(12) United States Patent
Hinderer et al.

(10) Patent No.: US 11,890,329 B2
(45) Date of Patent: Feb. 6, 2024

(54) AAV9-MEDIATED GENE THERAPY FOR TREATING MUCOPOLYSACCHARIDOSIS TYPE I

(71) Applicant: The Trustees of the University of Pennsylvania, Philadelphia, PA (US)

(72) Inventors: Christian Hinderer, New Orleans, LA (US); James M. Wilson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 770 days.

(21) Appl. No.: 16/624,084

(22) PCT Filed: Jul. 5, 2018

(86) PCT No.: PCT/US2018/040957
§ 371 (c)(1),
(2) Date: Dec. 18, 2019

(87) PCT Pub. No.: WO2019/010335
PCT Pub. Date: Jan. 10, 2019

(65) Prior Publication Data
US 2020/0147185 A1    May 14, 2020

Related U.S. Application Data

(60) Provisional application No. 62/529,385, filed on Jul. 6, 2017, provisional application No. 62/530,614, filed on Jul. 10, 2017, provisional application No. 62/616,106, filed on Jan. 11, 2018.

(51) Int. Cl.
| | |
|---|---|
| *A61K 38/47* | (2006.01) |
| *A61K 9/00* | (2006.01) |
| *A61K 31/343* | (2006.01) |
| *A61K 31/439* | (2006.01) |
| *A61K 35/76* | (2015.01) |
| *A61K 45/06* | (2006.01) |
| *C12N 7/00* | (2006.01) |
| *C12N 9/24* | (2006.01) |
| *C12N 15/86* | (2006.01) |
| *A61P 3/00* | (2006.01) |
| *A61K 48/00* | (2006.01) |

(52) U.S. Cl.
CPC ............ *A61K 38/47* (2013.01); *A61K 9/0019* (2013.01); *A61K 31/343* (2013.01); *A61K 31/439* (2013.01); *A61K 35/76* (2013.01); *A61K 45/06* (2013.01); *A61P 3/00* (2018.01); *C12N 7/00* (2013.01); *C12N 9/2402* (2013.01); *C12N 15/86* (2013.01); *C12Y 302/01076* (2013.01); *A61K 48/00* (2013.01); *A61K 48/0083* (2013.01); *C12N 2750/14121* (2013.01); *C12N 2750/14132* (2013.01); *C12N 2750/14143* (2013.01)

(58) Field of Classification Search
CPC ............................... A61K 35/76; A61K 38/47
See application file for complete search history.

(56) References Cited

U.S. PATENT DOCUMENTS

| | | |
|---|---|---|
| 5,478,745 A | 12/1995 | Samulski et al. |
| 6,149,909 A | 11/2000 | Scott et al. |
| 6,426,208 B1 | 7/2002 | Kakkis et al. |
| 6,596,535 B1 | 7/2003 | Carter |
| 7,125,717 B2 | 10/2006 | Carter |
| 7,282,199 B2 | 10/2007 | Gao et al. |
| 7,456,683 B2 | 11/2008 | Takano et al. |
| 7,588,772 B2 | 9/2009 | Kay et al. |
| 7,790,449 B2 | 9/2010 | Gao et al. |
| 7,906,111 B2 | 3/2011 | Wilson et al. |
| 8,318,480 B2 | 11/2012 | Gao et al. |
| 8,927,514 B2 | 1/2015 | Chatterjee et al. |
| 9,102,949 B2 | 8/2015 | Gao et al. |
| 9,585,971 B2 | 3/2017 | Deverman et al. |
| 9,827,295 B2 | 11/2017 | Mcivor et al. |
| 10,137,176 B2 | 11/2018 | Wilson et al. |
| 2005/0057114 A1 | 3/2005 | Calico |
| 2006/0057114 A1 | 3/2006 | Whitley et al. |
| 2007/0036760 A1 | 2/2007 | Wilson et al. |
| 2009/0062144 A1 | 3/2009 | Guo |
| 2009/0197338 A1 | 8/2009 | Vandenberghe et al. |
| 2010/0047174 A1 | 2/2010 | Kay et al. |
| 2012/0225933 A1 | 9/2012 | Gonzalez Aseguinolaza et al. |

(Continued)

FOREIGN PATENT DOCUMENTS

| | | |
|---|---|---|
| CN | 102869779 A | 1/2013 |
| EP | 1310571 | 2/2006 |

(Continued)

OTHER PUBLICATIONS

Aldenhoven et al., The Clinical Outcome of Hurler Syndrome after Stem Cell Transplantation, Biology of Blood and Marrow Transplantation, vol. 14(5): 485-498, 2008 (ePub May 2008).

Andersen et al., Herpesvirus-mediated gene delivery into the rat brain: specificity and efficiency of the neuron-specific enolase promoter, Cell. Mol. Neurobiol., vol. 13(5): 503-15, Oct. 1993.

Arbuthnot et al., In vitro and in vivo hepatoma cell-specific expression of a gene transferred with an adenoviral vector, Hum. Gene Ther., vol. 7(13): 1503-14, Aug. 1996.

Ashton LJ et al. Immunoquantification and enzyme kinetics of alpha-L-iduronidase in cultured fibroblasts from normal controls and mucopolysaccharidosis type I patients. Am J Hum Genet. Apr. 1992;50(4):787-94. (Apr. 1992).

(Continued)

*Primary Examiner* — Kevin E Weddington
(74) *Attorney, Agent, or Firm* — Howson & Howson; Cathy A. Kodroff

(57) ABSTRACT

A co-therapeutic regimen comprising AAV9-mediated intrathecal/intracisternal and/or systemic delivery of an expression cassette containing a hIDUA gene and two or more immunosuppressants is provided herein. Also provided are methods useful for treating hIDUA deficiency (MPSI) and the symptoms associated with Hurler, Hurler-Scheie and Scheie syndromes.

37 Claims, 23 Drawing Sheets

Figure 1:
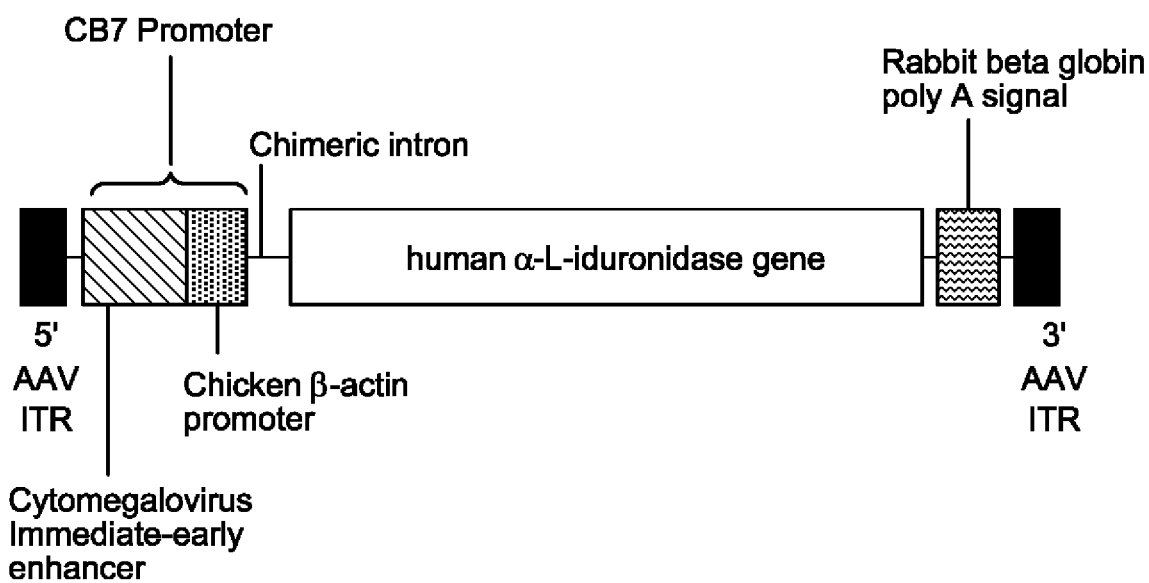

Specification includes a Sequence Listing.

(56) References Cited

U.S. PATENT DOCUMENTS

| | | |
|---|---|---|
| 2013/0045186 A1 | 2/2013 | Gao et al. |
| 2013/0225666 A1 | 8/2013 | Kaspar et al. |
| 2014/0017212 A1 | 1/2014 | Rebar |
| 2015/0315612 A1 | 11/2015 | Wilson et al. |
| 2015/0349911 A1 | 12/2015 | Otsubo |
| 2016/0000887 A1 | 1/2016 | Wilson et al. |
| 2016/0120960 A1 | 5/2016 | Mcivor et al. |
| 2016/0136293 A1 | 5/2016 | Littman et al. |
| 2018/0036388 A1 | 2/2018 | Mcivor et al. |
| 2019/0038772 A1 | 2/2019 | Hinderer et al. |
| 2019/0111116 A1 | 4/2019 | Wilson et al. |
| 2019/0269799 A1 | 9/2019 | Laoharawee et al. |
| 2019/0358303 A1 | 11/2019 | Yoo et al. |
| 2020/0147185 A1 | 5/2020 | Hinderer et al. |
| 2021/0275647 A1 | 9/2021 | Yoo et al. |
| 2023/0059395 A1 | 2/2023 | Pakola et al. |

FOREIGN PATENT DOCUMENTS

| | | | |
|---|---|---|---|
| JP | 2002/514429 | 5/2002 | |
| JP | 2004-504016 | 2/2004 | |
| JP | 2016-523835 | 8/2016 | |
| RU | 2196988 C2 | 5/2002 | |
| WO | WO 1993/010244 | 5/1993 | |
| WO | WO-1998/010088 | 3/1998 | |
| WO | WO-1999/058691 | 11/1999 | |
| WO | WO 2002/002597 | 1/2002 | |
| WO | WO 2002/004616 | 1/2002 | |
| WO | WO-2003/042397 | 5/2003 | |
| WO | WO-2005/033321 | 4/2005 | |
| WO | WO-2006/110689 | 10/2006 | |
| WO | WO-2011/126808 | 10/2011 | |
| WO | WO-2011/154520 | 12/2011 | |
| WO | WO-2012/112832 | 8/2012 | |
| WO | WO-2012/145601 | 10/2012 | |
| WO | WO-2014/151341 | 9/2014 | |
| WO | WO-2014/186579 | 11/2014 | |
| WO | WO-2017/100676 | 6/2015 | |
| WO | WO 2015/164723 | 10/2015 | |
| WO | WO-2016/049230 | 3/2016 | |
| WO | WO-2016/055437 | 4/2016 | |
| WO | WO-2016/187017 | 11/2016 | |
| WO | WO 2017/024198 | 2/2017 | |
| WO | WO-2017/024204 | 2/2017 | |
| WO | WO-2017/070678 | 4/2017 | |
| WO | WO-2017/100674 | 6/2017 | |
| WO | WO-2017/100704 | 6/2017 | |
| WO | WO-2017/123757 | 7/2017 | |
| WO | WO-2017/136500 | 8/2017 | |
| WO | WO-2017/160360 | 9/2017 | |
| WO | WO 2018/093925 | 5/2018 | |
| WO | WO-2019/010335 | 1/2019 | |
| WO | WO-2019010335 A1 * | 1/2019 | ........... A61K 31/343 |
| WO | WO 2018/144441 | 8/2019 | |
| WO | WO 2020/018665 | 1/2020 | |
| WO | WO 2021/150570 | 7/2021 | |
| WO | WO 2022/170082 A1 | 8/2022 | |

OTHER PUBLICATIONS

Belting et al., Glypican-1 is a vehicle for polyamine uptake in mammalian cells: a pivital role for nitrosothiol-derived nitric oxide, Journal of Biological Chemistry, vol. 278(47): 47181-47189, Nov. 2003.

Belting et al., Proteoglycan involvement in polyamine uptake, Biochemical Journal, vol. 338: 317-323, Mar. 1999.

Bertola et al. "IDUA mutational profiling of a cohort of 102 European patients with mucopolysaccharidosis type I: identification and characterization of 35 novel α-L-iduronidase (IDUA) alleles." Hum Mutat. Jun. 2011;32(6):E2189-210. doi: 10.1002/humu. 21479, Epub Mar. 10, 2011.

Belur et al., AAV Vector-Mediated Iduronidase Gene Delivery in a Murine Model of Mucopolysaccharidosis Type I: Comparing Different Routes of Delivery to the CNS (Abstract from Poster Session), The American Society of Gene & Cell Therapy, May 17, 2013.

Boshart et al. "A very strong enhancer is located upstream of an immediate early gene of human cytomegalovirus." Cell. Jun. 1985;41(2):521-30, (Jun. 1985).

Bradbury et al., A review of gene therapy in canine and feline models of lysosomal storage disorders, Human Gene Therapy Clinical Development, vol. 26(1): 27-37, Mar. 2015.

Bremer et al., A novel mucopolysaccharidosis type I associated splice site mutation and IDUA splice variants, Mol. Genet. Metab., vol. 104(3): 289-294, Nov. 2011 (ePub Jul. 2011).

Cai et al., Arginase I and polyamines act downstream from cyclic AMP in overcoming inhibition of axonal growth MAG and myelin in vitro, Neuron, vol. 35(4): 711-719, Aug. 2002.

Calcedo et al., Worldwide Epidemiology of Neutralizing Antibodies to Adeno-Associated Viruses, Journal of Infectious Diseases, vol. 199(3): 381-390, Feb. 2009.

Chen et al., Expression of rat bone sialoprotein promoter in transgenic mice, J. Bone Miner, Res., vol. 11(5):654-64, May 1996.

Chen et al., Glycosaminoglycan storage in neuroanatomical regions of mucopolysaccharidosis I dogs following intrathecal recombinant human iduronidase, Apmis, vol. 119(8): 513-521, Aug. 2011 (May 2011).

Chkioua L et al. Molecular analysis of mucopolysaccharidosis type I in Tunisia: identification of novel mutation and eight Novel polymorphisms. Diagn Pathol. Apr. 26, 2011;6:39. doi: 10.1186/1746-1596-6-39. Published online Apr. 26, 2011.

Chkioua L et al. Mucopolysaccharidosis type I: molecular characteristics of two novel alpha-L-iduronidase mutations in Tunisian patients. Diagn Pathol. Jun. 3, 2011;6:47. doi: 10.1186/1746-1596-6-47. Published online Jun. 3, 2011.

Ciron et al., Human alpha-Iduronidase Gene Transfer Mediated by Adeno-Associated Virus Types 1, 2, and 5 in the Brain of Nonhuman Primates: Vector Diffusion and Biodistribution, Human Gene Therapy, vol. 20:350-360, Apr. 2009.

Cotugno et al., Impact of Age at Administration, Lysosomal Storage, and Transgene Regulatory Elements on AAV2/8-Mediated Rat Liver Transduction, PLoS One, vol. 7(3):e33286, Mar. 13, 2012.

Deng et al., Increased synthesis of spermidine as a result of upregulation of arginase I promotes axonal regeneration in culture and in vivo, The Journal of Neuroscience, vol. 29: 9545-9552, Jul. 2009.

Desmaris, et al., Prevention of neuropathology in the mouse model of Hurler syndrome. Ann Neurol. Jul. 2004;56(1):68-76, First published: Jun. 28, 2004.

Devereux et al., A comprehensive set of sequence analysis programs for the VAX, Nucleic Acids Res., vol. 12:387-395, Jan. 1984.

Dickson et al., Early versus late treatment of spinal cord compression with longterm intrathecal enzyme replacement therapy in canine mucopolysaccharidosis type I, Mol. Genet. Metab., vol. 101: 115-122, Oct. 2010 (ePub Jul. 2010).

Dickson et al., Immune tolerance improves the efficacy of enzyme replacement therapy in canine mucopolysaccharidosis I, J Clin Invest, vol. 118: 2868-2876, Aug. 2008.

Duque, et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

Fisher et al. "Transduction with recombinant adeno-associated virus for gene therapy is limited by leading-strand synthesis." J Virol. Jan. 1996;70(1):520-32. (Jan. 1996).

Fu et al., Production and characterization of soluble human lysosomal enzyme α-iduronidase with high activity from culture media of transgenic tobacco BY-2 cells, Plant Science, vol. 177(6): 668-675, Dec. 2009.

Gossen et al. "Tight control of gene expression in mammalian cells by tetracycline-responsive promoters." Proc Natl Acad Sci USA. Jun. 15, 1992;89(12):5547-51. (Jun. 1992).

Gossen et al. "Transcriptional activation by tetracyclines in mammalian cells." Science. Jun. 23, 1995;268(5218):1766-9, (Jun. 1995).

(56) References Cited

OTHER PUBLICATIONS

Gao et al., Activated CREB is sufficient to overcome inhibitors in myelin and promote spinal axon regeneration in vivo, Neuron, vol. 44: 609-621, Nov. 2004.

Gao et al., Adeno-associated viruses undergo substantial evolution in primates during natural infections, PNAS, vol. 100(10): 6081-6086, May 2003 (ePub Apr. 2003).

GenBank Accession No. AAS99264, capsid protein VP1 [Adeno-associated virus 9], Jun. 2004.

GenBank Accession No. K03104.1, Human cytomegalovirus major immediate-early gene, enhancer, Aug. 1993.

GenBank Accession No. NC001401, Adeno-associated virus-2, complete genome, Aug. 2018.

GenBank Accession No. NP_000194.2, alpha-L-iduronidase isoform a precursor [*Homo sapiens*], Mar. 2019.

GenBank Accession No. V00882.1, Rabbit (*O. cuniculus*) gene for beta-globin, Nov. 2006.

GenBank Accession No. X00182.1, Gallus cytoplasmic beta-actin gene, Nov. 2006.

Gray et al., Optimizing promoters for recombinant adeno-associated virus-mediated gene expression in the peripheral and central nervous system using self-complementary vectors, Hu Gene Ther, vol. 22(9): 1143-1153, Sep. 2011 (ePub Jun. 2011).

Grimm et al., Titration of AAV-2 particles via a novel capsid ELISA: packaging of genomes can limit production of recombinant AAV-2, Gene Therapy, vol. 6(7):1322-1330, Jul. 1999.

Gurda et al., Evaluation of AAV-mediated Gene Therapy for Central Nervous System Disease in Canine Mucopolysaccharidosis VII, Molecular Therapy, Feb. 2016 (ePub Oct. 2015).

Hall, BioEdit: a user-friendly biological sequence alignment editor and analysis program for Windows 95/98/NT, Nucl. Acids. Symp. Ser., vol. 41: 95-98, Jan. 1999.

Hansal et al., Induction of antigen-specific hyporesponsiveness by transplantation of hemopoietic cells containing an MHC class I transgene regulated by a lymphocyte-specific promoter, J. Immunol., vol. 161: 1063-8, Aug. 1998.

Hartung et al. "Correction of metabolic, craniofacial, and neurologic abnormalities in MPS I mice treated at birth with adeno-associated virus vector transducing the human alpha-L-iduronidase gene." Mol Ther. Jun. 2004;9(6):866-75, (Jun. 2004).

Harvey et al. "Inducible control of gene expression: prospects for gene therapy." Curr Opin Chem Biol. Aug. 1998;2(4):512-8, (Aug. 1998).

Haskins et al., The pathology of the feline model of mucopolysaccharidosis I, Am. J. Pathol., vol. 112: 27, Jul. 1983.

Haurigot et al., Whole body correction of mucopolysaccharidosis TITA by intracerebrospinal fluid gene therapy, Journal of Clinical Investigation, vol. 123(8): 3254-3271, Jul. 2013.

He et al., Characterization and downstream mannose phosphorylation of human recombinant α-L-iduronidase produced in *Arabidopsis* complex glycan-deficient (cgl) seeds, Plant Biotechnol J., vol. 11(9): 1034-1043, Dec. 2013.

Hinderer et al., Intrathecal Gene Therapy Corrects CNS Pathology in a Feline Model of Mucopolysaccharidosis I., Molecular Therapy, vol. 22(12):2018-27, Dec. 2014 (ePub Jul. 2014).

Hinderer et al., Liver-directed gene therapy corrects cardiovascular lesions in feline mucopolysaccharidosis type I, PNAS, vol. III: 14894-14899, Oct. 2014 (ePub Sep. 2014).

Hinderer et al., Neonatal Systemic AAV Induces Tolerance to CNS Gene Therapy in MPS I Dogs and Nonhuman Primates, Molecular Therapy, vol. 23(8):1298-1307, Aug. 2015.

Hinderer et al., Neonatal tolerance induction enables accurate evaluation of gene therapy for MPS I in a canine model, Molecular Genetics and Metabolism, vol. 119(1-2):124-30, Sep. 2016 (ePub Jun. 2016).

HRSA.gov, Newborn Screening for Mucopolysaccharidosis Type 1 (MPS I): A Systematic Review of Evidence Report of Final Findings, Final Version 1.1, pp. 1-11, Mar. 2015.

Hayashi et al. "Human thyroxine-binding globulin gene: complete sequence and transcriptional regulation," Mol Endocrinol, Aug. 1993;7(8):1049-60, (Aug. 1993).

Jani, et al., Generation, validation, and large scale production of adenoviral recombinants with large size inserts such as a 6.3 kb human dystrophin cDNA. J Virol Methods. Mar. 1997;64(2):111-24.

Kakkis et al., Enzyme replacement therapy in feline mucopolysaccharidosis I, Mol Genet Metabol, vol. 72(3): 199-208, Feb. 2001.

Kakkis et al., Successful induction of immune tolerance to enzyme replacement therapy in canine mucopolysaccharidosis I, PNAS, vol. 101(3): 829-34, Jan. 2004.

Kalb, Regulation of motor neuron dendrite growth by NMDA receptor activation, Development, vol. 120:3063-3071, Nov. 1994.

Lawrence et al., Disease-specific non-reducing end carbohydrate biomarkers for mucopolysaccharidoses, Nature Chemical Biology, vol. 8: 197-204, Jan. 2012.

Li et al. "Synthetic muscle promoters: activities exceeding naturally occurring regulatory sequences." Nat Biotechnol, Mar. 1999;17(3):241-5, (Mar. 1999).

Lock et al., Absolute determination of single-stranded and self-complementary adeno-associated viral vector genome titers by droplet digital PCR, Hu Gene Therapy Methods, vol. 25(2):115-25, Apr. 2014 (ePub Feb. 2014).

Lock et al., Rapid, simple, and versatile manufacturing of recombinant adeno-associated viral vectors at scale, Human Gene Therapy, vol. 21(10):1259-1271, Oct. 2010.

Lykken, et al., Recent progress and considerations for AAV gene therapies targeting the central nervous system. J Neurodev Disord. May 18, 2018; 10(1):16. doi: 10.1186/s11689-018-9234-0, Published online May 18, 2018.

MacDonald ME et al. Huntington disease-linked locus D4S111 exposed as the alpha-L-iduronidase gene. Somat Cell Mol Genet. Jul. 1991;17(4):421-5.

Magari et al. "Pharmacologic control of a humanized gene therapy system implanted into nude mice." J Clin Invest. Dec. 1, 1997;100(11):2865-72, (Dec. 1997).

McCarty et al., Self-complementary recombinant adeno-associated virus (scAAV) vectors promote efficient transduction independently of DNA synthesis, Gene Therapy, vol. 8(16): 1248-1254, Aug. 2001.

Menon et al., Architecture of the canine IDUA gene and mutation underlying canine mucopolysaccharidosis I, Genomics, vol. 14: 763-768, Nov. 1992.

Merrifield, Solid Phase Peptide Synthesis. I. The Synthesis of a Tetrapeptide, J. Am. Chem. Soc., vol. 85(14):2149, Jul. 1963.

Meyer et al., Improving Single Injection CSF Delivery of AAV9-mediated Gene Therapy for SMA: A Dose-response Study in Mice and Nonhuman Primates, Molecular Therapy, vol. 23(3):477-487, Mar. 2015.

Michelfelder, et al., Peptide ligands incorporated into the threefold spike capsid domain to re-direct gene transduction of AAV8 and AAV9 in vivo. PLoS One. 2011;6(8):e23101. doi: 10.1371/journal.pone.0023101. Epub Aug. 5, 2011.

Miyatake et al., Transcriptional targeting of herpes simplex virus for cell-specific replication., J. Virol., vol. 71: 5124-32, Jul. 1997.

Mizushima and Nagata, pEF-BOS, a powerful mammalian expression vector. Nucleic Acids Res. Sep. 11, 1990;18(17):5322.

No et al. "Ecdysone-inducible gene expression in mammalian cells and transgenic mice." Proc Natl Acad Sci USA. Apr. 16, 1996;93(8):3346-51. (Apr. 1996).

Pearson et al., Improved tools for biological sequence comparison, PNAS, vol. 85: 2444-2448, Apr. 1988.

Piccioli et al., Neuroantibodies: ectopic expression of a recombinant anti-substance P antibody in the central nervous system of transgenic mice, Neuron, vol. 15: 373-84, Aug. 1995.

Piccioli et al., Neuroantibodies: molecular cloning of a monoclonal antibody against substance P for expression in the central nervous system, PNAS, vol. 88: 5611-5, Jul. 1991.

Ponder et al., Immune response hinders therapy for lysosomal storage diseases, J. Clin Invest., vol. 118(8)2686-2689, Jul. 24, 2008.

(56) References Cited

OTHER PUBLICATIONS

Rome et al., Direct demonstration of binding of a lysosomal enzyme, alpha-L-iduronidase, to receptors on cultured fibroblasts, PNAS, vol. 76: 2331-2334, May 1979.
Sandig et al., HBV-derived promoters direct liver-specific expression of an adenovirally transduced LDL receptor gene Ther., vol. 3: 1002-9, Nov. 1996.
Scott et al. "Human alpha-L-iduronidase: cDNA isolation and expression." Proc Natl Acad Sci USA, Nov. 1, 1991;88(21):9695-9. (Nov. 1991).
Scott et al. "Multiple polymorphisms within the alpha-L-iduronidase gene (IDUA): implications for a role in modification of MPS-I disease phenotype." Hum Mol Genet. Sep. 1993;2(9):1471-3, (Sep. 1993).
Scott et al. "PCR detection of two RFLPs in exon I of the alpha-L-iduronidase (IDUA) gene." Hum Genet. Nov. 1992;90(3):327. (Nov. 1992).
Scott et al. "Structure and sequence of the human alpha-L-iduronidase gene." Genomics. Aug. 1992;13(4):1311-3. (Aug. 1992).
Scott et al. alpha-L-iduronidase mutations (Q70X and P533R) associate with a severe Hurler phenotype. Hum Mutat. 1992;1(4):333-9.
Scott et al.. Chromosomal localization of the human alpha-L-iduronidase gene (IDUA) to 4p16.3. Am J Hum Genet. Nov. 1990;47(5):802-7.
Shull et al., Enzyme replacement in a canine model of Hurler syndrome, PNAS, vol. 91: 12937-12941, Dec. 1994.
Shull et al., Morphologic and biochemical studies of canine mucopolysaccharidosis I, Am J Pathol, vol. 114: 487-95, Mar. 1984.
Small Business Innovation Research-Small Business Technology Transfer, AAV Mediated Gene Transfer to the CNS for MPS I (Award Information), Retrieved from SBIR/STTR web site at https://www.sbir.gov/sbirsearch/detail/391096, Jan. 1, 2012.
Sommer et al., Quantification of adeno-associated virus particles and empty capsids by optical density measurement, Molec. Ther, vol. 7:122-128, Jan. 2003.
Stein et al., The osteocalcin gene: a model for multiple parameters of skeletal-specific transcriptional control, Mol. Biol. Rep., vol. 24: 185-96, Aug. 1997.
Tarantal et al., Intrapulmonary and intramyocardial gene transfer in rhesus monkeys (*Macaca mulatta*): safety and efficiency of HIV-1-derived lentiviral vectors for fetal gene delivery, Mol Ther, vol. 12: 87-98, Jul. 2005.
Teng et al. "Identification and characterization of-3c-g acceptor splice site mutation in human alpha-L-iduronidase associated with mucopolysaccharidosis type IH/S." Clin Genet. Feb. 2000;57(2):131-6, (First published: Feb. 2000).
Vera et al., Immune response to intrathecal enzyme replacement therapy in mucopolysaccharidosis I patients, Pediatr. Res., vol. 74: 712-720, Dec. 2013.
Velazquez, et al., Effective Depletion of Pre-existing Anti-AAV Antibodies Requires Broad Immune Targeting. Mol Ther Methods Clin Dev. Jan. 25, 2017;4:159-168. doi: 10.1016/j.omtm.2017.01.003. eCollection Mar. 17, 2017. Published online Jan. 25, 2017.
Vite et al., Correction of clinical manifestations of canine mucopolysaccharidosis I with neonatal retroviral vector gene therapy, Molecular Therapy, vol. 15: 1423-1431, Aug. 2007.
Vite et al., Features of brain MRI in dogs with treated and untreated mucopolysaccharidosis type I, Comp. Med., vol. 63: 163-173, Apr. 2013.
Walkley et al., Secondary lipid accumulation in lysosomal disease, Biochim. Biophys., vol. 1793: 726-736, Apr. 2009.
Wang et al., Hepatic gene transfer in neonatal mice by adeno-associated virus serotype 8 vector, Human Gene Therapy, vol. 23: 533-539, May 2012.
Wang et al., Impact of pre-existing immunity on gene transfer to nonhuman primate liver with adeno-associated virus 8 vectors, Human Gene Therapy, vol. 22: 1389-1401, Nov. 2011.

Wang et al. "Ligand-inducible and liver-specific target gene expression in transgenic mice." Nat Biotechnol, Mar. 1997;15(3):23 9-43, (Mar. 1997).
Wang et al. "Positive and negative regulation of gene expression in eukaryotic cells with an inducible transcriptional regulator." Gene Ther. May 1997;4(5):432-41, (May 1997).
Wang, et al., Adeno-associated virus serotype 8 efficiently delivers genes to muscle and heart. Nat Biotechnol. Mar. 2005;23(3):321-8, Epub Feb. 27, 2005.
Watson et al., Intrathecal administration of AAV vectors for the treatment of lysosomal storage in the brains of MPS I mice, Gene Therapy, vol. 13:917-925, Feb. 16, 2006.
Welch et al., Single chain fragment anti-heparan sulfate antibody targets the polyamine transport system and attenuates polyamine-dependent cell proliferation, International Journal of Oncology, vol. 32: 749-756, Apr. 2008.
Wobus et al., Monoclonal antibodies against the adeno-associated virus type 2 (AAV-2) capsid: epitope mapping and identification of capsid domains involved in AAV-2-cell interaction and neutralization of AAV-2 infection, J. Virol, vol. 74: 9281-9293, Oct. 2000.
Wolf et al., Direct gene transfer to the CNS prevents emergence of neurologic disease in a murine model of mucopolysaccharidosis type I, Neurobiology of Disease, vol. 43(1):123-133, Jul. 2011.
Wright, Manufacturing and characterizing AAV-based vectors for use in clinical studies, Gene Therapy, vol. 15(11):840-848, Apr. 2008.
Xia et al., MetaboAnalyst 2.0—a comprehensive server for metabolomic data analysis, Nucleic Acids Research, Jul. 2012 (ePub May 2012).
Xia et al., MetaboAnalyst 3.0—making metabolomics more meaningful, Nucleic Acids Research, Jul. 2015 (ePub Apr. 2015).
Xia et al., MetaboAnalyst: a web server for metabolomic data analysis and interpretation, Nucleic Acids Research, vol. 37: W652-W660, Jul. 2009.
Yan, et al., Human thyroxine binding globulin (TBG) promoter directs efficient and sustaining transgene expression in liver-specific pattern. Gene. Sep. 15, 2012;506(2):289-94, doi: 10.1016/j.gene.2012.07.009. Epub Jul. 20, 2012.
Yogalingam et al. "Identification and molecular characterization of alpha-L-iduronidase mutations present in mucopolysaccharidosis type I patients undergoing enzyme replacement therapy." Hum Mutat. Sep. 2004;24(3):199-207. (First published: Jul. 26, 2004).
"Alpha-L-iduronidase precursor [*Homo sapiens*]," Web page <https://www.ncbi.nlm.nih.gov/protein/110611239?sat-17&satkey-19459260>, 3 pages, Oct. 27, 2012, retrieved on Mar. 3, 2018, NCBI Reference Sequence NP_000194.2.
"Alpha-L-iduronidase precursor [*Homo sapiens*]," Web page <https://www.ncbi.nlm.nih.gov/protein/110611239?sat-17&satkey-23266850>, 3 pages, Feb. 17, 2013, retrieved on Mar. 3, 2018, NCBI Reference Sequence NP_000194.2.
"*Homo sapiens* iduronidase, alpha-L- (IDUA), mRNA," Web page <https://www.ncbi.nlm.nih.gov/nuccore/110611238?sat=17&satkey=23266850>, 4 pages, Feb. 17, 2013, retrieved on Mar. 8, 2018, NCBI Reference Sequence NM_000203.3.
International Search Report and Written Opinion issued on International Patent Application No. PCT/US2017/016133, dated Apr. 5, 2017.
U.S. Appl. No. 62/226,357, filed Dec. 11, 2015.
U.S. Appl. No. 62/266,341, filed Dec. 11, 2015.
U.S. Appl. No. 62/266,347, filed Dec. 11, 2015.
U.S. Appl. No. 62/266,351, filed Dec. 11, 2015.
U.S. Appl. No. 62/290,547, filed Feb. 3, 2016.
U.S. Appl. No. 62/322,055, filed Apr. 13, 2016.
U.S. Appl. No. 62/322,071, filed Apr. 13, 2016.
U.S. Appl. No. 62/322,083, filed Apr. 13, 2016.
U.S. Appl. No. 62/322,098, filed Apr. 13, 2016.
U.S. Appl. No. 62/323,271, filed Apr. 16, 2016.
U.S. Appl. No. 62/337,178, filed May 16, 2016.
U.S. Appl. No. 62/367,798, filed Jul. 28, 2016.
U.S. Appl. No. 62/452,560, filed Jan. 31, 2017.
Third Office Action issued in Chinese Patent Application No. 201480010987.3 dated Aug. 15, 2019 with unofficial English translation provided by the Agent.

(56) References Cited

OTHER PUBLICATIONS

Response filed Sep. 24, 201 in European Patent Application No. 14770186.6 in reply to the May 15, 2019 communication under Rule 71(3) EPC indicating intention to grant a European patent.
Response filed Sep. 10, 2018 in reply to the May 17, 2018 communication pursuant to Article 94(3) EPC in European Patent Application No. 14770186.6.
Communication pursuant to Article 94(3) EPC dated Sep. 6, 2019 in European Patent Application No. 17706915.0.
Office Action dated Oct. 23, 2019 in Mexican Patent Application No. MX/a/2015/012739 with unofficial English translation provided by the Agent.
Third-party submission under 37 CFR 1.290 and Concise Description of Relevance dated Jul. 7, 2016 with respect to U.S. Appl. No. 14/769,596.
International Search Report and Written Opinion issued on parent International Patent Application No. PCT/US14/25509, dated Aug. 19, 2014.
International Search Report and Written Opinion issued on International Patent Application No. PCT/US18/40957, dated Oct. 8, 2018.
Extended European search report issued on European Patent Application No. 14770186.6, dated Aug. 5, 2016.
Communication pursuant to Rule 70(2) and 70a (2) EPC issued on European Patent Application No. 14770186.6, dated Aug. 23, 2016.
Reply to communication pursuant to Rule 70(2) and 70a (2) EPC dated Aug. 23, 2016 issued on European Patent Application No. 14770186.6, filed Feb. 20, 2017.
Communication pursuant to Rule 94(3) EPC issued on European Patent Application No. 14770186.6, dated May 17, 2018.
First Office Action issued in Chinese Patent Application No. 201480010987.3 dated Jan. 22, 2018 with unofficial English translation.
Second Office Action issued in Chinese Patent Application No. 201480010987.3 dated Dec. 6, 2018 with unofficial English translation.
First Office Action issued in Japanese Patent Application No. 2016-501864 dated Jan. 31, 2018 with unofficial English translation.
First Office Action issued on Russian Patent Application No. 2015144234 dated Sep. 14, 2017 with unofficial English translation.
Second Office Action issued in Russian Patent Application No. 2015144234 dated Feb. 12, 2018 with unofficial English translation.
Third Office Action issued in Russian Patent Application No. 2015144234 dated Oct. 11, 2018 with unofficial English translation.
Second Office Action issued on Japanese Patent Application No. 2016-501864 dated Dec. 20, 2018 with unofficial English translation.
An Office Action issued on Australian Patent Application No. 2014235096 dated Mar. 8, 2019.
Restriction requirement issued on U.S. Appl. No. 14/769,596, dated May 8, 2017.
Response filed on Sep. 26, 2017 in reply to the May 8, 2017 Restriction requirement with respect to U.S. Appl. No. 14/769,596.
Nonfinal Office Action issued on U.S. Appl. No. 14/769,596, dated Nov. 3, 2017.
Response filed on Mar. 5, 2018 in reply to the Nov. 3, 2017 Office Action vith respect to U.S. Appl. No. 14/769,596.
Final Office Action issued on U.S. Appl. No. 14/769,596, dated May 18, 2018.
Response filed on Jun. 27, 2018 in reply to the May 18, 2018 Office Action with respect to U.S. Appl. No. 14/769,596.
Non-Final Office Action issued on U.S. Appl. No. 16/166,346, dated Dec. 3, 2019.
Office Action issued on U.S. Appl. No. 16/166,346, dated Dec. 5, 2019.
Restriction Requirement issued on U.S. Appl. No. 16/075,056, dated Feb. 4, 2020.
Cardone et al., Correction of Hunter syndrome in the MPSII mouse model by AAV2/8-mediated gene delivery, Human Molecular Genetics, vol. 15(7):1225-1236, Jan. 2006.
Office Action dated Mar. 9, 2020 issued in corresponding Canadian Patent Application No. 2,901,328, and Response filed Jul. 9, 2020.
Office Action dated Mar. 20, 2020 issued in corresponding Korean Patent Application No. 10-2015-7022504, with translation provide by local Agent.
Response filed Jun. 30, 2020 in reply to the Mar. 20, 2020 Office Action with respect to corresponding Korean Patent Application No. 10-2015-7022504.
Communication dated Jul. 27, 2020 issued in corresponding European Patent Application No. 17706915.0.
Extended European Search Report dated Oct. 2, 2020 issued in corresponding European Patent Application No. 20170476.4.
Swain et al., Adeno-associated virus serotypes 9 and rh10 mediate strong neuronal transduction of the dog brain, Gene Therapy, vol. 21:28-36, Jan. 2014.
Wang, R.Y., RGX-111 Gene Therapy for the Treatment of Severe Mucopolysaccharidosis Type I (MPS I): Interim Analysis of the First in Human Study and a Single Patient IND, Feb. 24, 2023, presentation at WORLDSymposium™ (https://www.regenxbio.com/wp-content/uploads/2023/02/RGX-111-WORLD23-FINAL.pdf).
Wang, R.Y., RGX-111 Gene Therapy for the Treatment of Severe Mucopolysaccharidosis Type I: Interim Analysis of the First in Human Study and a Single Patient IND, Feb. 9, 2022, presentation at WORLDSymposium™ (https://www.regenxbio.com/wp-content/uploads/2022/02/FINAL-WORLD22_111_002andSP_IND.pdf).
Podetz-Pedersen, K.M., Neurologic Recovery in MPS I and MPS II Mice by AAV9-Mediated Gene Transfer to the CNS After the Development of Cognitive Dysfunction, Hum Gene Ther, Jan. 2023, 34(1-2):8-18.
Olfest, J.R., Phenotypic correction and long-term expression of factor VIII in hemophilic mice by immunotolerization and nonviral gene transfer using the Sleeping Beauty transposon system, Blood: Gene Therapy, 2005, 105(7):2691-2698, Apr. 1, 2005.
Wang, R.Y., et al., First in human Intracistemal Dosing of RGX 111 (Adeno associated Virus 9 / Human Alpha 1 Iduronidase) for a 20-Month-old Child with Mucopolysaccharidosis Type I (MPSI): 1 Year Follow up, 14th International Congress of Inborn Errors of Metabolism, Nov. 21-23, 2021, Sydney, Australia, presentation (https://www.iciem2021.com.au/iciem2021/Poster/Posters/poster_59.pdf).
Hinderer, Christian, "Intrathecal Adeno-Associated Virus Vector Delivery for Mucopolysaccharidosis Type I" (2015). Publicly Accessible Penn Dissertations. 1763 (https://repository.upenn.edu/edissertations/1763).
Vance, M., AAV Gene Therapy for MPS-1 associated Corneal Blindness, Sci. Rep., 2016, 6:22131, epub Feb. 22, 2016.
Belur et al., 2015, "Non-Invasive Intranasal Administration of AAV9-Iduronidase Prevents Emergence of Neurologic Disease and Neurocognitive Dysfunction in a Murine Model of Mucopolysaccharidosis Type I," Molecular Therapy, 23(1):s281, #706.
Bragonzi et al., 2000, "A new Chinese hamster ovary cell line expressing α2,6-sialyltransferase used as universal host for the production of human-like sialylated recombinant glycoproteins," Biochimica et Biophysica Acta (BBA)—General Subjects, 1474(3):273-282.
Calias et al., 2014, "Intrathercal delivery of protein therapeutics to the brain: a critical reassessment," Pharmacology & Therapeutics, 144(2):114-122.
Gray et al., 2013, "Global CNS Gene Delivery and Evasion of Anti-AAV Neutralizing Antibodies by Intrathecal AAV Administration in Non-Human Primates," Gene Therapy, 20(4):450-459.
Jung et al., 2013, "Characterization of α-l-Iduronidase (Aldurazyme®) and its complexes," Journal of Proteomics, 80:26-33.
Lee et al., 2015,"Effects of N-glycosylation on protein conformation and dynamics: Protein Data Bank analysis and molecular dynamics simulation study," Scientific Reports, 5, 8926:1-7.
Solá and Griebenow, 2009, "Effects of Glycosylation on the Stability of Protein Pharmaceuticals," Journal of Pharmaceutical Sciences, 98(4):1223-1245.
Unger et al., 1994, "Recombinant α-l-iduronidase: characterization of the purified enzyme and correction of mucopolysaccharidosis type I fibroblasts," Biochemical Journal, 304:43-49.

(56) References Cited

OTHER PUBLICATIONS

Wynn et al., 2009, "Use of Enzyme Replacement Therapy (Laronidase) before Hematopoietic Stem Cell Transplantation for Mucopolysaccharidosis I: Experience in 18 Patients" The Journal of Pediatrics, 154(1):135-139.
Belichenko et al., 2005, "Penetration, diffusion, and uptake of recombinant human α-l-iduronidase after intraventricular injection into the rat brain," Molecular Genetics and Metabolism, 86(1-2):141-149.
Cohen-Pfeffer et al., 2017, "Intracerebroventricular Delivery as a Safe, Long-Term Route of Drug Administration," Pediatric Neurology, 67:23-25.
Dickson et al., 2007, "Intrathecal enzyme replacement therapy: Successful treatment of brain disease via the cerebrospinal fluid," Molecular Genetics and Metabolism, 91(1):61-68.
Drake et al., 2000, "CSF shunts 50 years on—past, present and future," Child's Nervous System, 16:800-804.
Kratzer et al., 2003, "Factors Affecting Liver Size: a Sonographic Survey of 2080 Subjects," Journal of Ultrasound Medicine, 22(11):1155-1161.
Moore et al., 2008, "The prevalence of and survival in Mucopolysaccharidosis I: Hurler, Hurler-Scheie and Scheie syndromes in the UK," Orphanet Journal of Rare Diseases, 3:24.
O'Reilly et al., 2013, "Gene therapy for rare diseases: summary of a National Institutes of Health workshop, Sep. 13, 2012," Human Gene Therapy, 24(4):355-362.
Raymond et al., 2012, "Production of highly sialylated monoclonal antibodies", Intech, Glycosylation and Structure:397-418.
Sawamoto et al., 2018, "Gene therapy for Mucopolysaccharidoses," Molecular Genetics and Metabolism, 123(2):59-68.
Slavc et al., 2018, "Best practices for the use of intracerebroventricular drug delivery devices," Molecular Genetics and Metabolism, 124:184-188.
Song et al., 2014, "In-Depth Method for the Characterization of Glycosylation in Manufactured Recombinant Monoclonal Antibody Drugs", Analytical Chemistry, 86(12):5661-5666 and Supplemental Data.
Stone et al., 2009, "Tyrosine sulfation: an increasingly recognised post-translational modification of secreted proteins", New Biotechnology, 25(5):299-317.
Wolf, D, 2010, "Molecular Therapy for Mucopolysaccharidosis Type I," A Dissertation Submitted to the Graduate School of the University of Minnesota (173 pages).
Clarke et al., 2009, "Long-term Efficacy and Safety of Laronidase in the Treatment of Mucopolysaccharidosis I," Pediatrics, 123(1):229-240 (abstract).
Office Action issued in corresponding Japanese Patent Application No. 2020-148103 dated Dec. 1, 2021, with unofficial English translation.
Office Action issued in corresponding Japanese Patent Application No. 2018-540838 dated Dec. 22, 2021, with unofficial English translation.
Examination Report dated May 17, 2022 issued in corresponding Australian Patent Application No. 2017215211.
Office Action dated Mar. 23, 2022 issued in corresponding Brazilian Patent Application No. BR112015021036-8, with unofficial English translation provided by local Agent.
Office Action dated Sep. 20, 2022 issued in corresponding Brazilian Patent Application No. BR112018015751-1, with unofficial English translation provided by local Agent.
International Search Report and Written Opinion dated Apr. 23, 2021 for PCT/US2021/014129.
Extended European Search report dated Oct. 5, 2020 for European Pat. App. No. 18748381.3.
Chen et al., "Glycoproteomics analysis of human liver tissue by combination of multiple enzyme digestion and hydrazide chemistry." J Proteome Res. Feb. 2009;8(2):651-61. doi: 10.1021/pr8008012. (Publication Date (Web): Jan. 21, 2009).

Ashley, Scott N., "Impact of Host Factors on The Adaptive Immune Response to AAV Gene Therapy" (2017). Publicly Accessible Penn Dissertations. 2171, https://repository.upenn.edu/edissertations/2171.
Belur, L.R., et al., Comparative Effectiveness of Intracerebroventricular, Intrathecal, and Intranasal Routes of AAV9 Vector Administration for Genetic Therapy of Neurologic Disease in Murine Mucopolysaccharidosis Type I, Front Mol Neurosci, May 10, 2021, 14:618360, eCollection 2021.
Belur, L.R., et al., Intranasal Adeno-Associated Virus Mediated Gene Delivery and Expression of Human Iduronidase in the Central Nervous System: A Noninvasive and Effective Approach for Prevention of Neurologic Disease in Mucopolysaccharidosis Type I, Hum Gene Ther, Jul. 2017, 28(7):576-587, Epub Apr. 2, 20170.
Belur, L.R., et al., Intravenous delivery for treatment of mucopolysaccharidosis type I: A comparison of AAV serotypes 9 and rh10, Mol Genet Metab Rep, May 20, 2020, 24:100604, eCollection Sep. 2020.
Cardone et al. "Correction of Hunter syndrome in the MPSII mouse model by AAV2/8-mediated gene delivery." Hum Mol Genet. Apr. 1, 2006;15(7):1225-36. Epub Feb. 2, 20067.
Hartung et al., Correction of Metabolic, Craniofacial, and Neurological Abnormalities in MPS I Mice Treated at Birth with Adeno-Associated Virus Vector Transducing the Human α-L-Iduronidase Gene, Molecular Therapy, vol. 9(6): 866-75, Jun. 2004.
Hinderer et al., Abnormal polyamine metabolism is unique to the neuropathic forms of MPS: potential for biomarker development and insight into pathogenesis, Human Molecular Genetics, 26(19):3837-3849, Oct. 1, 2017.
Hinderer et al., Evaluation of Intrathecal Routes of Administration for Adeno- Associated Viral Vectors in Large Animals, Human Gene Therapy, 2018, 29(1): 15-24, epub Oct. 3, 2017.
Hinderer et al., Widespread gene transfer in the central nervous system of cynomolgus macaques following delivery of AAV9 into the cisterna magna, Molecular Therapy: Methods and Clinical Development, Dec. 10, 2014, 1, 14051.
Hordeaux J et al., Safe and Sustained Expression of Human Iduronidase After Intrathecal Administration of Adeno-Associated Virus Serotype 9 in Infant Rhesus Monkeys, Human Gene Therapy, Aug. 16, 2019, (ePublished Jun. 10, 2019), 30(8):957-966.
Hordeaux J et al., Toxicology Study of Intra-Cisterna Magna Adeno- Associated Virus 9 Expressing Human Alpha-L-Iduronidase in Rhesus Macaques, 2018, Molecular Therapy: Methods & Clinical Development, Jul. 14, 2018, 10:79-88.
Ohlfest Jr et al., Phenotypic correction and long-term expression of factor VIII in hemophilic mice by immunotolerization and nonviral gene transfer using the Sleeping Beauty transposon system, Gene Therapy, Apr. 1, 2005, (ePublished Dec. 2, 2004), 105(7):2691-2698.
Aldenhoven et al., Hematopoietic cell transplantation for mucopolysaccharidosis patients is safe and effective: results after implementation of international guidelines. Biol Blood Marrow Transplant 2015;21:1106-9.
Aldenhoven et al., Long-term outcome of Hurler syndrome patients after hematopoietic cell transplantation: an international multicenter study, Blood 2015; 125(13):2164-72.
Beck et al., The natural history of MPS I: global perspectives from the MPS I Registry. Genet Med 2014; 16(10):759-65.
Bharucha-Goebel et al., Review of CSF and peripheral immune responses following intrathecal gene transfer for giant axonal neuropathy intrathecal gene transfer for giant axonal neuropathy. American Society of Gene & Cell Therapy 20th Annual Meeting; Washington, DC. May 10-13, 2017. Abstract No. 522.
Boelens et al., Current international perspectives on hematopoietic stem cell transplantation for inherited metabolic disorders. Pediatr Clin N Am 2010;57:123-45.
De Ru et al., Enzyme replacement therapy and/or hematopoietic stem cell transplantation at diagnosis in patients with mucopolysaccharidosis type I: results of a European consensus procedure, Orphanet J Rare Dis 2011;6:55.

(56) References Cited

OTHER PUBLICATIONS

Dickson et al., Initial experience with intrathecal recombinant human alpha-L- iduronidase for spinal cord compression in two mucopolysaccharidosis I patients [abstract], Mol Genet Metab 2008a;93(2):S19.
Dickson et al., Intrathecal recombinant human α-L-iduronidase alleviates spinal cord compression symptoms and is well-tolerated in attenuated MPS I patients [abstract], Mol Genet Metab 2008b;93(3):247.
El-Agroudy et al., Efficacy and safety of early tacrolimus conversion to sirolumus after kidney transplantation: Long-term results of a prospective randomized study. Indian J Nephrol 2017;27(1)28-36.
Ellinwood et al., Bone marrow transplantation for feline mucopolysaccharidosis I, Mol Genet Metab 2007;91(3):239-50.
Field et al., Comprehensive assessment of hemorrhage risks and outcomes after stereotactic brain biopsy, J Neurosurg. Apr. 2001. 94(4):545-51.
Gray et al., Preclinical differences of intravascular AAV9 delivery to neurons and glia: a comparative study of adult mice and nonhuman primates, Mol Ther 2011; 19(6): 1058-69. E-pub: Apr. 12, 2011.
Malone et al., Complications Following Stereotactic Needle Biopsy of Intracranial Tumors, World Neurosurg, Oct. 2015; 84(4): 1084-9.
Mitchell et al., Outcomes of haematopoietic stem cell transplantation for inherited metabolic disorders: a report from the Australian and New Zealand Children's Haematology Oncology Group and the Australian Bone Marrow Transplant Recipient Registry, Pediatr Transplantation 2013; 17(6):582-8.
Munoz-Rojas et al., Intrathecal enzyme replacement therapy in a patient with mucopolysaccharidosis type I and symptomatic spinal cord compression, American Journal of Medical Genetics Part A, vol. 146A:2538-2544, Jan. 2008.
Nestrasil et al., Intrathecal enzyme replacement therapy reverses cognitive decline in mucopolysaccharidosis type I. Am J Med Genet A 2017; 173(3):780-3.
De Simone et al., Everolimus With Reduced Tacrolimus Improves Renal Function in De Novo Liver Transplant Recipients: A Randomized Controlled Trial. American Journal of Transplantation 2012; 12: 3008-3020.
Pagon RA, Adam MP, Ardinger HH, et al., editors. GeneReviews [Internet]. Seattle, WA: University of Washington, Seattle; 1993-2017.
Passini et al., Translational fidelity of intrathecal delivery of self-complementary AAV9-survival motor neuron 1 for spinal muscular atrophy, Hum Gene Ther 2014;25(7):619-30.
Shaprio et al., Neurocognition across the spectrum of mucopolysaccharidosis type I: age, severity, and treatment, Mol Genet Metab 2015;116(1-2):61-8.
Sifuentes et al., A follow-up study of Mps I patients treated with laronidase enzyme replacement therapy for 6 years, Mol Genet Metab 2007;90(2):171-80.
Tanaka et al., Long-term efficacy of hematopoietic stem cell transplantation on brain involvement in patients with mucopolysaccharidosis type II: a nationwide survey in Japan. Mol Genet Metab 2012;107(3):513-20.
Tardieu et al., Intracerebral administration of adeno-associated viral vector serotype rh. 10 carrying human SGSH and SUMF1 cDNAs in children with mucopolysaccharidosis type IIIA disease: results of a Phase I/II trial, Hum Gene Ther 2014;25(6):506-16.
Tian et al., Ventricular Access Devices Are Safe and Effective in the Treatment of Posthemorrhagic Ventricular Dilatation prior to Shunt Placement, Pediatr Neurosurg 2012;48:13-20.
uniQure, Positive topline results announced from Phase I/II trial in Sanfilippo B syndrome patients using uniQure's novel AAV5-based gene therapy [press release], Available from: URL: https://globenewswire.com/newsrelease/2015/09/U.S. Appl. No. 19/769,451/10149930/en/Positive- Topline-Results-Announced-From-Phase-I-II-Trial-in-Sanfilippo-B-Syndrome- Patients-Using-uniQure-s-Novel-AAV5-Based-Gene-Therapy.html. Sep. 19, 2015. Accessed Nov. 17, 2016.

Vite et al., Biodistribution and pharmacodynamics of recombinant human alpha- L-iduronidase (rhIDU) in mucopolysaccharidosis type I-affected cats following multiple intrathecal administrations, Mol Genet Metab 2011; 103(3):268-74.
Wraith et al., Enzyme replacement therapy in patients who have mucopolysaccharidosis I and are younger than 5 years: results of a multinational study of recombinant human alpha-L-iduronidase (laronidase), Pediatrics 2007;120(1):e37-46.
Wraith et al. Enzyme replacement therapy for mucopolysaccharidosis I: a randomized, double-blinded, placebo-controlled, multinational study of recombinant human alpha-L-iduronidase (laronidase), J Pediatr 2004;144(5):581-8.
Clarke LA. Mucopolysaccharidosis Type I. Oct. 3, 20021 [Updated Feb. 2, 20215]. In: Adam MP, Mirzaa GM, Pagon RA, et al., editors. GeneReviews® [Internet]. Seattle (WA): University of Washington, Seattle; 1993-2023.
Hinderer, Christian, "Intrathecal Adeno-Associated Virus Vector Delivery for Mucopolysaccharidosis Type I" (2015). Publicly Accessible Penn Dissertations. 1763 (https://repository.upenn.edu/edissertations/1763); Date available: Oct. 26, 2018.
International Search Report and Written Opinion issued on International Patent Application No. PCT/US17/16133, dated May 4, 2017.
Extended European search report issued on corresponding European Patent Application No. 14770186.6, dated Aug. 5, 2016.
Communication pursuant to Rule 70(2) and 70a (2) EPC issued on corresponding European Patent Application No. 14770186.6, dated Aug. 23, 2016.
Reply to communication pursuant to Rule 70(2) and 70a (2) EPC of Aug. 23, 2016issued on corresponding European Patent Application No. 14770186.6, filed Feb. 20, 2017.
Communication pursuant to Rule 94(3) EPC issued on corresponding European Patent Application No. 14770186.6, dated May 17, 2018.
First Office Action issued in corresponding Chinese Patent Application No. 201480010987.3 dated Jan. 22, 2018 with unofficial English translation.
Second Office Action issued in corresponding Chinese Patent Application No. 201480010987.3 dated Dec. 6, 2018 with unofficial English translation.
First Office Action issued in corresponding Japanese Patent Application No. 2016-501864 dated Jan. 31, 2018 with unofficial English translation.
Third Office Action issued in corresponding Chinese Patent Application No. 201480010987.3 dated Aug. 15, 2019 with unofficial English translation provided by the Agent.
Response filed Sep. 24, 2019 in the corresponding European Patent Application No. 14770186.6 in reply to the May 15, 2019 communication under Rule 71(3) EPC.
Response filed Sep. 10, 2018 in reply to the May 17, 2018 communication pursuant to Article 94(3) EPC in the corresponding European Patent Application No. 14770186.6.
Communication pursuant to Article 94(3) EPC dated Sep. 6, 2019 in the European Patent Application No. 17706915.0.
Office Action dated Oct. 23, 2019 in the corresponding Mexican Patent Application No. MX/a/2015/012739 with unofficial English translation provided by the Agent.
Restriction Requirement dated May 8, 2017 in U.S. Appl. No. 14/769,596.
Response filed Sep. 26, 2017 in reply to the Restriction Requirement in U.S. Appl. No. 14/769,596.
Non-final Office Action dated Nov. 3, 2017 in U.S. Appl. No. 14/769,596.
Response filed Mar. 5, 2018 in reply to the Non-final Office Action in U.S. Appl. No. 14/769,596.
Final Office Action dated May 18, 2018 in U.S. Appl. No. 14/769,596.
Response filed Jun. 27, 2018 in reply to the final Office Action in U.S. Appl. No. 14/769,596.
First Office Action issued on corresponding Russian Patent Application No. 2015144234 dated Sep. 14, 2017 with unofficial English translation.

(56) References Cited

OTHER PUBLICATIONS

Second Office Action issued in corresponding Russian Patent Application No. 2015144234 dated Feb. 12, 2018 with unofficial English translation.
Third Office Action issued in corresponding Russian Patent Application No. 2015144234 dated Oct. 11, 2018 with unofficial English translation.
Second Office Action issued on corresponding Japanese Patent Application No. 2016-501864 dispatched Dec. 20, 2018 with unofficial English translation.
An Office Action issued on corresponding Australian Patent Application No. 2014235096 dated Mar. 8, 2019.
Restriction Requirement dated Feb. 4, 2020 in U.S. Appl. No. 16/075,056 (corresponding US Application Publication US 2019/0038772A1), and Response filed Apr. 3, 2020.
Non-Final Office Action dated Jul. 8, 2020 in in U.S. Appl. No. 16/075,056, and Response filed Nov. 13, 2020.
Office Action dated Dec. 1, 2021 issued in corresponding Japanese Patent Application No. 2020-148103.
Office Action dated Feb. 3, 2021 issued in corresponding Japanese Patent Application No. 2018-540838, and Response filed Jul. 2, 2021.
Communication dated Jul. 15, 2021 issued in corresponding European Patent Application No. 18746390.6, and Response filed Nov. 24, 2021.
Office Action dated Dec. 22, 2021 issued in corresponding Japanese Patent Application No. 2018-540838.
Office Action issued on Brazilian Patent Application No. BR112018015751-1, dated Sep. 20, 2022.
Communication pursuant to Article 94(3) EPC dated Mar. 15, 2023 issued in European Patent Application No. 20170476.4.
Communication pursuant to Article 94(3) EPC issued Jul. 21, 2020 in European Patent Application No. 17706915.0.
Official Action issued in Canadian Patent Application No. 2,901,328 dated Mar. 9, 2020 and response filed Jul. 9, 2020.
Extended European Search Report issued on European Patent Application No. 20170476.4, dated Oct. 2, 2020.
First Examination Report issued on Indian National Stage Patent Application No. 7302/DELNP/2015, dated Nov. 26, 2019, and Response filed Aug. 26, 2020.
Non-Final Office Action issued on Korean Patent Application No. 10-2015- 7022504, dated Mar. 20, 2020.
Non-Final Office Action issued on U.S. Appl. No. 16/166,346 (Corresponding US Patent Application Publication 2019/011116 A1), dated Dec. 3, 2019.
Response field on Mar. 31, 2020 in reply to the Dec. 3, 2020 Office Action with respect to U.S. Appl. No. 16/166,346.
US Provisional U.S. Appl. No. 62/529,385, filed Jul. 13, 2017.
US Provisional U.S. Appl. No. 62/530,614, filed Jul. 14, 2017.
US Provisional Patent Application No. 62/616, 106, filed Jan. 25, 2018.
International Preliminary Report on Patentability on International Patent Application No. PCT/US2018/040957, dated Jan. 7, 2020.
US Provisional U.S. Appl. No. 61/788,724, filed Mar. 15, 2013.
Response filed Jun. 30, 2020 in reply to the Mar. 20, 2020 Non-Final Office Action to the Korean Patent Application No. 10-2015-7022504.
Office Action issued on Mexican Patent Application No. MX/a/2015/012739, dated Jul. 23, 2020.
Notice of Allowance issued on U.S. Appl. No. 16/166,346, dated Jun. 1, 2020.
Office Action issued in corresponding Brazilian Patent Application No. BR112015021036-8, dated May 25, 2022, with unofficial English translation.
Examination Report issued in corresponding Australian Patent Application No. 2017215211, dated May 17, 2022.
Office Action dated Feb. 23, 2023 issued in corresponding Israeli Patent Application No. 260959, with unofficial translation provided by local agent.
Office Action dated Jul. 27, 2022 issued in related Japanese Patent Application No. 2020-500131, with unofficial translation provided by local agent.
Office Action dated Oct. 30, 2022 issued in related Israeli Patent Application No. 271780.
Final Office Action dated Feb. 24, 2023 issued in corresponding Japanese Patent Application No. 2020-500131, with unofficial translation provided by local Agent.
Communication dated Jul. 15, 2021 issued in corresponding European Patent Application No. 18746390.6.
Communication dated Mar. 15, 2023 issued in corresponding European Patent Application No. 20170476.4.

\* cited by examiner

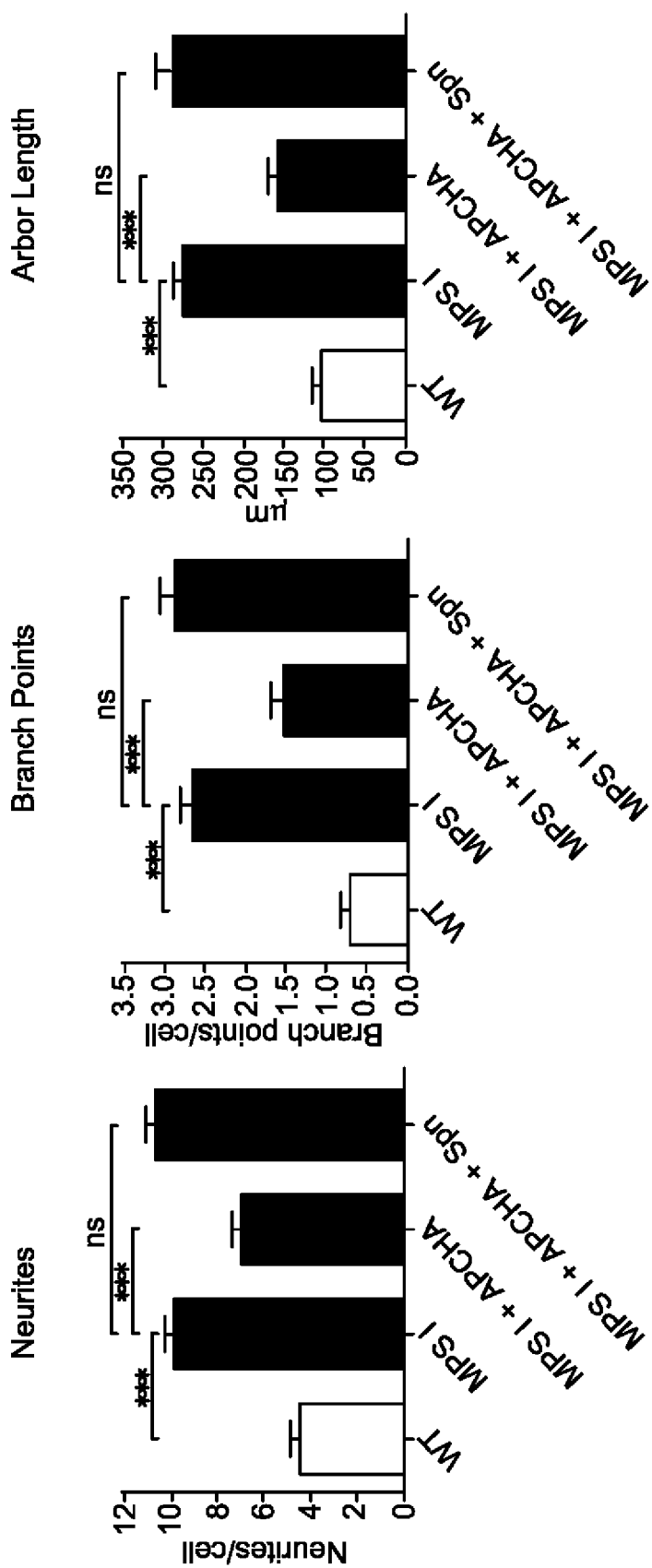

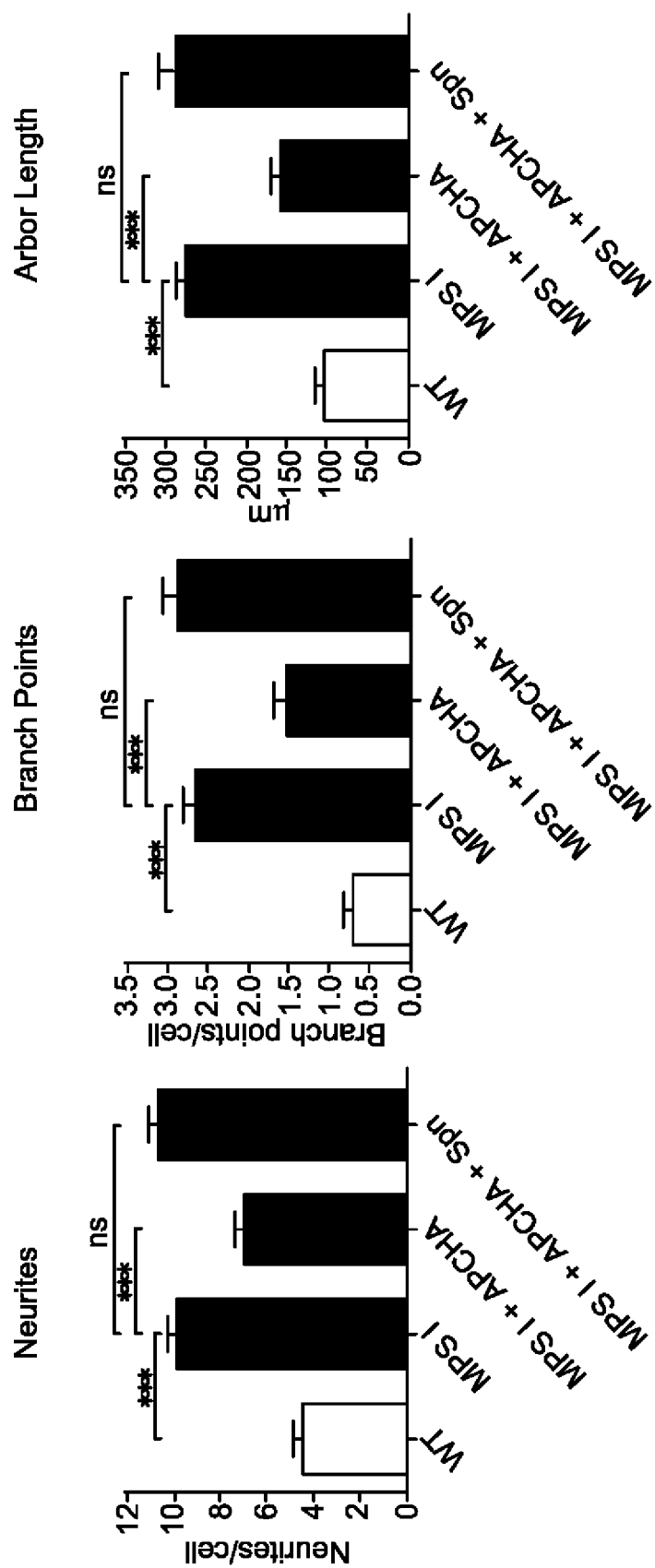

AAV9-MEDIATED GENE THERAPY FOR TREATING MUCOPOLYSACCHARIDOSIS TYPE I

CROSS-REFERENCE TO RELATED APPLICATIONS

This is a National Stage Entry under 35 U.S.C. 371 of International Patent Application No. PCT/US2018/040957, filed Jul. 5, 2018, which claims priority to U.S. Provisional Patent Application No. 62/529,385, filed Jul. 6, 2017; U.S. Provisional Patent Application No. 62/530,614, filed Jul. 10, 2017; and U.S. Provisional Patent Application No. 62/616, 106, filed Jan. 11, 2018. These applications are incorporated by reference herein.

STATEMENT OF FEDERALLY FUNDED RESEARCH

This application includes work which was supported in part by grants from the US Government, National Institutes of Health (NIH) numbers, R01DK54481, P40OD010939, and P30ES013508. The US government may have certain rights in this invention.

1. INTRODUCTION

The invention relates to a gene therapy approach for treating Mucopolysaccharidosis Type I (MPS I), including patients diagnosed with Hurler, Hurler-Scheie and/or Scheie syndromes.

2. BACKGROUND OF THE INVENTION

The mucopolysaccharidoses are a group of inherited disorders caused by a deficiency in specific lysosomal enzymes involved in the degradation of glycosaminoglycans (GAG), also called mucopolysaccharides. The accumulation of partially-degraded GAG causes interference with cell, tissue, and organ function. Over time, the GAG accumulates within cells, blood, and connective tissue, resulting in increasing cellular and organ damage. One of the most serious of the mucopolysaccharidosis (MPS) disorders, MPS I, is caused by a deficiency of the enzyme α-L-iduronidase (IDUA). Specifically, alpha-L-iduronidase is reported to remove terminal iduronic acid residues from two GAGS called heparan sulfate and dermatan sulfate. Alpha-L-iduronidase is located in lysosomes, compartments within cells that digest and recycle different types of molecules. The IDUA gene has been reported to provide instructions for producing the alpha-L-iduronidase enzyme, which is essential for the breakdown of large sugar molecules called glycosaminoglycans (GAGs). More than 100 mutations in the IDUA gene have been found to cause mucopolysaccharidosis type I (MPS I). Mutations that change one DNA building block (nucleotide)—single nucleotide polymorphisms or "SNPs" are the most common.

Mutations that cause MPS I reduce or completely eliminate the function of alpha-L-iduronidase leads to three clinical syndromes: Hurler, Hurler-Scheie and Scheie syndromes. Each is inherited in an autosomal recessive manner with the extent of enzyme deficiency being directly related to the severity of the clinical phenotype. Hurler syndrome represents the most severe manifestation of IDUA deficiency and usually occurs in the setting of a total absence of enzyme activity due to two null mutations. The clinical diagnosis is established before 2 years of age and is associated with multiple somatic pathologies. In addition, natural history data have firmly established that patients with Hurler syndrome genotype have CNS involvement, which leads to severe cognitive defects and mental retardation. Hurler-Scheie syndrome is a more attenuated form that is usually diagnosed between 2 and 8 years of age. In contrast to Hurler syndrome, Hurler-Scheie patients have a (theoretical) small amount of residual IDUA activity leading to a later onset of clinical manifestations and more attenuated progression of disease. Despite a more attenuated phenotype, some Hurler-Scheie patients experience multiple symptoms of CNS pathology related to IDUA deficiency, including neurocognitive decline as evidenced by drop in IQ. Scheie syndrome is the mildest form of MPS I. Symptoms generally begin to appear after age 5, with diagnosis most commonly made after age 10. Children with Scheie syndrome have normal intelligence or may have mild learning disabilities; some may have psychiatric problems. Glaucoma, retinal degeneration, and clouded corneas may significantly impair vision. Other problems include carpal tunnel syndrome or other nerve compression, stiff joints, claw hands and deformed feet, a short neck, and aortic valve disease. Some affected individuals also have obstructive airway disease and sleep apnea. Persons with Scheie syndrome can live into adulthood.

With respect to the clinical syndromes, the current standard of care for Hurler syndrome is hematopoietic stem cell transplantation (HSCT) such as bone marrow transplantation (BMT) or umbilical cord blood transplantations (UCBT). The procedure is done as early as possible, and before the age of two, to impact on both somatic and CNS aspects of the disease. However, HSCT for MPS I remains associated with a significant amount of morbidity and a 20% mortality rate. If transplantation is not an option, then enzyme replacement therapy (ERT) may be started which requires a weekly infusion of enzyme for the life of the patient. ERT does not impact on the progression of CNS disease but does partially improve the somatic manifestations. Organomegaly is significantly improved although aspects of the disease in the skeletal system, eye and heart are only partially improved. Patients may require surgery to stabilize the hip and knee and to treat carpal tunnel syndrome and finger contractions. Cardiac disease is treated medically although surgery may eventually be required.

ERT for MPS I provides exogenous enzyme for uptake into lysosomes and increased catabolism of GAG. Although the lysosomal enzymes function internally, cell-surface mannose-6-phosphate receptors are capable of binding, internalizing, and delivering these enzymes to the lysosomes. Recombinant IDUA (Aldurazyme®, BioMarin) is approved by FDA for patients with Hurler and Hurler-Scheie forms of MPS I and for patients with the Scheie form who have moderate to severe symptoms and was shown to improve pulmonary function and walking capacity. ERT has also been observed to reduce hepatomegaly in MPS I patients, as well as the levels of urinary GAG. However, because intravenous enzyme does not easily cross into the brain, ERT does not currently address the neurological symptoms experienced by some MPS I patients.

Complications of ERT revolve around immune response to the recombinant enzyme which can range from mild to full-blown anaphylaxis as well as complications of life-long peripheral access such as local and systemic infections. Up to 91% of patients receiving Aldurazyme develop antibodies to the enzyme, although it is not clear how much it affects efficacy. Furthermore, ERT requires weekly i.v. infusions, administered over a period of 3-8 hours in a hospital setting, which significantly impacts patient quality of life and, and at a high expense, is a major strain on health care reimbursement systems.

In light of these limitations, a treatment that can more effectively correct the morbidity associated with MPS I remains an unmet medical need.

3. SUMMARY OF THE INVENTION

A replication deficient adeno-associated virus ("AAV") to deliver a human alpha-L-iduronidase (hIDUA) gene to the CNS of patients (human subjects) diagnosed with mucopolysaccharidosis type I (MPS I) is provided herein. The recombinant AAV ("rAAV") vector used for delivering the hIDUA gene ("rAAV.hIDUA") should have a tropism for the CNS (e.g., an rAAV bearing an AAV9 capsid), and the hIDUA transgene should be controlled by specific expression control elements, e.g., a hybrid of cytomegalovirus (CMV) enhancer and the chicken beta actin promoter (CB7). Pharmaceutical compositions suitable for intrathecal/intra-cisternal administration comprise a suspension of rAAV.hIDUA vectors in a formulation buffer comprising a physiologically compatible aqueous buffer, a surfactant and optional excipients.

A therapeutic regimen useful for treatment of an alpha-L-iduronidase deficiency in a human patient is provided. In certain embodiments, the regimen comprises administering to the patient: (a) a recombinant AAV (rAAV) having an AAV9 capsid and a nucleic acid comprising a sequence encoding human α-L-iduronidase (hIDUA) under control of regulatory sequences which direct expression thereof in the patient, wherein the human hIDUA coding sequence has the nucleotide sequence of SEQ ID NO: 1 or a sequence at least about 80% identical to SEQ ID NO: 1 which encodes a functional hIDUA, (b) at least a first immunosuppressive agent selected from at least one of a glucocorticoid, a steroid, an antimetabolite, a T-cell inhibitor, a macrolide, or a cytostatic agent: and (c) at least a second immunosuppressive agent selected from at least one of a glucocorticoid, a steroid, an antimetabolite, a T-cell inhibitor, a macrolide, or a cytostatic agent, wherein administration of at least one immunosuppressive agent begins prior to or on the same day as delivery of the AAV vector; and wherein administration of at least one of the immunosuppressive agents continues for at least 8 weeks post-vector administration. The patients may be dosed initially with an intravenous steroid followed by an oral steroid. In certain embodiments, the immunosuppressive agents are one or more corticosteroids and optionally, mycophenolate mofetil (MMF), and/or one or more macrolides. The one or more macrolides may be a calcineurin inhibitor (e.g., tacrolimus), an mTOR inhibitor (e.g., sirolimus, temsirolimus, everolimus, or another rapalog), or combinations thereof. In certain embodiments, dosing the patient with steroids is discontinued 12-weeks post vector dosing. In certain embodiments, mycophenolate mofetil (MMF) and tacrolimus are delivered for 0 to 15 days pre-vector administration. In certain embodiments, the immunosuppressive agents are mycophenolate mofetil (MMF) and sirolimus. In certain embodiments, wherein when the immunosuppressive agents comprise both tacrolimus and sirolimus, a low dose of each is used to maintain a blood trough level of about 4 ng/mL to about 8 ng/ml, or a total of about 8 ng/mL to about 16 ng/mL. In certain embodiments, wherein the immunosuppressive agents comprise only one of tacrolimus or sirolimus, the total dose is in the range of about 16 ng/mL to about 24 ng/mL. In certain embodiments, wherein only one of tacrolimus or sirolimus is used, the initial loading dose is about 3 mg/m$^2$. In certain embodiments, the immunosuppressive therapy is started at about day −14 to day −1 prior to vector administration. In certain embodiments, the encoded hIDUA has the sequence selected from: (a) about amino acid 1 to about 653 of SEQ ID NO: 2 (Genbank NP_000193); and (b) a synthetic human enzyme comprising a heterologous leader sequence fused to about acids 27 to about 653 of SEQ ID NO: 2. In certain embodiments, wherein the nucleic acid sequence further comprises a 5' inverted terminal repeat (ITR) sequence, a chicken beta actin intron, a CB7 promoter, a polyA signal, and/or a 3' ITR sequence. In certain embodiments, wherein the rAAV is in a suspension having a pH of 6 to 9. In certain embodiments, the rAAV is delivered via intrathecal injection. In certain embodiments, the rAAV comprising the hIDUA gene is dosed intravenously. In certain embodiments, efficacy of therapy is assessed by measuring auditory capacity changes, optionally by auditory brainstem testing. In certain embodiments, the rAAV is formulated for intrathecal injection to a human subject, to administer a total flat dose of: (i) about $1.2 \times 10^{12}$ to about $6.0 \times 10^{12}$ GC or about $6.0 \times 10^{12}$ to about $3.0 \times 10^{13}$ GC to a human subject ≥4 months to <9 months of age; (ii) about $2 \times 10^{12}$ to about $6.0 \times 10^{13}$ or about $1.0 \times 10^{13}$ to about $5.0 \times 10^{13}$ GC to a human subject ≥9 months to <18 months of age; (iii) about $2.2 \times 10^{12}$ to about $1.1 \times 10^{13}$ GC or about $1.1 \times 10^{13}$ to about $5.5 \times 10^{13}$ GC to a human subject ≥9 months to <18 months of age.

A composition is provided which comprises a recombinant AAV vector comprising a heterologous nucleic acid encoding human α-L-iduronidase (hIDUA) formulated for intrathecal injection to a human subject in need thereof, to administer a total flat dose of: (a) about $1.2 \times 10^{12}$ to about $6.0 \times 10^{12}$ GC or about $6.0 \times 10^{12}$ to about $3.0 \times 10^{13}$ GC to a human subject ≥4 months to <9 months of age; or (b) about $2 \times 10^{12}$ to about $6.0 \times 10^{13}$ GC or about $1.0 \times 10^{13}$ to about $5.0 \times 10^{13}$ GC to a human subject ≥9 months to <18 months of age; or (c) about $2.2 \times 10^{12}$ to about $1.1 \times 10^{13}$ GC or about $1.1 \times 10^{13}$ to about $5.5 \times 10^{13}$ GC to a human subject ≥9 months to <18 months of age. In certain embodiments, the human hIDUA coding sequence has the nucleotide sequence of SEQ ID NO: 1 or a sequence at least about 80% identical to SEQ ID NO: 1 which encodes a functional hIDUA. In certain embodiments, the composition used a co-therapy with: (i) at least a first immunosuppressive agent selected from at least one of: and (ii) at least a second immunosuppressive agent selected from at least one of a glucocorticoid, a steroid, an antimetabolite, a T-cell inhibitor, a macrolide, or a cytostatic agent, wherein dosing of the immunosuppressive agents begins prior to or on the same day as delivery of the AAV vector; and wherein dosing with at least one of the immunosuppressive agents continues for at least 8 weeks post-vector administration.

Immunosuppressive agents for use in a combination therapy with a recombinant AAV vector comprising a heterologous nucleic acid encoding human α-L-iduronidase (hIDUA) are provided. In certain embodiments, the human hIDUA coding sequence has the nucleotide sequence of SEQ ID NO: 1 or a sequence at least about 80% identical to SEQ ID NO: 1 which encodes a functional hIDUA. In certain embodiments, the immunosuppressive agents comprise: (a) a composition comprising at least a first immunosuppressive agent selected from at least one of a glucocorticoid, a steroid, an antimetabolite, a T-cell inhibitor, a macrolide, or a cytostatic agent; and (b) a composition comprising at least a second immunosuppressive agent selected from at least one of a glucocorticoid, a steroid, an antimetabolite, a T-cell inhibitor, a macrolide, or a cytostatic agent, wherein dosing of the immunosuppressive agents begins prior to or on the same day as delivery of the AAV vector; and wherein dosing of at least one of the immunosuppressive agents continues for at least 8 weeks post-vector administration. In certain embodiments, the AAV vector is formulated for intrathecal injection to a human subject in need thereof, to administer a total flat dose of: (i) about $1.2 \times 10^{12}$ to about $6.0 \times 10^{12}$ GC or about $6.0 \times 10^{12}$ to about $3.0 \times 10^{13}$ GC to a human subject ≥4 months to <9 months of age; or (ii) about $2 \times 10^{12}$ to about $6.0 \times 10^{13}$ GC or about $1.0 \times 10^{13}$ to about $5.0 \times 10^{13}$ GC to a human subject ≥9 months to <18 months of age; or (iii) about $2.2 \times 10^{12}$ to about $1.1 \times 10^{13}$ GC or about $1.1 \times 10^{13}$ to about $5.5 \times 10^{13}$ GC to a human subject ≥9 months to <18 months of age.

Such rAAV.hIDUA vector preparations can be administered to human subjects by intrathecal/intracisternal injection to achieve therapeutic levels of hIDUA expression in the CNS. Patients who are candidates for treatment are pediatric and adult patients with MPSI and/or the symptoms associated with Hurler, Hurler-Scheie and Scheie.

Such rAAV.hIDUA vector preparations can be administered to human subjects by intrathecal/intracisternal injection to achieve therapeutic levels of hIDUA expression in the CNS. Patients who are candidates for treatment are pediatric and adult patients with MPSI and/or the symptoms associated with Hurler, Hurler-Scheie and Scheie.

Therapeutically effective intrathecal/intracisternal doses of the rAAV.hIDUA for MPSI patients range from about $1 \times 10^{11}$ to $7.0 \times 10^{14}$ GC (flat doses)—the equivalent of $10^9$ to $5 \times 10^{10}$ GC/g brain mass of the patient. Alternatively, the following therapeutically effective flat doses can be administered to patients of the indicated age group:

Newborns: about $1 \times 10^{11}$ to about $3 \times 10^{14}$ GC;
3-9 months: about $6 \times 10^{12}$ to about $3 \times 10^{14}$ GC;
9 months-6 years: about $6 \times 10^{12}$ to about $3 \times 10^{14}$ GC;
3-6 years: about $1.2 \times 10^{13}$ to about $6 \times 10^{14}$ GC;
6-12 years: about $1.2 \times 10^{13}$ to about $6 \times 10^{14}$ GC;
12+ years: about $1.4 \times 10^{13}$ to about $7.0 \times 10^{14}$ GC;
18+ years (adult): about $1.4 \times 10^{13}$ to about $7.0 \times 10^{14}$ GC.

In other embodiments, the following therapeutically effective flat doses are administered to an MPS patient of the age group:

Newborns: about $3.8 \times 10^{12}$ to about $1.9 \times 10^{14}$ GC;
3-9 months: about $6 \times 10^{12}$ to about $3 \times 10^{14}$ GC;
9-36 months: about $10^{13}$ to about $5 \times 10^{13}$ GC;
6-12 years: about $1.2 \times 10^{13}$ to about $6 \times 10^{14}$ GC;
3-12 years: about $1.2 \times 10^{13}$ to about $6 \times 10^{14}$ GC;
12+ years: about $1.4 \times 10^{13}$ to about $7.0 \times 10^{14}$ GC;
18+ years (adult): about $1.4 \times 10^{13}$ to about $7.0 \times 10^{14}$ GC.

In certain embodiments, one or more of these ranges are used for patients of any age at a dose of $1.2 \times 10^{12}$ total genome copies (GC) ($2.0 \times 10^9$ GC/g brain mass) or $6 \times 10^{12}$ total GC ($1 \times 10^{10}$ GC/g brain mass) is administered to a patient that is greater than or equal to (≥) 4 month to less than (<) 9 months. In certain embodiments, a flat dose of $2 \times 10^{12}$ total GC ($2.0 \times 10^9$ GC/g brain mass) or $1 \times 10^{13}$ total GC ($1 \times 10^{10}$ GC/g brain mass) is administered to a patient that is greater than or equal to (≥) 9 month to less than (<) 18 months. In certain embodiments, a flat dose of $2.2 \times 10^{12}$ total GC ($2.0 \times 10^9$ GC/g brain mass) or $1.1 \times 10^{13}$ total GC ($1 \times 10^{10}$ GC/g brain mass) is administered to a patient that is greater than or equal to (≥) 18 month to less than (<) 3 years. In certain embodiments, a flat dose of $6.0 \times 10^{12}$ ($1.0 \times 10^{10}$ GC/g brain mass) or $3 \times 10^{13}$ total genome copies (GC) ($5 \times 10^{10}$ GC/g brain mass) is administered to a patient that is greater than or equal to (≥) 4 month to less than (<) 9 months. In certain embodiments, a flat dose of $1.0 \times 10^{13}$ ($1.0 \times 10^{10}$ GC/g brain mass) or $5.0 \times 10^{13}$ total GC ($5 \times 10^{10}$ GC/g brain mass) is administered to a patient that is greater than or equal to (≥) 9 month to less than (<) 18 months. In certain embodiments, a flat dose of $1.1 \times 10^{13}$ ($1.0 \times 10^{10}$ GC/g brain mass) or $5.5 \times 10^{13}$ total GC ($5 \times 10^{10}$ GC/g brain mass) is administered to a patient that is greater than or equal to (≥) 18 month to less than (<) 3 years. In certain embodiments, a flat dose of $2.6 \times 10^{12}$ genome copies (GC) ($2.0 \times 10^9$ GC/g brain mass) is administered to a patient that is 6 years old or older than 6 years old. In certain embodiments, a flat dose of $1.3 \times 10^{13}$ (GC) ($1.0 \times 10^{10}$ GC/g brain mass) is administered to a patient that is 6 years old or older than 6 years old. In some embodiments, the dose administered to a 12+ year old MPSI patient (including 18+ year old) is $1.4 \times 10^{13}$ genome copies (GC) ($1.1 \times 10^{10}$ GC/g brain mass). In some embodiments, the dose administered to a 12+ year old MPSI patient (including 18+ year old) is $7 \times 10^{13}$ GC ($5.6 \times 10^{10}$ GC/g brain mass). In still a further embodiment, the dose administered to an MPSI patient is at least about $4 \times 10^8$ GC/g brain mass to about $4 \times 10^{11}$ GC/g brain mass. In certain embodiments, the dose administered to MPS I newborns ranges from about $1.4 \times 10^{11}$ to about $1.4 \times 10^{14}$ GC; the dose administered to infants 3-9 months ranges from about $2.4 \times 10^{11}$ to about $2.4 \times 10^{14}$ GC; the dose administered to MPS I children 9-36 months ranges: about $4 \times 10^{11}$ to about $4 \times 10^{14}$ GC; the dose administered to MPS I children 3-12 years: ranges from about $4.8 \times 10^{11}$ to about $4.8 \times 10^{14}$ GC; the dose administered to children and adults 12+ years ranges from about $5.6 \times 10^{11}$ to about $5.6 \times 10^{14}$ GC.

The goal of the treatment is to functionally replace the patient's defective alpha-L-iduronidase via rAAV-based CNS-directed gene therapy to treat disease. Efficacy of the therapy can be measured by assessing (a) the prevention of neurocognitive decline in patients with MPSI; and (b) reductions in biomarkers of disease, e.g., GAG levels and/or IDUA or hexosaminidase (Hex) enzyme activity in the CSF, serum and/or urine, and/or liver and spleen volumes. Neurocognition can be determined by measuring intelligence quotient (IQ), e.g., as measured by Bayley's Infantile Development Scale for Hurler subjects or as measured by the Wechsler Abbreviated Scale of Intelligence (WASI) for Hurler-Scheie subjects. Other appropriate measures of neurocognitive development and function may be utilized, e.g., assessing developmental quotient (DQ) using Bayley Scales of Infant Development (BSID-III), assessing memory using the Hopkins Verbal Learning Test, and/or using Tests of Variables of Attention (TOVA). Auditory capacity changes measured by auditory brainstem response (ABR) testing.

Prior to treatment, the MPSI patient can be assessed for neutralizing antibodies (Nab) to the capsid of the rAAV vector used to deliver the hIDUA gene. Such Nabs can interfere with transduction efficiency and reduce therapeutic efficacy. MPS I patients that have a baseline serum Nab titer ≤1:5 are good candidates for treatment with the rAAV.hIDUA gene therapy protocol. Treatment of MPS I patients with titers of serum Nab>1:5 may require a combination therapy, such as transient co-treatment with an immunosuppressant before and/or during treatment with rAAV.hIDUA vector delivery. Optionally, immunosuppressive co-therapy may be used as a precautionary measure without prior assessment of neutralizing antibodies to the AAV vector capsid and/or other components of the formulation. In certain embodiments, prior immunosuppression therapy may be desirable to prevent potential adverse immune reaction to the hIDUA transgene product, especially in patients who have virtually no levels of IDUA activity, where the transgene product may be seen as "foreign."

Results of non-clinical studies in mice, dogs and NHPs described in the Examples infra are consistent with the development of an immune response to hIDUA and neuroinflammation. While a similar reaction may not occur in human subjects, as a precaution immunosuppression therapy is recommended for all recipients of rAAV-hIDUA.

Combinations of gene therapy delivery of the rAAV.hIDUA to the CNS accompanied by systemic delivery of hIDUA are encompassed by the methods of the invention. Systemic delivery can be accomplished using ERT (e.g., using Aldurazyme®), or additional gene therapy using an rAAV.hIDUA with tropism for the liver (e.g., an rAAV.hIDUA bearing an AAV8 capsid).

In certain embodiments, the patient is administered an AAV.hIDUA via liver-directed injections in order to tolerize the patient to hIDUA, and the patient is subsequently administered AAV.hIDUA via intrathecal/intracisternal injections when the patient is an infant, child, and/or adult to express therapeutic concentrations of hIDUA in the CNS.

The benefits of the invention are illustrated by the Examples, infra, which demonstrate that IT administration of rAAV9.IDUA in animal studies resulted in widespread distribution of vector within the CNS. Moreover, single doses of rAAV9 vector delivering fIDUA, cIDUA, or hIDUA were successful in dose-dependently ameliorating or completely reversing the histological and biochemical manifestations of CNS-related MPS I in both 3-7 month old feline and 1 month old canine animal models. Similarly, single IT doses of rAAV9.IDUA were clinically well tolerated in macaques, including when injected as infants, for at least 2 years after injection. The only adverse effects associated with rAAV9.IDUA administration in the animals were related to immune responses to the transgene across all species that were tested.

As shown in the Examples, the beneficial effect of rAAV9.IDUA treatment was limited by development of anti-IDUA antibody responses. At the highest doses evaluated in either non-tolerized MPS I dogs (Example 3) or rhesus macaques (Example 7) adverse effects were observed. The characteristics of the changes and the time of onset indicate that these effects were mediated by an immunologic response to the transgene product. In Example 3, both dogs at the highest dose had high CSF WBC counts and protein levels accompanied by pain and hindlimb weakness. These animals had histopathologic lesions in the spinal cord and dorsal root ganglia that were attributed to an immunologic response to the transgene expressed in motor and sensory neurons, which were not observed in animals at the lower 2 doses. In a toxicology study in rhesus macaques (Example 7), both humoral and cell-mediated immunologic responses to hIDUA were observed and were characterized by increased nucleated cell counts and anti-IDUA antibodies in CSF, and weak anti-IDUA T-cell responses in peripheral blood. Unlike the dogs, adverse clinical signs did not occur, neuronal necrosis within the spinal cord was not observed, and the monkeys appeared to tolerate treatment. However, CNS lesions were observed in the spinal cord at Days 90 and 180 consisting of bilateral axonal degeneration in the white matter dorsal funiculi. These axonal changes are considered to be secondary to an immunologically mediated effect on the neurons in the dorsal root ganglia.

The acquired immunologic responses to human proteins observed in the nonclinical species may not be predictive of either the nature or magnitude of the same responses in humans. Nonetheless, in preferred embodiments, human subjects should be prophylactically treated with immunosuppressive agents, particularly individuals who do not express any hIDUA and therefore are not expected to be tolerant to this enzyme. The data in the Examples, infra, show that in neonatal dogs and nonhuman primates tolerized to either cIDUA or hIDUA prior to administration of the rAAV9.IDUA construct, sustained transduction and IDUA expression were achieved. In contrast, animals that had not been previously tolerized to IDUA generally mounted an immune response to both IDUA and to AAV9 capsid antigens. In sum, the data in the examples indicate that immunosuppressive treatment could also enhance the efficacy of rAAV9.IDUA.

In some embodiments, subjects who receive rAAV9.IDUA also receive an IS regimen consisting of corticosteroids (methylprednisolone 10 mg/kg IV once on Day 1 predose and oral prednisone starting at 0.5 mg/kg/day on Day 2 with gradual tapering and discontinuation by Week 12), tacrolimus (1.0 mg twice daily PO Day 2 to Week 24) with target blood level of 4 to 8 ng/mL and tapering over 8 weeks between Week 24 and 32, and sirolimus (a loading dose of 1 mg/$m_2$ every 4 hours×3 doses on Day −2 and then from Day −1: sirolimus 0.5 mg/$m_2$/day divided in twice a day dosing with target blood level of 4 to 8 ng/ml until Week 48). In some embodiments, the initial combination immunosuppressive therapy will be reduced sequentially with first discontinuing prednisone followed by tacrolimus and finally sirolimus.

Still other aspects and advantages of the invention will be apparent from the detailed description of the invention.

4. BRIEF DESCRIPTION OF THE FIGURES

FIG. 1 is a schematic representation of a vector genome which is packaged into an AAV as described herein. In the vector genome, the major components of the expression cassette flanked by the AAV 5' and 3' inverted terminal repeat (ITR)s vector genome are depicted. These include the cytomegalovirus immediate-early enhancer, CB7 promoter, a chimeric intron, a human alpha-L-iduronidase coding sequence (gene), and a rabbit beta globin poly A signal.

Figure 2A:
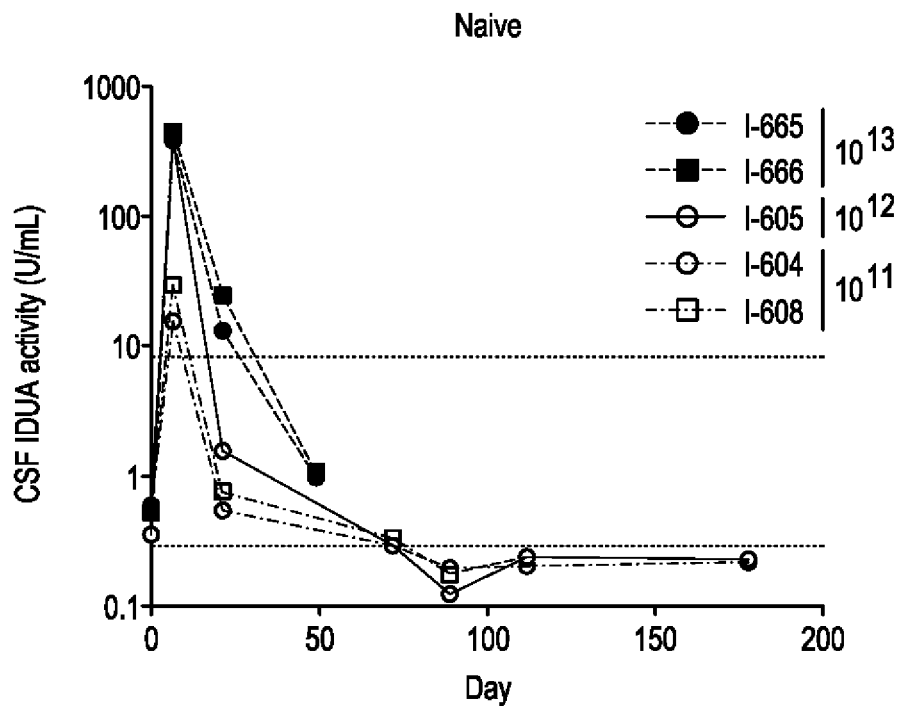
Figure 2B:
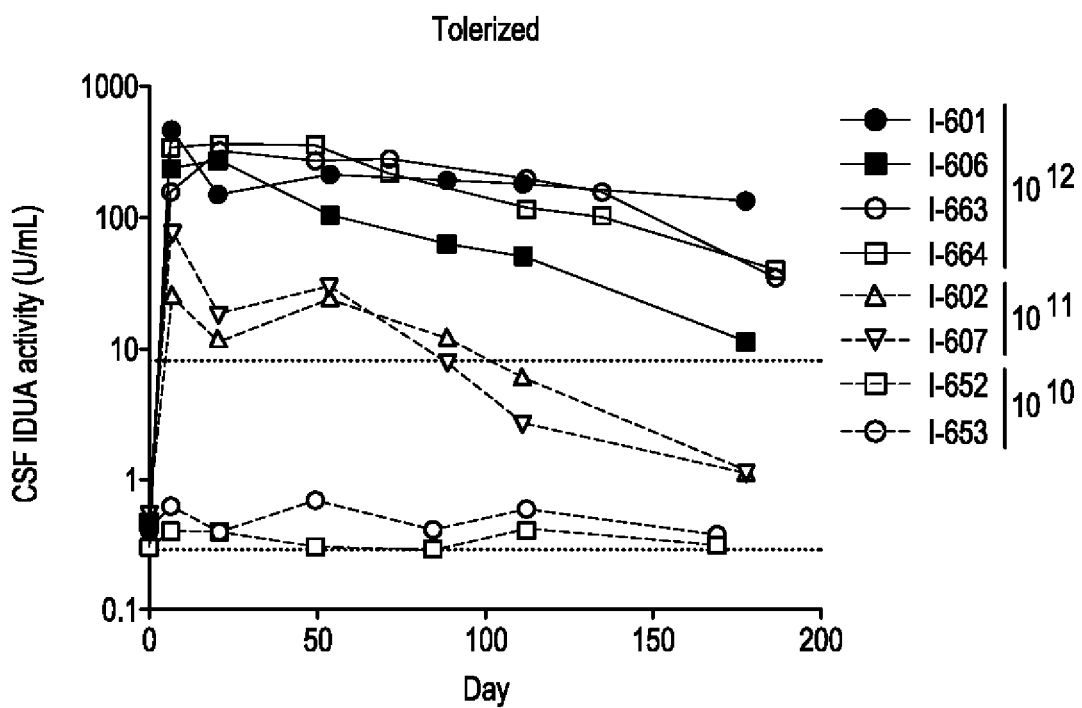

FIGS. 2A-2B show CSF IDUA activity in naïve (FIG. 2A) or tolerized (FIG. 2B) MPS I dogs treated with intrathecal injection with AAV9 expressing human IDUA. Dogs were treated at one month of age with an intrathecal injection of the vector into the cisterna magna. IDUA activity was measured in subsequent CSF samples. Vector doses (GC/kg) are indicated for each animal. The dashed lines represent animals treated with intrathecal vector only. The solid lines with filled symbols represent animals pretreated on postnatal day 5 with intravenous AAV8 expressing human IDUA from a liver-specific promoter. Solid lines with open symbols represent animals pretreated on postnatal day 7 and 14 with intravenous infusion of recombinant human IDUA. Animals I-665 and I-666 were euthanized on day 36 due to neurological signs. The horizontal dashed line represents mean CSF IDUA activity in normal dogs. The dotted line indicates the assay limit of quantification.

Figure 3:
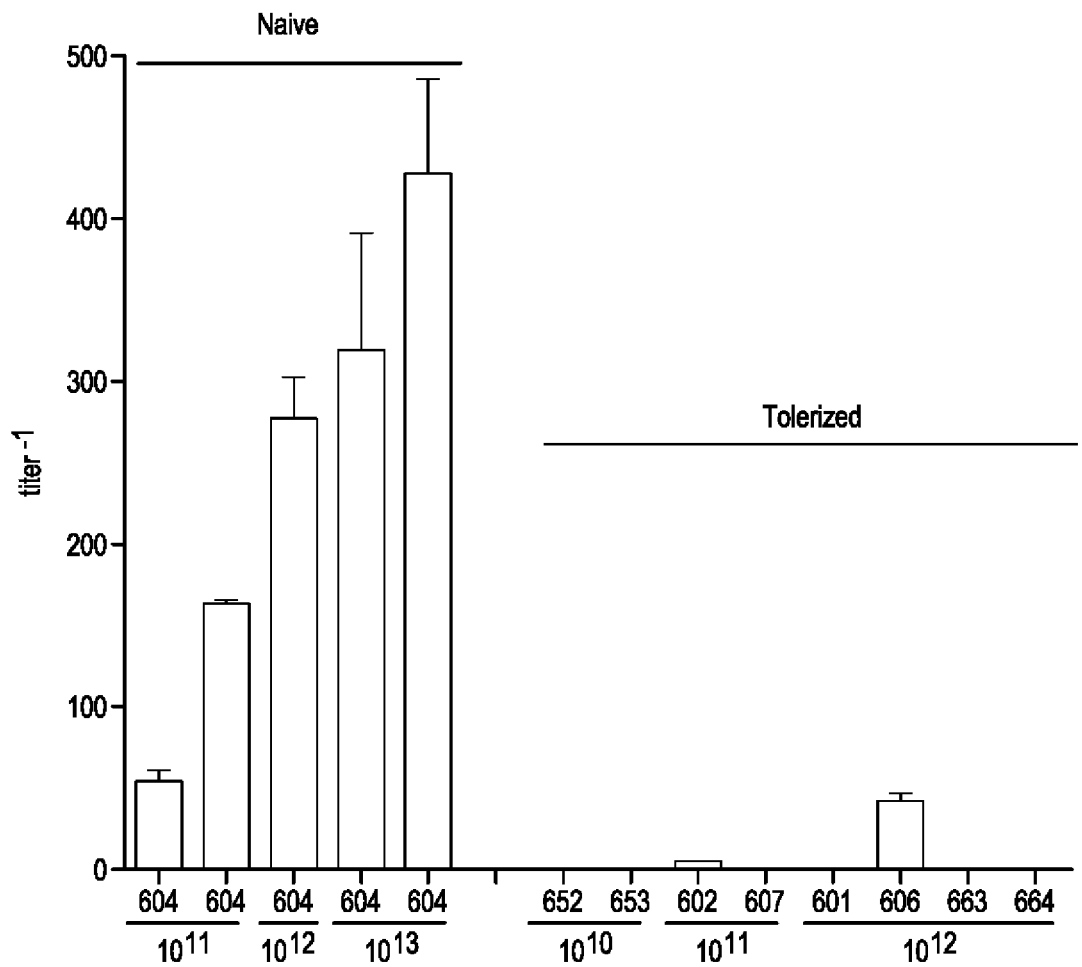

FIG. 3 shows CSF antibody titers against human IDUA. Antibody titers against human IDUA were measured by ELISA in CSF samples collected 50 days post vector administration. CSF samples tested from 1-665 and 1-666 were collected at the time of necropsy (day 36 post injection). Error bars=SEM. Antibody titers were significantly lower in the animals pre-treated as neonates with AAV8 vector (I-652, I-653, I-602, I-607, I-601, I-606) or recombinant human IDUA (I-663, I-664) compared with controls treated with IT vector alone (I-604, I-608, I-605, I-665, I-666) (Mann-Whitney test).

Figure 4A:
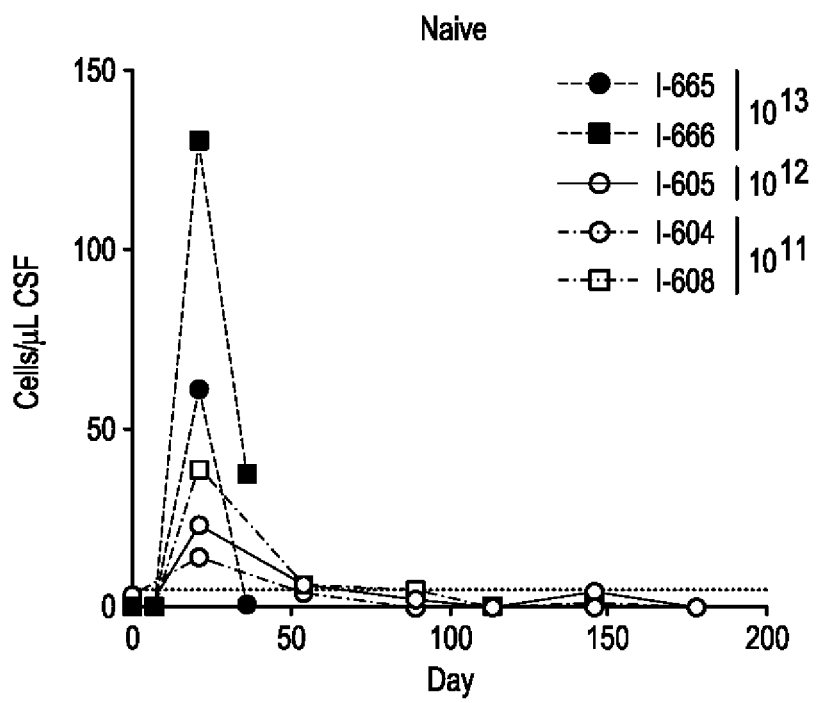
Figure 4B:
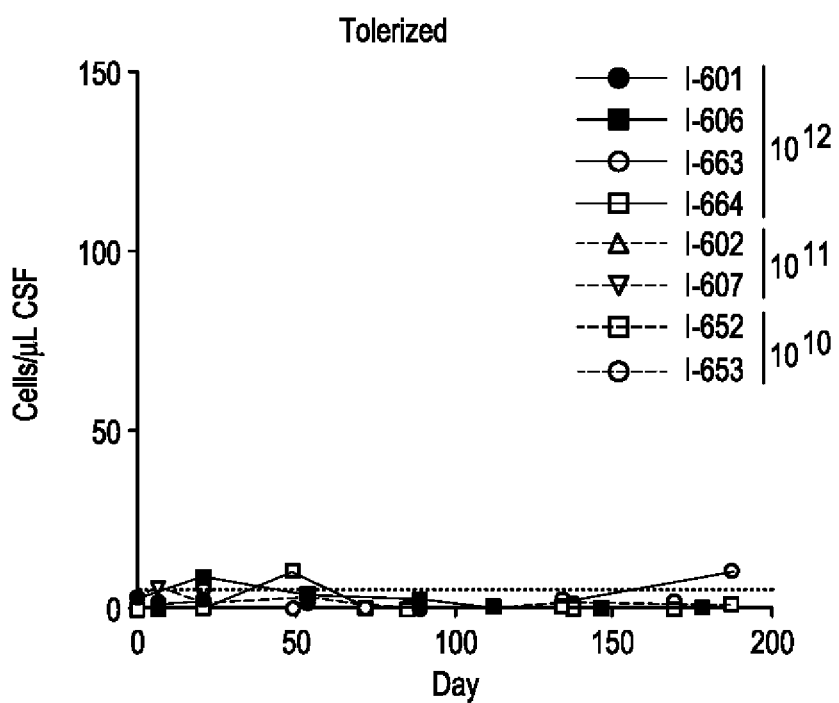

FIGS. 4A-4B shows CSF nucleated cell counts following intrathecal AAV9 injection. Total nucleated cell counts were measured in CSF samples from naïve dogs treated with intrathecal AAV9 (FIG. 4A)) as well as animals treated as neonates with systemic recombinant human IDUA (I-663 and I-664) or an AAV8 vector expressing IDUA before receiving intrathecal AAV9 (FIG. 4B)). Nucleated cell counts were significantly elevated on day 21 after vector injection in the naïve animals compared with those pre-treated as neonates with AAV8 vector or recombinant human IDUA (Mann-Whitney test).

Figure 5:
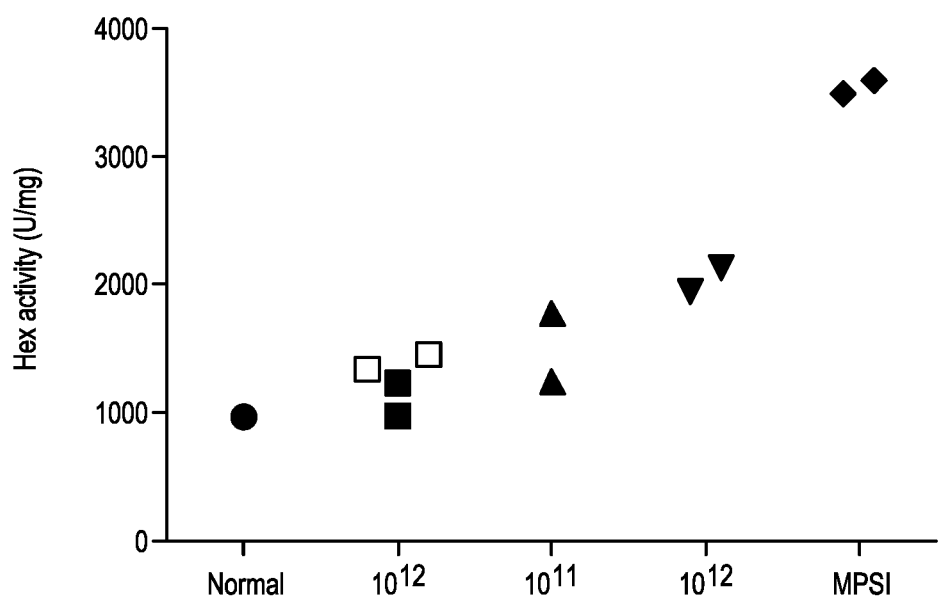

FIG. 5 shows normalization of brain hexosaminidase activity in human IDUA tolerant MPS I dogs treated with intrathecal AAV9. Hex activity was measured in samples collected from 6 brain regions (frontal cortex, temporal cortex, occipital cortex, hippocampus, medulla, and cerebellum). The mean activity is shown for a normal control dog, untreated MPS I dogs, and the 8 hIDUA tolerant dogs treated with intrathecal injection of AAV9 expressing human IDUA. Open symbols indicate animals tolerized with infusion of recombinant human IDUA. Hex activity was significantly reduced in the high dose cohort compared to untreated controls (Kruskal-Wallis test followed by Dunn's multiple comparisons test).

Figure 6A:
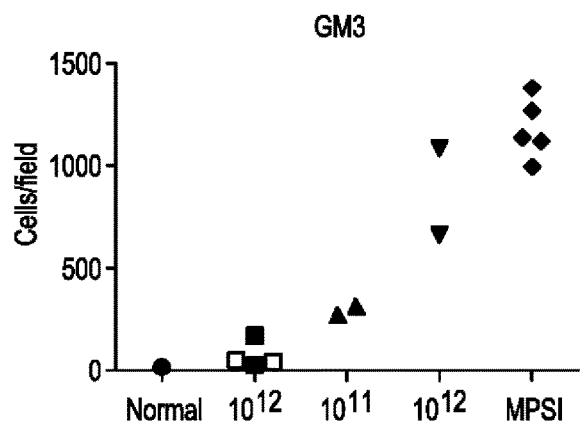
Figure 6B:
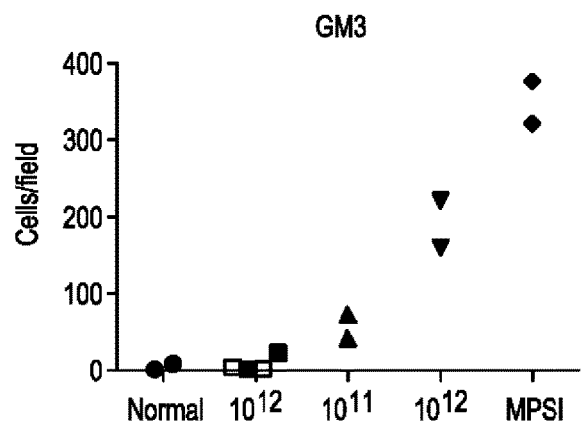

FIGS. 6A-6B shows dose-dependent correction of brain storage lesions in human IDUA tolerant dogs treated with intrathecal injection of AAV9 expressing human IDUA. Brains were sectioned and stained for LIMP2 and GM3. Meningeal GAG accumulation was imaged using Alcian blue staining. Automated quantification of GM3 (FIG. 6A) and LIMP2 (FIG. 6B) positive cells was performed on cortical brain images (n=10 per animal). Open symbols indicate animals tolerized with infusion of recombinant human IDUA. GM3 and LIMP2 were significantly reduced in the high dose cohort compared to untreated controls (Kruskal-Wallis test followed by Dunn's multiple comparisons test).

Figure 7:
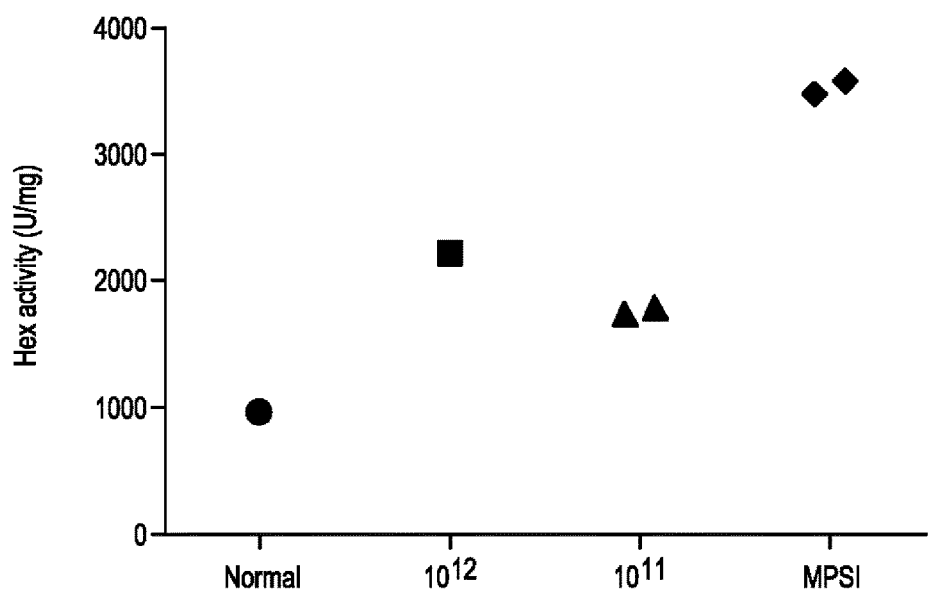

FIG. 7 shows partial normalization of brain hexosaminidase activity in naïve dogs treated with intrathecal injection of AAV9 expressing human IDUA. Hexosaminidase activity was measured in samples collected from 6 brain regions (frontal cortex, temporal cortex, occipital cortex, hippocampus, medulla, and cerebellum). The mean activity is shown for a normal control dog, untreated MPS I dogs, and dogs treated with intrathecal AAV9 expressing human IDUA at one month of age with doses of $10^{12}$ GC/kg or $10^{11}$ GC/kg.

Figure 8:
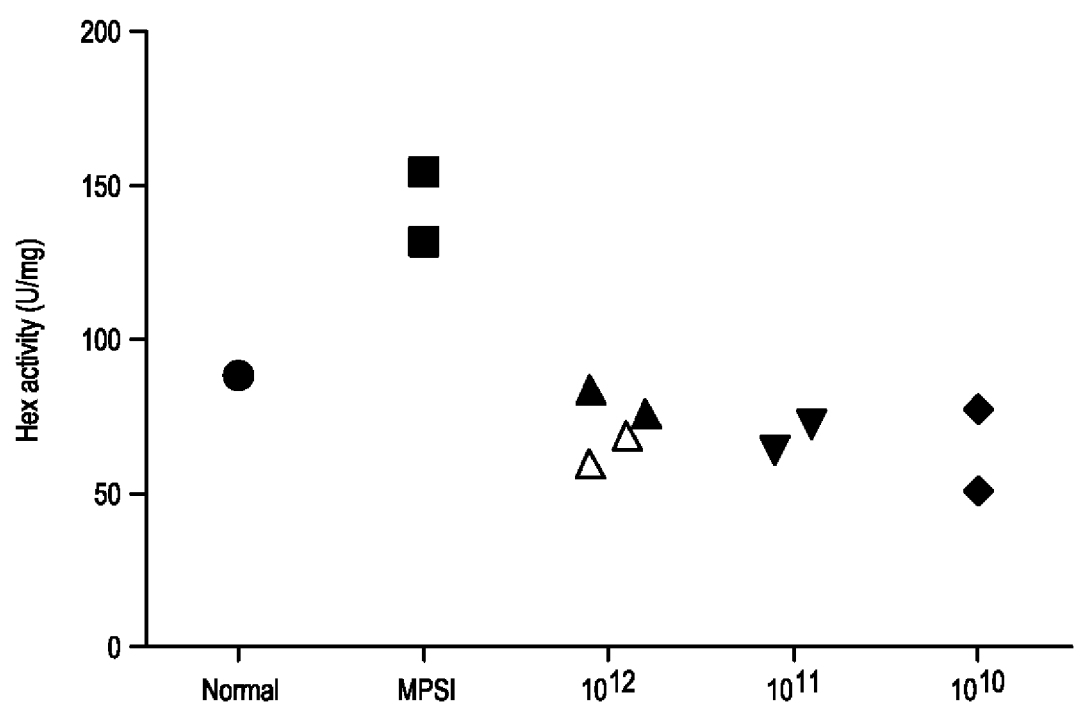

FIG. 8 shows normalization of CSF hexosaminidase activity after IT AAV9 treatment in hIDUA tolerant dogs. Hex activity was measured in CSF of MPS I dogs tolerized to human IDUA at the end of the study. Open symbols indicate animals tolerized with infusion of recombinant human IDUA. CSF hex activity was significantly reduced in all treated animals relative to untreated MPS I controls (Mann-Whitney test).

Figure 9:
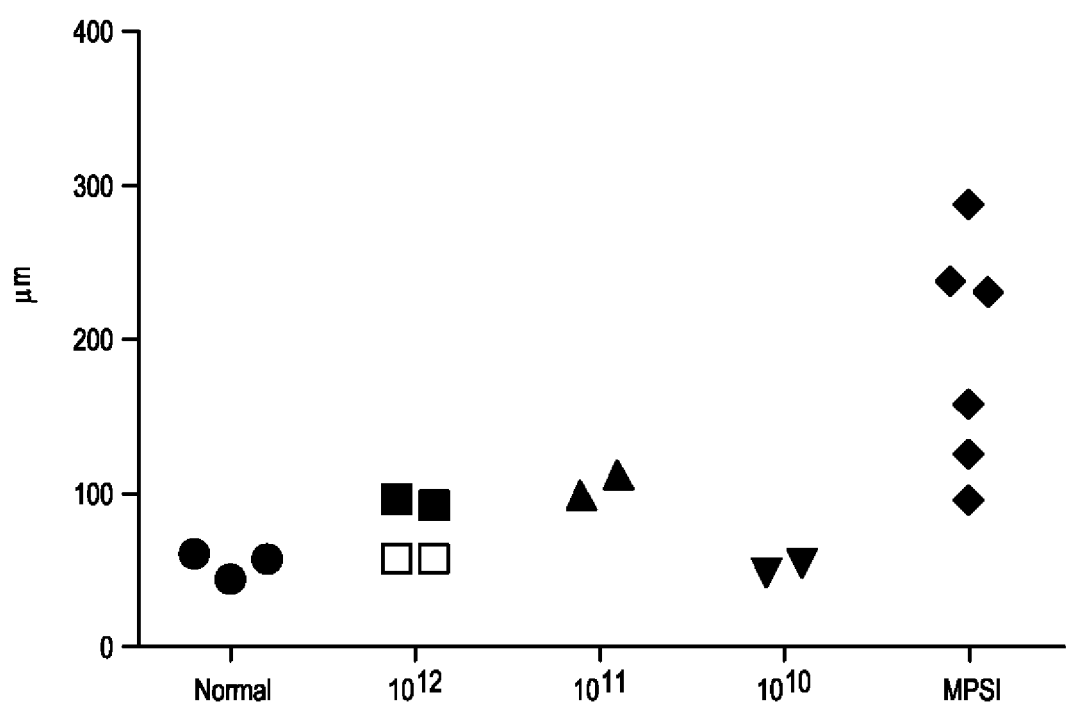

FIG. 9 shows resolution of cervical meningeal thickening in hIDUA tolerant dogs treated with intrathecal AAV9 expressing human IDUA. The average total thickness of the meninges was measured on H&E stained sections of the cervical spinal cord. Open symbols indicate animals tolerized with infusion of recombinant human IDUA. Meningeal thickness was significantly reduced in all treated animals relative to untreated MPS I controls (Mann-Whitney test).

Figure 10A:
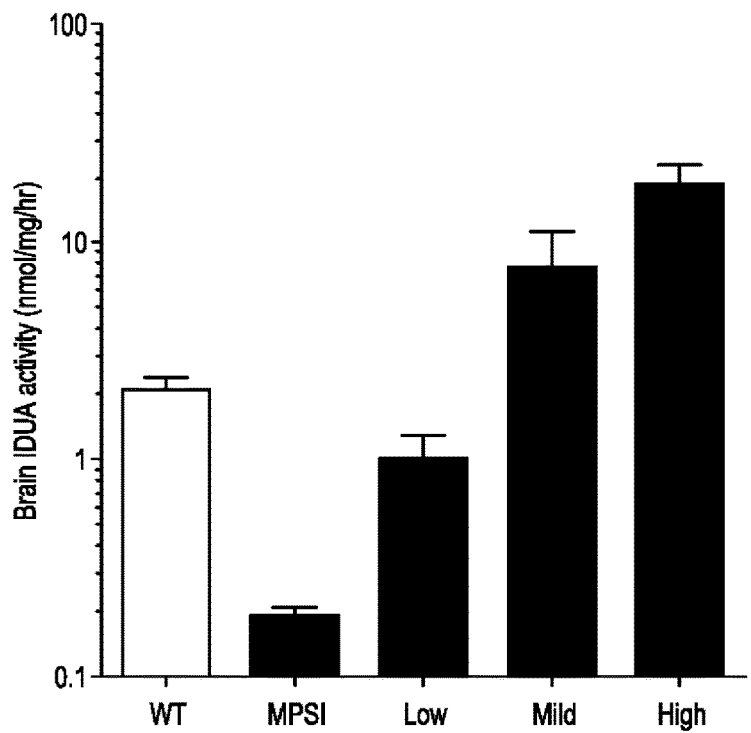
Figure 10B:
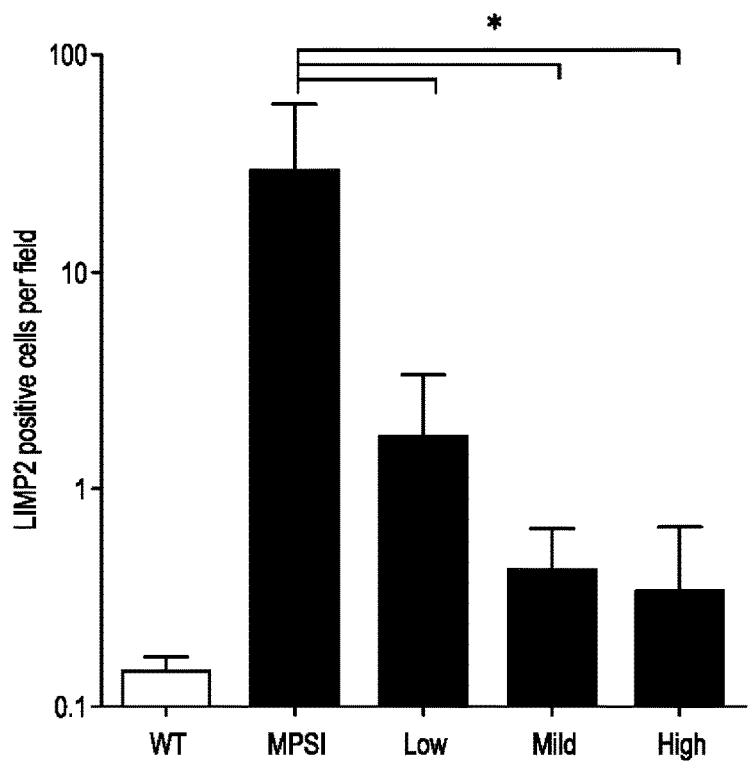

FIGS. 10A-10B provide a comparison of enzyme expression and correction of brain storage lesions in MPS I mice treated with IT AAV9. MPS I mice were treated at 2-3 months of age with an ICV injection of AAV9.CB.hIDUA at one of three doses: $3 \times 10^8$ GC (low), $3 \times 10^9$ GC (mid), or $3 \times 10^{10}$ GC (high). FIG. 10A is from one cohort of animals that was sacrificed at 3 weeks post vector injection, and brains were harvested for measurement of IDUA activity. FIG. 10B shows a second cohort of animals sacrificed 3 months after injection; brains were stained for the lysosomal membrane protein LIMP2. Cells staining positive for LIMP2 were quantified by a blinded reviewer in 4 cortical brain sections. *p<0.05, one-way ANOVA followed by Dunnett's test.

Figure 11:
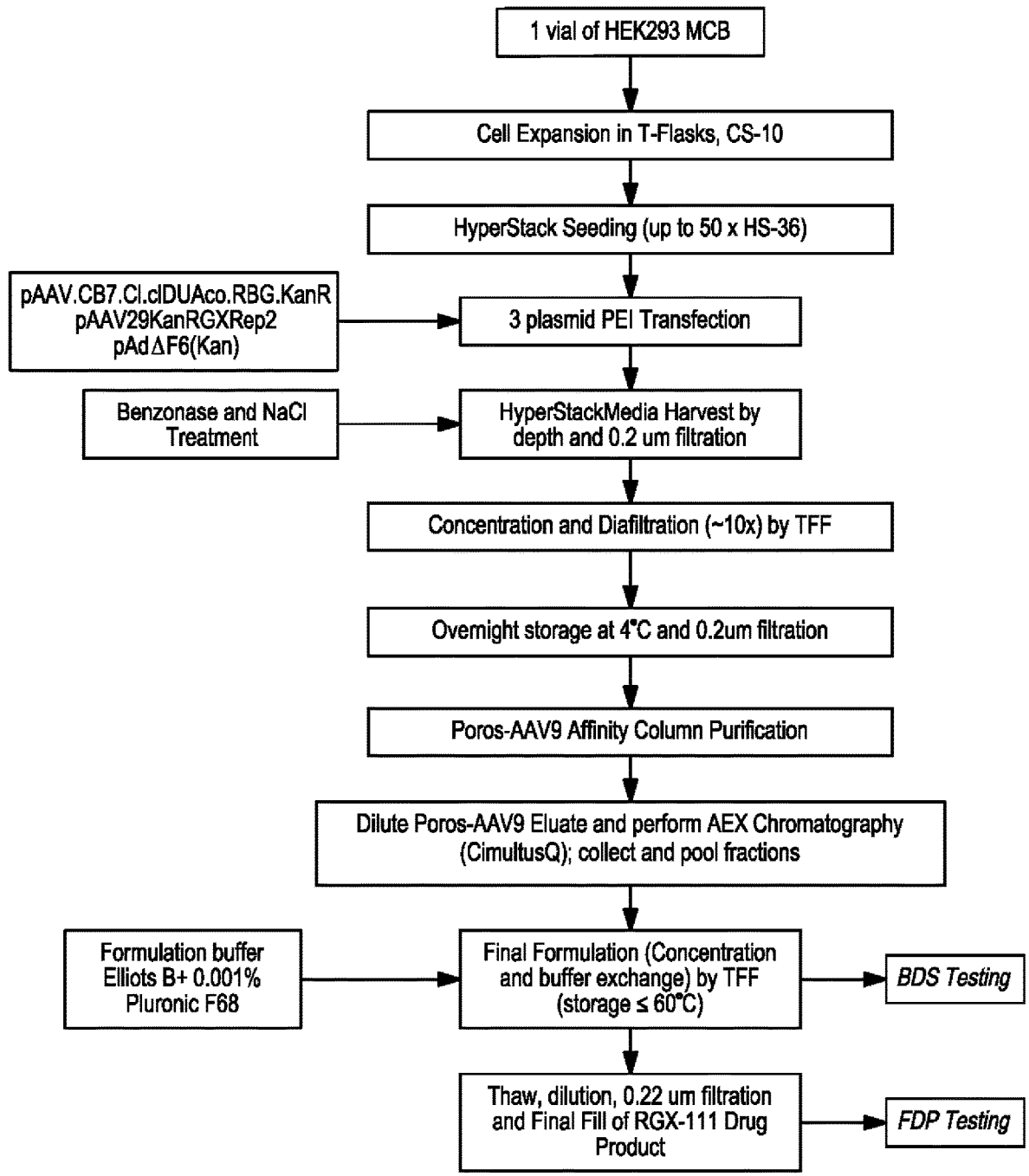

FIG. 11 provides a manufacturing process flow diagram.

Figure 12:
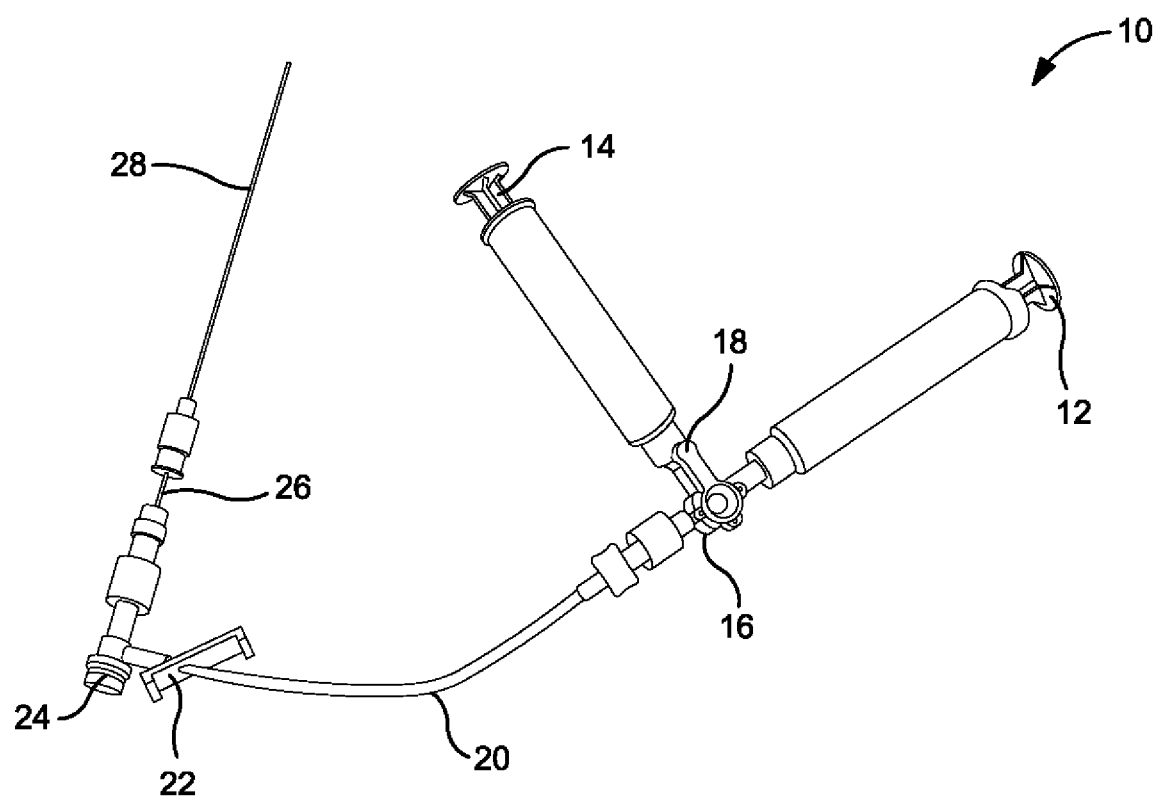

FIG. 12 is an image of apparatus (10) for intracisternal delivery of a pharmaceutical composition, including optional introducer needle for coaxial insertion method (28), which includes a 10 cc vector syringe (12), a 10 cc prefilled flush syringe (14), a T-connector extension set (including tubing (20), a clip at the end of the tubing (22) and connector (24)), a 22 G×5" spinal needle (26), an optional 18 G×3.5" introducer needle (28). Also illustrated is the 4-way stopcock with swivel male luer lock (16).

Figure 13:
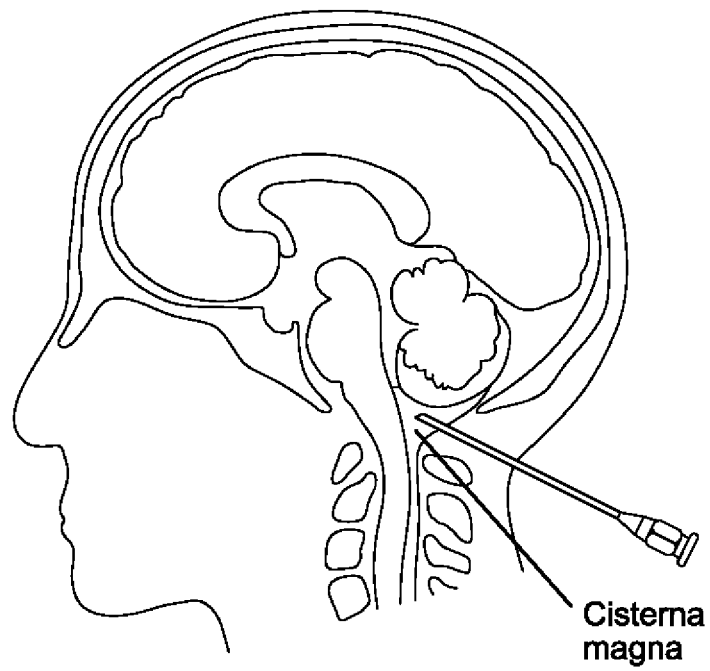

FIG. 13 provides a schematic illustration of an intracisternal injection.

Figure 14:
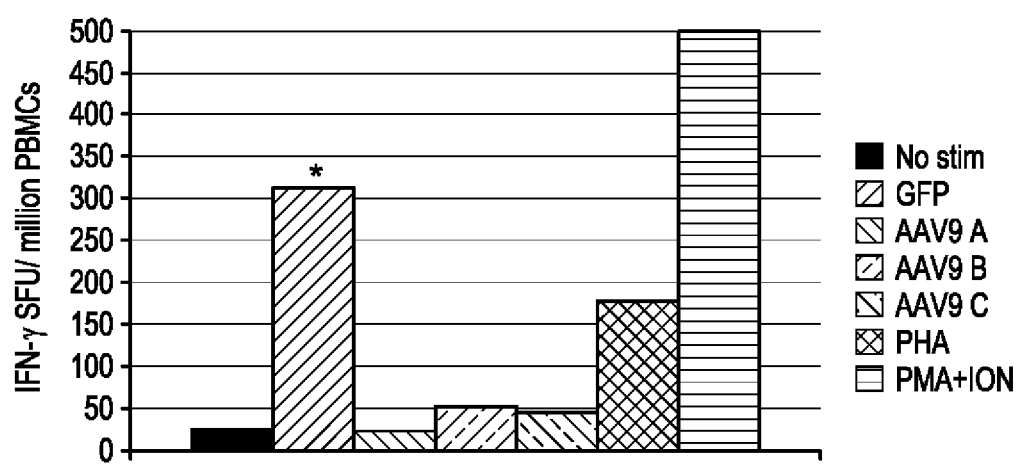

FIG. 14 illustrates encephalitis and transgene specific T cell responses in dogs treated with ICV AAV9. One-year-old MPS I dogs were treated with a single ICV or IC injection of an AAV9 vector expressing GFP. All animals were sacrificed 14 days after injection, except for I-567 which was found dead 12 days after injection. Brains were divided into coronal sections, which revealed gross lesions near the injection site (arrowheads) in ICV treated animals. Tissue sections from the brain regions surrounding the gross lesions were stained with hematoxylin and eosin. Peripheral blood mononuclear cells were collected from one ICV treated dog (I-565) at the time of necropsy, and T cell responses against the AAV9 capsid and GFP protein were measured by interferon-γ ELISPOT (FIG. 14). T cell responses to the GFP transgene product were measured using a single pool of overlapping 15 amino acids long peptides covering the full GFP sequence. The peptides comprising the AAV9 capsid protein were divided into three pools (designated pool A-C). *=positive response, defined as >3-fold background (unstimulated cells) and greater than 55 spots per million cells. Phytohemagglutinin (PHA) and ionomycin with phorbol 12-myristate 13-acetate (PMA) served as positive controls for T cell activation.

Figure 15:
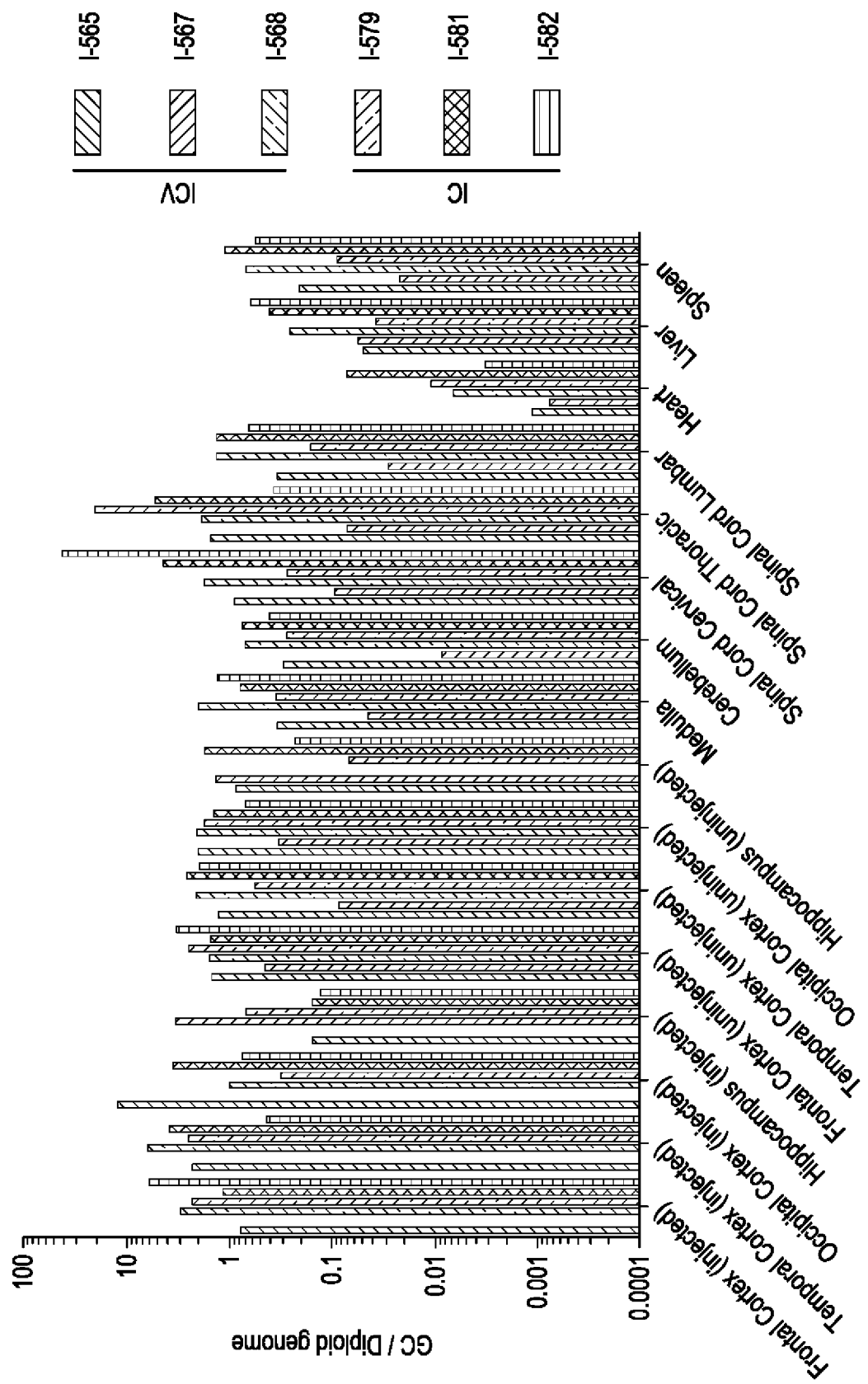

FIG. 15 is a bar chart illustrating vector biodistribution in dogs treated with ICV or IC AAV9. Dogs were sacrificed 14 days after injection with a single ICV or IC injection of an AAV9 vector expressing GFP, except for animal I-567 which was necropsied 12 days after injection. Vector genomes were detected in tissue samples by quantitative PCR. Values are expressed as vector genome copies per diploid cell (GC/diploid genome). Brain samples collected from the hippocampus or cerebral cortex are indicated as either injected or uninjected hemisphere for the ICV treated dogs; for the IC treated animals these are the right and left hemispheres, respectively. Samples were not collected for PCR from the injected cerebral hemisphere of animal I-567.

Figure 16:
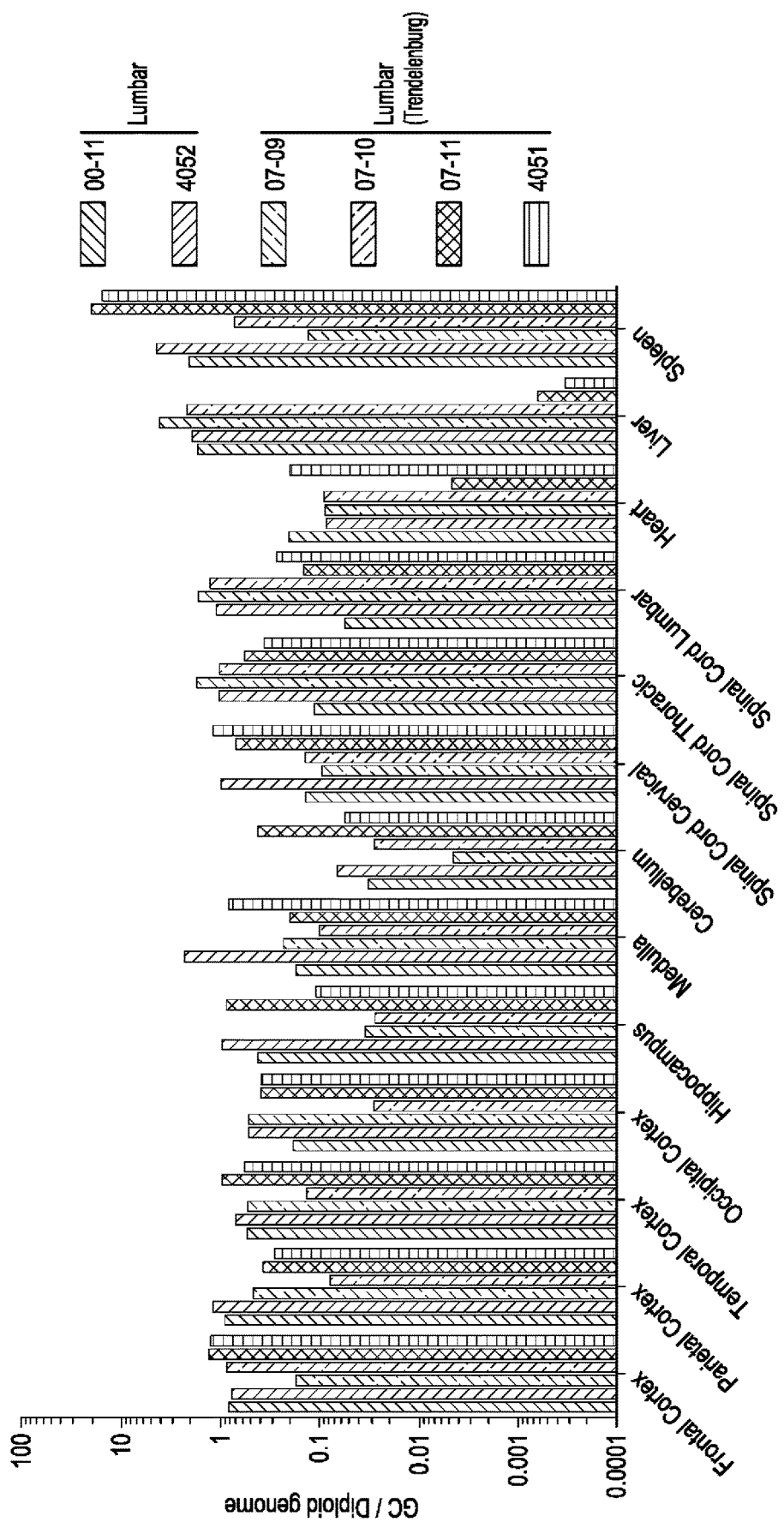

FIG. 16 is a bar chart showing vector biodistribution in NHPs treated with intrathecal AAV9. NHPs were sacrificed 14 days after intrathecal injection via lumbar puncture of an AAV9 vector diluted in 5 mL of Iohexol 180. Two of the animals were placed in the Trendelenburg position for 10 minutes after injection. Vector genomes were detected in tissue samples by quantitative PCR. Values are expressed as vector genome copies per diploid cell (GC/diploid genome).

Figure 17A:
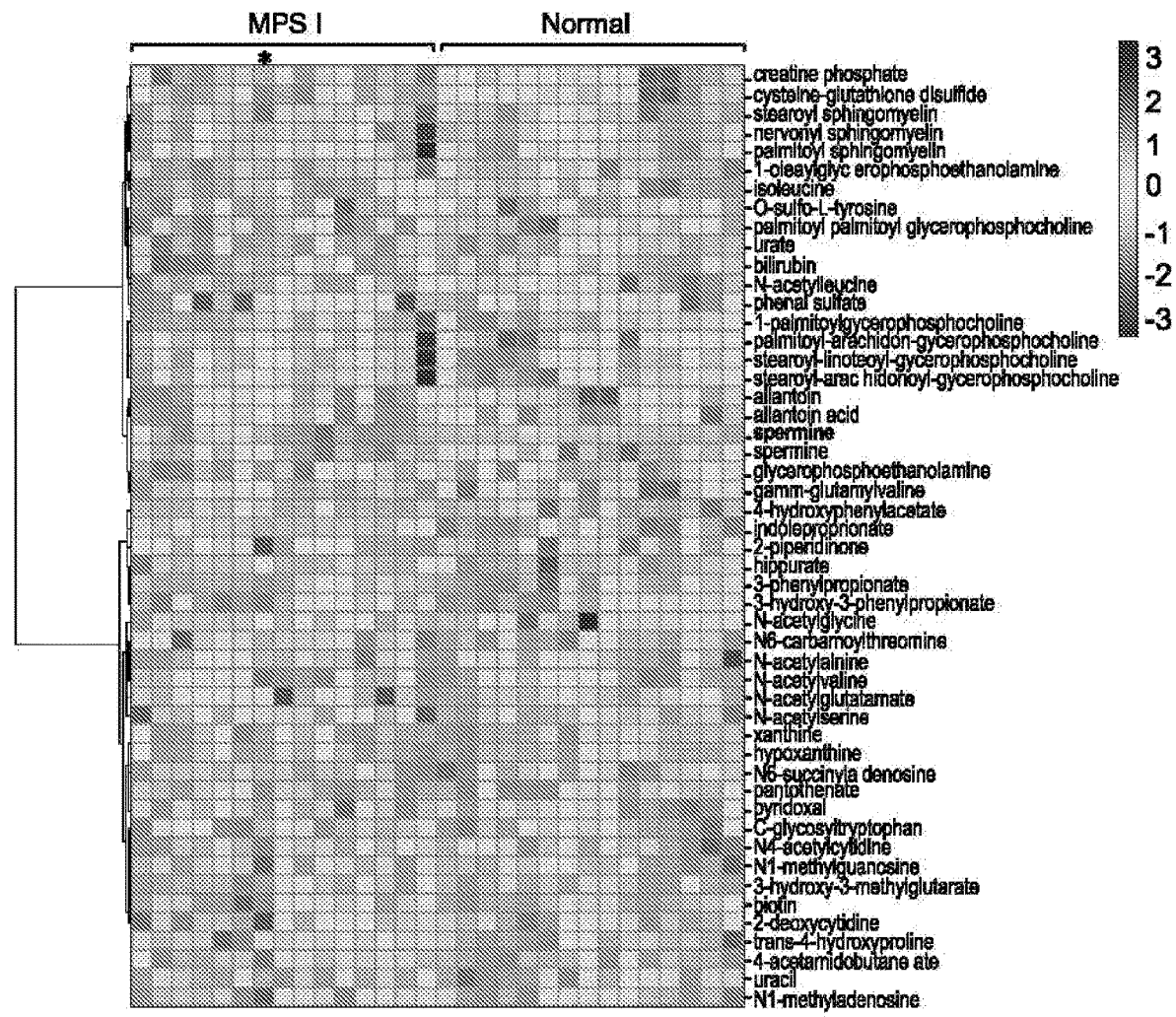
Figure 17B:
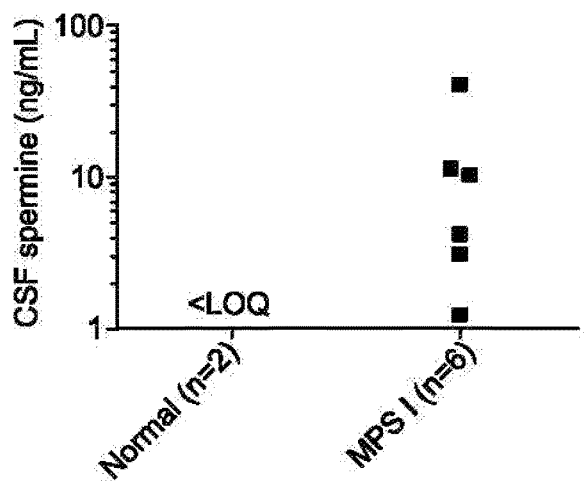

FIGS. 17A-17B illustrate elevated CSF spermine in MPS I. A high throughput LC/MS and GC/MS metabolite screen was performed on CSF samples from MPS I dogs (n=15) and normal controls (n=15). FIG. 17A shows a heatmap of the top 100 differentially detected metabolites (ANOVA). The youngest animal in the MPS I cohort (28 days of age) is indicated by an asterisk. FIG. 17B is a graph showing spermine concentration measured by a quantitative isotope dilution LC/MS assay in CSF samples from 6 infants with MPS I and 2 normal infants.

FIGS. 18A-18F illustrate spermine dependent aberrant neurite growth in MPS I neurons. Cortical neurons harvested from E18 wild-type or MPS I mouse embryos were treated with spermine (50 ng/mL) or the spermine synthase inhibitor APCHA 24 hours after plating. Neurite number, length and branching were quantified for 45-65 randomly selected neurons from duplicate cultures per treatment condition by a blinded reviewer. FIG. 18A is a bar chart providing neurites for MPSI, MPSI+APCHA, or MPSI+APCHA+spermine, as compared to a wild-type. FIG. 18B is a bar chart providing branch points for MPSI, MPSI+APCHA, or MPSI+APCHA+spermine, as compared to a wild-type. FIG. 18C is a bar chart providing arbor length for MPSI, MPSI+APCHA, or MPSI+APCHA+spermine, as compared to a wild-type *** $p<0.0001$ (ANOVA followed by Dunnett's test). FIG. 18D is a bar chart comparing neurites/cell for wild-type treated with spermine as compared to wild-type. FIG. 18E is a bar chart comparing branch points/cell for wild-type treated with spermine as compared to wild-type. FIG. 18F is a bar chart comparing arbor length/cell for wild-type treated with spermine as compared to wild-type.

Figure 19A:
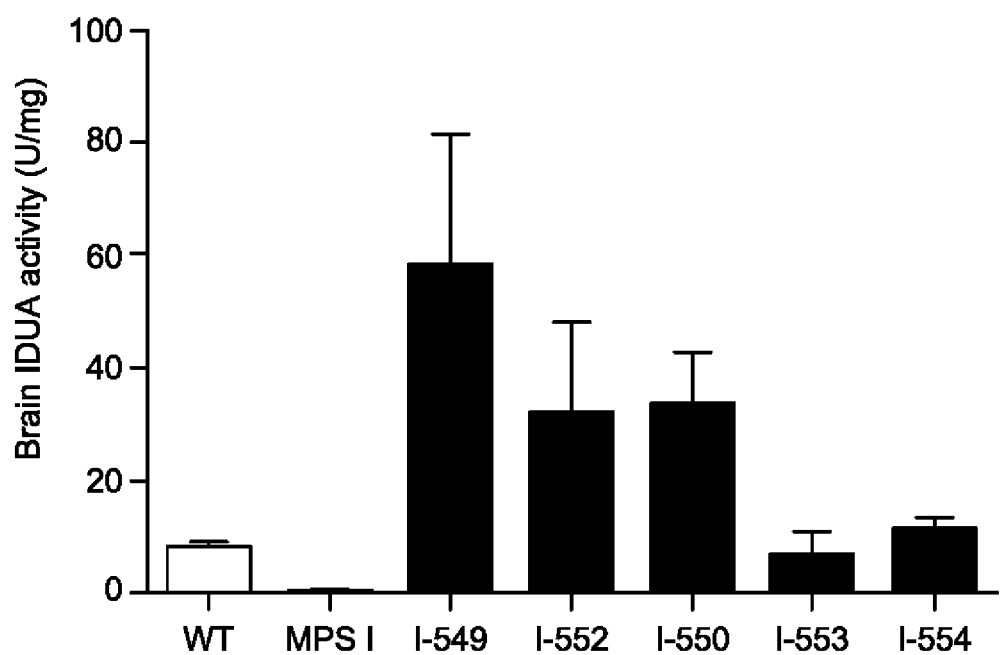
Figure 19B:
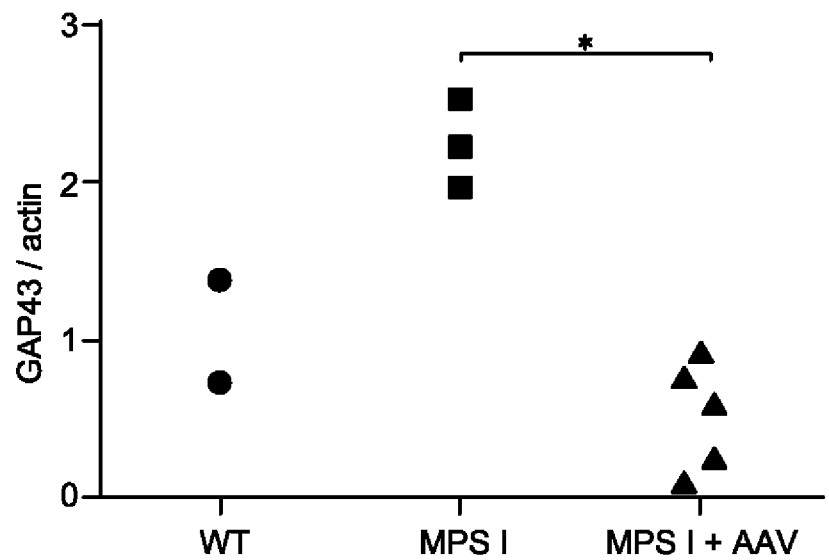
Figure 19C:
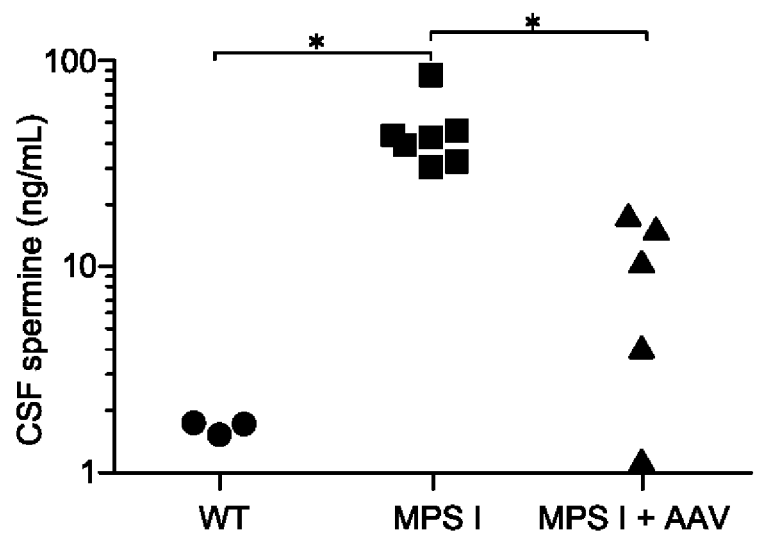

FIGS. 19A-19C illustrate normalization of CSF spermine levels and brain GAP43 expression in MPS I dogs following gene therapy. Five MPS I dogs were treated with an intrathecal injection of an AAV9 vector expressing canine IDUA at one month of age. Two of the dogs (I-549, I-552) were tolerized to IDUA by liver directed gene therapy on postnatal day 1 in order to prevent the antibody response that is elicited to IDUA in some MPS I dogs. FIG. 19A is a bar chart showing the results of IDUA activity measured in brain tissue six months after intrathecal vector injection. FIGS. 19B and C are graphs showing results following measurement of GAP43 in cortical brain samples quantified relative to β-actin by densitometry. CSF spermine was measured at the time of sacrifice by isotope dilution LC/MS (E). Untreated MPS I dogs (n=3) and normal dogs (n=2) served as controls. * $p<0.05$ (Kruskal-Wallis test followed by Dunn's test).

Figure 20A:
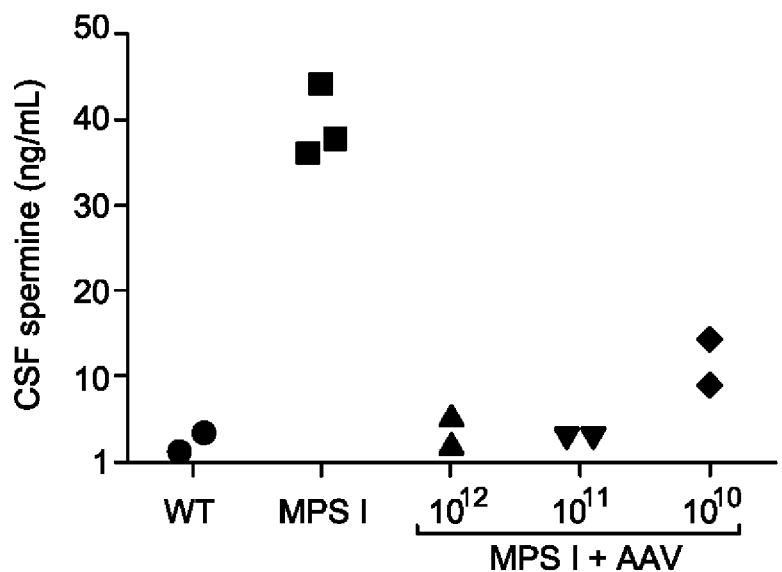
Figure 20B:
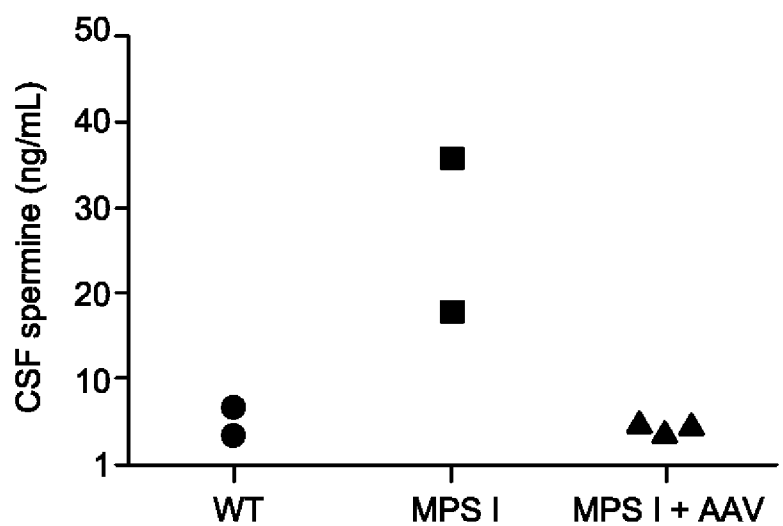

FIGS. 20A-20B are graphs which illustrate the use of spermine as a CSF biomarker for evaluation of CNS directed gene therapy in MPS I. Six MPS I dogs tolerized to human IDUA at birth were treated with intrathecal AAV9 expressing human IDUA (1012 GC/kg, n=2, 1011 GC/kg, n=2, 1010 GC/kg, n=2) at one month of age. FIG. 20A provides results following measurement of CSF spermine levels measured six months after treatment. Three MPS I cats were treated with intrathecal AAV9 expressing feline IDUA (1012 GC/kg). FIG. 20B provides results following quantification of CSF spermine six months after treatment. Untreated MPS I dogs (n=3) and normal dogs (n=2) served as controls.

Figure 21:
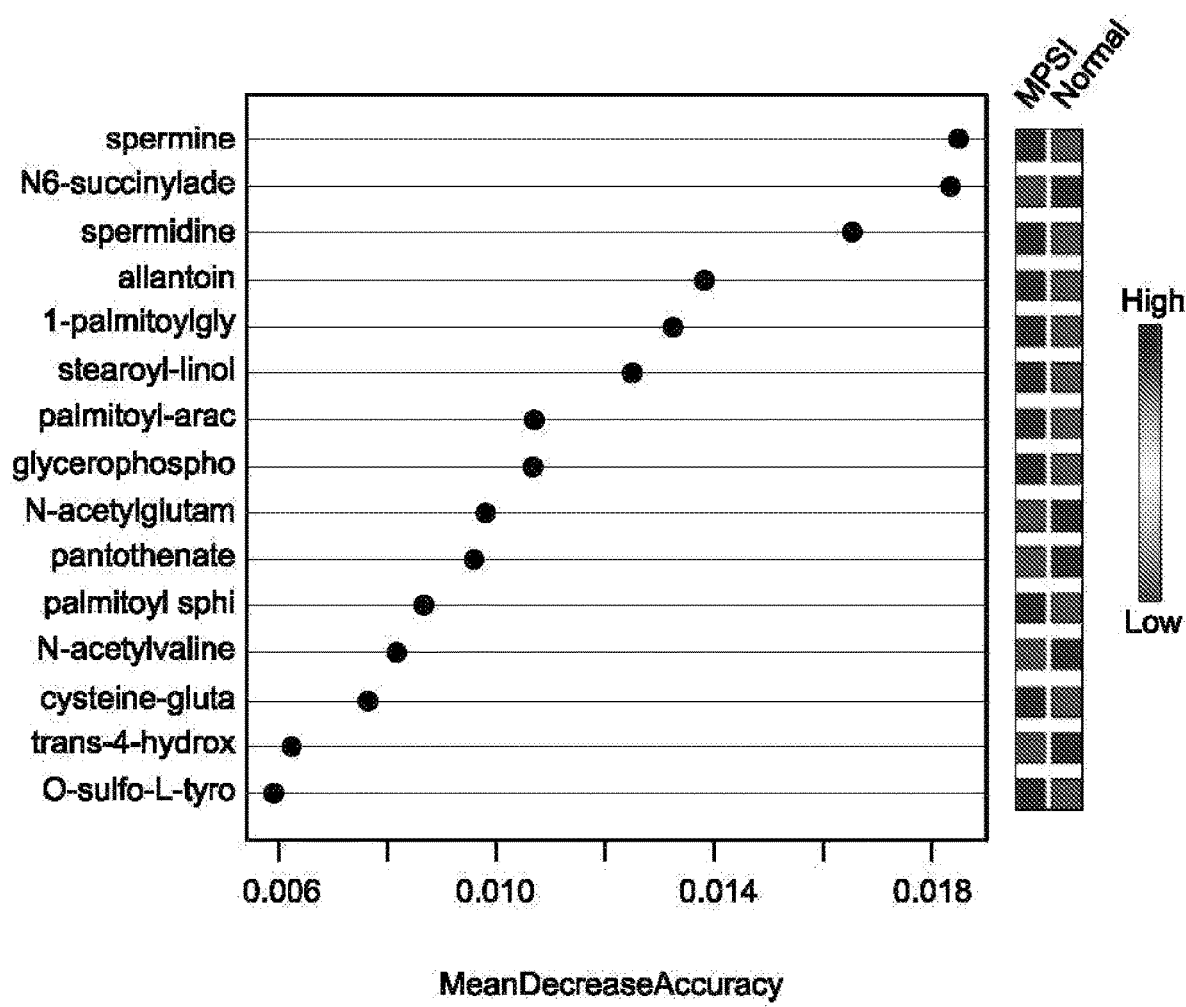

FIG. 21 illustrates the mean decrease accuracy for metabolites identified by random forest analysis.

Figure 22:
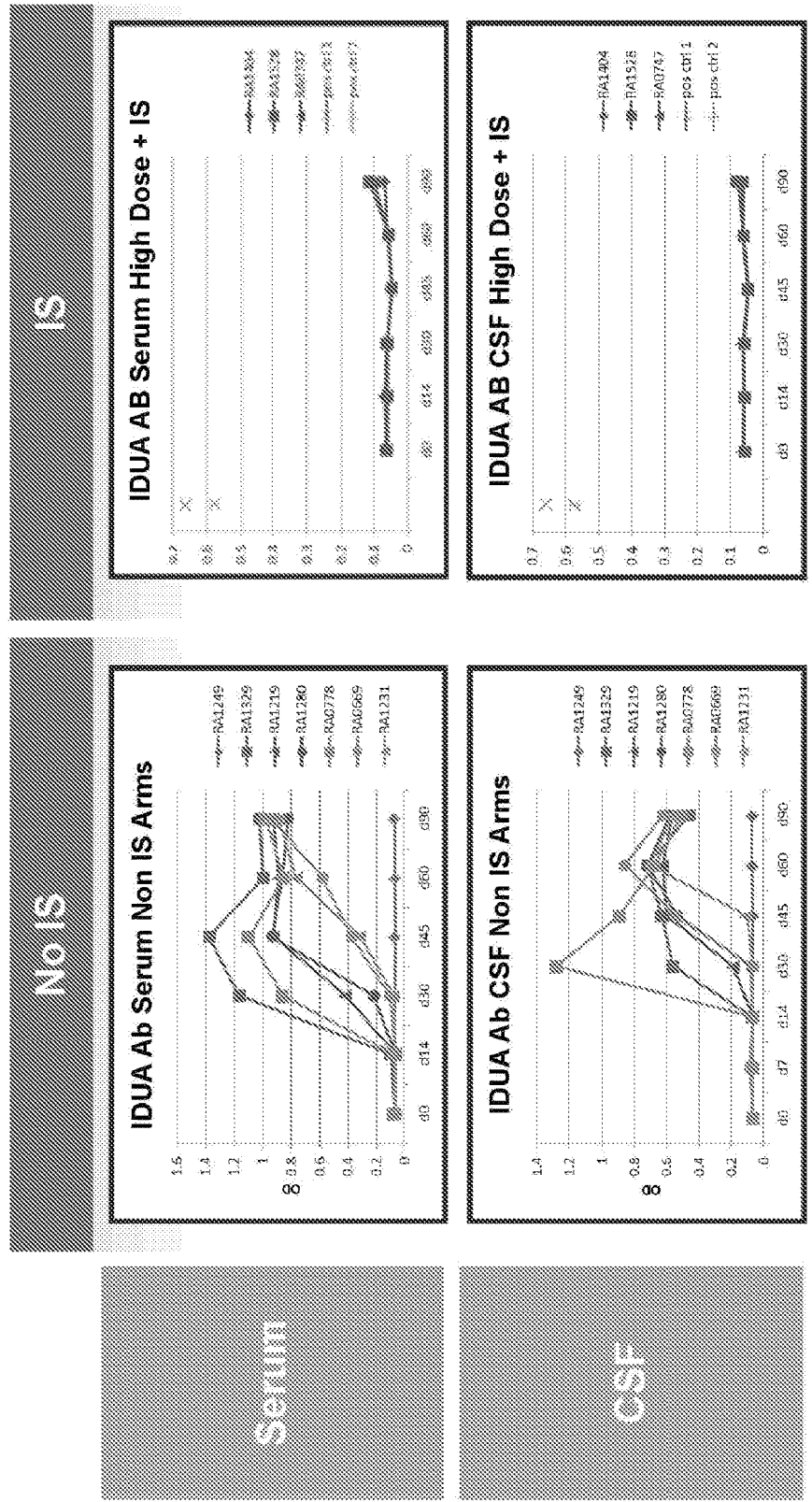
Figure 23:
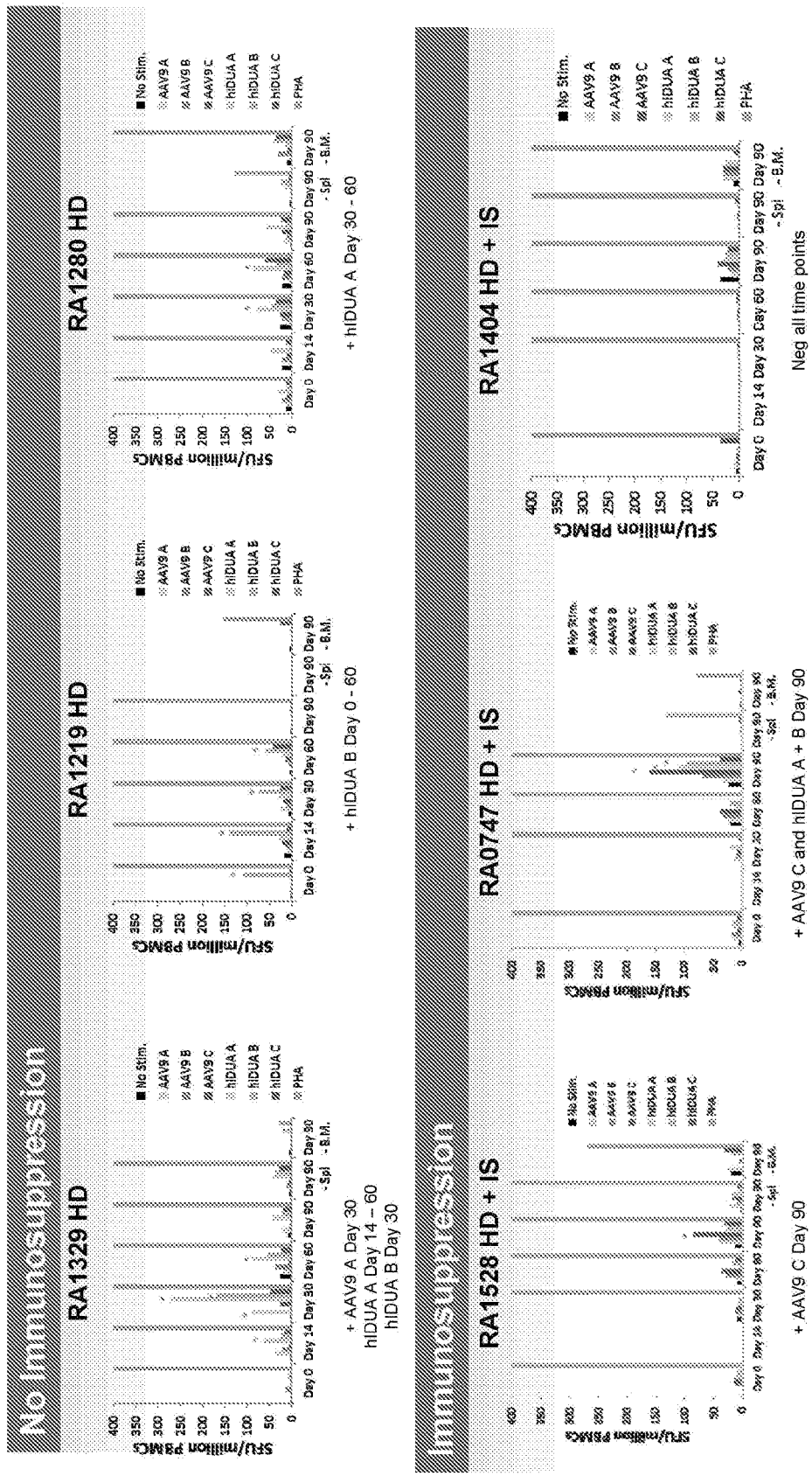

FIG. 22-23 provide data from the non-human safety studies using the AAV9.hIDUA vector described in Example 7.

FIG. 22 shows serum and cerebrospinal fluid from non-human primates without immunosuppression (no IS) and with immunosuppression (IS) from day 0 through day 90. The numbers in the legend reflect individual animals.

FIG. 23 shows the impact of immunosuppression on T cell immune response at high dose (HD), with immunosuppression (IS) and without immunosuppression. ElisSpots were run for the vector capsid (AAV9) and transgene (hIDUA). Cells were stimulated as shown. Results are provided in spot forming units (SFU)/million peripheral blood mononuclear cells (PBMCs).

5. DETAILED DESCRIPTION OF THE INVENTION

A replication deficient adeno-associated virus ("AAV") to deliver a human alpha-L-iduronidase (hIDUA) gene to the CNS of patients (human subjects) diagnosed with mucopolysaccharidosis type I (MPS I) is provided herein. The recombinant AAV ("rAAV") vector used for delivering the hIDUA gene ("rAAV.hIDUA") has tropism for the CNS (e.g., an rAAV bearing an AAV9 capsid), and the hIDUA transgene is controlled by specific expression control elements, e.g., a hybrid of cytomegalovirus (CMV) enhancer and the chicken beta actin promoter (CB7). In certain embodiments, pharmaceutical compositions suitable for intrathecal, intracisternal, and systemic administration are provided, which comprise a suspension of rAAV.hIDUA vectors in a formulation buffer comprising a physiologically compatible aqueous buffer, a surfactant and optional excipients. The rAAV suspension is further characterized in that:

(i) the rAAV Genome Copy (GC) titer is at least $1\times10^9$ GC/mL to $1\times10^{14}$ GC/mL (+/−20%);

(ii) the rAAV Empty/Full particle ratio is between 0.01 and 0.05 (95%-99% free of empty capsids), or in other embodiments at least about 50, at least about 80%, at least about 85%, or at least about 90%, free of empty capsids, as determined by SDS-PAGE analysis (see Example 6D); and/or (iii) a dose of at least about $4\times10^8$ GC/g brain mass to about $4\times10^{11}$ GC/g brain mass of the rAAV suspension has potency.

Potency can be measured by in vitro/cell culture assays, e.g., the in vitro potency assay described in Example 6G, in which Huh7 or HEK293 cells are transduced with a known multiplicity of rAAV GCs per cell and the supernatant is assayed for IDUA activity 72 hours post-transduction. The function (activity) and/or the potency of hIDUA may be measured in a suitable in vitro assay, e.g., by its ability to cleave a fluorogenic substrate, 4-Methylumbelliferyl alpha-L-iduronide. The specific activity is >7,500 pmol/min/mg, as measured under the described conditions. See Activity Assay Protocol on www.RnDSystems.com. Other suitable methods of measuring enzyme activity have been described [see, e.g., Kakkis, E. D., et al (1994). Protein Expression Purif. 5: 225-232; Rome, L. H., et al (1979). Proc. Natl. Acad. Sci. USA 76: 2331-2334], including those described herein. Activity may also be assessed using the method described, e.g., E. Oussoren, et al, Mol Genet Metab. 2013 August; 109(4):377-81. doi: 10.1016/j.ymgme.2013.05.016. Epub 2013 Jun. 4.

Patients who are candidates for treatment are pediatric and adult patients with MPSI and/or the symptoms associated with Hurler, Hurler-Scheie and Scheie.

Therapeutically effective intrathecal/intracisternal doses of the rAAV.hIDUA for MPSI patients range from about $1\times10^{11}$ to $7.0\times10^{14}$ GC (flat doses)—the equivalent of $10^9$ to $5\times10^{10}$ GC/g brain mass of the patient. Alternatively, the following therapeutically effective flat doses can be administered to patients of the indicated age group:

Newborns: about $1\times10^{11}$ to about $3\times10^{14}$ GC;
3-9 months: about $6\times10^{12}$ to about $3\times10^{14}$ GC;
9 months-6 years: about $6\times10^{12}$ to about $3\times10^{14}$ GC;
Under 3 years old (newborns up to 3 years): about $1\times10^{11}$ to about $1.2\times10^{13}$ GC
3-6 years: about $1.2\times10^{13}$ to about $6\times10^{14}$ GC;
6-12 years: about $1.2\times10^{13}$ to about $6\times10^{14}$ GC;
12+ years: about $1.4\times10^{13}$ to about $7.0\times10^{14}$ GC;
18+ years (adult): about $1.4\times10^{13}$ to about $7.0\times10^{14}$ GC.

In other embodiments, the following therapeutically effective flat doses are administered to an MPS patient of the age group:

Newborns: about $3.8\times10^{12}$ to about $1.9\times10^{14}$ GC;
3-9 months: about $6\times10^{12}$ to about $3\times10^{14}$ GC;
9-36 months: about $10^{13}$ to about $5\times10^{13}$ GC;
Under 3 years old (newborns up to 3 years): about $1\times10^{11}$ to about $1.2\times10^{13}$ GC
6-12 years: about $1.2\times10^{13}$ to about $6\times10^{14}$ GC;
3-12 years: about $1.2\times10^{13}$ to about $6\times10^{14}$ GC;
12+ years: about $1.4\times10^{13}$ to about $7.0\times10^{14}$ GC;
18+ years (adult): about $1.4\times10^{13}$ to about $7.0\times10^{14}$ GC.

In certain embodiments, one or more of these ranges are used for patients of any age. In certain embodiments, a flat dose of $1.2\times10^{12}$ total genome copies (GC) ($2.0\times10^{9}$ GC/g brain mass) or $6\times10^{12}$ total GC ($1\times10^{10}$ GC/g brain mass) is administered to a patient that is greater than or equal to ($\geq$) 4 month to less than (<) 9 months. In certain embodiments, a flat dose of $2\times10^{12}$ total GC ($2.0\times10^{9}$ GC/g brain mass) or $1\times10^{13}$ total GC ($1\times10^{10}$ GC/g brain mass) is administered to a patient that is greater than or equal to ($\geq$) 9 month to less than (<) 18 months. In certain embodiments, a flat dose of $2.2\times10^{12}$ total GC ($2.0\times10^{9}$ GC/g brain mass) or $1.1\times10^{13}$ total GC ($1\times10^{10}$ GC/g brain mass) is administered to a patient that is greater than or equal to ($\geq$) 18 month to less than (<) 3 years. In certain embodiments, a flat dose of $6\times10^{12}$ ($1.0\times10^{10}$ GC/g brain mass) or $3\times10^{13}$ total genome copies (GC) ($5\times10^{10}$ GC/g brain mass) is administered to a patient that is greater than or equal to ($\geq$) 4 month to less than (<) 9 months. In certain embodiments, a flat dose of $1.0\times10^{13}$ ($1.0\times10^{10}$ GC/g brain mass) or $5.0\times10^{13}$ total GC ($5\times10^{10}$ GC/g brain mass) is administered to a patient that is greater than or equal to ($\geq$) 9 month to less than (<) 18 months. In certain embodiments, a flat dose of $1.1\times10^{13}$ ($1.0\times10^{10}$ GC/g brain mass) or $5.5\times10^{13}$ total GC ($5\times10^{10}$ GC/g brain mass) is administered to a patient that is greater than or equal to ($\geq$) 18 month to less than (<) 3 years. In certain embodiments, a flat dose of $2.6\times10^{12}$ genome copies (GC) ($2.0\times10^{9}$ GC/g brain mass) is administered to a patient that is 6 years old or older than 6 years old. In certain embodiments, a flat dose of $1.3\times10^{13}$ (GC) ($1.0\times10^{10}$ GC/g brain mass) is administered to a patient that is 6 years old or older than 6 years old. In some embodiments, the dose administered to a 12+ year old MPSI patient (including 18+ year old) is $1.4\times10^{13}$ genome copies (GC) ($1.1\times10^{10}$ GC/g brain mass). In some embodiments, the dose administered to a 12+ year old MPSI patient (including 18+ year old) is $7\times10^{13}$ GC ($5.6\times10^{10}$ GC/g brain mass). In still a further embodiment, the dose administered to an MPSI patient is at least about $4\times10^{8}$ GC/g brain mass to about $4\times10^{11}$ GC/g brain mass. In certain embodiments, the dose administered to MPS I newborns ranges from about $1.4\times10^{11}$ to about $1.4\times10^{14}$ GC; the dose administered to infants 3-9 months ranges from about $2.4\times10^{11}$ to about $2.4\times10^{14}$ GC; the dose administered to MPS I children 9-36 months ranges: about $4\times10^{11}$ to about $4\times10^{14}$ GC; the dose administered to MPS I children 3-12 years: ranges from about $4.8\times10^{11}$ to about $4.8\times10^{14}$ GC; the dose administered to children and adults 12+ years ranges from about $5.6\times10^{11}$ to about $5.6\times10^{14}$ GC.

The goal of the treatment is to functionally replace the patient's defective alpha-L-iduronidase via rAAV-based CNS-directed gene therapy as a viable approach to treat disease. As expressed from the rAAV vector described herein, expression levels of at least about 2% of normal levels as detected in the CSF, serum, neurons, or other tissue or fluid, may provide therapeutic effect. However, higher expression levels may be achieved. Such expression levels may be from 2% to about 100% of normal functional human IDUA levels. In certain embodiments, higher than normal expression levels may be detected in CSF, serum, or other tissue or fluid.

The invention also provides for the manufacture and characterization of the rAAv.hIDUA pharmaceutical compositions (Example 6, infra).

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular, suboccipital/intracisternal, and/or C1-2 puncture. For example, material may be introduced for diffusion throughout the subarachnoid space by means of lumbar puncture. In another example, injection may be into the cisterna magna.

As used herein, the terms "intracisternal delivery" or "intracisternal administration" refer to a route of administration for drugs directly into the cerebrospinal fluid of the brain ventricles or within the cisterna magna cerebellomedularis, more specifically via a suboccipital puncture or by direct injection into the cisterna magna or via permanently positioned tube. FIG. 13 provides an illustration as to how an intracisternal injection would be made.

As used herein, a "therapeutically effective amount" refers to the amount of the AAV9.hIDUA composition which delivers and expresses in the target cells an amount of enzyme sufficient to ameliorate or treat one or more of the symptoms of MPSI Hurler, and/or Hurler-Scheie and/or Scheie syndromes. "Treatment" may include preventing the worsening of the symptoms of one of the MPSI syndromes and possibly reversal of one or more of the symptoms thereof. Method of assessing therapeutic effectiveness (efficacy) are described in detail below (see, e.g., Section 5.2.3, infra).

A "therapeutically effective amount" for human patients may be predicted based on an animal model. Examples of a suitable feline model and a suitable canine model are described herein. See, C. Hinderer et al, Molecular Therapy (2014); 22 12, 2018-2027; A. Bradbury, et al, Human Gene Therapy Clinical Development. March 2015, 26(1): 27-37, which are incorporated herein by reference. With respect to the canine model, the model is typically an immune suppressed animal model, or a tolerized animal, as intravenous administration in dogs has been observed to elicit a strong, sustained antibody response to human IDUA, whereas in human patients, administration is well tolerated. In these models, reversal of certain symptoms may be observed and/or prevention of progression of certain symptoms may be observed. For example, correction of corneal clouding may be observed, and/or correction of lesions in the central nervous system (CNS) is observed, and/or reversal of perivascular and/or meningeal gag storage is observed.

As used herein a "functional human alpha-L-iduronidase" refers to a human alpha-L-iduronidase enzyme which functions normally in humans without MPS1 or an associated syndrome such as Hurler, Hurler-Scheie and/or Scheie syndromes. Conversely, a human alpha-L-iduronidase enzyme variant which causes MPS1 or one of these syndromes is considered non-functional. In one embodiment, a functional human alpha-1-iduronidase has the amino acid sequence of a wild-type human alpha-L-iduronidase described by Bremer et al, Mol. Genet. Metab. 104 (3): 289-294 (2011), NCBI Reference Sequence NP_000194.2, reproduced in SEQ ID NO:2 (653 amino acids). However, several naturally occurring functional polymorphisms (variants) of this sequence have been described and may be encompassed within the scope of this invention. Such variants have been described; see, e.g., in WO 2014/151341, which is incorporated herein by reference, as well as in, e.g., UniProtKB/Swiss-Prot; www.uniprot.org/uniprot/P35475, also incorporated by reference.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

As used herein, an "expression cassette" refers to a nucleic acid molecule which comprises an IDUA gene, promoter, and may include other regulatory sequences therefor, which cassette may be delivered via a genetic element (e.g., a plasmid) to a packaging host cell and packaged into the capsid of a viral vector (e.g., a viral particle). Typically, such an expression cassette for generating a viral vector contains the IDUA coding sequence described herein flanked by packaging signals of the viral genome and other expression control sequences such as those described herein.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

As used herein, the term "operably linked" refers to both expression control sequences that are contiguous with the gene of interest and expression control sequences that act in trans or at a distance to control the gene of interest.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

As used herein, "recombinant AAV9 viral particle" refers to nuclease-resistant particle (NRP) which has an AAV9 capsid, the capsid having packaged therein a heterologous nucleic acid molecule comprising an expression cassette for a desired gene product. Such an expression cassette typically contains an AAV 5' and/or 3' inverted terminal repeat sequence flanking a gene sequence, in which the gene sequence is operably linked to expression control sequences. These and other suitable elements of the expression cassette are described in more detail below and may alternatively be referred to herein as the transgene genomic sequences. This may also be referred to as a "full" AAV capsid. Such a rAAV viral particle is termed "pharmacologically active" when it delivers the transgene to a host cell which is capable of expressing the desired gene product carried by the expression cassette.

In many instances, rAAV particles are referred to as DNase resistant. However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a transgene to a host cell and protects these packaged genomic sequences from degradation (digestion) during nuclease incubation steps designed to remove contaminating nucleic acids which may be present from the production process.

As used herein, "AAV9 capsid" refers to the AAV9 having the amino acid sequence of GenBank accession: AAS99264, is incorporated by reference herein and the AAV vp1 capsid protein is reproduced in SEQ ID NO:7. Some variation from this encoded sequence is encompassed by the present invention, which may include sequences having about 99% identity to the referenced amino acid sequence in GenBank accession: AAS99264 and U.S. Pat. No. 7,906,111 (also WO 2005/033321) (i.e., less than about 1% variation from the referenced sequence). Such AAV may include, e.g., natural isolates (e.g., hu31 or hu32), or variants of AAV9 having amino acid substitutions, deletions or additions, e.g., including but not limited to amino acid substitutions selected from alternate residues "recruited" from the corresponding position in any other AAV capsid aligned with the AAV9 capsid; e.g., such as described in U.S. Pat. Nos. 9,102,949, 8,927,514, US2015/349911; and WO 2016/049230A1. However, in other embodiments, other variants of AAV9, or AAV9 capsids having at least about 95% identity to the above-referenced sequences may be selected. See, e.g., US Published Patent Application No. 2015/0079038. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

The term "AAV9 intermediate" or "AAV9 vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

The term "about" encompasses a variation within and including ±10%, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

5.1. AAV.hIDUA Constructs and Formulations 5.1.1. Expression Cassettes

In certain embodiments, an AAV vector that comprises an expression cassette containing a hIDUA gene characterized by having the nucleotide sequence of SEQ ID NO: 1 is provided. This sequence, developed by the inventors, has an identity of about 83% with the published gene coding sequence of Genbank NP000194.2 encoding SEQ ID NO: 2. In another embodiment, the expression cassette contains a hIDUA gene characterized by having the nucleotide sequence at least about 80% identical to SEQ ID NO: 1 and encodes a functional human alpha-L-iduronidase. In another embodiment, the sequence is at least about 85% identity to SEQ ID NO: 1 or at least about 90% identical to SEQ ID NO:1 and encodes a functional human alpha-L-iduronidase. In one embodiment, the sequence is at least about 95% identical to SEQ ID NO:1, at least about 97% identical to SEQ ID NO:1, or at least about 99% identical to SEQ ID NO: 1 and encodes a functional human alpha-L-iduronidase. In one embodiment, this encompasses full-length hIDUA gene, including the leader peptide sequences of the human alpha-L-iduronidase (i.e., encoding about amino acid 26, or about amino acid 27, to about amino acid 653 of SEQ ID NO:2), corresponding to about 1 to about 78 of SEQ ID NO:1. In another embodiment, the hIDUA gene encodes a functional synthetic human alpha-L-iduronidase enzyme which is synthetic peptide comprising a heterologous leader sequence fused to the secreted portion of a functional alpha-L-iduronidase enzyme, i.e., about amino acids 27 to about 653 of SEQ ID NO: 2 or one of the functional variants thereof which are identified herein. Still further expression cassettes include those identified in SEQ ID NO: 5 and SEQ ID NO: 6. In each, the expression cassettes are flanked by AAV2 5' and 3' ITRs. Further, each contains a promoter, enhancer, hIDUA gene, and a polyA.

In another embodiment, a functional human alpha-L-iduronidase may include a synthetic amino acid sequence in which all or a portion of the first 26 amino acids of SEQ ID NO:2, which correspond to the leader (signal) peptide, are replaced with a heterologous leader peptide. This leader peptide, e.g., such as the leader peptides from interleukin-2 (IL-2) or oncostatin, can improve transport of the enzyme out of the cell through its secretory pathway into the circulation. Suitable leader peptides are preferably, although not necessarily of human original. Suitable leader peptides may be chosen from proline.bic.nus.edu.sg/spdb/zhang270.htm, which is incorporated by reference herein, or may be determined using a variety of computational programs for determining the leader (signal) peptide in a selected protein. Although not limited, such sequences may be from about 15 to about 50 amino acids in length, or about 19 to about 28 amino acids in length, or may be larger or smaller as required. In addition, at least one in vitro assay has been described as being useful to assess the enzymatic activity of an IDUA enzyme [see, e.g., Kakkis et al, Mol Genet Metabol, 2001 March; 72(3): 199-208].

Identity or similarity with respect to a sequence is defined herein as the percentage of amino acid residues in the candidate sequence that are identical (i.e., same residue) or similar (i.e., amino acid residue from the same group based on common side-chain properties, see below) with the peptide and polypeptide regions provided herein, after aligning the sequences and introducing gaps, if necessary, to achieve the maximum percent sequence identity. Percent (%) identity is a measure of the relationship between two polynucleotides or two polypeptides, as determined by comparing their nucleotide or amino acid sequences, respectively. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology. There are a number of algorithms, and computer programs based thereon, which are available to be used the literature and/or publicly or commercially available for performing alignments and percent identity. The selection of the algorithm or program is not a limitation of the present invention.

Examples of suitable alignment programs including, e.g., the software CLUSTALW under Unix and then be imported into the Bioedit program (Hall, T. A. 1999, BioEdit: a user-friendly biological sequence alignment editor and analysis program for Windows 95/98/NT. Nucl. Acids. Symp. Ser. 41:95-98); the Wisconsin Sequence Analysis Package, version 9.1 (Devereux J. et al., Nucleic Acids Res., 12:387-395, 1984, available from Genetics Computer Group, Madison, Wis., USA). The programs BESTFIT and GAP, may be used to determine the % identity between two polynucleotides and the % identity between two polypeptide sequences.

Other programs for determining identity and/or similarity between sequences include, e.g., the BLAST family of programs available from the National Center for Biotechnology Information (NCB), Bethesda, Md., USA and accessible through the home page of the NCBI at www.ncbi.nlm.nih.gov), the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used; and FASTA (Pearson W. R. and Lipman D. J., Proc. Natl. Acad. Sci. USA, 85:2444-2448, 1988, available as part of the Wisconsin Sequence Analysis Package). SeqWeb Software (a web-based interface to the GCG Wisconsin Package: Gap program).

In some embodiments, the cassette is designed to be expressed from a recombinant adeno-associated virus, the vector genome also contains AAV inverted terminal repeats (ITRs). In one embodiment, the rAAV is pseudotyped, i.e., the AAV capsid is from a different source AAV than that the AAV which provides the ITRs. In one embodiment, the ITRs of AAV serotype 2 are used. However, ITRs from other suitable sources may be selected. Optionally, the AAV may be a self-complementary AAV.

The expression cassettes described herein utilized AAV 5' inverted terminal repeat (ITR) and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and/or 3' ITRs are used. Where a pseudotyped AAV is to be produced, the ITRs in the expression are selected from a source which differs from the AAV source of the capsid. For example, AAV2 ITRs may be selected for use with an AAV capsid having a particular efficiency for targeting CNS or tissues or cells within the CNS. In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. However, other sources of AAV ITRs may be utilized.

In one embodiment, the expression cassette is designed for expression and secretion in the central nervous system (CNS), including the cerebral spinal fluid and brain. In a particularly desired embodiment, the expression cassette is useful for expression in both the CNS and in the liver, thereby allowing treatment of both the systemic and CNS-related effects of MPSI, Hurler, Hurler-Scheie and Scheie syndromes. For example, the inventors have observed that certain constitutive promoters (e.g., CMV) do not drive expression at desired levels when delivered intrathecally, thereby providing suboptimal hIDUA expression levels. However, the chicken beta-actin promoter drives expression well both upon intrathecal delivery and systemic delivery. Thus, this is a particularly desirable promoter. Other promoters may be selected, but expression cassettes containing same may not have all of the advantages of those with a chicken beta-actin promoter. A variety of chicken beta-actin promoters have been described alone, or in combination with various enhancer elements (e.g., CB7 is a chicken beta-actin promoter with cytomegalovirus enhancer elements, a CAG promoter, which includes the promoter, the first exon and first intron of chicken beta actin, and the splice acceptor of the rabbit beta-globin gene), a CBh promoter [S J Gray et al, Hu Gene Ther, 2011 September; 22(9): 1143-1153].

Examples of promoters that are tissue-specific are well known for liver and other tissues (albumin, Miyatake et al., (1997) *J. Virol.*, 71:5124-32; hepatitis B virus core promoter, Sandig et al., (1996) *Gene Ther.*, 3:1002-9; alpha-fetoprotein (AFP), Arbuthnot et al., (1996) *Hum. Gene Ther.*, 7:1503-14), bone osteocalcin (Stein et al., (1997)*Mol. Biol. Rep.*, 24:185-96); bone sialoprotein (Chen et al., (1996) *J. Bone Miner. Res.*, 11:654-64), lymphocytes (CD2, Hansal et al., (1998) *J. Immunol*, 161:1063-8; immunoglobulin heavy chain; T cell receptor chain), neuronal such as neuron-specific enolase (NSE) promoter (Andersen et al., (1993) *Cell. Mol. Neurobiol.*, 13:503-15), neurofilament light-chain gene (Piccioli et al, (1991) *Proc. Natl. Acad. Sci. USA*, 88:5611-5), and the neuron-specific vgf gene (Piccioli et al., (1995) *Neuron*, 15:373-84), among others. Alternatively, a regulatable promoter may be selected. See, e.g., WO 2011/126808B2, incorporated by reference herein.

In one embodiment, the expression cassette comprises one or more expression enhancers. In one embodiment, the expression cassette contains two or more expression enhancers. These enhancers may be the same or may be different. For example, an enhancer may include an Alpha mic/bik enhancer or a CMV enhancer. This enhancer may be present in two copies which are located adjacent to one another. Alternatively, the dual copies of the enhancer may be separated by one or more sequences. In still another embodiment, the expression cassette further contains an intron, e.g., a chicken beta-actin intron, a human β-globulin intron, and/or a commercially available Promega® intron. Other suitable introns include those known in the art, e.g., such as are described in WO 2011/126808.

Further, an expression cassette of the invention is provided with a suitable polyadenylation signal. In one embodiment, the polyA sequence is a rabbit globulin poly A. See, e.g., WO 2014/151341. Alternatively, another polyA, e.g., a human growth hormone (hGH) polyadenylation sequence, an SV50 polyA, or a synthetic polyA. Still other conventional regulatory elements may be additional or optionally included in an expression cassette.

5.1.2. Production of rAAV.hIDUA Viral Particles

In certain embodiments, a recombinant adeno-associated virus (rAAV) particle is provided which has an AAV capsid and having packaged therein a AAV inverted terminal repeats, a human alpha-L-iduronidase (hIDUA) gene under the control of regulatory sequences which control expression thereof, wherein said hIDUA gene has a sequence shown in SEQ ID NO: 1 or a sequence at least about 95% identical thereto which encodes a functional human alpha-L-iduronidase. See also, schematic in FIG. 1. In one embodiment, the hIDUA expression cassette is flanked by an AAV5' ITR and an AAV3' ITR. In another embodiment, the AAV may be a single stranded AAV.

For intrathecal delivery, AAV9 is particularly desirable. The sequences of AAV9 and methods of generating vectors based on the AAV9 capsid are described in U.S. Pat. No. 7,906,111; US2015/0315612; WO 2012/112832; which are incorporated herein by reference. Optionally, an rAAV9.hIDUA vector as described herein may be co-administered with a vector designed to specifically target the liver. Any of a number of rAAV vectors with liver tropism can be used. Examples of AAV which may be selected as sources for capsids of rAAV include, e.g., rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689], and rh10 [WO 2003/042397], AAV3B;

AAVdj [US 2010/0047174]. One particularly desirable rAAV is AAV2/8.TBG.hIDUA.co.

In many instances, rAAV particles are referred to as DNase resistant. However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

Methods of preparing AAV-based vectors are known. See, e.g., US Published Patent Application No. 2007/0036760 (Feb. 15, 2007), which is incorporated by reference herein. The use of AAV capsids of AAV9 are particularly well suited for the compositions and methods described herein. Additionally, the sequences of AAV8 and methods of generating vectors based on the AAV8 capsid are described in U.S. Pat. No. 7,282,199 B2, U.S. Pat. Nos. 7,790,449, and 8,318,480, which are incorporated herein by reference. However, other AAV capsids may be selected or generated for use in the invention. The sequences of a number of such AAV are provided in the above-cited U.S. Pat. No. 7,282,199 B2, U.S. Pat. Nos. 7,790,449, 8,318,480, and 7,906,111, and/or are available from GenBank. The sequences of any of the AAV capsids can be readily generated synthetically or using a variety of molecular biology and genetic engineering techniques. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, oligonucleotides encoding peptides (e.g., CDRs) or the peptides themselves can generated synthetically, e.g., by the well-known solid phase peptide synthesis methods (Merrifield, (1962) *J. Am. Chem. Soc.*, 85:2149; Stewart and Young, Solid Phase Peptide Synthesis (Freeman, San Francisco, 1969) pp. 27-62). These and other suitable production methods are within the knowledge of those of skill in the art and are not a limitation of the present invention.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid; a functional rep gene; an expression cassette composed of, at a minimum, AAV inverted terminal repeats (ITRs) and a transgene; and sufficient helper functions to permit packaging of the expression cassette into the AAV capsid protein.

To calculate empty and full particle content, VP3 band volumes for a selected sample (e.g., in examples herein an iodixanol gradient-purified preparation where #of GC=#of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy* (1999) 6:1322-1330; Sommer et al., *Molec. Ther.* (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAV9 particles having packaged genomic sequences from genome-deficient AAV9 intermediates involves subjecting a suspension comprising recombinant AAV9 viral particles and AAV 9 capsid intermediates to fast performance liquid chromatography, wherein the AAV9 viral particles and AAV9 intermediates are bound to a strong anion exchange resin equilibrated at a pH of 10.2, and subjected to a salt gradient while monitoring eluate for ultraviolet absorbance at about 260 and about 280. Although less optimal for rAAV9, the pH may be in the range of about 10.0 to 10.4. In this method, the AAV9 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/9 serotype. Under these ionic conditions, a significant percentage of residual cellular DNA and proteins flow through the column, while AAV particles are efficiently captured.

The rAAV.hIDUA vector can be manufactured as shown in the flow diagram shown in FIG. 11, which is described in more detail in Section 5.4 and Example 5, infra.

5.1.3. Pharmaceutical Formulations of rAAV.hIDUA

The rAAV9.hIDUA formulation is a suspension containing an effective amount of AAV.hIDUA vector suspended in an aqueous solution containing saline, a surfactant, and a physiologically compatible salt or mixture of salts. Suitably, the formulation is adjusted to a physiologically acceptable pH, e.g., in the range of pH 6 to 8, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of 6.8 to about 7.2 may be desired. However, other pHs within the broadest ranges and these subranges may be selected for other route of delivery.

A suitable surfactant, or combination of surfactants, may be selected from among nonionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly (propylene oxide)) flanked by two hydrophilic chains of polyoxyethylene (poly (ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one embodiment, the formulation may contain, e.g., a concentration of at least about $1 \times 10^9$ GC/mL to about $3 \times 10^{13}$ GC/mL, as measured by oqPCR or digital droplet PCR (ddPCR) as described in, e.g., M. Lock et al, Hu Gene Therapy Methods, Hum Gene Ther Methods. 2014 April; 25(2):115-25. doi: 10.1089/hgtb.2013.131. Epub 2014 Feb. 14, which is incorporated herein by reference.

In one embodiment, a frozen composition which contains an rAAV in a buffer solution as described herein, in frozen form, is provided. Optionally, one or more surfactants (e.g., Pluronic F68), stabilizers or preservatives is present in this composition. Suitably, for use, a composition is thawed and titrated to the desired dose with a suitable diluent, e.g., sterile saline or a buffered saline.

In one example, the formulation may contain, e.g., buffered saline solution comprising one or more of sodium chloride, sodium bicarbonate, dextrose, magnesium sulfate (e.g., magnesium sulfate·$7H_2O$), magnesium chloride potassium chloride, calcium chloride (e.g., calcium chloride·$2H_2O$), sodium phosphate (e.g., dibasic sodium phosphate), and mixtures thereof, in water. The formulation may also contain, e.g., dextrose and/or a poloxamer, as described herein. Suitably, for intrathecal delivery, the osmolarity is within a range compatible with cerebrospinal fluid (e.g., about 275 to about 290); see, e.g., emedicine.medscape.com/article/2093316-overview. Optionally, for intrathecal delivery, a commercially available diluent may be used as a suspending agent, or in combination with another suspending agent and other optional excipients. See, e.g., Elliotts B® solution [Lukare Medical].

In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In certain embodiments, a kit is provided which includes a concentrated vector suspended in a formulation (optionally frozen), optional dilution buffer, and devices and other components required for intrathecal administration are provided. In another embodiment, the kit may additional or alternatively include components for intravenous delivery. In one embodiment, the kit provides sufficient buffer to allow for injection. Such buffer may allow for about a 1:1 to a 1:5 dilution of the concentrated vector, or more. In other embodiments, higher or lower amounts of buffer or sterile water are included to allow for dose titration and other adjustments by the treating clinician. In still other embodiments, one or more components of the device are included in the kit.

In certain embodiments, dilution may be performed in a clinical pharmacy in a laminar air flow cabinet using aseptic technique as follows. Withdraw a pre-defined volume of the suspension containing the AAV9.hIDUA (which may have been previously frozen) using a syringe and needle-less vial adapters, then cap the syringe with a sterile, stainless steel blunt needle covered with a plastic needle sheath. Withdraw a pre-defined volume of diluent using a syringe and needle-less vial adapters, then cap the syringe with a sterile, stainless steel blunt needle covered with a plastic needle sheath. Deliver the diluent, then the suspension containing the AAV9.hIDUA, into a third "dosing" syringe using aseptic technique to ensure sterility of the outside of the syringe is maintained. Cap the syringe using a tip cap and mix via inversion. Remove the cap and prime to the desired delivery volume, cap, label, and package in a sterile bag that can be transported to the operating room for use within 6 hours.

5.2. Gene Therapy Protocol

5.2.1 Target Patient Populations

Provided herein are methods for treating type I mucopolysaccharidosis comprising delivering a therapeutically effective amount of a modified hIDUA expression cassette as described herein is provided. In particular, provided herein are methods for preventing, treating, and/or ameliorating neurocognitive decline in a patient diagnosed with MPS I, comprising delivering a therapeutically effective amount of a rAAV.hIDUA described herein to a patient in need thereof. A "therapeutically effective amount" of the rAAV.hIDUA vector described herein may correct one or more of the symptoms identified in any one of the following paragraphs.

Patients who are candidates for treatment are pediatric and adult patients with MPSI and/or the symptoms associated with Hurler, Hurler-Scheie and Scheie. MPSI disorders are a spectrum of disease from early severe (Hurler) to later onset (Scheie) forms. Hurler syndrome is typically characterized by no (0%) IDUA enzyme activity and diagnosed early and is characterized by developmental delay, hepatosplenomegaly, skeletal involvement, corneal clouding, joint involvement, deafness, cardiac involvement, and death during the first decade of life. Hurler-Scheie patients have been observed to have some IDUA enzyme activity (greater than 0% but typically less than 2%) and by having variable intellectual effects, respiratory disease, obstructive airway disease, cardiovascular disease, joint stiffness/contractures, skeletal abnormalities, decreased visual acuity, and death in teens or twenties. Patients with Scheie syndrome typically have at least 2% of "normal" IDUA enzyme activity, and are diagnosed later; such patients typically have normal intelligence, but have hepatosplenomegaly, joint involvement, nerve entrapment, deafness, cardiac involvement, and a normal life span. See, also, Newborn Screening for Mucopolysaccharidosis Type 1 (MPS I): A Systematic Review of Evidence Report of Final Findings, Final Version 1.1, Prepared for: MATERNAL AND CHILD HEALTH BUREAU. www.hrsa.gov/advisorycommitrees/mchbadvisory/-heritabledisorders/nominatecondition/reviews/mps1finalreport.pdf.

The compositions of the present invention avoid complications of long-term enzyme replacement therapy (ERT) related to immune response to the recombinant enzyme which can range from mild to full-blown anaphylaxis as well as complications of life-long peripheral access such as local and systemic infections. In contrast to ERT, the composition of the invention does not require life-long, repeated weekly injections. Without wishing to be bound by theory, the therapeutic method described herein is believed to be useful for correcting at least the central nervous system phenotype associated with MPSI disorders by providing efficient, long-term gene transfer afforded by vectors with high transduction efficiency which provide continuous, elevated circulating IDUA levels, which provides therapeutic leverage outside the CNS compartment. In addition, provided herein are methods for providing active tolerance and preventing antibody formation against the enzyme by a variety of routes, including by direct systemic delivery of the enzyme in protein form or in the form of rAAV-hIDUA prior to AAV-mediated delivery into CNS.

In some embodiments, patients diagnosed with Hurler syndrome are treated in accordance with the methods described herein. In some embodiments, patients diagnosed with Hurler-Scheie syndrome are treated in accordance with the methods described herein. In some embodiments, patients diagnosed with Scheie syndrome are treated in accordance with the methods described herein. In some embodiments, pediatric subjects with MPS I who have neurocognitive deficit are treated in accordance with the methods described herein.

In certain embodiments, newborn babies (3 months old or younger) are treated in accordance with the methods described herein. In certain embodiments, babies that are 3 months old to 9 months old are treated in accordance with the methods described herein. In certain embodiments, children that are 9 months old to 36 months old are treated in accordance with the methods described herein. In certain embodiments, children that are 3 years old to 12 years old are treated in accordance with the methods described herein. In certain embodiments, children that are 12 years old to 18 years old are treated in accordance with the methods described herein. In certain embodiments, adults that are 18 years old or older are treated in accordance with the methods described herein.

In one embodiment, a patient may have Hurler syndrome and is a male or female of at least about 3 months to less than 12 months of age. In another embodiment, a patient may have an MPSI condition and be between about 49 months (over 4 years old) to about 72 months (6 years) of age. In another embodiment, a patient may be male or female Hurler-Scheie patient and be at least about 6 years to up to 18 years of age. In other embodiments, the subjects may be older or younger, and may be male or female.

Suitably, patients selected for treatment may include those having one or more of the following characteristics: a documented diagnosis of MPS I confirmed by the lacking or diminished IDUA enzyme activity as measured in plasma, fibroblasts, or leukocytes; documented evidence of early-stage neurocognitive deficit due to MPS I, defined as either of the following, if not explainable by any other neurological or psychiatric factors:—A score of 1 standard deviation below mean on IQ testing or in 1 domain of neuropsychological function (language, memory, attention or non-verbal ability), OR—Documented historical evidence of a decline of greater than 1 standard deviation on sequential testing. Alternatively, increased GAGS in urine or genetic tests may be used.

Prior to treatment, subjects, e.g., infants, preferably undergo genotyping to identify MPS I patients, i.e., patients that have mutations in the gene encoding hIDUA. In certain populations, the subject may be older, e.g., under 3 years to up to 72 months (6 years), or even older. Prior to treatment, the MPS I patient can be assessed for neutralizing antibodies (Nab) to the AAV serotype used to deliver the hIDUA gene. In certain embodiments, MPS I patients with neutralizing antibody titers to AAV that are less than or equal to 5 are treated in accordance with any one or more of the methods described herein.

Prior to treatment, the MPSI patient can be assessed for neutralizing antibodies (Nab) to the capsid of the AAV vector used to deliver the hIDUA gene. Such Nabs can interfere with transduction efficiency and reduce therapeutic efficacy. MPS I patients that have a baseline serum Nab titer ≤1:5 are good candidates for treatment with the rAAV.hIDUA gene therapy protocol. Treatment of MPS I patients with titers of serum Nab>1:5 may require a combination therapy, such as transient co-treatment with an immunosuppressant before and/or during treatment with rAAV.hIDUA vector delivery. Optionally, immunosuppressive co-therapy may be used as a precautionary measure without prior assessment of neutralizing antibodies to the AAV vector capsid and/or other components of the formulation. Prior immunosuppression therapy may be desirable to prevent potential adverse immune reaction to the hIDUA transgene product, especially in patients who have virtually no levels of IDUA activity, where the transgene product may be seen as "foreign." Results of non-clinical studies in mice, dogs and NHPs described infra are consistent with the development of an immune response to hIDUA and neuroinflammation. While a similar reaction may not occur in human subjects, as a precaution immunosuppression therapy is recommended for all recipients of rAAV-hIDUA.

Immunosuppressants for such co-therapy include, but are not limited to, a glucocorticoid, steroids, antimetabolites, T-cell inhibitors, a macrolide), and cytostatic agents including an alkylating agent, an anti-metabolite, a cytotoxic antibiotic, an antibody, or an agent active on immunophilin. The one or more macrolides selected are immunosuppressants. In certain embodiments the macrolide is a non-antibiotic immunosuppressant. These non-antibiotic immunosuppressants may have different mechanisms of action. In certain embodiments, calcineurin inhibitor (e.g., tacrolimus), an mTOR inhibitor (e.g., sirolimus, temsirolimus, everolimus, or another rapalog), or combinations thereof. Another suitable non-antibiotic immunosuppressant may be pimecrolimus.

The immune suppressant may include a nitrogen mustard, nitrosourea, platinum compound, methotrexate, azathioprine, mycophenolate mofetil, methotrexate, leflunomide (Arava), cyclophosphamide, chlorambucil (Leukeran), a chloroquine (e.g., hydroxychloroquine), quinine sulfate, mefloquine, a combination of atovaquone and proguanil, sulfasalazine, mercaptopurine, fluorouracil, dactinomycin, an anthracycline, mitomycin C, bleomycin, mithramycin, IL-2 receptor-(CD25-) or CD3-directed antibodies, anti-IL-2 antibodies, abatacept (Orencia), adalimumab (Humira), anakinra (Kineret), certolizumab (Cimzia), etanercept (Enbrel), golimumab (Simponi), infliximab (Remicade), rituximab (Rituxan), tocilizumab (Actemra) and tofacitinib (Xeljanz), cyclosporine, tacrolimus, mTOR inhibitors (such as sirolimus (i.e., rapamycin), temsirolimus, or a rapalog), IFN-β, IFN-γ, an opioid, or TNF-α (tumor necrosis factor-alpha) binding agent, and combinations of these drugs. In certain embodiments, the immunosuppressive therapy may be started 0, 1, 2, 7, or more days prior to the gene therapy administration. Such therapy may involve co-administration of two or more drugs, the on the same day. In one embodiment, the two or more drugs may be. e.g., one or more corticosteroids (e.g., a prednelisone or prednisone) and optionally, MMF, and/or a calcinuerin inhibitor (e.g., tacrolimus), and/or an mTOR inhibitor (temsirolimus or sirolimus (i.e., rapamycin)). In one embodiment, the two or more drugs are micophenolate mofetil (MMF) and/or sirolimus. In another embodiment, the two or more drugs may be, e.g., methylprednisolone, prednisone, tacrolimus, and/or sirolimus. In certain embodiments, the immunosuppressive regimen consists of corticosteroids, tacrolimus and sirolimus. In certain embodiments, the drugs are MMF and tacrolimus for 0 to 15 days pre-vector delivery and maintaining for about 8 weeks with MMF and/or throughout follow-up appointments with tacrolimus. One or more of these drugs may be continued after gene therapy administration, at the same dose or an adjusted dose. In certain embodiments, patients are dosed initially with an IV steroid (e.g., methylprednisolone) to load the dose, followed by with an oral steroid (e.g., prednisolone) that is gradually tapered down so that the patient is off steroids by week 12. The corticosteroid treatment is supplemented by tacrolimus (for 24 weeks) and/or sirolimus (for 12 weeks), and can be further supplemented with MMF. When using both tacrolimus and sirolimus, the dose of each should be a low dose adjusted to maintain a blood trough level of about 4 ng/mL to about 8 ng/ml, or a total of about 8 ng/mL to about 16 ng/mL. In certain embodiments, when only one of these agents is used, the total dose for tacrolimus and/or sirolimus may be in the range of about 16 ng/mL to about 24 ng/mL. If only one of the agents is used, the label dose (higher dose) should be employed; e.g., tacrolimus at 0.15-0.20 mg/kg/day given as two divided doses every 12 hours; and sirolimus at 1 mg/m$^2$/day; the loading dose should be 3 mg/m$^2$. If MMF is added to the regimen, the dose for tacrolimus and/or sirolimus can be maintained since the mechanisms of action differ. These and other therapies may be started at about day −14 to day −1 (e.g., day −2, day 0, etc), and continue to about to up to about 1 week (7 days), or up to about 60 days, or up to about 12 weeks, or up to about 16 weeks, or up to about 24 weeks, or up to about 48 weeks, or longer, as needed. In certain embodiments, a tacrolimus-free regimen is selected.

Nevertheless, in one embodiment, patients having one or more of the following characteristics may be excluded from treatment at the discretion of their caring physician:

Has a contraindication for an IC injection, including any of the following:
  Review of baseline MRI testing shows a contraindication for an IC injection.
  History of prior head/neck surgery, which resulted in a contraindication to IC injection.
  Has any contraindication to CT (or contrast) or to general anesthesia.
  Has any contraindication to MRI (or gadolinium).
  Has estimated glomerular filtration rate (eGFR)<30 mL/min/1.73 m$^2$
Has any neurocognitive deficit not attributable to MPS I or diagnosis of a neuropsychiatric condition.
Has any history of a hypersensitivity reaction to one or more of tacrolimus, sirolimus, prednisone, methylprednisolone, or prednisolone.
Has any condition that would not be appropriate for immunosuppressive therapy (e.g., absolute neutrophil count <1.3×10$^3$/μL, platelet count <100×10$^3$/μL, and hemoglobin <12 g/dL [male] or <10 g/dL [female]).
Has any contraindication to lumbar puncture.
Has undergone HSCT.
Has received laronidase via IT administration within 6 months prior to treatment.
Has received IT laronidase at any time and experienced a significant adverse event considered related to IT administration that would put the patient at undue risk.
Any history of lymphoma or history of another cancer, other than squamous cell or basal cell carcinoma of the skin, that has not been in full remission for at least 3 months before treatment.
Alanine aminotransferase (ALT) or aspartate aminotransferase (AST)>3×upper limit of normal (ULN) or total bilirubin >1.5×ULN, unless the patient has a previously known history of Gilbert's syndrome and a fractionated bilirubin that shows conjugated bilirubin <35% of total bilirubin.
History of human immunodeficiency virus (HIV)-positive test, history of active or recurrent hepatitis B or hepatitis C, or positive screening tests for hepatitis B, hepatitis C, or HIV.
Is pregnant, <6 weeks post-partum, breastfeeding, or planning to become pregnant (self or partner)

History of alcohol or substance abuse within 1 year before treatment.

Has a serious or unstable medical or psychological condition that, would compromise the patient's safety.

Uncontrolled seizures.

In other embodiments, a caring physician may determine that the presence of one or more of these physical characteristics (medical history) should not preclude treatment as provided herein.

Considering that HSCT is the standard of care in children with MPS I in the US, the subject may be an adult ≥18 years of age. Enrollment of children ≥6 years old will only start if no safety concerns are identified at 8 weeks post-gene therapy in this subject.

In other countries, e.g., Brazil, HSCT and/or ERT is limited and the unmet medical need in patients with Hurler syndrome is significant. Enrolling patients <3 years old is, therefore, justified as these patients have the greatest prospect for benefit from treatment with rAAV9.hIDUA. Eligible patients include those with the severe form of MPS I and are at risk for early-stage neurocognitive deficit. The pharmacodynamic effect of AAV9.hIDUA may be measured using biomarkers of disease and efficacy of AAV9.hIDUA in subjects with Hurler syndrome may be measured using cognitive function.

In such populations, a patient may meet the following criteria. In certain embodiments, subject must meet all of the following inclusion criteria:

1) A male or female <3 years of age.
2) The subject's legal guardian(s) is(are) willing and able to provide written, signed informed consent after the nature of the study has been explained, and prior to any study-related procedures.
3) Has a documented diagnosis of severe MPS I-Hurler:
4) presence of clinical signs and symptoms compatible with MPS I-Hurler, and/or
5) homozygosity or compound heterozygosity for mutations exclusively associated with the severe phenotype.
6) Has an intelligent quotient (IQ) score of ≥55
7) Has sufficient auditory and visual capacity, with or without aids, to complete the required protocol testing and willing to be compliant with wearing the aid, if applicable, on testing days.

In certain embodiments, treatment of a subject who meets any of the following exclusion criteria is ineligible for treatment.

8) Has a contraindication for an IC injection, including any of the following:
   a) Review of baseline magnetic resonance imaging (MRI) testing by an adjudication panel of neuroradiologists/neurosurgeons shows a contraindication for an IC injection.
   b) History of prior head/neck surgery, which resulted in a contraindication to IC injection, based on review of available information by an adjudication panel of neuroradiologists/neurosurgeons.
   c) Has any contraindication to computed tomography (CT) (or contrast) or to general anesthesia.
   d) Has any contraindication to MRI (or gadolinium).
   e) Has estimated glomerular filtration rate (eGFR)<30 mL/min/1.73 m$^2$
9) Has any neurocognitive deficit not attributable to MPS I or has a diagnosis of a neuropsychiatric condition that may, in the opinion of the PI, confound interpretation of study results.
10) Has any contraindication to lumbar puncture.
11) Has undergone hematopoietic stem cell transplantation (HSCT)
12) Has had prior treatment with an AAV-based gene therapy product
13) Has received intrathecal (IT) laronidase at any time and experienced a significant AE considered related to IT administration that, in the opinion of the PI, would put the subject at undue risk.
14) Has any history of lymphoma or history of another cancer other than squamous cell or basal cell carcinoma of the skin that has not been in full remission for at least 3 months before screening.
15) Uncontrolled hypertension (systolic blood pressure [BP]>180 mmHg, diastolic BP>100 mmHg) despite maximal medical treatment.
16) Has a platelet count <100,000 per microliter (µL)
17) Has alanine aminotransferase (ALT) or aspartate aminotransferase (AST)>3× upper limit of normal (ULN) or total bilirubin >1.5×ULN at screening, unless the subject has a previously known history of Gilbert's syndrome.
18) Has a history of human immunodeficiency virus (HIV) or hepatitis B or hepatitis C virus infection, or positive screening tests for hepatitis B surface antigen or hepatitis B core antibody, or hepatitis C or HIV antibodies.
19) Received any investigational product within 30 days or 5 half-lives before signing of the Informed Consent Form (ICF), whichever is longer
20) Is a first-degree family member of a clinical site employee or any other individual involved in the conduct of the study, or is a clinical site employee, or any other individual involved in the conduct of the study.
21) Has a clinically significant ECG abnormality that, in the opinion of the PI, would compromise the subject's safety.
22) Has a serious or unstable medical or psychological condition that, in the opinion of the PI, would compromise the subject's safety or successful participation in the study or interpretation of study results.
23) Has a (cerebral) ventricular shunt that in the opinion of the site neuroradiologist/neurosurgeon and in discussion with the Medical Monitor, may impact the administration and proper dosing of the subject.

In certain embodiments, subjects may be precluded from treatment (excluded) based on the following criteria related to immunosuppressive therapy:

21) A history of a hypersensitivity reaction to tacrolimus, sirolimus, or prednisone;
22) A history of a primary immunodeficiency (e.g., common variable immunodeficiency syndrome), splenectomy, or any underlying condition that predisposes the subject to infection.
23) Herpes zoster, cytomegalovirus, or Epstein Barr virus (EBV) infection that has not completely resolved at least 12 weeks prior to screening.
24) Any infection requiring hospitalization or treatment with parenteral anti-infectives not resolved at least 8 weeks prior to Visit 2.
25) Any active infection requiring oral anti-infectives (including antivirals) within 10 days prior to Visit 2.
26) History of active tuberculosis (TB) or a positive Quantiferon-TB Gold test during screening.
27) Any live vaccine within 8 weeks prior to signing the ICF.
28) Major surgery within 8 weeks before signing the ICF or major surgery planned during the study period.

29) Anticipate the need for adenoidectomy or tonsillectomy within 6 months of enrollment. If adenoidectomy or tonsillectomy is anticipated, it should be performed prior to screening.
30) Absolute neutrophil count <1.3×103/μL.
31) Any condition or laboratory abnormality that the clinician believes would not be appropriate for immunosuppressive therapy.

5.2.2. Dosages & Mode of Administration

Pharmaceutical compositions suitable for administration to patients comprise a suspension of rAAV.hIDUA vectors in a formulation buffer comprising a physiologically compatible aqueous buffer, a surfactant and optional excipients. In certain embodiments, a pharmaceutical composition described herein is administered intrathecally. In other embodiments, a pharmaceutical composition described herein is administered intracisternally. In other embodiments, a pharmaceutical composition described herein is administered intravenously. In certain embodiments, the pharmaceutical composition is delivered via a peripheral vein by infusion over 20 minutes (±5 minutes). However, this time may be adjusted as needed or desired. However, still other routes of administration may be selected. Alternatively or additionally, routes of administration may be combined, if desired.

While a single administration of the rAAV is anticipated to be effective, administration may be repeated (e.g., quarterly, bi-annually, annually, or as otherwise needed, particularly in treatment of newborns. Optionally, an initial dose of a therapeutically effective amount may be delivered over split infusion/injection sessions, taking into consideration the age and ability of the subject to tolerate infusions/injections. However, repeated weekly injections of a full therapeutic dose are not required, providing an advantage to the patient in terms of both comfort and therapeutic outcome.

In some embodiments, the rAAV suspension has an rAAV Genome Copy (GC) titer that is at least $1×10^9$ GC/mL. In certain embodiments, the rAAV Empty/Full particle ratio in the rAAV suspension is between 0.01 and 0.05 (95%-99% free of empty capsids). In some embodiments, an MPS I patient in need thereof is administered a dose of at least about $4×10^8$ GC/g brain mass to about $4×10^{11}$ GC/g brain mass of the rAAV suspension.

Therapeutically effective intrathecal/intracisternal doses of the rAAV.hIDUA for MPSI patients range from about $1×10^{11}$ to $7.0×10^{14}$ $^{GC}$ (flat doses)—the equivalent of $10^9$ to $5×10^{10}$ GC/g brain mass of the patient. Alternatively, the following therapeutically effective flat doses can be administered to patients of the indicated age group:

Newborns: about $1×10^{11}$ to about $3×10^{14}$ GC;
3-9 months: about $6×10^{12}$ to about $3×10^{14}$ GC;
≥4 to <9 months: about $1.2×10^{12}$ to about $6.0×10^{12}$;
≥9 to <18 months: about $2×10^{12}$ to about $1.0×10^{13}$;
≥18 months to <3 years: about $2.2×10^{12}$ to about $1.1×10^{13}$;
9 months-6 years: about $6×10^{12}$ to about $3×10^{14}$ GC;
Under 3 years old (newborns up to 3 years): about $1×10^{11}$ to about $1.2×10^{13}$ GC;
3-6 years: about $1.2×10^{13}$ to about $6×10^{14}$ GC;
6-12 years: about $1.2×10^{13}$ to about $6×10^{14}$ GC;
12+ years: about $1.4×10^{13}$ to about $7.0×10^{14}$ GC;
18+ years (adult): about $1.4×10^{13}$ to about $7.0×10^{14}$ GC.

In other embodiments, the following therapeutically effective flat doses are administered to an MPS patient of the age group:

Newborns: about $3.8×10^{12}$ to about $1.9×10^{14}$ GC;
3-9 months: about $6×10^{12}$ to about $3×10^{14}$ GC;
≥4 to <9 months: about $6.0×10^{12}$ to about $3.0×10^{13}$;
≥9 to <18 months: about $1.0×10^{13}$ to about $5.0×10^{13}$;
≥18 months to <3 years: about $1.1×10^{13}$ to about $5.5×10^{13}$;
9-36 months: about $10^{13}$ to about $5×10^{13}$ GC;
Under 3 years old (newborns up to 3 years): about $1×10^{11}$ to about $1.2×10^{13}$ GC;
6-12 years: about $1.2×10^{13}$ to about $6×10^{14}$ GC;
3-12 years: about $1.2×10^{13}$ to about $6×10^{14}$ GC;
12+ years: about $1.4×10^{13}$ to about $7.0×10^{14}$ GC;
18+ years (adult): about $1.4×10^{13}$ to about $7.0×10^{14}$ GC.

In certain embodiments, one or more of these ranges are used for patients of any age. In certain embodiments, a flat dose of $1.2×10^{12}$ total genome copies (GC) ($2.0×10^9$ GC/g brain mass) or $6×10^{12}$ total GC ($1×10^{10}$ GC/g brain mass) is administered to a patient that is greater than or equal to (≥) 4 month to less than (<) 9 months. In certain embodiments, a flat dose of $2×10^{12}$ total GC ($2.0×10^9$ GC/g brain mass) or $1×10^{13}$ total GC ($1×10^{10}$ GC/g brain mass) is administered to a patient that is greater than or equal to (≥) 9 month to less than (<) 18 months. In certain embodiments, a flat dose of $2.2×10^{12}$ total GC ($2.0×10^9$ GC/g brain mass) or $1.1×10^{13}$ total GC ($1×10^{10}$ GC/g brain mass) is administered to a patient that is greater than or equal to (≥) 18 month to less than (<) 3 years. In certain embodiments, a flat dose of $6.0×10^{12}$ ($1.0×10^{10}$ GC/g brain mass) or $3×10^{13}$ total genome copies (GC) ($5×10^{10}$ GC/g brain mass) is administered to a patient that is greater than or equal to (≥) 4 month to less than (<) 9 months. In certain embodiments, a flat dose of $1.0×10^{13}$ ($1.0×10^{10}$ GC/g brain mass) or $5.0×10^{13}$ total GC ($5×10^{10}$ GC/g brain mass) is administered to a patient that is greater than or equal to (≥) 9 month to less than (<) 18 months. In certain embodiments, a flat dose of $1.1×10^{13}$ ($1.0×10^{10}$ GC/g brain mass) or $5.5×10^{13}$ total GC ($5×10^{10}$ GC/g brain mass) is administered to a patient that is greater than or equal to (≥) 18 month to less than (<) 3 years. In certain embodiments, a flat dose of $2.6×10^{12}$ genome copies (GC) ($2.0×10^9$ GC/g brain mass) is administered to a patient that is 6 years old or older than 6 years old. In certain embodiments, a flat dose of $1.3×10^{13}$ (GC) ($1.0×10^{10}$ GC/g brain mass) is administered to a patient that is 6 years old or older than 6 years old. In some embodiments, the dose administered to a 12+ year old MPSI patient (including 18+ year old) is $1.4×10^{13}$ genome copies (GC) ($1.1×10^{10}$ GC/g brain mass). In some embodiments, the dose administered to a 12+ year old MPSI patient (including 18+ year old) is $7×10^{13}$ GC ($5.6×10^{10}$ GC/g brain mass). In still a further embodiment, the dose administered to an MPSI patient is at least about $4×10^8$ GC/g brain mass to about $4×10^{11}$ GC/g brain mass. In certain embodiments, the dose administered to MPS I newborns ranges from about $1.4×10^{11}$ to about $1.4×10^{14}$ GC; the dose administered to infants 3-9 months ranges from about $2.4×10^{11}$ to about $2.4×10^{14}$ GC; the dose administered to MPS I children 9-36 months ranges: about $4×10^{11}$ to about $4×10^{14}$ GC; the dose administered to MPS I children 3-12 years: ranges from about $4.8×10^{11}$ to about $4.8×10^{14}$ GC; the dose administered to children and adults 12+ years ranges from about $5.6×10^{11}$ to about $5.6×10^{14}$ GC.

Suitable volumes for delivery of these doses and concentrations may be determined by one of skill in the art. For example, volumes of about 1 μL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

In one embodiment for intrathecal delivery, the patients are adult subjects and the dose comprises about $1\times10^8$ GC to $5\times10^{14}$ GC. In another embodiment, the dose comprises about $3.8\times10^{12}$ to about $1.9\times10^{14}$ GC. In a further embodiment, the patients are infant subjects of at least about 3 months to up to 12 months of age, at least about 3 months to up to 24 months, or at least about 3 months to up to 36 months, at least about 3 months to up to 6 years, at least six months to up to 6 years, at least 12 months up to 6 years, having Hurler syndrome and the dose comprises at least the equivalent of $4\times10^8$ GC rAAV9.hIDUA/g brain mass to $3\times10^{12}$ GC rAAV9.hIDUA/g brain mass. In another example, the patients are children of up to 3 years having Hurler syndrome and the dose comprises the equivalent of at least $4\times10^8$ GC rAAV9.hIDUA/g brain mass to $5\times10^{10}$ GC rAAV9.hIDUA/g brain mass. In another example, the patients are children of at least about 6 years to up to 18 years of age having Hurler-Scheie syndrome and the dose comprises the equivalent of at least $4\times10^8$ GC rAAV9.hIDUA/g brain mass to $3\times10^{12}$ GC rAAV9.hIDUA/g brain mass.

5.2.3. Monitoring Efficacy

Efficacy of the therapy can be measured by assessing (a) the prevention of neurocognitive decline in patients with MPSI; and (b) reductions in biomarkers of disease, e.g., GAG levels and/or enzyme activity in the CSF, serum and/or urine, and/or liver and spleen volumes. Neurocognition can be determined by measuring intelligence quotient (IQ), e.g., as measured by Bayley's Infantile Development Scale for Hurler subjects or as measured by the Wechsler Abbreviated Scale of Intelligence (WASI) for Hurler-Scheie subjects. Other appropriate measures of neurocognitive development and function may be utilized, e.g., assessing developmental quotient (DQ) using Bayley Scales of Infant Development (BSID-III), assessing memory using the Hopkins Verbal Learning Test, and/or using Tests of Variables of Attention (TOVA). Auditory capacity changes measured by auditory brainstem response (ABR) testing. Other neuropsychological function, such as vineland adaptive behavior scales (e.g., Vineland II), visual processing, fine motor, communication, socialization, daily living skills, and emotional and behavioral health are monitored. Magnetic Resonance Imaging (MRI) of brain to acquire volumetric, diffusion tensor imaging (DTI), and resting state data, median nerve cross-sectional area by ultrasonography, improvement in spinal cord compression, safety, liver size and spleen size are also administered.

Optionally, other measures of efficacy may include evaluation of biomarkers (e.g., spermine and other polyamines as described herein) and clinical outcomes. Urine is evaluated for total GAG content, concentration of GAG relative to creatinine, as well as MPS I specific pGAGs. Serum and/or plasma is evaluated for IDUA activity, anti-IDUA antibodies, pGAG, and concentration of the heparin cofactor II-thrombin complex and markers of inflammation. CSF is evaluated for IDUA activity, anti-IDUA antibodies, hexosaminidase (hex) activity, and pGAG (such as heparan sulfate and dermatan sulfate). The presence of neutralizing antibodies to vector (e.g., AAV9) and binding antibodies to anti-IDUA antibodies may be assessed in CSF and serum. T-cell response to vector capsid (e.g., AAV9) or the hIDUA transgene product may be assessed by ELISPOT assay. Pharmacokinetics of IDUA expression in CSF, serum, and urine as well as vector concentration (PCR to AAV9 DNA) may also be monitored.

Combinations of gene therapy delivery of the rAAV.hIDUA to the CNS accompanied by systemic delivery of hIDUA are encompassed by the methods of the invention. Systemic delivery can be accomplished using ERT (e.g., using Aldurazyme®), or additional gene therapy using an rAAV.hIDUA with tropism for the liver (e.g., an rAAV.hIDUA bearing an AAV8 capsid).

Additional measures of clinical efficacy associated with systemic delivery may include, e.g., Orthopedic Measures, such as bone mineral density, bone mineral content, bone geometry and strength, Bone Density measured by dual energy x-ray absorptiometry (DXA); Height (Z-scores for standing height/lying-length-for-age); Markers of Bone Metabolism: Measurements of Serum osteocalcin (OCN) and bone-specific alkaline phosphatase (BSAP), carboxyterminal telopeptide of type I collagen (ICTP) and carboxy-terminal telopeptide a1 chain of type I collagen (CTX); Flexibility and Muscle Strength: Biodex and Physical Therapy evaluations, including 6 minute walk study (The Biodex III isokinetic strength testing system is used to assess strength at the knee and elbow for each participant); Active Joint Range of Motion (ROM); Child Health Assessment Questionnaire/Health Assessment Questionnaire (CHAQ/HAQ) Disability Index Score; Electromyographic (EMG) and/or Oxygen Utilization to Monitor an individual's cardiorespiratory fitness: peak oxygen uptake (VO2 peak) during exercise testing; Apnea/Hypopnea Index (AHI); Forced Vital Capacity (FVC); Left Ventricular Mass (LVM).

In certain embodiments, a method of diagnosing and/or treating MPSI in a patient, or monitoring treatment, is provided. The method involves obtaining a cerebrospinal fluid or plasma sample from a human patient suspected of having MPSI; detecting spermine concentration levels in the sample; diagnosing the patient with a mucopolysaccharidosis selected from MPS I in the patient having spermine concentrations in excess of 1 ng/mL; and delivering an effective amount of human alpha-L-iduronidase (hIDUA) to the diagnosed patient as provided herein, e.g., using a device as described herein.

In another aspect, the method involves monitoring and adjusting MPSI therapy.

Such method involves obtaining a cerebrospinal fluid or plasma sample from a human patient undergoing therapy for MPSI; detecting spermine concentration levels in the sample by performing a mass spectral analysis; adjusting dosing levels of the MPSI therapeutic. For example, "normal" human spermine concentrations are about 1 ng/mL or less in cerebrospinal fluid. However, patients having untreated MPSI may have spermine concentration levels of greater than 2 ng/mL and up to about 100 ng/mL. If a patient has levels approaching normal levels, dosing of any companion ERT may be lowered. Conversely, if a patient has higher than desired spermine levels, higher doses, or an additional therapy, e.g., ERT may be provided to the patient.

Spermine concentration may be determined using a suitable assay. For example the assay described in J Sanchez-Lopez, et al, "Underivatives polyamine analysis is plant samples by ion pair liquid chromatography coupled with electrospray tandem mass spectrometry," Plant Physiology and Biochemistry, 47 (2009): 592-598, avail online 28 Feb. 2009; M R Hakkinen et al, "Analysis of underivatized polyamines by reversed phase liquid chromatography with electrospray tandem mass spectrometry", J Pharm Biomec Analysis, 44 (2007): 625-634, quantitative isotope dilution liquid chromatography (LC)/mass spectrometry (MS) assay. Other suitable assays may be used.

In some embodiments, efficacy of a therapeutic described herein is determined by assessing neurocognition at week 52 post-dose in pediatric subjects with MPS I who have an early-stage neurocognitive deficit. In some embodiments, efficacy of a therapeutic described herein is determined by assessing the relationship of CSF glycosaminoglycans (GAG) to neurocognition in an MPS I patient. In some embodiments, efficacy of a therapeutic described herein is determined by evaluating the effect of the therapeutic on physical changes to the CNS in an MPS I patient as measured by magnetic resonance imaging (MRI), e.g., volumetric analysis of gray and white matter and CSF ventricles. In some embodiments, efficacy of a therapeutic described herein is determined by evaluating the pharmacodynamic effect of the therapeutic on biomarkers, (e.g., GAG, HS) in cerebrospinal fluid (CSF), serum, and urine of an MPS I patient. In some embodiments, efficacy of a therapeutic described herein is determined by evaluating the impact of the therapeutic on quality of life (QOL) of an MPS I patient. In some embodiments, efficacy of a therapeutic described herein is determined by evaluating the impact of the therapeutic on motor function of an MPS I patient. In some embodiments, efficacy of a therapeutic described herein is determined by evaluating the effect of the therapeutic on growth and on developmental milestones of an MPS I patient.

As expressed from the rAAV vector described herein, expression levels of at least about 2% as detected in the CSF, serum, or other tissue, may provide therapeutic effect. However, higher expression levels may be achieved. Such expression levels may be from 2% to about 100% of normal functional human IDUA levels. In certain embodiments, higher than normal expression levels may be detected in CSF, serum, or other tissue.

In certain embodiments, the methods of treating, preventing, and/or ameliorating MPS I and/or symptoms thereof described herein result in a significant increase in intelligence quotient (IQ) in treated patients, as assessed using Bayley's Infantile Development Scale for Hurler subjects. In certain embodiments, the methods of treating, preventing, and/or ameliorating MPS I and/or symptoms thereof described herein result in a significant increase in neurocognitive IQ in treated patients, as measured by Wechsler Abbreviated Scale of Intelligence (WASI) for Hurler-Scheie subjects. In certain embodiments, the methods of treating, preventing, and/or ameliorating MPS I and/or symptoms thereof described herein result in a significant increase in neurocognitive DQ in treated patients, as assessed using Bayley Scales of Infant Development.

In certain embodiments, the methods of treating, preventing, and/or ameliorating MPS I and/or symptoms thereof described herein result in a significant increase in functional human IDUA levels. In certain embodiments, the methods of treating, preventing, and/or ameliorating MPS I and/or symptoms thereof described herein result in a significant decrease in GAG levels, as measured in a sample of a patient's serum, urine and/or cerebrospinal fluid (CSF).

5.3. Combination Therapies

Combinations of gene therapy delivery of the rAAV.hIDUA to the CNS accompanied by systemic delivery of hIDUA are encompassed by the methods of the invention. Systemic delivery can be accomplished using ERT (e.g., using Aldurazyme®), or additional gene therapy using an rAAV.hIDUA with tropism for the liver (e.g., an rAAV.hIDUA bearing an AAV8 capsid).

In certain embodiments, an intrathecal administration of rAAV9.hIDUA is be co-administered with a second AAV.hIDUA injection, e.g., directed to the liver. In such an instance, the vectors may be same. For example, the vectors may have the same capsid and/or the same vector genomic sequences. Alternatively, the vector may be different. For example, each of the vector stocks may designed with different regulatory sequences (e.g., each with a different tissue-specific promoter), e.g., a liver-specific promoter and a CNS-specific promoter. Additionally, or alternatively, each of the vector stocks may have different capsids. For example, a vector stock to be directed to the liver may have a capsid selected from AAV8, AAVrh64R1, AAVrh64R2, rh8, rh10, AAV3B, or AAVdj, among others. In such a regimen, the doses of each vector stock may be adjusted so that the total vector delivered intrathecally is within the range of about $1\times10^8$ GC to $\times1\times10^{14}$ GC; in other embodiments, the combined vector delivered by both routes is in the range of $1\times10^{11}$ to $1\times10^{16}$. Alternatively, each vector may be delivered in an amount of about $10^8$ GC to about $10^{12}$ GC/vector. Such doses may be delivered substantially simultaneously, or at different times, e.g., from about 1 day to about 12 weeks apart, or about 3 days to about 30 days, or other suitable times.

In some embodiments, the patient is co-administered an AAV.hIDUA via liver-directed and intrathecal injections. In some embodiments, a method for treatment comprises: (a) dosing a patient having MPS I and/or the symptoms associated with Hurler, Hurler-Scheie and Scheie syndromes with a sufficient amount of hIDUA enzyme or liver directed rAAV-hIDUA to induce transgene-specific tolerance; and (b) administering an rAAV.hIDUA to the patient's CNS, which rAAV.hIDUA directs expression of therapeutic levels of hIDUA in the patient.

In a further embodiment, a method of treating a human patient having MPSI and/or the symptoms associated with Hurler, Hurler-Scheie and Scheie syndromes is provided which involves tolerizing a patient having MPSI and/or the symptoms associated with Hurler, Hurler-Scheie and Scheie syndromes with a sufficient amount of hIDUA enzyme or liver-directed rAAV-hIDUA to induce transgene-specific tolerance, followed by CNS-directed rAAV-mediated delivery of hIDUA to the patient. In certain embodiments, the patient is administered an rAAV.hIDUA via liver-directed injections e.g., when the patient is less than 4 weeks old (neonatal stage) or an infant in order to tolerize the patient to hIDUA, and the patient is subsequently administered rAAV.hIDUA via intrathecal injections when the patient is an infant, child, and/or adult to express therapeutic concentrations of hIDUA in the CNS.

In one example, the MPSI patient is tolerized by delivering hIDUA to the patient within about two weeks of birth, e.g., within about 0 to about 14 days, or about 1 day to 12 days, or about day 3 to about day 10, or about day 5 to about day 8, i.e., the patient is a newborn infant. In other embodiments, older infants may be selected. The tolerizing dose of hIDUA may be delivered via rAAV. However, in another embodiment, the dose is delivered by direct delivery of the enzyme (enzyme replacement therapy). Methods of producing recombinant hIDUA in Chinese hamster ovary (CHO) cells and soluble rhIDUA in tobacco cells [L H Fu, et al, Plant Science (Impact Factor: 3.61). December 2009; 177

(6):668-675] or plant seeds [X He et al, Plant Biotechnol J. 2013 December; 11(9): 1034-1043] have been described in the literature.

Additionally, a recombinant hIDUA is commercially produced as Aldurazyme® (laronidase); a fusion protein of an anti-human insulin receptor monoclonal antibody and alpha-L-iduronidase [AGT-181; ArmaGen, Inc] may be useful. Although currently less preferred, the enzyme may be delivered via "naked" DNA, RNA, or another suitable vector. In one embodiment, the enzyme is delivered to the patient intravenously and/or intrathecally. In another embodiment, another route of administration is used (e.g., intramuscular, subcutaneous, etc). In one embodiment, the MPSI patient selected for tolerizing is incapable of expressing any detectable amounts of hIDUA prior to initiation of the tolerizing dose. When recombinant human IDUA enzyme is delivered, intrathecal rhIDUA injections may consist of about 0.58 mg/kg body weight or about 0.25 mg to about 2 mg total rhIDUA per injection (e.g., intravenous or intrathecal). For example, 3 cc of enzyme (e.g., approximately 1.74 mg Aldurazyme® (laronidase)) diluted with 6 cc of Elliotts Be solution for a total injection of 9 cc. Alternatively, a higher or lower dose is selected. Similarly, when expressed from a vector, lower expressed protein levels may be delivered. In one embodiment, the amount of hIDUA delivered for tolerizing is lower than a therapeutically effective amount. However, other doses may be selected.

Typically, following administration of the tolerizing dose, the therapeutic dose is delivered to the subject, e.g., within about three days to about 6 months post-tolerizing dose, more preferably, about 7 days to about 1-month post-tolerizing dose. However, other time points within these ranges may be selected, as may longer or shorter waiting periods.

In certain embodiments, an immune co-therapy may be delivered in combination with a sole gene therapy vector or a combination of gene therapy vectors as described herein. As an alternative, immunosuppressive therapy may be given in addition to the vector—before, during and/or subsequent to vector administration. Immunosuppressive therapy can include prednisolone, mycophenolate mofetil (MMF) and tacrolimus or sirolimus as described supra. In another embodiment, immunosuppressive therapy may begin about two days before the vector dosing and may include a single intravenous dose of methylprednisolone about two days before the vector, an oral dose of prednisone, an oral dose of tacrolimus, and an oral dose of sirolimus. The prednisone is orally dosed daily from about two days prior to vector administration to about 16 weeks from treatment. The tacrolimus is orally dosed daily from about two days prior to vector administration to about 24 weeks from treatment. In certain embodiments, a tacrolimus-free regimen described infra may be preferred. The sirolimus may be orally dosed daily from about two days prior to vector administration to about 48 weeks from treatment.

In certain embodiments, a therapeutic regimen useful for treatment of an alpha-L-iduronidase deficiency in a human patient involves administering to the patient: (a) a recombinant AAV (rAAV) having an AAV9 capsid and a nucleic acid comprising a sequence encoding human α-L-iduronidase (hIDUA) under control of regulatory sequences which direct expression thereof in the patient, wherein the human hIDUA coding sequence has the nucleotide sequence of SEQ ID NO: 1 or a sequence at least about 80% identical to SEQ ID NO: 1 which encodes a functional hIDUA; (b) at least a first immunosuppressive agent selected from at least one of a glucocorticoid, a steroid, an antimetabolite, a T-cell inhibitor, a macrolide, or a cytostatic agent: and (c) at least a second immunosuppressive agent selected from at least one of a glucocorticoid, a steroid, an antimetabolite, a T-cell inhibitor, a macrolide, or a cytostatic agent, wherein administration of at least one immunosuppressive agent begins prior to or on the same day as delivery of the AAV vector; and wherein administration of at least one of the immunosuppressive agents continues for at least 8 weeks post-vector administration. The patients may be dosed initially with an intravenous steroid followed by an oral steroid. In certain embodiments, a combination of immunosuppressive agents includes one or more corticosteroids and optionally, mycophenolate mofetil (MMF), and/or a calcinuerin inhibitor, and/or an mTOR inhibitor. The one or more calcineurin inhibitor may be tacrolimus. The one or more mTOR inhibitor may be temsirolimus or sirolimus, or another rapalog (e.g., everolimus). In certain embodiments, the dosing the patients with steroids is discontinued 12-weeks post vector dosing. In certain embodiments, mycophenolate mofetil (MMF) and tacrolimus are delivered for 0 to 15 days pre-vector administration. In certain embodiments, the immunosuppressive agents are mycophenolate mofetil (MMF) and sirolimus.

In embodiments, wherein the immunosuppressive agents comprise both tacrolimus and sirolimus, a low dose of each may be used to maintain a blood trough level of about 4 ng/mL to about 8 ng/ml, or a total of about 8 ng/mL to about 16 ng/mL. In embodiments wherein the immunosuppressive agents comprise only one of tacrolimus or sirolimus, the total dose is in the range of about 16 ng/mL to about 24 ng/mL. In certain embodiments wherein only one of tacrolimus or sirolimus is used, the initial loading dose may be about 3 mg/m$^2$.

In certain embodiments, the immunosuppressive therapy is started at about day −14 to day −1 prior to vector administration.

In certain embodiments, the encoded hIDUA has the sequence selected from: (a) about amino acid 1 to about 653 of SEQ ID NO: 2 (Genbank NP_000193); or (b) a synthetic human enzyme comprising a heterologous leader sequence fused to about acids 27 to about 653 of SEQ ID NO: 2.

In certain embodiments, the nucleic acid sequence packaged within the AAV capsid further comprises a 5' inverted terminal repeat (ITR) sequence, a chicken beta actin intron, a CB7 promoter, a polyA signal, and/or a 3' ITR sequence.

In certain embodiments, the rAAV is in a suspension having a pH of 6 to 9.

In certain embodiments, the rAAV is delivered via intrathecal injection.

In certain embodiments, the regimen further comprises co-administering an rAAV comprising the hIDUA gene intravenously.

In certain embodiments, efficacy of therapy includes measuring auditory capacity changes, optionally by auditory brain stem testing.

In certain embodiments, a composition is provided which comprises a recombinant AAV vector comprising a heterologous nucleic acid encoding human α-L-iduronidase (hIDUA), wherein the human hIDUA coding sequence has the nucleotide sequence of SEQ ID NO: 1 or a sequence at least about 80% identical to SEQ ID NO: 1 which encodes a functional hIDUA for use as in a therapeutic regimen which further comprises: (b) at least a first immunosuppressive agent selected from at least one of: and (c) at least a second immunosuppressive agent selected from at least one of a glucocorticoid, a steroid, an anti-metabolites, a T-cell inhibitor, a macrolide, or a cytostatic agent, wherein dosing of the immunosuppressive agents begins prior to or on the same day as delivery of the AAV vector; and wherein dosing with at least one of the immunosuppressive agents continues for at least 8 weeks post-vector administration. In certain embodiments, the macrolide is one or more anti-calcineurin inhibitor, one or more mTOR inhibitor, or combinations thereof.

In certain embodiments, one or more compositions are provided which contain at least one immunosuppressive agent for use in a combination therapy with a recombinant AAV vector comprising a heterologous nucleic acid encoding human α-L-iduronidase (hIDUA), wherein the human hIDUA coding sequence has the nucleotide sequence of SEQ ID NO: 1 or a sequence at least about 80% identical to SEQ ID NO: 1 which encodes a functional hIDUA, wherein the immunosuppressive agents comprise: (a) a composition comprising at least a first immunosuppressive agent selected from at least one of a glucocorticoid, a steroid, an antimetabolite, a T-cell inhibitor, a macrolide, or a cytostatic agent; and (b) a composition comprising at least a second immunosuppressive agent selected from at least one of a glucocorticoid, a steroid, an antimetabolite, a T-cell inhibitor, a macrolide, or a cytostatic agent, wherein dosing of the immunosuppressive agents begins prior to or on the same day as delivery of the AAV vector; and wherein dosing of at least one of the immunosuppressive agents continues for at least 8 weeks post-vector administration. In certain embodiments, the macrolide is one or more anti-calcineurin inhibitor, one or more mTOR inhibitor, or combinations thereof 5.4. Manufacture The invention provides for the manufacture of the rAAV.hIDUA pharmaceutical compositions described herein (Example 5, infra). An illustrative manufacturing process is provided in FIG. 11. The rAAV.hIDUA vector can be manufactured as shown in the flow diagram shown in FIG. 11. Briefly, cells are manufactured in a suitable cell culture (e.g., HEK 293) cells. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed by anion exchange resin chromatography are used to purify the vector drug product and to remove empty capsids. These methods are described in more detail in International Patent Application No. PCT/US2016/065970, filed Dec. 9, 2016 and its priority documents, U.S. Patent Application Nos. 62/322,071, filed Apr. 13, 2016 and 62/226,357, filed Dec. 11, 2015 and entitled "Scalable Purification Method for AAV9", which is incorporated by reference herein. Purification methods for AAV8, International Patent Application No. PCT/US2016/065976, filed Dec. 9, 2016 and is priority documents US Patent Application Nos. 62/322,098, filed Apr. 13, 2016 and 62/266,341, filed Dec. 11, 2015, and rh10, International Patent Application No. PCT/US16/66013, filed Dec. 9, 2016 and its priority documents, U.S. Patent Application No. 62/322,055, filed Apr. 13, 2016 and 62/266,347, entitled "Scalable Purification Method for AAVrh10", also filed Dec. 11, 2015, and for AAV1, International Patent Application No. PCT/US2016/065974, filed Dec. 9, 2016 and its priority documents US Patent Application Nos. 62/322,083, filed Apr. 13, 2016 and 62/26,351, for "Scalable Purification Method for AAV1", filed Dec. 11, 2015, are all incorporated by reference herein.

5.5 Apparatus and Method for Delivery of a Pharmaceutical Composition into Cerebrospinal Fluid In one aspect, the vectors provided herein may be administered intrathecally via the method and/or the device provided in this section and described further in the Examples and FIG. 12. Alternatively, other devices and methods may be selected. The method comprises the steps of advancing a spinal needle into the cisterna magna of a patient, connecting a length of flexible tubing to a proximal hub of the spinal needle and an output port of a valve to a proximal end of the flexible tubing, and after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve. After connecting the first and second vessels to the valve, a path for fluid flow is opened between the vector inlet port and the outlet port of the valve and the pharmaceutical composition is injected into the patient through the spinal needle, and after injecting the pharmaceutical composition, a path for fluid flow is opened through the flush inlet port and the outlet port of the valve and the isotonic solution is injected into the spinal needle to flush the pharmaceutical composition into the patient.

In another aspect, a device for intracisternal delivery of a pharmaceutical composition is provided. The device includes a first vessel containing an amount of a pharmaceutical composition, a second vessel containing an isotonic solution, and a spinal needle through which the pharmaceutical composition may be ejected from the device directly into cerebrospinal fluid within the cisterna magna of a patient. The device further includes a valve having a first inlet port interconnected to the first vessel, a second inlet port interconnected to the second vessel, an outlet port interconnected to the spinal needle, and a luer lock for controlling flow of the pharmaceutical composition and isotonic solution through the spinal needle.

As used herein, the term Computed Tomography (CT) refers to radiography in which a three-dimensional image of a body structure is constructed by computer from a series of plane cross-sectional images made along an axis.

The apparatus or medical device 10 as shown in FIG. 12 includes one or more vessels, 12 and 14, interconnected via a valve 16. The vessels, 12 and 14, provide a fresh source of a pharmaceutical composition, drug, vector, or like substance and a fresh source of an isotonic solution such as saline, respectively. The vessels, 12 and 14, may be any form of medical device that enables injection of fluids into a patient.

By way of example, each vessel, 12 and 14, may be provided in the form of a syringe, cannula, or the like. For instance, in the illustrated embodiment, the vessel 12 is provided as a separate syringe containing an amount of a pharmaceutical composition and is referred to herein as a "vector syringe". Merely for purposes of example, the vessel 12 may contain about 10 cc of a pharmaceutical composition or the like.

Likewise, the vessel 14 may be provided in the form of a separate syringe, cannula, or the like that contains an amount of saline solution and may be referred to as a "flush syringe". Merely for purposes of example, the vessel 14 may contain about 10 cc of a saline solution.

As an alternative, the vessels 12 and 14 may be provided in forms other than syringes and may be integrated into a single device, such as an integrated medical injection device have a pair of separate chambers, one for the pharmaceutical composition and one for saline solution. Also, the size of the chambers or vessels may be provided as needed to contain a desired amount of fluid.

In the illustrated embodiment, the valve 16 is provided as a 4-way stopcock having a swivel male luer lock 18. The valve 16 interconnects the vessels 12 and 14 (i.e., the vector syringe and flush syringe in the illustrated embodiment), and the swivel male luer lock enables a path through the valve 16 to be closed or opened to each of the vessels 12 and 14. In this way, the path through the valve 16 may be closed to both the vector syringe and flush syringe or may be open to a selected one of the vector syringe and flush syringe. As an alternative to a 4-way stopcock, the valve may be a 3-way stopcock or fluid control device.

In the illustrated embodiment, the valve 16 is connected to one end of a length of extension tubing 20 or the like conduit for fluid. The tubing 20 may be selected based on a desired length or internal volume. Merely by way of example, the tubing may be about 6 to 7 inches in length.

In the illustrated embodiment, an opposite end 22 of the tubing 12 is connected to a T-connector extension set 24 which, in turn, is connected to a spinal needle 26. By way of example, the needle 26 may be a five inch, 22 or 25-gauge spinal needle. In addition, as an option, the spinal needle 26 may be connected to an introducer needle 28, such as a three and a half inch, 18-gauge introducer needle.

In use, the spinal needle 26 and/or optional introducer needle 28 may be advanced into a patient towards the cisterna magna. After needle advancement, Computed Tomography (CT) images may be obtained that permit visualization of the needle 26 and/or 28 and relevant soft tissues (e.g., paraspinal muscles, bone, brainstem, and spinal cord). Correct needle placement is confirmed by observation of Cerebrospinal Fluid (CSF) in the needle hub and visualization of a needle tip within the cisterna magna. Thereafter, the relatively short extension tubing 20 may be attached to the inserted spinal needle 26, and the 4-way stopcock 16 may then be attached to the opposite end of the tubing 20.

The above assembly is permitted to become "self-primed" with the patient's CSF. Thereafter, the prefilled normal saline flush syringe 14 is attached to a flush inlet port of the 4-way stopcock 16 and then the vector syringe 12 containing a pharmaceutical composition is attached to a vector inlet port of the 4-way stopcock 16. Thereafter, the output port of the stopcock 16 is opened to the vector syringe 12, and the contents of the vector syringe may be slowly injected through the valve 16 and assembled apparatus and into the patient over a period of time. Merely for purposes of example, this period of time may be approximately 1-2 minutes and/or any other time of desire.

After the contents of the vector syringe 12 are injected, the swivel lock 18 on the stopcock 16 is turned to a second position so that the stopcock 16 and needle assembly can be flushed with a desired amount of normal saline using the attached prefilled flush syringe 14. Merely by way of example, 1 to 2 cc of normal saline may be used; although greater or lesser amounts may be used as needed. The normal saline ensures that all or most of the pharmaceutical composition is forced to be injected through the assembled device and into the patient and so that little or none of the pharmaceutical composition remains in the assembled device.

After the assembled device has been flushed with the saline, the assembled device in its entirely, including the needle(s), extension tubing, stopcock, and syringes are slowly removed from the subject and placed onto a surgical tray for discarding into a biohazard waste receptacle or hard container (for the needle(s)).

A screening process may be undertaken by a principal investigator which may ultimately lead to an intracisternal (IC) procedure. The principal investigator may describe the process, procedure, the administration procedure itself, and all potential safety risks in order for the subject (or designated caregiver) to be fully informed. Medical history, concomitant medications, physical exam, vital signs, electrocardiogram (ECG), and laboratory testing results are obtained or performed and provided to a neuroradiologist, neurosurgeon, and anesthesiologist for use in screening assessment of subject eligibility for the IC procedure.

To allow adequate time to review eligibility, the following procedures may be performed at any time between the first screening visit and up to one week prior to a study visit. For example, on "Day 0", Head/Neck Magnetic Resonance Imaging (MRI) with and without gadolinium (i.e., eGFR>30 mL/min/1.73 m2) may be obtained. In addition to the Head/Neck MRI, the investigator may determine the need for any further evaluation of the neck via flexion/extension studies. The MRI protocol may include T1, T2, DTI, FLAIR, and CINE protocol images.

In addition, Head/Neck MRA/MRV may be obtained as per institutional protocol (i.e., subjects with a history of intra/transdural operations may be excluded or may need further testing (e.g., radionucleotide cisternography)) that allows for adequate evaluation of CSF flow and identification of possible blockage or lack of communication between CSF spaces.

The neuroradiologist, neurosurgeon, and anesthesiologist ultimately discuss and determine the eligibility of each subject for the IC procedures based on all available information (scans, medical history, physical exam, labs, etc.). An Anesthesia pre-op evaluation may also be obtained from "Day −28" to "Day 1" that provides a detailed assessment of airway, neck (shortened/thickened) and head range-of-motion (degree of neck flexion), keeping in mind the special physiologic needs of a MPS subject.

Prior to an IC procedure, the CT Suite will confirm the following equipment and medications are present:

Adult lumbar puncture (LP) kit (supplied per institution);

BD (Becton Dickinson) 22 or 25 gauge×3-7" spinal needle (Quincke bevel);

Coaxial introducer needle, used at the discretion of the interventionalist (for introduction of spinal needle);

4 way small bore stopcock with swivel (Spin) male luer lock;

T-connector extension set (tubing) with female luer lock adapter, approximate length of 6.7 inches;

Omnipaque 180 (iohexol), for intrathecal administration;
Iodinated contrast for intravenous (IV) administration;
1% lidocaine solution for injection (if not supplied in adult LP kit);
Prefilled 10 cc normal saline (sterile) flush syringe;
Radiopaque marker(s);
Surgical prep equipment/shaving razor;
Pillows/supports to allow proper positioning of intubated subject;
Endotracheal intubation equipment, general anesthesia machine and mechanical ventilator;
Intraoperative neurophysiological monitoring (IONM) equipment (and required personnel); and
10 cc syringe containing vector; prepared and transported to CT/Operating Room (OR) suite in accordance with separate Pharmacy Manual.

Informed Consent for the procedure are confirmed and documented within the medical record and/or study file. Separate consent for the procedure from radiology and anesthesiology staff is obtained as per institutional requirements. Subject has intravenous access placed within the appropriate hospital care unit according to institutional guidelines (e.g., two IV access sites). Intravenous fluids are administered at the discretion of the anesthesiologist. At the discretion of the anesthesiologist and per institutional guidelines, subject may be induced and undergo endotracheal intubation with administration of general anesthesia in an appropriate patient care unit, holding area or the surgical/CT procedure suite.

A lumbar puncture is performed, first to remove 5 cc of cerebrospinal fluid (CSF) and subsequently to inject contrast (Omnipaque 180) intrathecally to aid visualization of the cisterna magna. Appropriate subject positioning maneuvers may be performed to facilitate diffusion of contrast into the cisterna magna.

Intraoperative neurophysiological monitoring (IONM) equipment is attached to the subject. Subject is placed onto the CT scanner table in the prone or lateral decubitus position. Adequate staff must be present to assure subject safety during transport and positioning. If deemed appropriate, subject may be positioned in a manner that provides neck flexion to the degree determined to be safe during pre-operative evaluation and with normal neurophysiologic monitor signals documented after positioning.

The following staff may be confirmed to be present and identified on-site: Interventionalist/neurosurgeon performing the procedure; Anesthesiologist and respiratory technician(s); Nurses and physician assistants; CT (or OR) technicians; Neurophysiology technician; and Site Coordinator. A "time-out" may be completed per Joint Commission/hospital protocol to verify correct subject, procedure, site, positioning, and presence of all necessary equipment in the room. The lead site investigator may then confirm with staff that he/she may proceed with prepping the subject.

The subject's skin under the skull base is shaved as appropriate. CT scout images are performed, followed by a pre-procedure planning CT with IV contrast, if deemed necessary by the interventionalist to localize the target location and to image vasculature. After the target site (cisterna magna) is identified and needle trajectory planned, the skin is prepped and draped using sterile technique as per institutional guidelines. A radiopaque marker is placed on the target skin location as indicated by the interventionalist. The skin under the marker is anesthetized via infiltration with 1% lidocaine. A 22 G or 25 G spinal needle is than advanced towards the cisterna magna, with the option to use a coaxial introducer needle.

After needle advancement, CT images are obtained using the thinnest CT slice thickness feasible using institutional equipment (ideally ≤2.5 mm). Serial CT images using the lowest radiation dose possible that allows for adequate visualization of the needle and relevant soft tissues (e.g., paraspinal muscles, bone, brainstem, and spinal cord) are obtained. Correct needle placement is confirmed by observation of CSF in the needle hub and visualization of needle tip within the cisterna magna.

The interventionalist confirms that the vector syringe is positioned close to, but outside of the sterile field. Prior to handling or administering the pharmaceutical composition in the vector syringe, gloves, mask, and eye protection are donned by staff assisting the procedure within the sterile field.

The extension tubing is attached to the inserted spinal needle, which is then attached to the 4-way stopcock. Once this apparatus is "self-primed" with the subject's CSF, the 10 cc prefilled normal saline flush syringe is attached to a flush inlet port of the 4-way stopcock. The vector syringe is then provided to the interventionalist and attached to a vector inlet port on the 4-way stop cock.

After the outlet port of the stopcock is opened to the vector syringe by placing the swivel lock of the stopcock in a first position, the contents of the vector syringe are injected slowly (over approximately 1-2 minutes), with care taken not to apply excessive force onto the plunger of the syringe during the injection. After the contents of the vector syringe are injected, the swivel lock of stopcock is turned to a second position so that the stopcock and needle assembly can be flushed with 1-2 cc of normal saline using the attached prefilled flush syringe.

When ready, the interventionist then alerts staff that he/she will remove the apparatus from the subject. In a single motion, the needle, extension tubing, stopcock, and syringes are slowly removed from the subject and placed onto a surgical tray for discarding into a biohazard waste receptacle or hard container (for the needle).

The needle insertion site is examined for signs of bleeding or CSF leakage and treated as indicated by the investigator. Site is dressed using gauze, surgical tape and/or Tegaderm dressing, as indicated. Subject is then removed from the CT scanner and placed supine onto a stretcher. Adequate staff is present to assure subject safety during transport and positioning.

Anesthesia is discontinued and subject cared for following institutional guidelines for post-anesthesia care. Neurophysiologic monitors are removed from the subject. The head of the stretcher on which the subject lies should be slightly raised (~30 degrees) during recovery. Subject is transported to a suitable post-anesthesia care unit as per institutional guidelines. After subject has adequately recovered consciousness and is in stable condition, he/she will be admitted to the appropriate floor/unit for protocol mandated assessments. Neurological assessments will be followed as per the protocol and the Primary Investigator oversees subject care in collaboration with hospital and research staff.

In one embodiment, a method for delivery of a composition provided herein comprises the steps of: advancing a spinal needle into the cisterna magna of a patient; connecting a length of flexible tubing to a proximal hub of the spinal needle and an output port of a valve to a proximal end of the flexible tubing; after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve; after connecting said first and second vessels to the valve, opening a path for fluid flow between the vector inlet port and the outlet port of the valve and injecting the pharmaceutical composition into the patient through the spinal needle; and after injecting the pharmaceutical composition, opening a path for fluid flow through the flush inlet port and the outlet port of the valve and injecting the isotonic solution into the spinal needle to flush the pharmaceutical composition into the patient. In certain embodiment, the method further comprises confirming proper placement of a distal tip of the spinal needle within the cisterna magna before connecting the tubing and valve to the hub of the spinal needle. In certain embodiments, the confirming step includes visualizing the distal tip of the spinal needle within the cisterna magna with Computed Tomography (CT) imaging. In certain embodiments, the confirming step includes observing the presence of the patient's cerebrospinal fluid in the hub of the spinal needle.

In the above-described method, the valve may be a stopcock with a swivel luer lock adapted to swivel to a first position permitting flow from the vector inlet port to the outlet port while simultaneously blocking flow through the flush inlet port and to a second position permitting flow from the flush inlet port to the outlet port while simultaneously blocking flow through the vector inlet port, and wherein the swivel luer lock is positioned into said first position when said pharmaceutical composition is injected the patient and is positioned into said second position when said pharmaceutical composition is being flushed into said patient by the isotonic solution. In certain embodiments, after injecting the isotonic solution into the spinal needle to flush the pharmaceutical composition into the patient, the spinal needle is withdrawn from the patient with the tubing, valve, and first and second vessels connected thereto as an assembly. In certain embodiments, the valve is a 4-way stopcock with a swivel male luer lock. In certain embodiments, the first and second vessels are separate syringes. In certain embodiments, a T-connector is located at the hub of the spinal needle and interconnects the tubing to the spinal needle. Optionally, the spinal needle includes an introducer needle at the distal end of the spinal needle. The spinal needle may be a five inch, 22 or 24-gauge spinal needle. In certain embodiments, the introducer needle is a 3.5 inch, 18-gauge introducer needle.

In certain aspects, the method utilizes a device which is composed of, at a minimum, a first vessel for containing an amount of a pharmaceutical composition; a second vessel for containing an isotonic solution; a spinal needle through which the pharmaceutical composition may be ejected from the device directly into cerebrospinal fluid within the cisterna magna of a patient; and a valve having a first inlet port interconnected to the first vessel, a second inlet port interconnected to the second vessel, an outlet port interconnected to the spinal needle, and a luer lock for controlling flow of the pharmaceutical composition and isotonic solution through the spinal needle. In certain embodiments, the valve is a stopcock with a swivel luer lock adapted to swivel to a first position permitting flow from the first inlet port to the outlet port while simultaneously blocking flow through the second inlet port and to a second position permitting flow from the second inlet port to the outlet port while simultaneously blocking flow through the first inlet port. Optionally, the valve is a 4-way stopcock with a swivel male luer lock. In certain embodiments, the first and second vessels are separate syringes. In certain embodiments, the spinal needle is interconnected to the valve via a length of flexible tubing.

A T-connector may interconnect the tubing to the spinal needle. In certain embodiments, the spinal needle is a five inch, 22 or 24-gauge spinal needle. In certain embodiments, the device further comprises an introducer needle connected to a distal end of the spinal needle. Optionally, the introducer needle is a 3.5 inch, 18-gauge introducer needle.

This method and this device may each optionally be used for intrathecal delivery of the compositions provided herein. Alternatively, other methods and devices may be used for such intrathecal delivery.

The following examples are illustrative only and are not a limitation on the invention described herein.

6. EXAMPLES

Example 1: Protocol for Treatment of Human Subjects

This Example relates to a gene therapy treatment for patients that have MPS I. In this example, the gene therapy vector, AAV9.CB7. hIDUA, a replication deficient adeno-associated viral vector 9 (AAV9) expressing a modified hIDUA gene encoding the wild-type hIDUA enzyme, is administered to the central nervous system (CNS) of the MPSI patients. Doses of the AAV vector are be injected directly into the CNS under general anesthesia. Efficacy of treatment is assessed using clinical measures of neurocognitive development and/or surrogate markers, including biomarkers, e.g., a decrease in pathogenic GAG and/or hexosaminidase concentration in the subject's CSF or serum, as described herein.

A. Gene Therapy Vector

An illustrative gene therapy vector, AAV9.CB.hIDUA, is described in Example 3. Expression from the transgene cassette is driven by a CB7 promoter, a hybrid between a CMV immediate early enhancer (C4) and the chicken beta actin promoter, while transcription from this promoter is enhanced by the presence of the chicken beta actin intron (CI). The polyA signal for the expression cassette is the RBG polyA. The vector is suspended in formulation buffer (Elliots B Solution, 0.001% Pluronic F68]. The manufacturing process is described in more detail in Example 5 below.

B. Dosing & Route of Administration

Patients that are ≥6 years old or older receive a single intrathecal/intracisternal dose of rAAV9.CB7.hIDUA of $2.6 \times 10^{12}$ GC ($2.0 \times 10^9$ GG/g brain mass) (low dose) or $1.3 \times 10^{13}$ GC ($1.0 \times 10^{10}$ GC/g brain mass (high dose)). For administration of vector, the subject is put under general anesthesia. A lumbar puncture is performed, first to remove 5 cc of CSF and subsequently to inject contrast IT to aid visualization of the cisterna magna. CT (with contrast) is utilized to guide needle insertion and administration of rAAV9.CB7.hIDUA into the suboccipital space.

In another embodiment, subjects who are less than three years of age (<3) with severe MPIS phenotype (Hurler syndrome) may be confirmed by a mutation(s) known to lead to Hurler syndrome may be treated with rAAV9.CB7.hIDUA in modified Elliotts Be Solution with 0.001% Pluronic® F68. In certain embodiments, the composition is administered as a single-dose via intracisternal administration at one of two dose levels: $1 \times 10^{10}$ GC/g brain mass and $5 \times 10^{10}$ GC/g brain mass. No subject will receive more than 1 dose of IP. Vector administration is as described above. The proposed starting clinical dose is $1 \times 10^{10}$ GC/g brain mass. The starting dose is 100-fold lower than the dose at which toxicity was observed in naïve (non-tolerized) dogs with MPS I ($1 \times 10^{11}$ GC/g brain mass) and similar to the lowest dose tested in NHP in the GLP toxicology study ($1.1 \times 10^{10}$ GC/g brain mass). In summary, the choice of $1 \times 10^{10}$ GC/g brain mass as the starting dose is justified for the following reasons: a) this is the lowest dose with a reasonable prospect of clinical benefit b) it maintains a reasonable safety margin to the dose where toxicity was observed in the dog model of MPS I c) although no NOAEL was identified in NHPs, in the absence of dose response related to the histopathological findings, lowering the dose is not expected to change the risk of this potential adverse finding. Importantly, none of the NHPs had any clinical manifestations associated with the histopathological findings. The higher dose of $5 \times 10^{10}$ GC/g brain mass is approximately 20-fold lower than the dose ($1 \times 10^{12}$ GC/g brain mass) at which toxicity was observed in MPS I dogs and approximately two fold lower than the highest dose ($1.1 \times 10^{11}$ GC/g brain mass) tested in NHPs in the GLP toxicology study described herein.

Total Dose Administered by Age

| Subject Age at Dosing | Assumed brain mass (g) | Dose 1 Total GC ($1.0 \times 10^{10}$ GC/g brain mass) | Dose 2 Total GC ($5 \times 10^{10}$ GC/g brain mass) |
|---|---|---|---|
| ≥ 4 to < 9 months | 600 | $6.0 \times 10^{12}$ | $3.0 \times 10^{13}$ |
| ≥ 9 to < 18 months | 1000 | $1.0 \times 10^{13}$ | $5.0 \times 10^{13}$ |
| ≥ 18 months to < 3 years | 1100 | $1.1 \times 10^{13}$ | $5.5 \times 10^{13}$ |

| Subject Age at Dosing | Assumed brain mass (g) | Dose 1 Total GC ($2.0 \times 10^{9}$ GC/g brain mass) | Dose 2 Total GC ($1 \times 10^{10}$ GC/g brain mass) |
|---|---|---|---|
| ≥ 4 to < 9 months | 600 | $1.2 \times 10^{12}$ | $3.0 \times 10^{13}$ |
| ≥ 9 to < 18 months | 1000 | $2 \times 10^{12}$ | $5.0 \times 10^{13}$ |
| ≥ 18 months to < 3 years | 1100 | $2.2 \times 10^{12}$ | $5.5 \times 10^{13}$ |

The AAV9.hIDUA is aseptically diluted using a diluent (similar in composition to the formulation buffer) to adjust the pH to near-physiological conditions as part of dose preparation. The total volume of product delivered for both the lower and higher doses will be 10 mL or less after appropriate dilutions are made prior to administration.

The following therapeutically effective flat doses are administered to patients of the indicated age group:
Newborns: about $1 \times 10^{11}$ to about $3 \times 10^{14}$ GC;
3-9 months: about $6 \times 10^{12}$ to about $3 \times 10^{14}$ GC;
9 months-6 years: about $6 \times 10^{12}$ to about $3 \times 10^{14}$ GC;
3-6 years: about $1.2 \times 10^{13}$ to about $6 \times 10^{14}$ GC;
6-12 years: about $1.2 \times 10^{13}$ to about $6 \times 10^{14}$ GC;
12+ years: about $1.4 \times 10^{13}$ to about $7.0 \times 10^{14}$ GC;
18+ years (adult): about $1.4 \times 10^{13}$ to about $7.0 \times 10^{14}$ GC.

In other embodiments, the following therapeutically effective flat doses are administered to an MPS patient of the age group:
Newborns: about $3.8 \times 10^{12}$ to about $1.9 \times 10^{14}$ GC;
3-9 months: about $6 \times 10^{12}$ to about $3 \times 10^{14}$ GC;
9-36 months: about $10^{13}$ to about $5 \times 10^{13}$ GC;
6-12 years: about $1.2 \times 10^{13}$ to about $6 \times 10^{14}$ GC;
3-12 years: about $1.2 \times 10^{13}$ to about $6 \times 10^{14}$ GC;
12+ years: about $1.4 \times 10^{13}$ to about $7.0 \times 10^{14}$ GC;
18+ years (adult): about $1.4 \times 10^{13}$ to about $7.0 \times 10^{14}$ GC.

In order to ensure that empty capsids are removed from the dose of rAAV9.CB7.hIDUA that is administered to patients, empty capsids are separated from vector particles by cesium chloride gradient ultracentrifugation or by ion exchange chromatography during the vector purification process, as discussed in Example 5 herein.

Immunosuppressive therapy may be given in addition to the vector. Immunosuppressive therapy includes corticosteroids (methylprednisolone 10 mg/kg intravenously [IV] once on Day −2 and oral prednisone starting at 0.5 mg/kg/day on Day −1 with gradual tapering and discontinuation by Week 16), tacrolimus (0.2 mg/kg/day by mouth [PO] Days −2 to Week 24), and sirolimus (once daily [QD] from Day −2 until the Week 48 visit). An illustrative sirolimus dose may include (6 mg PO Day −2 then 2 mg QD from Day −1 until the Week 48 visit). Sirolimus dose adjustments can be made to maintain whole blood trough concentrations within 16-24 ng/mL. Adjustments may also be made to the other drugs in the regimen, including delivering the drugs for a shorter or longer time period. In most subjects, dose adjustments can be based on the equation: new dose=current dose×(target concentration/current concentration). Subjects may continue on the new maintenance dose for at least 7-14 days before further dosage adjustment with concentration monitoring. Optionally, patients can be permitted to remain on a stable regimen of intravenous enzyme replacement therapy (ERT, e.g., ALDURAZYME™ [laronidase], as well as any supportive measures (e.g., physical therapy). Patients are monitored for any adverse event. Serious adverse events may include possible drug-induced liver injury with hyperbilirubinemia defined as ALT ~3× the ULN and bilirubin ~2×ULN (>35% direct) termed "Hy's Law" events.

In some embodiments, the immunosuppressive therapy regimen is as follows:
Corticosteroids
In the morning of vector administration (Day 1 predose), patients receive methylprednisolone 10 mg/kg IV (maximum of 500 mg) over at least 30 minutes. The methylprednisolone is administered before the lumbar puncture and intrathecal (IC) injection of rAAV9.CB7.hIDS. Premedication with acetaminophen and an antihistamine is optional.

On Day 2, oral prednisone is started with the goal to discontinue prednisone by Week 12. The dose of prednisone is as follows: Day 2 to the end of Week 2: 0.5 mg/kg/day. Week 3 and 4: 0.35 mg/kg/day. Week 5-8: 0.2 mg/kg/day. Week 9-12: 0.1 mg/kg.

Prednisone is discontinued after Week 12. The exact dose of prednisone can be adjusted to the next higher clinically practical dose.

Sirolimus: 2 days prior to vector administration (Day −2): a loading dose of sirolimus 1 mg/m² every 4 hours×3 doses is administered. From Day −1: sirolimus 0.5 mg/m/day divided in twice a day dosing with target blood level of 4-8 ng/ml. Sirolimus is discontinued after the Week 48 visit.

Tacrolimus: Tacrolimus is started on Day 2 (the day following rAAV9.CB7.hIDUA administration) at a dose of 1 mg twice daily and adjusted to achieve a blood level 4-8 ng/mL for 24 Weeks. Starting at Week 24 visit, tacrolimus is tapered off over 8 weeks. At week 24 the dose is decreased by approximately 50%. At Week 28 the dose is further decreased by approximately 50%. Tacrolimus is discontinued at Week 32.

In other embodiments, immunosuppressive therapy for patients under 3 years old is as follows:
Corticosteroids
In the morning of vector administration (Day 1 predose), patients will receive methylprednisolone 10 mg/kg IV (maximum of 500 mg) over at least 30 minutes. The methylprednisolone should be administered before the lumbar puncture and IC injection of AAV9.hIDUA. Premedication with acetaminophen and an antihistamine is optional at the discretion of the investigator.

On Day 2, oral prednisone will be started with the goal to discontinue prednisone by Week 12. The dose of prednisone will be as follows:

Day 2 to the end of Week 2: 0.5 mg/kg/day
Week 3 and 4: 0.35 mg/kg/day
Week 5-8: 0.2 mg/kg/day
Week 9-12: 0.1 mg/kg Prednisone will be discontinued after Week 12. The exact dose of prednisone can be adjusted to the next higher clinically practical dose.

Sirolimus 2 days prior to vector administration (Day −2): a loading dose of sirolimus 1 mg/m2 every 4 hours×3 doses will be administered From Day −1: sirolimus 0.5 mg/m2/day divided in twice a day dosing with target blood level of 1-3 ng/ml Sirolimus will be discontinued after the Week 48 visit.

Tacrolimus

Tacrolimus will be started on Day 2 (the day following AAV9.hIDUA administration) at a dose of 0.05 mg/kg twice daily and adjusted to achieve a blood level 2-4 ng/mL for 24 Weeks.

Starting at Week 24 visit, tacrolimus will be tapered off over 8 weeks. At week 24 the dose will be decreased by approximately 50%. At Week 28 the dose will be further decreased by approximately 50%. Tacrolimus will be discontinued at Week 32.

Tacrolimus and sirolimus blood level monitoring

C. Patient Subpopulations

Suitable patients may include those:

having documented diagnosis of MPS I confirmed by enzyme activity, as measured in plasma, fibroblasts, or leukocytes.

Having documented evidence (medical records) of early-stage neurocognitive deficit due to MPS I, defined as either of the following, if not explainable by any other neurologic or psychiatric factors:

A score of ≥1 standard deviation below mean on IQ testing or in 1 domain of neuropsychological function (verbal comprehension, memory, attention, or perceptual reasoning).

Documented historical evidence (medical records) of a decline of >1 standard deviation on sequential testing.

Has sufficient auditory and visual capacity, with or without aids, to complete the required protocol testing and willing to be compliant with wearing the aid, if applicable, on testing days.

Optionally, has been on a stable regimen of ERT (i.e., ALDURAZYME® [laronidase] IV) for at least 6 months.

Prior to treatment, patients are screened and one or more of the following criteria may indicate this therapy is not suitable for the patient:

Has a contraindication for an IC injection, including any of the following:

Review of baseline MRI testing shows a contraindication for an IC injection.

History of prior head/neck surgery, which resulted in a contraindication to IC injection.

Has any contraindication to CT (or contrast) or to general anesthesia.

Has any contraindication to MRI (or gadolinium).

Has estimated glomerular filtration rate (eGFR)<30 mL/min/1.73 m$^2$.

Has any neurocognitive deficit not attributable to MPS I or diagnosis of a neuropsychiatric condition.

Has any history of a hypersensitivity reaction to sirolimus, MMF, or prednisolone.

Has any condition that would not be appropriate for immunosuppressive therapy (e.g., absolute neutrophil count <1.3×10$^3$/μL, platelet count <100×10$^3$/μL, and hemoglobin <12 g/dL [male] or <10 g/dL [female]).

Has any contraindication to lumbar puncture.

Has undergone HSCT.

Has received laronidase via IT administration within 6 months prior to treatment.

Has received IT laronidase at any time and experienced a significant adverse event considered related to IT administration that would put the patient at undue risk.

Any history of lymphoma or history of another cancer, other than squamous cell or basal cell carcinoma of the skin, that has not been in full remission for at least 3 months before treatment.

Alanine aminotransferase (ALT) or aspartate aminotransferase (AST)>3× upper limit of normal (ULN) or total bilirubin >1.5×ULN, unless the patient has a previously known history of Gilbert's syndrome and a fractionated bilirubin that shows conjugated bilirubin <35% of total bilirubin.

History of human immunodeficiency virus (HIV)-positive test, history of active or recurrent hepatitis B or hepatitis C, or positive screening tests for hepatitis B, hepatitis C, or HIV.

Is pregnant, <6 weeks post-partum, breastfeeding, or planning to become pregnant (self or partner)

History of alcohol or substance abuse within 1 year before treatment.

Has a serious or unstable medical or psychological condition that, would compromise the patient's safety.

Uncontrolled seizures.

Suitable patients include, male or female subjects in age:

Newborns;
3-9 months of age;
≥4 to <9 months of age;
≥9 to <18 months of age;
9-36 months of age;
≥18 months to <3 years of age;
3-12 years of age;
12+ years of age
18+ years of age In certain embodiments, suitable patients include a male or female under 3 years of age and, one or more, or all of the following:

1) The subject's legal guardian(s) is(are) willing and able to provide written, signed informed consent after the nature of the study has been explained, and prior to any study-related procedures.

2) Has a documented diagnosis of severe MPS I-Hurler:
 a) presence of clinical signs and symptoms compatible with MPS I-H, and/or
 b) homozygosity or compound heterozygosity for mutations exclusively associated with the severe phenotype.

3) Has an intelligent quotient (IQ) score of ≥55

4) Has sufficient auditory and visual capacity, with or without aids, to complete the required protocol testing and willing to be compliant with wearing the aid, if applicable, on testing days.

A subject who meets any of the following exclusion criteria will not be eligible to participate in the study:

5) Has a contraindication for an IC injection, including any of the following:
   a) Review of baseline magnetic resonance imaging (MRI) testing by an adjudication panel of neuroradiologists/neurosurgeons shows a contraindication for an IC injection.
   b) History of prior head/neck surgery, which resulted in a contraindication to IC injection, based on review of available information by an adjudication panel of neuroradiologists/neurosurgeons.
   c) Has any contraindication to computed tomography (CT) (or contrast) or to general anesthesia.
   d) Has any contraindication to MRI (or gadolinium).
   e) Has estimated glomerular filtration rate (eGFR)<30 mL/min/1.73 m2.
6) Has any neurocognitive deficit not attributable to MPS I or has a diagnosis of a neuropsychiatric condition that may, in the opinion of the physician, confound interpretation of study results.
7) Has any contraindication to lumbar puncture.
8) Has undergone hematopoietic stem cell transplantation (HSCT)
9) Has had prior treatment with an AAV-based gene therapy product
10) Has received intrathecal (IT) laronidase at any time and experienced a significant AE considered related to IT administration that, in the opinion of the physician, would put the subject at undue risk.
11) Has any history of lymphoma or history of another cancer other than squamous cell or basal cell carcinoma of the skin that has not been in full remission for at least 3 months before screening.
12) Uncontrolled hypertension (systolic blood pressure [BP]>180 mmHg, diastolic BP>100 mmHg) despite maximal medical treatment.
13) Has a platelet count <100,000 per microliter (µL)
14) Has alanine aminotransferase (ALT) or aspartate aminotransferase (AST)>3× upper limit of normal (ULN) or total bilirubin >1.5×ULN at screening, unless the subject has a previously known history of Gilbert's syndrome.
15) Has a history of human immunodeficiency virus (HIV) or hepatitis B or hepatitis C virus infection, or positive screening tests for hepatitis B surface antigen or hepatitis B core antibody, or hepatitis C or HIV antibodies.
16) Received any investigational product within 30 days or 5 half-lives before signing of the Informed Consent Form (ICF), whichever is longer
17) Is a first-degree family member of a clinical site employee or any other individual involved in the conduct of the study, or is a clinical site employee, or any other individual involved in the conduct of the study.
18) Has a clinically significant ECG abnormality that, in the opinion of the PI, would compromise the subject's safety.
19) Has a serious or unstable medical or psychological condition that, in the opinion of the PI, would compromise the subject's safety or successful participation in the study or interpretation of study results.
20) Has a (cerebral) ventricular shunt that in the opinion of the site neuroradiologist/neurosurgeon and in discussion with the Medical Monitor, may impact the administration and proper dosing of the subject Exclusion criteria related to immunosuppressive therapy:
21) A history of a hypersensitivity reaction to tacrolimus, sirolimus, or prednisone
22) A history of a primary immunodeficiency (e.g., common variable immunodeficiency syndrome), splenectomy, or any underlying condition that predisposes the subject to infection
23) Herpes zoster, cytomegalovirus, or Epstein Barr virus (EBV) infection that has not completely resolved at least 12 weeks prior to screening
24) Any infection requiring hospitalization or treatment with parenteral anti-infectives not resolved at least 8 weeks prior to Visit 2
25) Any active infection requiring oral anti-infectives (including antivirals) within 10 days prior to Visit 2
26) History of active tuberculosis (TB) or a positive Quantiferon-TB Gold test during screening
27) Any live vaccine within 8 weeks prior to signing the ICF
28) Major surgery within 8 weeks before signing the ICF or major surgery planned during the study period
29) Anticipate the need for adenoidectomy or tonsillectomy within 6 months of enrollment. If adenoidectomy or tonsillectomy is anticipated, it should be performed prior to screening.
30) Absolute neutrophil count <$1.3\times10^3$/µL
31) Any condition or laboratory abnormality that the clinician believes would not be appropriate for immunosuppressive therapy D. Measuring Clinical Objectives Primary clinical objectives include preventing and/or optionally reversing the neurocognitive decline and/or slowing or arresting neurodevelopmental decline associated with MPSI defects. Clinical objectives are determined by measuring intelligence quotient (IQ), e.g., as measured by Bayley Scale of Infant and Toddler Development, Third Edition (Bayley-III) and/or the Wechsler Preschool and Primary Scales of Intelligence, Fourth Edition (WPPSI-IV)] and adaptive behavior (Vineland-2) for Hurler subjects. or as measured by WASI for Hurler-Scheie subjects. Other appropriate measures of neurocognitive development and function are utilized, e.g., assessing developmental quotient (DQ) using Bayley Scales of Infant Development (BSID-III), assessing memory using the Hopkins Verbal Learning Test, and/or using WASI-I and/or Bayler-III, and/or Tests of Variables of Attention (TOVA).

Secondary endpoints include evaluation of biomarkers and clinical outcomes. Urine is evaluated for total glycosaminoglycan(s) (GAG) content, as well as MPS I specific pGAGs. Serum is evaluated for IDUA activity, anti-IDUA antibodies, pGAG, and concentration of the heparin cofactor II-thrombin complex. Since animal data indicates there may be systemic effects, plasma is monitored for biomarkers (GAGS and IDUA). CSF is evaluated for IDUA activity, anti-IDUA antibodies, hexosaminidase (hex) activity, and pGAG. The presence of neutralizing antibodies to vector (e.g., AAV9) and binding antibodies to IDUA may be assessed in CSF and serum, T-cell response to vector capsid (e.g., AAV9) may be assessed by ELISPOT assay, and the pharmacokinetics of IDUA expression in CSF, serum, and urine, as well as vector concentration (quantitative PCR (qPCR) to AAV9 DNA) may be monitored. Vector shedding in CSF, plasma and urine may be monitored.

Exploratory endpoints may include, one or more of: Immunogenicity measurements, e.g., Neutralizing antibodies to AAV9 and binding antibodies to IDUA in CSF and serum, Enzyme-linked immunospot (ELISPOT) assay: T-cell response to AAV9 and IDUA, and Flow cytometry: AAV- and IDUA-specific regulatory T cells. Other exploratory endpoints may include, CNS structural abnormalities assessed by magnetic resonance imaging (MRI) of the brain; Liver and spleen volume assessed by ultrasound of the abdomen; Auditory capacity changes measured by auditory brainstem response (ABR) testing; biomarkers in plasma (GAGS and IDUA), CSF (GAGs, IDUA and spermine), and urine (GAGs); Viral shedding: Vector concentration (quantitative polymerase chain reaction [qPCR] to AAV9.hIDUA deoxyribonucleic acid [DNA]) in CSF, serum, and urine; effect on systemic manifestation of disease (as compared to CSF) and quality of life.

Example 2: Neonatal Systemic AAV Induces Tolerance to CNS Gene Therapy in MPS I Dogs and Nonhuman Primates This example demonstrates in both dogs and nonhuman primates that liver directed gene transfer using an adeno-associated virus (AAV) vector in neonates induces a persistent state of immunological tolerance to the transgene, substantially improving the efficacy of subsequent vector administration targeting the central nervous system (CNS). This approach was applied to a canine model of the lysosomal storage disease mucopolysaccharidosis type I (MPS I), which is characterized by progressive CNS disease due to deficient activity of the enzyme α-1-iduronidase (IDUA). CNS targeted gene transfer using intrathecal AAV delivery in one-month-old MPS I dogs resulted in antibody induction to canine IDUA, which partially attenuated the improvement in brain lesions. MPS I dogs treated systemically in the first week of life with a vector expressing canine IDUA did not develop antibodies against the enzyme and exhibited robust expression in the CNS upon intrathecal AAV delivery at one month of age, resulting in complete correction of brain storage lesions. Newborn rhesus monkeys treated systemically with an AAV vector expressing human IDUA likewise developed tolerance to the transgene, resulting in drastically higher CSF IDUA expression and absence of antibody induction after subsequent CNS gene therapy. These findings suggest the possibility of improving the efficacy and safety of gene therapy by inducing tolerance to the transgene during a critical period in immunological development.

A. Materials and Methods

1. Vector Production

The test articles consisted of an AAV9 capsid packaging an expression construct consisting of a chicken beta actin promoter (CB7), a chimeric intron (CI), a codon-optimized canine IDUA transgene (cIDUA) and a polyadenylation signal (RBG). The expression construct was flanked by AAV serotype 2 inverted terminal repeats. This vector is designated as either AAV2/9.CB7.CI.cIDUA.RBG or AAV9.CB7.CI.cIDUA.RBG. Some animals were also treated intravenously as neonates with a different vector to induce tolerance to the canine IDUA protein. This vector consisted of an AAV8 capsid packaging an expression construct consisting of a liver specific thyroid hormone binding globulin promoter (TBG), an artificial intron (PI), the codon-optimized canine IDUA transgene (cIDUA) and a polyadenylation signal (RBG). The expression construct was flanked by AAV serotype 2 inverted terminal repeats. Vectors were produced by triple transfection of 293 cells and purified on iodixanol gradients as previously described [L Wang et al, Human gene therapy 22, 1389-1401 (2011); published online Epub November].

2. Animals

The MPS I dog colony was maintained at the University of Pennsylvania School of Veterinary Medicine under NIH and USDA guidelines for the care and use of animals in research. All MPS I dog study protocols were approved by the University of Pennsylvania Institutional Animal Care and Use Committee. For vector injections in neonatal MPS I dogs, the AAV8 vector was diluted in 0.5-1 mL of sterile saline, and injected via the jugular vein. Intrathecal injections of AAV9 vectors and CSF collection were performed via the suboccipital approach as previously described [C. Hinderer, et al, Intrathecal Gene Therapy Corrects CNS Pathology in a Feline Model of Mucopolysaccharidosis I. Molecular therapy: the journal of the American Society of Gene Therapy, (2014); published online Epub July 16]. A total of 9 MPS I dogs were included in this study. Genotype was confirmed at birth by PCR and serum enzyme assay. Six dogs were administered an IV injection of the AAV serotype 8 vector ($5 \times 10^{12}$ genome copies per kilogram [GC/kg] body weight) on either the first (N=3) or seventh (N=3) day of life. One animal died on postnatal day 3. The remaining 5 treated animals as well as 3 naïve MPS I dogs were treated with intrathecal AAV9 ($10^{12}$ GC/kg) at one month of age. Blood was collected from a peripheral vessel weekly for the first seven weeks of life then monthly thereafter. CSF (1 mL) was collected at the time of intrathecal vector injection (one month of age), on days 7 and 21 after injection, and monthly thereafter. Euthanasia was performed by administration of sodium pentobarbital (80 mg/kg IV). Five animals were euthanized at 9 months of age; were euthanized at 11 months of age. Untreated MPS I and controls were euthanized between 6 and 26 months of age. Tissues were collected and processed as previously described [Hinderer et al, 2014].

All animal procedures conformed to the requirements of the Animal Welfare Act and protocols were approved prior to implementation by the Institutional Animal Care and Use Committee at the University of California, Davis. Activities related to animal care were performed as per California National Primate Research Center standard operating procedures. Normally cycling, adult female rhesus monkeys (*Macaca mulatta*; N=4) with a history of prior pregnancy were bred and identified as pregnant, using established methods [A F Tarantal, in The Laboratory Primate. (2005), pp. 317-352]. All dams selected for the study were pre-screened to ensure they were seronegative for AAV antibodies. Fetuses were monitored sonographically during gestation to confirm normal growth and development [A F Tarantal (2005)] and newborns were delivered by cesarean section at term (160±2 days gestation) according to established protocols [A. F. Tarantal, et al, Mol Ther 12, 87-98 (2005); published online Epub July]. Newborns were placed in incubators post-delivery and nursery-reared for the study. Infant health, food intake, and body weights were recorded daily or weekly (dependent on age) in the nursery according to established protocols. At birth all animals were administered the selected AAV vector IV. At one-month postnatal age and at subsequent monthly time points (up to 2 months post-transfer, to date) infants were sedated with ketamine (10 mg/kg intramuscularly, IM) and dexmedetomidine (0.015-0.075 mg/kg IM) in preparation for collection of CSF (~0.5 ml; pre-injection then weekly or monthly) and for intrathecal injection via the suboccipital approach (~0.5 ml volume; 1 month and immediately after collection of CSF), all under aseptic conditions. Blood samples were collected at birth then monthly from a peripheral vessel (~3-6 ml) to monitor CBCs and clinical chemistry panels, and for collection of serum and plasma. The reversal atipamezole was given IM at a comparable dose to dexmedetomidine when sample collection was completed.

DNA was isolated from tissues and vector genomes quantified by TaqMan PCR as described [L Wang, 2011]. Assays for IDUA and Hex activity were performed as described [Hinderer et al, 2014].

CSF pGAG measurement was performed by the Glycotechnology Core at the University of California, San Diego using previously described methods [R. Lawrence, et al, Nature chemical biology 8, 197-204 (2012); published online Epub February]. Briefly, GAG was extracted from CSF samples and digested to disaccharides with heparinase I, II, and III. Disaccharides were tagged with aniline $^{12}$C by reductive coupling and dried by speed vac. Dried samples were reconstituted in LC-MS grade water and spiked with a known concentration of $^{12}$C-aniline tagged standard. Samples were analyzed on a LTQ Orbitrap Discovery electrospray ionization mass spectrometer (Thermo Scientific) equipped with Thermo Scientific Ultimate 3000 HPLC system.

The ELISA for antibodies to canine IDUA was performed as described [Hinderer et al, 2014], except that the expression construct contained the canine cDNA under the control of the thyroid hormone binding globulin promoter, and the cIDUA protein was produced in Huh7 cells. The detection antibody used was HRP-conjugated sheep anti-canine (Pierce, Rockford, Ill.). The assay for antibodies to human IDUA in rhesus monkeys was identical, except that Aldurazyme (Genzyme, Cambridge, Mass.) 10 µg/mL, was used for coating antigen and the detection antibody was polyclonal goat anti-human (Jackson ImmunoResearch Laboratories, West Grove, Pa.).

Histological analysis of MPS I dog brains was performed as previously described [C. Hinderer, 2014] with the following modifications for quantifying neurons positive for monosialodihexosylganglioside (GM3), cholesterol, and lysosomal membrane protein (LIMP2) storage: Images of LIMP2- and filipin-stained sections of cerebral cortex were taken with a 10× objective such that the border between layer I (molecular layer) and layer II formed the upper border of the image. A total of 10 images were acquired from each animal. Images of GM3-stained brain sections were taken with a 4× objective from the area directly below the cerebral cortex surface including the cerebral molecular layer. Seven images from each animal were analyzed. All images were processed with ImageJ software (Rasband W. S., National Institutes of Health, USA; rsb.info.nih.gov/ij/) using the "Threshold" and "Analyze particles" modules as described previously [M. Aldenboven et al, Biology of Blood and Marrow Transplantation 14, 485-498 (2008); published online Epub May].

B. Results

1. Antibody Induction to Canine IDUA after Intrathecal AAV9-Mediated Gene Transfer in MPS I Dogs The canine model of MPS I faithfully recapitulates many of the manifestations of the human disease [E. Kakkis, et al, Molecular genetics and metabolism 83, 163-174 (2004); published online Epub September-October; R. M. Shull, et al, Am J Pathol 114, 487-495 (1984)]. These animals have no detectable IDUA activity due to a splice site mutation that results in retention of the first intron of IDUA [K. Menon et al, (Genomics 14, 763-768 (1992)]. Given the absence of detectable IDUA expression in these animals, we anticipated that they will model the immune response to intrathecal gene therapy that would occur in patients with the severe form of MPS I, as these individuals generally carry alleles that produce no full length IDUA, leaving them immunologically naïve to the protein [N. J. Terlato, G. F. Cox, Can mucopolysaccharidosis type I disease severity be predicted based on a patient's genotype? A comprehensive review of the literature. Genetics in medicine: official journal of the American College of Medical Genetics 5, 286-294 (2003); published online Epub July-August]. The brains of MPS I dogs show the characteristic pathology associated with MPS I, including widespread storage of gangliosides such as GM3 in neurons, as well as abnormal accumulation of cholesterol and lysosomal membrane proteins including LIMP2 [R. M. Shull, et al, Am J Pathol 114, 487-495 (1984)]. MPS I dogs also exhibit prominent storage of glycosaminoglycans (GAGs) in the meninges, resulting in significant meningeal thickening, a process which contributes to spinal cord compression in some MPS I patients [E. Kachur, et al, Neurosurgery 47, 223-228 (2000); published online Epub July; A. Taccone, et al, Pediatric Radiology 23, 349-352 (1993); published online Epub September; S. Vijay, J. E. Wraith, Clinical presentation and follow-up of patients with the attenuated phenotype of mucopolysaccharidosis type I. Acta Paediatrica 94, 872-877 (2005)].

Three (3) dogs were initially treated at one month of age with an intrathecal injection of an AAV9 vector carrying the canine IDUA sequence under the control of a ubiquitous promoter. The injection was well tolerated in all animals; no clinical signs were observed throughout the study. CSF analyses were generally unremarkable, with only a mild transient elevation of CSF lymphocytes occurring in 2 animals. A single CSF sample in one animal showed a marked pleocytosis consisting primarily of monocytoid cells. A subsequent tap showed no evidence of pleocytosis, and at the time of euthanasia, there was no histological evidence of inflammation in the brain or spinal cord of any treated animal.

The vector was distributed throughout the CNS, transducing cells in all analyzed regions of the brain and spinal cord. All animals exhibited supraphysiologic expression of IDUA in CSF, which declined to the normal range in one animal and to below normal levels in two animals over the course of 3 months, after which CSF enzyme levels were essentially stable for 5 months until the animals were euthanized. The absence of clinical signs, vector genome loss, or histological evidence of encephalitis indicated that the decline in CSF IDUA activity was not due to killing of transduced cells by cytotoxic T lymphocytes, which was also supported by persistent residual CSF IDUA activity. Instead, the decline in CSF IDUA activity was associated with the induction of high titer antibodies against canine IDUA.

B. Induction of Tolerance to IDUA by Neonatal Gene Transfer

To determine whether neonatal expression of canine IDUA could induce immune tolerance to the enzyme in MPS I dogs, 6 animals were treated with an IV injection of an AAV serotype 8 vector expressing canine IDUA from a liver selective promoter on either the first (N=3) or the seventh (N=3) day after birth. One of the dogs treated on postnatal day one died two days after treatment. Overall survival of neonates was similar to historical data for untreated MPS I dogs, which have approximately 20% mortality in the first two weeks of life [Vite, R. et al, Molecular therapy: the journal of the American Society of Gene Therapy 15, 1423-1431 (2007); published online Epub August]. The cause of this early mortality in MPS I dogs has not been determined; in this treated animal postmortem examination showed systemic lesions typical of MPS I as well as possible evidence of a systemic bacterial infection. Treated animals demonstrated an elevation in serum IDUA followed by a rapid decline. This is consistent with observations of transient expression due to vector genome loss during hepatocyte division in previous studies utilizing non-integrating vectors for hepatic gene transfer in newborns [L. Wang, et al, Human gene therapy 23, 533-539 (2012); published online Epub May].

At one month of age, the five surviving dogs that received IV AAV8 in the first week of life were given an injection of an AAV9 vector using an intrathecal approach. All 5 animals exhibited peak levels of greater than 30-fold of normal levels of IDUA in CSF following intrathecal vector injection, with long term CSF enzyme levels 3- to 100-fold higher than those achieved in naïve animals. Antibodies to canine IDUA were undetectable in the CSF of dogs treated on postnatal day 1, and were only slightly above the limit of detection in the animals treated on postnatal day 7, suggesting a state of immune tolerance to the enzyme in both groups.

2. Correction of Biochemical and Histological Abnormalities in the CNS of MPS I Dogs The lysosomal enzyme Hexosaminidase (Hex) is upregulated in tissues of MPS I animals, and the elevated Hex activity in both brain tissue and CSF serves as a useful marker for the aberrant cellular processes occurring downstream of IDUA deficiency [Hinderer et al (2014)]. Measurement of CSF Hex activity at the time of intrathecal vector delivery (~1 month postnatal) revealed abnormally elevated Hex activity in all MPS I dogs. The animals treated with intrathecal AAV9 alone exhibited modest reductions in CSF Hex activity, with only the animal with the highest residual IDUA expression reaching the normal range of Hex activity. All 5 animals treated with neonatal systemic gene transfer followed by intrathecal vector administration demonstrated complete normalization of CSF Hex. Hex activity in brain tissue samples showed a greater response to therapy than CSF Hex, with substantial reductions in brain Hex activity in all treated animals, although the effect was slightly diminished in the two intrathecal-only treated animals with the lowest CSF IDUA levels.

GAG concentrations in CSF were measured using an assay specific for the non-reducing end of the pathologic GAGS (pGAG) that accumulate due to IDUA deficiency [R. Lawrence, et al; Nature chemical biology 8, 197-204 (2012); published online Epub February]. All animals exhibited a marked reduction in CSF pGAG concentration 3 weeks after intrathecal AAV injection. This reduction was sustained at day 112, although the dogs that were not immune tolerant to IDUA maintained higher residual CSF pGAG than immune tolerant dogs. Histological analysis revealed severe storage lesions throughout the brains of untreated MPS I dogs, with widespread neuronal accumulation of GM3, cholesterol, and LIMP2. The animals treated with intrathecal AAV9 alone demonstrated substantial improvements in storage lesions, although only the animal with the highest CSF IDUA experienced complete resolution of neuronal storage. The other two intrathecal-treated dogs had residual storage lesions. CNS storage lesions were completely reversed in all 5 dogs treated with neonatal AAV8 systemic gene transfer followed by intrathecal AAV9 administration. In addition to the storage lesions in the brain parenchyma, untreated MPS I dogs showed accumulation of GAGS in meninges visible by Alcian blue stain. This meningeal GAG accumulation and the resulting thickening of the meninges is implicated in many cases of spinal cord compression requiring surgical intervention, and also likely contributes to the development of communicating hydrocephalus in some MPS I patients by interfering with normal routes of CSF resorption. All treated animals showed evidence of improvement in meningeal GAG storage. While the meninges appeared almost completely normal in all tolerant dogs and one nontolerant dog, the two nontolerant animals with the lowest CSF IDUA activity retained some GAG storage.

3. Induction of Tolerance to Human IDUA in Newborn Rhesus Macaques

To assess whether the neonatal window for immune tolerance induction that was observed in MPS I dogs could also be found in primates, a similar study was performed in newborn rhesus monkeys (N=4). Because these animals are not IDUA deficient, the human IDUA transgene was used to model the immune response that might be expected against a species-specific transgene in a patient lacking active endogenous protein. Two newborn rhesus monkeys were administered AAV8 vector expressing human IDUA from a liver specific promoter IV at birth. Both demonstrated a brief increase in serum IDUA activity. Two additional newborns were administered an AAV8 vector expressing an irrelevant transgene (human factor IX) IV at birth. All four animals were administered AAV9 vector expressing human IDUA at one-month postnatal age by intrathecal injection. Similar to the MPS I dogs, the IDUA naïve animals exhibited declining CSF IDUA activity 3 weeks after injection, with a return to near baseline levels by 2 months post-administration. These animals also developed transgene specific antibodies in the CSF. The two animals administered IDUA gene transfer IV at birth did not develop antibodies to human IDUA in CSF, and maintained CSF enzyme activity greater than 10-fold normal two months after intrathecal AAV9 administration. All animals remained robust and healthy during the study period with no evidence of adverse effects, normal growth trajectories, and complete blood counts (CBCs) and chemistry panels within normal limits based on age and when compared to historical controls.

C. Discussion

Immune activation to a wild type therapeutic protein is a potential concern for any recessive disease. Antibody responses to protein replacement therapy have been particularly challenging for some LSDs, as antibodies can interfere with the distribution and uptake of the intravenously delivered enzyme [E. J. Langereis, et al, Molecular genetics and metabolism, (2014); published online Epub October 29]. Antibodies may be equally problematic for gene therapies targeting these disorders, as they could interfere with cross-correction mediated by enzyme secreted from transduced cells.

This study demonstrated that intrathecal AAV9 delivery can effectively target cells throughout the CNS in dogs and achieve sufficient expression to correct the biochemical and histological abnormalities associated with MPS I in the brain of a large animal. Vector biodistribution data showed that there was less than one vector genome per cell in the brain, indicating that the widespread reduction in storage pathology observed was due to cross-correction by secreted enzyme. However, of the three animals treated with intrathecal vector alone, two developed sufficiently robust anti-transgene antibody responses to prevent complete resolution of CNS storage lesions. Only the animal that maintained near-normal CSF IDUA activity after antibody induction to the transgene demonstrated a complete response to CNS gene therapy. From this outcome, it is concluded that IDUA activity in CSF is a reasonable predictor of efficacy following intrathecal gene transfer, with approximately normal levels required for full therapeutic benefit. This is consistent with our findings with intrathecal gene therapy in MPS I cats [Hinderer (2014)]. MPS I cats generally exhibited weaker antibody responses to intrathecal gene transfer and more stable CSF IDUA activity than MPS I dogs. This may relate to the underlying mutation in the two models, as MPS I cats express an inactive mutant IDUA, potentially rendering them partially immunologically tolerant to the enzyme. Importantly, the present data in MPS I dogs indicates that even for MPS I patients with severe disease who, like the dogs, have no residual IDUA expression, the anti-transgene antibody response that is likely to occur after intrathecal gene transfer does not result in adverse clinical events, and substantial efficacy is retained despite the antibody response. However, these data also suggest that preventing antibody responses against IDUA in the CNS could improve the efficacy of intrathecal gene therapy for MPS I.

Using liver-directed gene transfer, the effect of early exposure to IDUA was tested on subsequent immune responses following intrathecal gene therapy. Neonatal IDUA expression induced tolerance to the enzyme in MPS I dogs, which greatly increased CSF enzyme levels achieved with intrathecal gene therapy at one month of age. The high CSF IDUA levels in the immune tolerant group consistently resulted in complete reversal of neuropathology, providing a strong example of the efficacy that is possible with intrathecal gene therapy for LSDs when interfering antibody responses are overcome. The finding that this neonatal window for induction of immune tolerance to a transgene also exists in nonhuman primates appears promising for translation to the clinic. There are several important limitations to the present study. Due to the increased risks associated with performing intrathecal vector injections in newborn MPS I pups, systemic gene transfer was used as a means of inducing tolerance rather than performing CNS directed gene therapy in neonates.

The approach used in this example had the advantage that intrathecal gene therapy was performed in an identical manner and at the same age in all experimental groups, allowing for direct comparison of CSF IDUA levels between animals without the confounding effects of differences in transduction efficiency in animals of different ages. This study also did not rule out the possibility that prior liver directed gene therapy contributed to the improved correction of brain pathology in immune tolerant animals, although this appears unlikely given that IDUA was undetectable in CSF in these animals at the time of intrathecal vector injection, and CSF Hex activity and pGAG concentration showed no evidence of correction before intrathecal gene transfer. This is consistent with prior studies in MPS I cats, in which extremely high serum IDUA activity had no effect on brain lesions [C. Hinderer, PNAS, 111: 14894-14899 (2014)]. Based on the observation that detectable antibody responses began to appear in the MPS I dogs treated on postnatal day 7, it is estimated that this period lasts no more than one to two weeks, which could serve as a useful starting point for human studies.

If human neonates are found to exhibit the same potential for transgene-specific immunological tolerance that have been demonstrated herein in dogs and nonhuman primates, neonatal gene transfer could have enormous potential to treat many genetic disorders for which immune responses limit the safety or efficacy of therapy. In order for clinical trials to be feasible, prenatal or newborn screening will be essential for identifying patients sufficiently early for this approach to be effective. For MPS I, newborn screening is now being implemented in several states, providing a potential opportunity to conduct first-in-human trials [P V Hopkins et al, J Pediatr, (2014); published online Epub October 18].

Example 3: Induction of Transgene-Specific Immune Tolerance Enables Accurate Evaluation of a Human Gene Therapy in a Canine Disease Model A. Materials and Methods The vector is a non-replicating recombinant adeno-associated virus (AAV) vector of serotype 9 expressing human iduronidase (hIDUA). The AAV9 serotype allows for efficient expression of the hIDUA product in the CNS following IC administration.

1. Vector Production:

The AAV-hIDUA vector genome plasmid pAAV.CB7.CI.hIDUAco.RBG (p3032) is 7,165 bp in size. The vector genome derived from this plasmid is a single-stranded DNA genome with AAV2 derived ITRs flanking the hIDUA expression cassette. Expression from the transgene cassette is driven by a CB7 promoter, a hybrid between a CMV immediate early enhancer (C4) and the chicken beta actin promoter, while transcription from this promoter is enhanced by the presence of the chicken beta actin intron (CI). The polyA signal for the expression cassette is the RBG polyA. The plasmid was constructed by codon-optimizing and synthesizing the hIDUA sequence and the resulting construct was then cloned into the plasmid pENN.AAV.CB7.CI.RBG (p1044), an AAV2 ITR-flanked expression cassette containing CB7, CI and RBG expression elements to give pAAV.CB7.CI.hIDUAco.RBG (p3032).

Description of the Sequence Elements

Inverted terminal repeats (ITR): AAV ITRs (GenBank #NC001401) are sequences that are identical on both ends, but in opposite orientation. The AAV2 ITR sequences function as both the origin of vector DNA replication and the packaging signal of the vector genome, when AAV and adenovirus helper functions are provided in trans. As such, the ITR sequences represent the only cis sequences required for vector genome replication and packaging.

CMV immediate early enhancer (382 bp, C4; GenBank #K03104.1). This element is present in the vector genome plasmid.

Chicken beta-actin promoter (282 bp; CB; GenBank #X00182.1) promoter and is used to drive high-level hIDUA expression.

Chicken beta-actin intron: The 973 bp intron from the chicken beta actin gene (GenBank #X00182.1) is present in the vector expression cassette. The intron is transcribed, but removed from the mature messenger RNA (mRNA) by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This is a common feature in gene vectors intended for increased level of gene expression. This element is present in both vector genome plasmids.

α-L-iduronidase coding sequence: The hIDUA sequence (Genbank NP_000194) was codon-optimized and synthesized [SEQ ID NO:1]. The encoded protein is 653 amino acids [SEQ ID NO:2] with a predicted molecular weight of 73 kD and an apparent molecular weight of 83 kD by SDS PAGE.

Polyadenylation Signal: The 127 bp rabbit beta-globin polyadenylation signal (GenBank #V00882.1) provides cis sequences for efficient polyadenylation of the antibody mRNA. This element functions as a signal for transcriptional termination, a specific cleavage event at the 3' end of the nascent transcript and addition of a long polyadenyl tail. This element is present in both vector genome plasmids.

Inverted terminal repeats (ITR): AAV ITRs (GenBank #NC001401) are sequences that are identical on both ends, but in opposite orientation. The AAV2 ITR sequences function as both the origin of vector DNA replication and the packaging signal of the vector genome, when AAV and adenovirus helper functions are provided in trans. As such, the ITR sequences represent the only cis sequences required for vector genome replication and packaging.

The construct was packaged in an AAV9 capsid, purified and titered as previously described in M. Lock et al, Human Gene Ther, 21: 1259-1271 (2010)].

2. Animal Procedures:

The MPS I dog colony was maintained at the University of Pennsylvania School of Veterinary Medicine under NIH and USDA guidelines for the care and use of animals in research. All study protocols were approved by the University of Pennsylvania Institutional Animal Care and Use Committee. For infusions of recombinant human IDUA, laronidase (Genzyme) was diluted 5-fold in saline immediately before use. Infusions were performed through a peripheral venous catheter over two hours. Intrathecal injections of AAV9 vectors and CSF collection were performed via the suboccipital approach as previously described [C. Hinderer, et al, (Mol. Ther. J. Am. Soc. Gene Ther. 22, 2018-2027 (2014)]. Euthanasia was performed by administration of sodium pentobarbital (80 mg/kg IV). Tissues were collected and processed as previously described [Hinderer (2014)].

3. Enzyme Assays:

IDUA and Hex activity were measured in tissue lysates and CSF as previously described [C. Hinderer, et al, (Mol. Ther. J. Am. Soc. Gene Ther. 22, 2018-2027 (2014))].

4. Anti-hIDUA ELISA:

Polystyrene ELISA plates were coated overnight at 4 degrees with recombinant human IDUA (Genzyme) diluted to 5 mg/mL in phosphate buffer pH 5.8. The plate was washed and blocked in 2% BSA in pH 5.8 phosphate buffer. The plate was incubated 1 hour at room temperature with CSF samples diluted 1:50 in PBS. The plate was washed and bound antibody detected with HRP conjugated anti-canine IgG (Pierce, Rockford, Ill.) diluted 1:10,000 in phosphate buffer with 2% BSA. The ELISA was developed with tetramethylbenzidine substrate for 15 minutes, then stopped with 2 N sulfuric acid and absorbance was measured at 450 nm. Titers were calculated from a standard curve of a serially diluted positive sample.

5. Histology, Biodistribution and Statistics:

Histological analysis brains was performed as previously described [Hinderer, 2014] with the following modifications for quantifying neurons positive for GM3, cholesterol, and LIMP2 storage: Images of LIMP2- and filipin-stained sections of cerebral cortex were taken with a 10× objective such that the border between layer I (molecular layer) and layer II formed the upper border of the image. A total of 10 images were acquired from each animal. Images of GM3-stained brain sections were taken with a 4× objective from the area directly below the cerebral cortex surface including the cerebral molecular layer. Seven images from each animal were analyzed. All images were processed with ImageJ software (Rasband W. S., National Institutes of Health, USA; rsb.info.nih.gov/ij/) using the "Threshold" and "Analyze particles" modules as described previously [M Aldenboven et al, Biology of Blood and Marrow Transplantation 14, 485-498 (2008); published online Epub May]. Quantification of thickness of the cervical meninges was performed on H&E stained sections of the cervical spinal cord. Fifteen measurements of total meningeal thickness were made per slide at 300 μm intervals.

Vector biodistribution was evaluated as follows. DNA was isolated from tissues and vector genomes quantified by TaqMan PCR as described [L. L. Wang, et al, Impact of Pre-Existing Immunity on Gene Transfer to Nonhuman Primate Liver with Adeno-Associated Virus 8 Vectors. Human gene therapy 22, 1389-1401 (2011); published online Epub November]. Data were evaluated using Kruskal-Wallis test followed by Dunn's test or Mann-Whitney test as appropriate. P<0.05 was considered statistically significant. All statistical analyses were performed using Prism 6.0 (GraphPad Software).

B. Results

1. Intrathecal AAV9 Expressing Human IDUA Elicits Robust Transgene-Specific Immunity in MPS I Dogs The MPS I dog carries an IDUA mutation resulting in inclusion of the first intron in the mature mRNA, creating an immediate stop codon. The mutation in MPS I dogs yields no detectable IDUA activity [K P Menon, et al, Genomics, 14: 763-768 (1992); N J Terlato, et al, Genet Med, 5: 286-294 (2003); X X He, et al, Mol. Genet Metab, 67: 106-112 (1999)]. In the absence of lysosomal IDUA activity, un-degraded GAGS accumulate in the cell [G N Sando, et al Cell, 12: 619-627 (2011)]. This primary GAG storage material in affected tissues can be directly detected histologically by Alcian blue staining [C. Hinderer, et al, Mol. Ther. J. Am. Soc. Gene Ther. 22, 2018-2027 (2014); N J Terloato et al (2003); R. M. Shull, et al, Am J Pathol 114, 487-95 (1984); R. M. Shull, et al, Proc. Natl. Acad. Sci. U.S.A. 91, 12937-12941 (1994); L. A. Clarke, et al., Pediatrics 123, 229-40 (2009); N. M. Ellinwood, et al., Mol. Genet. Metab. 91, 239-250 (2007); M. E. Haskins, et al, Am. J. Pathol. 112, 27 (1983); A. Chen, et al, Apmis 119, 513-521 (2011)]. In addition to the primary GAG storage pathology, lysosomal GAG accumulation leads to a characteristic cascade of cellular abnormalities. The un-degraded GAGS cause lysosomal distention, which are visible on histology by increased staining for lysosomal membrane proteins such as LIMP2. Neurons also exhibit secondary accumulation of substances such as gangliosides (e.g. GM3) and un-esterified cholesterol. Lysosomal storage also induces aberrant overexpression of lysosomal enzymes such as hexosaminidase (Hex).

Three MPS I dogs were treated at one month of age with a single intrathecal injection into the cisterna magna of a clinical candidate AAV9 vector expressing human IDUA. Vector doses ranged from $10^{11}$ genome copies per kg (GC/kg) (n=2) to $10^{12}$ GC/kg (n=1). The procedure was well tolerated in all subjects. IDUA activity in CSF rapidly increased following vector administration, exceeding that of normal controls by day 7 (FIG. 2A, Naïve). However, by day 21 post vector administration, CSF IDUA levels fell to baseline, accompanied by an elevation in CSF anti-hIDUA antibody titers (FIG. 2A, Naïve). Day 21 CSF samples also revealed a lymphocytic pleocytosis in all animals (FIG. 4A, Naïve). In this cohort, the elevated CSF antibodies and cell counts were not associated with clinical signs or other laboratory abnormalities, and the pleocytosis spontaneously resolved. At the time of necropsy six months after injection, histological evaluation revealed no evidence of pathology in the brain or spinal cord. Vector biodistribution demonstrated widespread CNS transduction and persistence of the vector genome.

Brain hexosaminidase overexpression was reduced relative to untreated MPS I dogs, although it was not normalized at either dose (FIG. 7). Histology also showed partial resolution of brain storage lesions by LIMP2 and GM3 immunostaining, which did not appear to be dose dependent.

Based on the favorable safety profile observed in these dogs, two additional MPS I dogs were treated with a 10-fold higher dose of vector ($10^{13}$ GC/kg). These dogs developed CSF pleocytosis with similar kinetics to the animals treated at the lower two doses (FIG. 4A, Naïve); however, in these two subjects the response was more pronounced, and the pleocytosis was temporally associated with the onset of neurological signs. Beginning 21 days after vector administration, the animals exhibited hyporeflexia and weakness of the hind limbs, and pain upon flexion of the neck. Pain and CSF pleocytosis began to resolve following treatment with analgesics and corticosteroids; however, the hind limb weakness persisted, and the animals were euthanized two weeks after symptom onset. Histopathology demonstrated robust transduction of spinal motor neurons, particularly in the lumbar spinal cord, and lymphocytic infiltrates surrounding transduced neurons. Systematic evaluation of sections throughout the brain and spinal cord confirmed that the pathology was primarily localized to the lumbar spinal cord, although occasional infiltrates were observed in the brain.

2. Neonatal Exposure to Human IDUA Through Hepatic Gene Transfer Induces Tolerance to Subsequent Intrathecal Gene Transfer In order to evaluate the AAV9 vector expressing human IDUA in the absence of an exaggerated immune response to the transgene, we attempted to induce immunological tolerance to the human protein through neonatal exposure. On postnatal day 5, six MPS I dogs were treated with a single intravenous injection of an AAV serotype 8 vector (AAV8) expressing human IDUA from a liver specific promoter. At one month of age the animals were treated with an intrathecal injection into the cisterna magna of different doses of the AAV9 vector expressing human IDUA in three cohorts (n=2 animals per cohort) as follows: $10^{10}$, $10^{11}$ and $10^{12}$ GC/kg. All animals exhibited a dose-dependent elevation in CSF IDUA activity similar to the non-tolerized dogs (FIG. 2A); however, in this cohort CSF enzyme expression persisted beyond day 21 and remained detectable for the duration of the experiment (FIG. 2B, Tolerized). CSF antibody responses were blunted compared with those observed when naïve (i.e., non-tolerized) animals were dosed with intrathecal vector; only two animals in the tolerized cohorts (1-602 and 1-606) exhibited detectable titers, which were approximately 20-fold lower than naïve animals treated with an equivalent vector dose (FIG. 3). Only the dog with the highest antibody titer in this cohort (I-606) exhibited elevated CSF lymphocytes at day 21, albeit at lower levels than in the naïve animals (FIGS. 4A and 4B). There were no clinical adverse events in these cohorts.

3. Intrathecal AAV9-Mediated hIDUA Expression Effects Dose-Dependent Correction of Brain Biochemical Abnormalities and Storage Lesions The six MPS I dogs tolerized to human IDUA through neonatal gene transfer were sacrificed 6 months post intrathecal AAV9 injection. Brain lysates demonstrated complete normalization of hexosaminidase activity at the highest vector dose, with partial correction at the lowest dose (FIG. 5). Hexosaminidase activity was normalized in CSF at all vector doses (FIG. 8). The thickening of the cervical meninges, which can contribute to spinal cord compression in MPS I patients, was reversed in animals treated at all doses (FIG. 9). Histological evaluation of the brain revealed dose-dependent decreases in LIMP2 and GM3 storage in the hIDUA tolerant dogs (FIGS. 6A-6B). Animals treated with the highest vector does exhibited LIMP2 and GM2 staining similar to normal controls; at the lowest dose, there were measurable improvements in some markers (LIMP2 and Hex), whereas GM2 accumulation was not clearly reduced. The low dose of $10^{10}$ GC/kg therefore appeared to be the minimum effective dose (MED).

The MED of IT AAV9.CB7.hIDUA was established in 8 MPS I dogs previously tolerized to human IDUA in order to evaluate efficacy in the absence of a confounding immune response to the human protein. Dogs were treated with IT AAV9.CB7.hIDUA at 1 month of age, and were euthanized for evaluation of brain storage pathology 6 months later. Establishment of the MED utilized well characterized histological measures of MPS I disease in CNS tissue including LIMP2 and GM3. All measures of lysosomal storage pathology were normalized at the highest dose evaluated ($10^{12}$ GC/kg body weight). Consistent improvement was also observed at a ten-fold lower dose ($10^{11}$ GC/kg body weight), although animals in this cohort did not reach the normal range for GM3 or LIMP2 storage. In the lowest dose group ($10^{10}$ GC/g body weight) histological evidence of lysosomal storage showed modest improvement by LIMP2 staining and minimal improvement in GM3 accumulation. We therefore estimate that 1010 GC/kg body weight is the MED for IT AAV9.CB7.hIDUA. The dose-dependent resolution of brain storage lesions correlated with CSF IDUA activity and was inversely correlated with CSF spermine concentration, indicating that CSF IDUA activity and CSF spermine could be useful biomarkers for the evaluation of AAV9.CB7.hIDUA pharmacodynamics in clinical studies.

These data indicate that the MED of AAV9.CB7.hIDUA is $10^{10}$ GC/kg in MPS I dogs.

AAV9.CB7.hIDUA administration was also evaluated in naïve MPS I dogs. MPS I dogs (5) received an intrathecal injection of AAV9.MPSI test vector at 1 month of age. All animals treated at $10^{11}$ GC/kg body weight and $10^{12}$ GC/kg body weight exhibited a mild self-limited lymphocytic pleocytosis. These animals appeared healthy throughout the study, and at necropsy 6 months after injection there was no evidence of inflammation in the brain, spinal cord, or meninges. The 2 dogs treated with a dose of $10^{13}$ GC/kg body weight appeared well initially, but 3 weeks post injection developed neurologic signs which coincided with a more severe pleocytosis and histological evidence of a T cell response to transduced cells, with mononuclear cells surrounding dying motor neurons in the lumbar spinal cord. These results are consistent with dose-dependent immunological toxicity mediated by lymphocytes targeting transduced spinal motor neurons. In view of the differences in sequence between the human and dog IDUA proteins, it is not surprising that human IDUA is immunogenic in the dog.

In the non-tolerized MPS I dogs, the MTD was $10^{12}$ GC/kg. Since the MTD is based on a canine immune response to a human protein, this is a conservative estimate of the MTD. Scaled to the 45 g brain mass of a one-month old dog, and with an average body weight of 2 kg, this dose would correspond to an MED of $9 \times 10^{10}$ total or $2 \times 10^9$ GC/g brain mass, or approximately $1.4 \times 10^{13}$ GC total ($1.1 \times 10^{10}$ GC/g brain mass) GC in an adult human (approximately 5× canine MED on GC/g brain mass basis).

4. Infusion of Recombinant hIDUA in Newborn MPS I Dogs is Sufficient to Induce Tolerance to Intrathecal AAV9-Mediated hIDUA Expression In order to determine whether hepatic expression of human IDUA was necessary for tolerance induction, we treated two MPS I dogs (I-663 and I-664) with infusions of recombinant human IDUA (0.58 mg/kg) on postnatal day 7 and 14 before intrathecal AAV9 injection at one month of age. Similar to dogs treated as newborns with a vector expressing human IDUA, the enzyme-treated dogs exhibited persistently high levels of CSF IDUA activity (FIGS. 2A-2B) and minimal antibody response against human IDUA (FIG. 2) or CSF pleocytosis (FIGS. 4A-4B3). Brain hexosaminidase activity was reduced (FIG. 5) and storage lesions were effectively cleared in both animals (FIGS. 6A-6B).

C. Discussion

Evaluating the efficacy of intrathecal AAV9 delivery for the treatment of MPS I required assessment of both the vector distribution that could be achieved via injection into the CSF, and the impact of that degree of transduction on disease-specific markers. These studies necessitated the use of an animal model that could accurately reflect the disease pathophysiology while also displaying sufficiently similar size and anatomy to allow for meaningful evaluation of the clinical delivery method and the resulting vector distribution. The canine model of MPS I faithfully replicates the human phenotype, exhibiting not only the same biochemical and histological lesions, but also many of the same clinical manifestations [K P Menon, et al, Genomics, 14: 763-8 (1992); R M Shull, et al, (1984); R M Shull et al, (1994); C Ciron et al, Ann Neurol, 60: 204-213 (2006); P. Dickson et al, Ann Neurol, 60: 204-213 (2006)]. Due to the phenotypic similarity to MPS I in humans, MPS I dogs were used extensively in the development of enzyme replacement therapy for the treatment of systemic disease [R M Shull et al, PNAS 91: 12937-12941 (1994); P. Dickson et al, J Clin Invest, 118: 2868-2876 (2008)]. MPS I dogs also mimic CNS manifestations of the disease, sporadically developing spinal cord compression and hydrocephalus [P. Dickson, et al, Mol. Genet. Metab. 99, S15-S15 (2010); P. I. Dickson, et al, Mol. Genet. Metab. 98, 70-70 (2009); C. H. Vite, et al, Comp. Med. 63, 163-173 (2013)]. Though cognitive studies have not been reported for MPS I dogs, the histological and biochemical manifestations in the brain have been well characterized, and faithfully recapitulate the findings in humans with the severe form of the disease [R M Shull (1984); C. Ciron (2006); S U Walkley, et al, Acta Neuropathol. (Berl.) 75, 611-620 (1988)]. MPS I dog brains demonstrate accumulation of lysosomal membrane proteins (LIMP2) and gangliosides (GM3), and upregulation of lysosomal enzymes such as hexosaminidase (Hex). Ganglioside accumulation correlates with cognitive function in MPS I and other lysosomal storage diseases, and thus is a critical marker for evaluating disease severity and therapeutic outcomes [S. U. Walkley, M. T. Vanier, Secondary lipid accumulation in lysosomal disease, Biochim. Biophys. Acta BBA—Mol. Cell Res. 1793, 726-736 (2009); G. Constantopoulos, et al, J. Neurochem. 34, 1399-1411 (1980)]. MPS I dogs also exhibit changes in neuronal morphology similar to those identified in patients [SU Walkley, (1988)]. These striking similarities made this a compelling model for the evaluation of intrathecal AAV delivery as a novel therapy for the CNS manifestations of MPS I in humans. The capacity of large animal models to replicate the route of administration that would be used clinically for IT AAV9 delivery, as well as the resulting vector distribution in the CNS, further supported the relevance of the MPS I dog for these studies.

Although the MPS I dog appeared to be an excellent model for evaluation of the clinical vector, the immune response to human IDUA presented a critical obstacle. From previous studies it is clear that the immune response to human IDUA in MPS I dogs is much more extreme than that observed in patients. Intravenous delivery of the protein in both dogs and MPS I patients often elicits antibodies; however, in dogs these responses are more robust, less likely to decline upon continued administration, and more often associated with anaphylactic responses to subsequent infusions [R M Shull, et al, 1994); E. Kakkis, et al, Proc Natl Acad Sci U A 101, 829-34 (2004)]. The difference in immune response to human IDUA in the CNS is even more striking; MPS I dogs treated with intrathecal infusions of the enzyme show evidence of meningitis as well as antibody responses detectable in CSF. In contrast, for both pediatric and adult MPS I patients treated with repeated IT infusions of the protein, there have been no similar adverse effects, and in the 5 patients that have been tested for CSF antibodies against IDUA only one has been positive [C. Ciron (2006); P. Dickson, et al, (2010); P. I. Dickson, et al, Mol. Genet. Metab. 98, 70-70 (2009); P. I. Dickson, et al, Mol. Genet. Metab. 101, 115-122 (2010); P. I. Dickson, et al, Mol. Genet. Metab. 93, 247-247 (2008); E. Kakkis, et al, Mol. Genet. Metab. 83, 163-174 (2004); T. C. Lund, et al, Mol. Genet. Metab. 111, S74 (2); M. Vera, et al, Pediatr. Res. 74, 712-720 (2013)]. Interestingly MPS I dogs also develop CSF antibodies against canine IDUA, albeit at lower levels than to the human enzyme, suggesting that this model has a greater overall tendency toward immunity to IDUA, which is exacerbated by the use of the non-species-specific protein. These marked differences in the outcome of both intravenous and intrathecal delivery of human IDUA in MPS I dogs and patients indicate a consistently exaggerated immune response to human IDUA in MPS I dogs, and suggest that preventing this response will be necessary to replicate the anticipated vector activity in humans. Inducing tolerance to the protein through neonatal exposure allowed for the evaluation of the efficacy of the human vector in this model without the interference of the exaggerated immune response. This provided critical information, allowing for the accurate determination of a minimum effective dose—an essential factor in the design of first-in-human gene therapy trials—in the most relevant animal model. More particularly, extensive dose-ranging studies were performed in MPS I dogs. The minimum effective dose was determined in immune-tolerant animals and is estimated to be a dose of $2 \times 10^9$ GC/g brain mass as determined by the oqPCR method described herein. Dose-ranging safety was performed in immune-competent (i.e., IDUA- and AAV-naïve) dogs and toxicity was observed at doses of $10^{12}$ GC/g. Based on the finding of dose-limiting toxicity (DLT) at $10^{12}$ GC/g in the stringent canine model of immune-mediated toxicity, a 10-fold lower dose will be administered in the formal Good Laboratory Practice (GLP) toxicology studies in rhesus macaques. The dose that is evaluated in the formal GLP nonhuman primate (NHP) toxicology studies will be $1.1 \times 10^{11}$ GC/g brain mass. If toxicity is not encountered, the clinical starting dose will be $1.1 \times 10^{10}$ GC/g brain mass. This starting dose is approximately 5-fold greater than the minimum effective dose (MED) in the canine MPS I model, and nearly as large as the doses that demonstrated reliable histological responses in MPS I dog and cat studies, supporting a reasonable expectation of clinical efficacy at this dose. The starting dose is also approximately 90-fold lower than the dose at which toxicity was observed in MPS I dogs and 10-fold lower than the dose tested in nonhuman primates, providing an acceptable safety margin to account for the potential of human subjects to exhibit greater sensitivity to vector- or transgene-related toxicity. Based on these data, the starting dose represents an acceptable benefit:risk profile, where the dose is expected to be in the therapeutic range (and, therefore, may offer clinical benefit), but is expected to be below toxic vector doses (and, therefore, should be reasonably safe). The calculation below depicts how the dose in dogs is extrapolated to a starting dose in humans: 1-month Dog Brain=45 grams; naïve Dog: MED $9\times10^{10}$ GC total ($2\times10^9$ GC/g brain mass). Adult Human Brain=1300 grams; Human: Starting Dose (5× canine MED). $1.4\times10^{13}$ GC total ($1.1\times10^{10}$ GC/g brain mass). Without this approach, the only options would be to extrapolate efficacy data from vectors with species-specific transgenes, which could have important differences in potency, or move studies to a less representative animal model that is more immune tolerant to the human protein. Pharmacologic immune suppression can also be employed in this setting, although the neonatal tolerance-induction protocol has the clear advantage of avoiding secondary consequences of the immune-suppressing drugs.

Though efficacy assessment was confounded by the immune response and loss of circulating IDUA in the non-tolerized dogs treated with the human vector, some useful data can be derived from these animals. While the strong immune response is not likely to represent the immune response in humans, it could inform monitoring plans for first-in-human studies by demonstrating key characteristics of immune-mediated toxicity. In this case, we observed that immune-mediated toxicity was dose dependent, the peak of the immune response occurred 3 weeks after vector administration, presented with focal motor symptoms likely due to high transduction of spinal motor neurons, and was accompanied by CSF pleocytosis. These findings could be directly integrated into the phase 1 trial protocol, with intensive monitoring for immune-mediated toxicity and neurological symptoms extending for several weeks after vector administration, and CSF analysis for pleocytosis occurring 2-4 weeks after injection. If neurological symptoms accompanied by pleocytosis appeared with similar kinetics in a human study subject, the findings in naïve dogs would suggest that the toxicity is due to an immune response (as opposed to overexpression toxicity, for example) and could guide therapeutic decisions.

A strong correlation emerged between vector dose, CSF enzyme levels, and correction of brain storage lesions in MPS I dogs that were tolerized to human IDUA. The relationship between IDUA activity in the CSF and correction of brain pathology could be a valuable observation as this approach advances into human trials, where IDUA activity detected in CSF may be a useful predictor of clinical response. Even more useful would be the identification of CSF markers that directly reflect the severity of CNS storage pathology. CSF biomarkers would be a valuable tool for evaluating correction of the underlying CNS pathology in MPS I patients, and the canine model could be an ideal system for identification of such markers. In this study, we evaluated one potential CSF biomarker, the enzyme hexosaminidase. While substantially elevated in brain tissue of MPS I dogs, Hex activity was only modestly elevated in the CSF. CSF Hex was normalized in all treated animals, regardless of the degree of tissue response. CSF Hex may therefore be useful to confirm vector activity in clinical studies, but is not likely to predict a therapeutic response. Future studies using the MPS I dog model may allow for evaluation of additional CSF markers and their correlation with brain storage lesions, which could ultimately yield powerful new tools to non-invasively evaluate the severity of CNS involvement in MPS I and the impact of novel therapeutics.

The present findings indicate that neonatal exposure to human IDUA can induce tolerance using two different sources of the enzyme. While Example 3 shows that AAV-mediated expression could induce transgene-specific tolerance in neonates, this Example shows that infusion of the recombinant enzyme could also induce tolerance. If this approach is generalizable to other proteins, it could be useful for more accurate preclinical evaluation of many human therapeutics in animal models. Further, if a similar approach could induce tolerance to foreign proteins in human neonates, it could have enormous potential to improve the efficacy of protein replacement therapies for diseases in which antibody responses to the normal protein limit efficacy. While most MPS I patients appear to tolerate intrathecal IDUA infusions, the vast majority develop serum antibodies against intravenous enzyme replacement, and these antibodies can diminish the response to therapy. Combining neonatal tolerance induction with a gene or protein replacement therapy may substantially improve patient outcomes. The availability of an approved recombinant enzyme would make MPS I an excellent candidate for an initial human trial of this approach. If human neonates exhibit the same window of 1-2 weeks for tolerance induction, newborn screening would be essential for identifying patients early enough for successful intervention. The ongoing implementation of newborn screening for MPS I and other lysosomal storage diseases will therefore be critically important for clinical evaluation of a neonatal tolerance-induction protocol.

Example 4—Intrathecal AAV-Mediated Human IDUA Gene Transfer in Juvenile Rhesus Macaques A. Intrathecal Delivery The purpose of this study was to evaluate the safety of intrathecal (IT) administration of AAV2/9.CB7.CI.hIDUAco.RBG, an AAV9 vector expressing human IDUA in one-month-old rhesus macaques, a model developmentally similar to a human infant at 6-9 months of age. In addition, this study evaluated whether antibodies to the transgene product in serum or cerebrospinal fluid (CSF) affected the safety of vector administration and the activity of human IDUA.

This study included 4 rhesus macaques. Pilot studies indicated that macaques can develop antibodies against human α-L-iduronidase (IDUA). As an antibody response to the human IDUA transgene product was anticipated in macaques, 2 of the animals were tolerized at birth by an intravenous (IV) administration of AAV8 vector expressing human IDUA from a liver-specific promoter (AAV2/8.TBG-.PI.COhIDUA.nRBG). To control for procedural effects and exposure to the AAV8 vector, the other 2 macaques were administered an AAV8 vector expressing an irrelevant transgene (human coagulation factor IX (AAV2/8.LSP.IVS2.hFIXco.WPRE.BGH) IV at birth. At 1 month postnatal age, all 4 animals were administered AAV2/9.CB7.CI.hIDUAco.RBG, an AAV9 vector expressing human IDUA at a dose of $3\times10^{12}$ GC/kg by IT injection. Animals were observed for 16 months post-administration at the time of report issuance and will remain on study for at least 1 more year. Endpoints assessed throughout the study include general observations, body weight, and comprehensive clinical pathology (blood cell counts with differentials and serum chemistries). In addition, IDUA enzyme activity and antibody responses to the transgene were measured in CSF.

This study revealed no vector related pathology and no (0) clinical sequelae. All animals exhibited normal growth trajectories. Serum chemistries and blood cell counts were within the normal range of historical control Rhesus macaques of comparable age and housing conditions. Antibodies to the transgene were detected in the CSF of the 2 non-tolerized animals, but not in the 2 animals tolerized to human IDUA as neonates. In both IDUA-tolerized animals, IDUA activity at least 15% greater than baseline levels was detectable in CSF throughout the study. In the non-tolerized animals, CSF IDUA activity rapidly increased after AAV9.MSPl test vector administration, but fell to baseline following antibody induction. The presence of transgene-specific antibodies in CSF did not impact on the safety of IT AAV9.CB7.hIDUA administration but did affect the ability to detect human IDUA levels in CSF.

In conclusion, intrathecal administration of a single dose of AAV9.CB7.hIDUA was well tolerated in one-month old Rhesus macaques at a dose of $3\times10^{12}$ GC/kg At this dose, levels of hIDUA of at least 15% above baseline were detectable in the CSF of animals that had been tolerized at birth to human IDUA; animals that had not been tolerized developed antibody responses to hIDUA that were detectable in the CSF and negatively correlated with hIDUA expression. No effects on growth, behavior, or clinical chemistry or hematology parameters were observed that were attributed to treatment, either in animals that were positive for anti-IDUA antibodies or animals that were not antibody-positive.

A. Materials and Methods

The vectors used in this study include an rAAV9.hIDUA, an rAAV8.hIDUA, and an AAV8 vector having an irrelevant transgene (hFIX).

Intrathecal (IT) administration via suboccipital puncture was selected because it is the proposed route for clinical use. This study evaluated a single vector dose which was scaled to the body mass of the animal. Two animals were administered with an IV injection of rAAV8.hIDUA ($10^{12}$ GC/kg) on postnatal Day 1 (study Day 0) in order to induce immunological tolerance to human IDUA. The control animals were administered a control vector expressing an irrelevant transgene (human factor IX) from a liver specific promoter (rAAV8.hFIX) on postnatal day 1. All animals were then administered IT AAV9.MPSI test vector by suboccipital puncture at 1 month of age (study Day 30).

B. Results and Conclusion

Four one-month-old rhesus macaques (*M. mulatta*) were administered IT $3\times10^{12}$ GC/kg rAAV9.hIDUA and monitored for more than 1 year post-vector administration. Two of these animals were tolerized at birth to the human IDUA protein.

There were no treatment-related effects on body weight or body weight gain and no treatment-related clinical signs. There no treatment-related effects on clinical chemistry or hematology parameters. Antibodies to the transgene product were detectable in the CSF of the 2 animals that were not pre-treated to induce tolerance to the human protein. There were no differences in the endpoints assessed (clinical signs, body weight, hematology and clinical chemistry) between tolerized and non-tolerized animals, indicating that CSF antibodies to the protein were not associated with apparent toxicity. In the IDUA tolerant animals, there was persistent IDUA expression in CSF at more than 2-fold baseline levels in 1 animal and approximately 15% over baseline in the other animal.

In conclusion, intrathecal administration of a single dose of rAAV9.CB7.hIDUA was well tolerated in one-month old rhesus macaques at a dose of $3\times10^{12}$ GC/kg. At this dose, levels of hIDUA of 115-200% of baseline were detectable in the CSF of animals that had been tolerized at birth to human IDUA; animals that had not been tolerized developed antibody responses to hIDUA that were detectable in the CSF and negatively correlated with hIDUA expression. No effects on growth, behavior, or clinical chemistry or hematology parameters were observed that were attributed to treatment, either in animals that were positive for anti-IDUA antibodies or animals that were not antibody-positive.

Example 5—Intrathecal AAV-Mediated Human IDUA Gene Transfer in Cynomolgus Macaques The vector consisted of an AAV9 capsid packaging an expression construct consisting of a cytomegalovirus promoter (CMV), a chimeric intron (PI), a codon-optimized human IDUA transgene (hIDUA) and a polyadenylation signal (SV40). The expression construct was flanked by AAV serotype 2 inverted terminal repeats. There is one vector used in this study, but this vector is designated as either, AAV2/9.CMV.PI.hIDUA.SV40, AAV2/9.CMV.PI.hIDUAco.SV40, AAV2/9.CMV.PI.hIDUAco.SV40PA or AAV9. CMV.PI.hIDUA.SV40.

A. Materials and Methods

This study included two female cynomolgus macaques (IDs 06-09 and 07-19). Both macaques received $10^{12}$ genome copies per kilogram of body weight (GC/kg) of AAV2/9.CMV.PI.hIDUAco.SV40PA. The intrathecal (IT) route via suboccipital puncture was selected because it is the proposed route for clinical use.

| Vector | Weight at injection (kg) | Dose/kg body weight | Total dose |
|---|---|---|---|
| AAV2/9.CMV.PI.hIDUAco.SV40PA | 3.90 | 1.00E+12 | 3.90E+12 |
| AAV2/9.CMV.PI.hIDUAco.SV40PA | 4.60 | 1.00E+12 | 4.60E+12 |

1. Dose per gram brain mass is based on a 90 g brain.

B. Results and Conclusions

Two adult female cynomolgus macaques were treated with an intrathecal injection of an AAV9 vector expressing human IDUA from a CMV promoter. Body weight, physical exams, and blood counts and serum chemistries were assessed on study Day 1, 7, 14, 28, 91, 118, 147, 182, 208, 239, 261, 294, 322, 350, 378, 413, 434, 462, 490, 518, 561, 589, 624, and 636 after vector administration, after which the animals were necropsied for analysis of histopathology and vector biodistribution. There were no vector-related clinical adverse events. One animal developed a femoral aneurysm 600 days after vector administration. This is believed to be secondary to repeated blood collection and is not likely to be treatment related. There were no treatment-related effects on clinical pathology parameters including terminal CSF parameters. Histopathology showed no evidence of CNS pathology, and no apparent vector-related abnormalities in peripheral organs. Biodistribution analysis indicated vector deposition throughout the brain and spinal cord of both NHPS that was one to two orders of magnitude higher than in peripheral organs with one exception. Significant liver distribution occurred in one animal without pre-existing neutralizing antibodies to the AAV9 capsid, whereas the animal with pre-existing serum antibodies to the vector exhibited minimal liver transduction. Immunostaining of brain sections from both animals demonstrated expression of human IDUA.

This study provided evidence that IT AAV9-mediated gene transfer can allow for long-term expression of IDUA in the brain. This study also provided preliminary evidence of the safety of this approach.

Example 6—Intracerebroventricular (ICV) AAV9.hIDUA Delivery in Mice in Setting of Pre-Existing Immunity to hIDUA This pilot study was designed to evaluate histological evidence of toxicity following intracerebroventricular (ICV) administration of an AAV9.hIDUA vector in treatment-naive mice, as well as mice with pre-existing antibodies against the transgene product, human iduronidase (IDUA).

The test article consisted of an AAV9 capsid packaging an expression construct consisting of a chicken beta actin promoter (CB7), a chimeric intron (CI), a codon-optimized human IDUA transgene (hIDUAco) and a polyadenylation signal (RBG). The expression construct was flanked by AAV serotype 2 inverted terminal repeats. This vector is designated as either AAV9.CB7.CI.hIDUA.RBG. The final product was diluted in Elliot's Formulation Buffer (EFB).

This non-GLP study was originally planned as an aid in designing a GLP toxicology study in pre-immunized mice, but the GLP study was not performed based on FDA feedback that the experimental design based on immunization against a non-species specific protein in normal mice is unlikely to be representative of patients previously treated with enzyme replacement therapy (ERT). At the time that the decision was made against performing a GLP toxicology study in pre-immunized mice, the initial pilot study was already underway. The results of the pilot study are included in this report.

This study included 100 adult C57BL/6 mice (50/sex). Half of the animals were immunized against human IDUA with a single intramuscular (IM) injection of recombinant human IDUA (Aldurazyme®) in adjuvant (TiterMax). Six months after immunization both the immunized animals and naïve animals were treated with an ICV injection of AAV9.hIDUA at 1 of 2 doses ($5\times10^{10}$ GC or $2.5\times10^{11}$ GC). Animals from each treatment group were sacrificed at 1 of 5 time points (Day 7, 14, 30, 60 or 90) after vector administration. The brain, spinal cord, heart, lung, liver, spleen, kidney and gonads were harvested for histopathology.

In the naïve (non-immunized) cohort (n=50, 25/sex), no animals died before the scheduled necropsy or demonstrated clinical abnormalities. Brain histopathology showed dilation of the lateral ventricle and a visible needle track in some animals, consistent with the ICV route of administration. Minimal to mild lymphocytic infiltration of the meninges and/or brain parenchyma occurred in 12 out of the 50 mice, and did not show a clear correlation with vector dose or time after injection. Hepatitis occurred in a manner that was both dose dependent and correlated with the time after vector administration. Minimal to moderate hepatitis occurred in all 5 animals in the high dose cohort sacrificed 14 days after vector administration. Only minimal hepatitis was observed in the high dose animals sacrificed at 7, 30, 60 or 90 days. In the low dose cohort only minimal hepatitis was observed; this occurred in 8 animals with no clear correlation with time after vector administration. Moderate myocarditis occurred in one animal in the high dose cohort 60 days after vector administration; 3 additional animals in the high dose cohort exhibited minimal myocarditis at 30 or 90 days post vector administration. Two animals in the low dose cohort exhibited minimal myocarditis and 1 exhibited mild myocarditis; all occurred 60 days post vector administration. There were no other potentially vector-related abnormalities observed in the naïve (non-immunized) cohort.

In the cohort that was immunized to human IDUA before vector administration (n=50, 25/sex) 3 animals died (2 males, 1 female); 2 that received a high dose ($2.5\times10^{11}$ GC) of AAV9.CB7.hIDUA, and 1 that received a low dose ($5\times10^{10}$ GC). All 3 died on study Day 18 or 19. Histopathology in the immunized group was consistent with a severe cell-mediated immune response to transduced cells in peripheral organs, with moderate to severe myocarditis occurring in 8 out of 50 animals and moderate to severe hepatitis occurring in 8 out of 50 animals. Both findings correlated with vector dose and timing of vector administration, with the most severe findings occurring 14 days after vector administration. Findings in the brain were less severe; moderate meningitis or encephalitis occurred in 3 animals treated with a high vector dose and 1 animal treated with a low vector dose. These findings did not correlate with the time of vector administration. Other findings in the brain were minimal or mild.

Overall the results in the naïve (non-immunized) cohort were consistent with the induction of an immune response to the human transgene, as evidenced by lymphocytic infiltration of the liver, and to a lesser degree the heart, both organs which are transduced by AAV9 that escapes to the peripheral circulation following IT injection[1,2]. In this setting toxicity was evident at the highest dose evaluated ($2.5\times10^{11}$ GC).

In the pre-immunized cohort, the immunization strategy appeared to induce a robust cell-mediated immune response to the transgene, resulting in moderate to severe myocarditis and hepatitis in some vector treated animals. Toxicity correlated with vector dose. Since the experimental design was based on immunization against a non-species specific protein in normal mice, the applicability to patients previously treated with ERT is unclear.

Example 7—AAV9.CB7.hIDUA Vector Injected Intrathecally (IT) in Non-Human Primates The following non-human primate (NHP) safety studies involved fluoroscopy guided suboccipital injection (cisterna magna) using two doses. The Low Dose (LD) was $1.1\times10^{10}$ GC/g and the High Dose (HD) was $1.1\times10^{11}$ GC/g (equivalent to canine maximum tolerated dose (MTD)). For the arm involving HD with immune suppression (IS), the protocol involved co-administration of MMF and Sirolimus as follows: MMF from Day −21 to Day 60 and Sirolimus from Day −21 until Day 90. There were no clinical findings and no clinically significant abnormalities in serum chemistry or hematology parameters in the tested NHP. There was evidence of anti-AAV and anti-hIDUA immune response and immune-mediated axonopathy. These data are provided in FIGS. 22-23 and the table below.

The histological findings are not shown. Axonopathy in dorsal columns (ascending sensory tracts) at high dose was found to have an axonopthy score 2 (0 to 4 scale) (vehicle control, normal). The dorsal root ganglia gangioneuritis at high dose was observed to have perineuronal inflammatory cells, neuronal degeneration, satellite cells activation and proliferation (vehicle control, normal).

For AAV9.hIDUA, neuronal degeneration is limited to DRG (data not shown). For the cervical spinal cord (ventral horns) for high dose without immunosuppression, no sign of inflammation around the motor neurons expression hIDUA is observed. For the cervical (DRG) for high dose without immunosuppression, inflammation is observed around DRG neurons expressing hIDUA. A prevalence of about 1-2 neuron per 100 is observed. The inflammatory infiltrate is shown to be primarily CD 20 positive B lymphocytes and CD3 positive T lymphocytes with few CD68 positive macrophages. Lymphocytes were clustered around hIDUA positive transduced neurons. Small inflammatory nodules replacing missing neurons.

Immunosuppression ameliorated but did not uniformly prevent immune-mediated DRG gangioneurites (data not shown). The results illustrated are four images from three different animals, all receiving the same vector, but having variations in their immune responses. ForRA1404 cervical (DRG), high dose with immunosuppression, MMR stopped @ day 36, axonopathy score is 0 and cumulative is 0. No inflammation around DRG neurons expressing hIDUA is observed. For RA0747 cervical (DRG) at high dose with immunosuppression, axonopathy score (cervical 1, cumulative 4), inflammation is observed around DRG neurons expressing hIDUA. CD3+T lymphocytes are not organized or clustered. No CD20+ positive B lymphocytes are observed in infiltrate. For a third animal (RA1528) cervical (DRG) at high dose with immunosuppression, axonapthy score was cervical 1, cumulative 4. Inflammation is observed around DRG neurons expressing hIDUA. CD3+T lymphocytes and CD20+ positive B lymphocytes are observed in clusters.

Immunosuppression ameliorated but did not uniformly prevent immune-mediated DRG gangioneurites. The data is presented in tabular form and includes control, low dose, high dose, and high dose with immunosuppression.

| Group | (1) Vehicle Control | (2) AAV9.hIDUA Low Dose* | (3) AAV9.hIDUA High Dose* | (4) AAV9.hIDUA High Dose + Immuno-suppression |
|---|---|---|---|---|
| Spinal Cord-Axonopathy | | | | |
| Cervical | 0/1 | 3/3 (1, 2, 1) | 2/3 (0, 2, 2) | 1/3 (0, 0, 1) |
| Thoracic | 0/1 | 3/3 (1, 1, 1) | 3/3 (1, 2, 1) | 2/3 (0, 0, 1) |
| Lumbar | 0/1 | 3/3 (2, 2, 1) | 3/3 (1, 2, 1) | 2/3 (0, 0, 2) |
| Dorsal Root Ganglia Gang lioneuritis | | | | |
| Cervical | 0/0 | 1/2 | 2/3 | 2/3 |
| Thoracis | 0/1 | 2/3 | 3/3 | 2/3 |
| Lumbar | 0/1 | 3/3 | 3/3 | 1/3 |

A. Safety and Biodistribution

This study evaluated the safety and biodistribution of AAV9.CB7.hIDUA for up to 180 days after administration by image-guided suboccipital puncture in rhesus macaques. Adult rhesus macaques (n=9, 6 females, 3 males, Groups 1A, B and C) were administered a single dose of $10^{13}$ GC AAV9.CB7.hIDUA by image guided suboccipital puncture, corresponding approximately to a dose of $1.1 \times 10^{11}$ GC/g of brain mass. An additional 3 animals (2 females, 1 male, Groups 2A and B) were administered a single dose of vehicle (Elliotts Be +0.001% Pluronic® F68) by image guided suboccipital puncture. Animals were euthanized and necropsied on Day 14 (Groups 1A and 2A), Day 90 (Groups 1B and 2B), or Day 180 (Group 1C) after test article or control article administration. Toxicity was evaluated by daily observations, and by physical exams, CBCs and serum chemistry panels, coagulation panels, and analysis of CSF cell counts, protein and glucose concentration on Study Days 0, 3, 7, 14, 21, 30, 45, 60 and 90. At necropsy, tissues were evaluated for gross lesions and examined microscopically by a pathologist. T cell responses against the vector capsid and transgene product were evaluated by ELISPOT, and antibody responses against the transgene product were measured in serum and CSF by ELISA. Vector biodistribution was assessed by qPCR.

There were no adverse events (AEs) associated with the administration procedure. From the first time point evaluated, Study Day 14, AAV vector genomes could be detected throughout the brain and spinal cord of all treated animals (levels around 104 GC/µg DNA) and were persistent at the same levels in the brain and spinal cord of animals euthanized and necropsied on Day 90 and 180. There was also significant vector distribution to peripheral organs, particularly the liver and spleen (105 to 106 GC/µg DNA), reticuloendothelial tissues (lymph nodes and bone marrow 103 to 104 GC/µg DNA), and heart (103 to 104 GC/µg DNA). These data suggest that vector spreads to the periphery and liver transduction is possible following intrathecal vector delivery.

An immune response, both humoral and T-cell mediated, was elicited to the human IDUA protein. This response seemed to correlate with transient CSF mononuclear pleocytosis, and with a histological finding of spinal cord dorsal white matter axonopathy (observed throughout the spinal cord at Days 90 and 180). These findings were not associated with clinical abnormalities or histological evidence of damage to tissues other than dorsal funiculi of the spinal cord. Based on this finding, a no observable adverse effect level (NOAEL) could not be defined with the testing of a single dose of $10^{13}$ GC (approximately $1.1 \times 10^{11}$ GC/g brain mass) in rhesus macaques.

1. Materials and Methods

An AAV9.hIDUA test vector was assessed (in Elliots B®+0.001% Pluronic® F68). This study included 12 rhesus macaques. Animals were randomly assigned to 5 groups. Study Groups 1A, 1B and 1C consisted of 1 male and 2 female macaques treated with test vector and euthanized and necropsied on Study Day 14±2; 90±2; or 180±2, respectively. Animals in Group 2A and 2B were treated with vehicle (Elliot's formulation buffer) and euthanized and necropsied on Day 14±2 or 90±2, respectively.

The IT route via image-guided suboccipital puncture was selected because it is the proposed route for clinical use. A dose of $10^{13}$ GC was selected, as this dose is similar (on a dose per gram brain mass basis) to the maximally tolerated dose in MPS I dogs, and is 10-fold greater than the proposed starting dose for first-in-human studies.

On Study Day 0, animals were anesthetized and placed on an X-ray table in the lateral decubitus position with the head flexed forward for CSF collection and dosing into the cisterna magna. The site of injection was sterilely prepped. Using aseptic technique, a 21-27 gauge, 1-1.5 inch Quincke spinal needle (Becton Dickinson) was advanced into the suboccipital space until the flow of CSF was observed. Up to 1.0 mL of CSF was collected for baseline analysis. Correct placement of the needle was verified via myelography, using a fluoroscope (OEC9800 C-Arm, GE). After CSF collection, a Luer access extension catheter was connected to the spinal needle to facilitate dosing of Iohexol (Trade Name: Omnipaque 180 mg/mL, General Electric Healthcare) contrast media and test or control article. Up to 1 mL of Iohexol was administered via the catheter and spinal needle. After confirming correct placement of the needle by observation of the contrast agent in the cisterna magna, a syringe containing the test article or vehicle (volume of 1.4 mL, equivalent to 1 mL plus the volume of syringe and linker dead space) was connected to the flexible linker and slowly injected over 20-60 seconds. The needle was removed and direct pressure applied to the puncture site.

2. Results

There were no adverse events associated with the vector administration procedure. AAV vector genomes were detected throughout the brain and spinal cord of all AAV9.hIDUA test vector—treated animals at all measured time points and levels were comparable across time in these tissues. There was also significant vector distribution to peripheral organs, especially the liver, and vector genome levels in peripheral tissues were also comparable across time. There were no clinical, gross, or histological findings in vehicle controls nor in test vector animals euthanized at 14 days. A mild, transient CSF mononuclear pleocytosis was observed in 5/6 AAV9.hIDUA—treated animals, peaking around 30 days post-dose.

Serum and CSF antibodies to hIDUA (the transgene product) were detected in 6/6 AAV9.hIDUA test vector—treated animals from day 21 and peripheral T cell responses to hIDUA peptides were observed in 4/6 test vector—treated animals at day 90, and 1/3 tested animal at day 180. Microscopically, in 6/6 AAV9.hIDUA test vector—treated animals, there was minimal to moderate axonopathy in the dorsal sensory white matter tracts of the spinal cord suggestive of cell body injury within the sensory neurons of the dorsal root ganglia (DRG not available for histological evaluation). The anatomic location of the axonopathy in the ascending dorsal sensory tracts suggests specific involvement of sensory neurons from the dorsal root ganglia. The fact that those neurons are usually heavily transduced after intrathecal AAV administration and the time course of CSF antibodies (from day 21), of CSF pleocytosis (peak at day 30), and the presence of transgene specific T-cell response in the majority of animals at day 90 suggest that a cell mediated cytotoxic immune response to hIDUA occurred in the dorsal root ganglia.

B. NHP Toxicity

The objectives of this exploratory GLP study were to evaluate the safety of IC administered AAV9.hIDUA test vector at 2 dose levels: $1 \times 10^{12}$ GC total ($1.1 \times 10^{10}$ GC/g of brain mass) and $1 \times 10^{13}$ GC total ($1.1 \times 10^{11}$ GC/g of brain mass) and to evaluate the effect of immunosuppressive therapy on the safety of IC administered R AAV9.hIDUA test vector at the high dose. The immunosuppressive regimen consisted of Sirolimus (rapamycin) and mycophenolate mofetil (MMF) given daily starting at least 2 weeks prior to AAV9.hIDUA test vector dosing and continuing through Day 60 (MMF) and Day 90 (Sirolimus) at doses that maintained plasma trough levels as close as possible to 10 to 15 mg/L for Sirolimus and 2 to 3.5 mg/mL for mycophenolate acid (active metabolite of MMF).

Adult rhesus macaques (N=9, 6 males and 3 females, Groups 2 to 4) were administered a single dose of either $1 \times 10^{12}$ or $10^{13}$ GC total AAV9.hIDUA by image-guided suboccipital puncture. An additional male animal (Group 1) was administered a single dose of vehicle (Elliotts B®+0.001% Pluronic® F68) by image-guided suboccipital puncture. Consistent with the study in Part A of this Example, there were AEs associated with the administration procedure, and no treatment-related effects on clinical general observations, body weight change, CBC, serum chemistry, or coagulation parameters. IS had an expected impact mostly on body weight and CBC.

AAV vector genomes were detected throughout the brain, spinal cord, and dorsal root ganglia of all AAV9.hIDUA test vector-treated animals. All but 1 AAV9.hIDUA test vector treated animals developed both humoral and T-cell immune responses to hIDUA that were not dose-dependent. IS prevented humoral immune responses against hIDUA only. IS does not prevent cellular immune response occurred between Day 60 and Day 90 in ⅔ of the IS animals against hIDUA or AAV9 capsid. Treatment-related findings were observed on histological analysis and consisted of minimal to mild spinal cord dorsal columns axonopathy that was not dose dependent. In the dorsal root ganglia that contain the neuronal cell bodies that project in the dorsal columns, there was minimal to moderate neuronal cell body degeneration with mononuclear cell infiltration. The dose level of AAV9.hIDUA did not impact the presence nor intensity of the findings in spinal cord and dorsal root ganglia. IS did not eliminate the axonopathy in the majority animals receiving IS. These data support the potential efficacy of IC administration of AAV9.hIDUA to reverse the CNS manifestations of MPS I, but also suggest that IS may be needed in the clinical setting to achieve optimal efficacy and safety.

Based on the observed findings of DRG neuronal degeneration, of T- and B-lymphocyte infiltration around sensory neurons expressing hIDUA, and of humoral and T-cell immune responses to hIDUA, it was concluded that immune-mediated destruction of a small proportion of transduced sensory neurons in the dorsal root ganglia led to the minimal-to-mild dorsal columns axonopathy by degeneration of the axons belonging to injured DRG neurons (die back phenomenon).

The findings of DRG neuronal degeneration and dorsal column axonopathy were present at similar incidence and severity in the low-dose ($1 \times 10^{12}$ GC) and high-dose ($1 \times 10^{13}$ GC) groups. Based on this finding, a NOAEL could not be defined in rhesus macaques injected IT with AAV9.hIDUA test vector. Incidence and severity of the finding were decreased in the high-dose ($1 \times 10^{13}$ GC) IS group, suggesting the cause of this finding was immune related.

C. Study Summary and Conclusions

These data show that immune-mediated destruction of DRG neurons may cause axonopathy. Perineuronal inflammatory infiltration was observed around DRG neurons expressing hIDUA and neuronal death. Mild to moderate axonopathy was observed in dorsal funiculi containing ascending axons originating from DRG. Animals with abnormal findings all have both humoral and T cell response to transgene product. Animals were clinically normal throughout the study. The immunosuppressive regimen used (MMF+sirolimus) attenuated but did not consistently prevent immune response to transgene. No correlation between axonopathy and anti-AAV9 response was observed. From this, it was concluded that immunosuppression is required in initial studies with AAV9.hIDUA to minimize the risk of immune mediated injury to neuronal cells. In conclusion, preclinical studies support the development of IT AAV9 based gene therapies to address neurocognitive symptoms in MPS I (AAV9.hIDUA). The results of pre-clinical studies necessitate the inclusion of immune suppression along with therapy with AAV9.hIDUA to minimize the risk of immune mediated toxicity

Example 8: Manufacture of rAAV9.CB7.hIDUA Vector

The AAV9.CB7.hIDUA is be produced by triple plasmid transfection of human HEK293 MCB cells with: (i) the hIDUA vector genome plasmid, (ii) an AAV helper plasmid termed pAAV29 containing the AAV rep2 and cap 9 wild-type genes and (iii) a helper adenovirus plasmid termed pAdΔF6(Kan). The size of the packaged vector genome is 4344nt.

Cloning of the plasmid pAAV.CV7.CI.hIDUAco.RGB above; the plasmid is 7,165 bp in size. The vector genome derived from this plasmid is a single-stranded DNA genome with AAV2 derived ITRs flanking the hIDUA expression cassette. Expression from the transgene cassette is driven by a CB7 promoter, a hybrid between a cytomegalovirus (CMV) immediate early enhancer (C4) and the chicken beta actin promoter, while transcription from this promoter is enhanced by the presence of the chicken beta actin intron (CI). The polyA signal for the expression cassette is the rabbit beta-globin (RBG) polyA. The plasmid was constructed by codon-optimizing and synthesizing the hIDUA sequence [SEQ ID NO: 1] and the resulting construct was then cloned into the plasmid pENN.AAV.CB7.CI.RBG (p1044), an AAV2 ITR-flanked expression cassette containing CB7, CI and RBG expression elements to give pAAV.CB7.CI.hIDUAco.RBG (p3032).

Cloning of the cis plasmid pAAV.CB7CIhIDUA.RGB.KanR: The vector genome was excised from p3032 using the PacI restriction enzyme and cloned into a pKSS-based plasmid backbone (p2017) containing the kanamycin resistance gene. The final vector genome plasmid is pAAV.CB7.CI.hIDUAco.RBG.KanR.

AAV2/9 helper plasmid pAAV29KanRRep2: The AAV2/9 helper plasmid pAAV29KanRRep2 encodes the 4 wild-type AAV2 rep proteins and the 3 wild-type AAV VP capsid proteins from AAV9. To create the chimeric packaging construct, first the AAV2 cap gene from plasmid p5E18, containing the wild type AAV2 rep and cap genes, was removed and replaced with a PCR fragment of the AAV9 cap gene amplified from liver DNA. The resulting plasmid was given the identifier pAAV2-9 (p0008). Note that the AAV p5 promoter which normally drives rep expression is moved in this construct from the 5' end of rep to the 3' end of cap. This arrangement serves to introduce a spacer between the promoter and the rep gene (i.e. the plasmid backbone), down-regulate expression of rep and increase the ability to support vector production. The plasmid backbone in p5E18 is from pBluescript KS. The AAV2/9 helper plasmid pAAV29KanRRep2 encodes the 4 wild-type AAV2 rep proteins, the 3 wild-type AAV VP capsid proteins from AAV9, and kanamycin resistance.

pAdDeltaF6(Kan) adenovirus helper plasmid is 15,770 bp in size. The plasmid contains the regions of adenovirus genome that are important for AAV replication, namely E2A, E4, and VA RNA (the adenovirus E1 functions are provided by the 293 cells), but does not contain other adenovirus replication or structural genes. The plasmid does not contain the cis elements critical for replication such as the adenoviral inverted terminal repeats and therefore, no infectious adenovirus is expected to be generated. It was derived from an E1, E3 deleted molecular clone of Ad5 (pBHG10, a pBR322 based plasmid). Deletions were introduced in the Ad5 DNA to remove expression of unnecessary adenovirus genes and reduce the amount of adenovirus DNA from 32 Kb to 12 kb. Finally, the ampicillin resistance gene was replaced by the kanamycin resistance gene to give pAdAF6 (Kan). The functional elements of the E2, E4 and VAI adenoviral genes necessary for AAV vector production remain in this plasmid. The adenoviral E1 essential gene functions are supplied by the HEK293 cells. DNA plasmid sequencing was performed by Qiagen Genomic Services and revealed 100% homology with the following important functional elements of the reference sequence pAdDeltaF6 (Kan) p1707FH-Q: E4 ORF6 3692-2808 bp; E2A DNA binding protein 11784-10194 bp; VA RNA region 12426-13378 bp.

A flow diagram summarizing the manufacturing process is provided in FIG. 11.

Cell Seeding: A qualified human embryonic kidney 293 cell line will be used for the production process. Cells will be expanded to 5×109-5×1010 cells using Corning T-flasks and CS-10, which will allow sufficient cell mass to be generated for seeding up to 50 HS-36 for vector production per BDS lot. Cells will be cultivated in medium composed of Dulbecco's Modified Eagle Medium (DMEM), supplemented with 10% gamma irradiated, US-sourced, Fetal Bovine Serum (FBS). The cells are anchorage dependent and cell disassociation will be accomplished using TrypLE Select, an animal product-free cell dissociation reagent. Cell seeding is accomplished using sterile, single-use disposable bioprocess bags and tubing sets. The cells will be maintained at 37° C. (±2° C.), in 5% (±0.5%) CO2 atmosphere. Cell culture media will be replaced with fresh, serum free DMEM media and transfected with the three production plasmids using an optimized PEI-based transfection method. All plasmids used in the production process will be produced in the context of a CMO quality system and infrastructure utilizing the most salient features of cGMP manufacturing; traceability, document control, and materials segregation.

Sufficient DNA plasmid transfection complex will be prepared in the BSC to transfect up to 50 HS-36 (per BDS batch). Initially a DNA/PEI mixture will be prepared containing 7.5 mg of pAAV.CB7.CI.hIDUAco.RBG.KanR vector genome plasmid, 150 mg of pAdDeltaF6(Kan), 75 mg of pAAV29KanRRep2 AAV helper plasmid and GMP grade PEI (PEIPro, PolyPlus Transfection SA). This plasmid ratio was determined to be optimal for AAV production in small scale optimization studies. After mixing well, the solution is allowed to sit at room temperature for 25 min. and then added to serum-free media to quench the reaction and then added to the HS-36's. The transfection mixture is equalized between all 36 layers of the HS-36 and the cells are incubated at 37° C. (±2° C.) in a 5% (±0.5%) CO2 atmosphere for 5 days.

Cell Media Harvesting: Transfected cells and media will be harvested from each HS-36 using disposable bioprocess bags by aseptically draining the medium out of the units. Following the harvest of media, the ~80-liter volume will be supplemented with MgCl2 to a final concentration of 2 mM (co-factor for Benzonase) and Benzonase nuclease (Cat #: 1.016797.0001, Merck Group) will be added to a final concentration of 25 units/ml. The product (in a disposable bioprocess bag) will be incubated at 37° C. for 2 hr in an incubator to provide sufficient time for enzymatic digestion of residual cellular and plasmid DNA present in the harvest as a result of the transfection procedure. This step is performed to minimize the amount of residual DNA in the final vector. After the incubation period, NaCl will be added to a final concentration of 500 mM to aid in the recovery of the product during filtration and downstream tangential flow filtration (see below steps 4 and 5).

Clarification: Cells and cellular debris will be removed from the product using a depth filter capsule (1.2 µm/0.22 um) connected in series as a sterile, closed tubing and bag set that is driven by a peristaltic pump. Clarification assures that downstream filters and chromatography columns will be protected from fouling and bioburden reduction filtration ensures that at the end of the filter train, any bioburden potentially introduced during the upstream production process will be removed before downstream purification. The harvest material will be passed through a Sartorius Sartoguard PES capsule filter (1.2/0.22 µm) (Sartorius Stedim Biotech Inc.).

Large-scale Tangential Flow Filtration: Volume reduction (10-fold) of the clarified product will be achieved by Tangential Flow Filtration (TFF) using a custom sterile, closed bioprocessing tubing, bag and membrane set. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface preventing membrane pore fouling. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This results in a modest purification of the clarified product, but also achieves buffer exchange compatible with the subsequent affinity column chromatography step. Accordingly, we utilize a 100 kDa, PES membrane for concentration that is then diafiltrated with 4 volumes of a buffer composed of: 20 mM Tris pH 7.5 and 400 mM NaCl. The diafiltered product will be stored overnight at 4° C. and then further clarified with a 1.2 µm/0.22 um depth filter capsule to remove any precipitated material.

Affinity Chromatography: The diafiltered product will be applied to a Capture Select™ Poros-AAV2/9 affinity resin (Life Technologies) that efficiently captures the AAV2/9 serotype. Under these ionic conditions, a significant percentage of residual cellular DNA and proteins flow through the column, while AAV particles are efficiently captured. Following application, the column is washed to remove additional feed impurities followed by a low pH step elution (400 mM NaCl, 20 mM Sodium Citrate; pH 2.5) that is immediately neutralized by collection into a 1/10th volume of a neutralization buffer (Bis Tris Propane, 200 mM, pH 10.2).

Anion Exchange Chromatography: To achieve further reduction of in-process impurities including empty AAV particles, the Poros-AAV2/9 elution pool is diluted 50-fold (20 mM Bis Tris Propane, 0.001% Pluronic F68; pH 10.2) to reduce ionic strength to enable binding to a CIMultus Q monolith matrix (BIA Separations). Following a low-salt wash, vector product is eluted using a 60 CV NaCl linear salt gradient (10-180 mM NaCl). This shallow salt gradient effectively separates capsid particles without a vector genome (empty particles) from particles containing vector genome (full particles) and results in a preparation enriched for full capsids. Fractions will be collected into tubes containing 1/100th volume of 0.1% pluronic F68 and 1/27th volume of Bis Tris pH 6.3 to minimize non-specific binding to tubes and the length of exposure to high pH respectively. The appropriate peak fraction will be collected, and the peak area assessed and compared to previous data for determination of the approximate vector yield.

Final Formulation and Sterile Filtration to yield the BDS: TFF will be used to achieve final formulation on the pooled AEX fractions with a 100 kDa membrane. This will be achieved by diafiltration with 4 volumes of formulation buffer (Elliots B solution, 0.001% Pluronic F68) and concentrated to yield the BDS, whereby the peak area from the anion exchange chromatography will be compared to previous data in order to estimate the concentration factor to achieve a titer of $\geq 5\times 10^{13}$ GC/ml. Samples will be removed for BDS testing (described in the section below). The filtered Purified Bulk will be stored in sterile polypropylene tubes and frozen at $\leq -60°$ C. in a quarantine location until release for Final Fill. Preliminary stability study indicates that the DP does not lose activity following freezing and thawing in our proposed formulation buffer. Additional studies are underway to assess stability following prolonged storage at $-80$ C.

Final Fill: The frozen BDS will be thawed, pooled, diluted to the target titer using the final formulation buffer, terminally filtered through a 0.22 um filter (Millipore, Billerica, Mass.) and filled into West Pharmaceutical's "Ready-to-Use" (pre-sterilized) 2 ml glass vials and 13 mm stoppers and seals at a fill volume $\geq 0.6$ ml to $<2.0$ ml per vial. Individually labeled vials will be labeled according to the specifications below. Labeled vials are stored at $\leq -60°$ C.

The vector (drug product) will be vialed at a single fixed concentration and the only variable will be the volume per vial. To achieve lower dose concentrations, the drug product will be diluted with Elliots B solution, 0.001% Pluronic F68. The high dose vector will be used directly without dilution while the low vector will require a 1:5 dilution in the formulation buffer which will be conducted by the pharmacy at the time of dosing.

Example 9: Testing of Vector

Characterization assays including serotype identity, empty particle content and transgene product identity are performed. Descriptions of the assays appear below.

A. Vector Genome Identity: DNA Sequencing

Viral Vector genomic DNA will be isolated and the sequence determined by 2-fold sequencing coverage using primer walking. Sequence alignment will be performed and compared to the expected sequence.

B. Vector Capsid Identity: AAV Capsid Mass spectrometry of VP3

Confirmation of the AAV2/9 serotype of the vector is achieved by an assay based upon analysis of peptides of the VP3 capsid protein by mass spectrometry (MS). The method involves multi-enzyme digestion (trypsin, chymotrypsin and endoproteinase Glu-C) of the VP3 protein band excised from SDS-PAGE gels followed by characterization on a UPLC-MS/MS on a Q-Exactive Orbitrap mass spectrometer to sequence the capsid protein. A tandem mass spectra (MS) method was developed that allows for subtraction of the host protein products and deriving capsid peptide sequence from mass spectra.

C. Genomic Copy (GC) Titer

The oqPCR based genomic copy titer will be determined over a range of serial dilutions and compared to the cognate plasmid standard (pAAV.CB7.CI.hIDUAco.RBG.KanR). The oqPCR assay utilizes sequential digestion with DNase I and Proteinase K, followed by qPCR analysis to measure encapsidated vector genomic copies. DNA detection will be accomplished using sequence specific primers targeting the RBG polyA region in combination with a fluorescently tagged probe hybridizing to this same region. Comparison to the plasmid DNA standard curve allows titer determination without the need of any post-PCR sample manipulation. A number of standards, validation samples and controls (for background and DNA contamination) have been introduced into the assay. This assay is currently not qualified, but will be qualified by the CMO. The assay will be qualified by establishing and defining assay parameters including sensitivity, limit of detection, range of qualification and intra and inter assay precision. An internal AAV9 reference lot will be established and used to perform the qualification studies. Note that our previous experience suggests that the titer obtained by the optimized qPCR assay described here is generally 2.5 fold higher than that achieved by our standard qPCR technique which was used for the generation of the pre-clinical data.

D. Empty to Full Particle Ratio

The total particle content of the drug product will be determined by SDS-PAGE analysis. A reference vector preparation purified on an iodixanol gradient is analyzed by various methods (analytical ultracentrifugation, electron microscopy and absorbance at 260/280 nm) to established that the preparation contains >95% genome-containing (full) particles. This reference material is serially diluted to known genome copy numbers (and thus by extension, particle numbers) and each dilution is run on an SDS PAGE gel along with a similar dilution series of the drug product. Peak area volumes of both the reference material and drug product VP3 protein bands are determined by densitometry and the reference material volumes are plotted versus particle number. The total particle concentration of the drug product is determined by extrapolation from this curve and the genome copy (GC) titer is then subtracted to obtain the empty particle titer. The empty to full particle ratio is the ratio of the empty particle titer to the GC titer.

E. Infectious Titer

The infectious unit (IU) assay is used to determine the productive uptake and replication of vector in RC32 cells (rep2 expressing HeLa cells). A 96-well end-point format has been employed similar to that previously published. Briefly, RC32 cells are co-infected by serial dilutions of rAAV9.CB.hIDUA and a uniform dilution of Ad5 with 12 replicates at each dilution of rAAV. Seventy-two hours after infection the cells are lysed, and qPCR performed to detect rAAV vector amplification over input. An end-point dilution TCID50 calculation (Spearman-Karber) is performed to determine a replicative titer expressed as IU/ml. Since "infectivity" values are dependent on particles coming into contact with cells, receptor binding, internalization, transport to the nucleus and genome replication, they are influenced by assay geometry and the presence of appropriate receptors and post-binding pathways in the cell line used. Receptors and post-binding pathways are not usually maintained in immortalized cell lines and thus infectivity assay titers are not an absolute measure of the number of "infectious" particles present. However, the ratio of encapsidated GC to "infectious units" (described as GC/IU ratio) can be used as a measure of product consistency from lot to lot.

The GC/IU ratio is a measure of product consistency. The oqPCR titer (GC/ml) is divided by the "infectious unit (IU/ml) to give the calculated GC/IU ratio.

F. Replication-competent AAV (rcAAV) Assay

A sample will be analyzed for the presence of replication competent AAV2/9 (rcAAV) that can potentially arise during the production process. A 3 passage assay has been developed consisting of cell-based amplification and passage followed by detection of rcAAV DNA by real-time qPCR (cap 9 target). The cell-based component consists of inoculating monolayers of HEK293 cells (P1) with dilutions of the test sample and wild-type human adenovirus type 5 (Ad5). $10^{10}$ GC of the vector product will be the maximal amount of the product tested. Due to the presence of adenovirus, replication competent AAV will amplify in the cell culture. After 2 days, a cell lysate is generated and Ad5 heat inactivated. The clarified lysate is then passed onto a second round of cells (P2) to enhance sensitivity (again in the presence of Ad5). After 2 days, a cell lysate is generated and Ad5 heat inactivated. The clarified lysate is then passed onto a third round of cells (P3) to maximize sensitivity (again in the presence of Ad5). After 2 days, cells are lysed to release DNA which is then subjected to qPCR to detect AAV9 cap sequences. Amplification of AAV9 cap sequences in an Ad5 dependent manner indicates the presence of rcAAV. The use of a AAV2/9 surrogate positive control containing AAV2 rep and AAV9 cap genes enables the Limit of Detection (LOD) of the assay to be determined (0.1, 1, 10 and 100 IU) and using a serial dilution of rAAV9.CB7.hIDUA vector ($1 \times 10^{10}$, $1 \times 10^9$, $1 \times 10^8$, $1 \times 10^7$ GC) the approximate level of rcAAV present in the test sample can be quantitated.

G. In Vitro Potency

To relate the qPCR GC titer to gene expression, an in vitro bioassay will be performed by transducing Huh7 or HEK293 cells with a known multiplicity of GCs per cell and assaying the supernatant for IDUA activity 72 hours post-transduction. IDUA activity is measured by incubating sample diluted in 0.1 ml water with 0.1 ml of 100 mmol/l 4 MU-iduronide at 37 degrees for 1-3 hours. The reaction is stopped by the addition of 2 ml 290 mmol/l glycine, 180 mmol/l sodium citrate, pH 10.9 and liberated 4 MU is quantified by comparing fluorescence to standard dilutions of 4 MU. Comparison to highly active pre-clinical and tox vector preparations will enable interpretation of product activity.

H. Total Protein, Capsid Protein, Protein Purity Determination and Capsid Protein Ratio Vector samples are first quantified for total protein against a Bovine Serum Albumin (BSA) protein standard curve using a bicinchoninic acid (BCA) assay. The determination is made by mixing equal parts of sample with a Micro-BCA reagent provided in the kit. The same procedure is applied to dilutions of a BSA Standard. The mixtures are incubated at 60° C. and absorbance measured at 562 nm. A standard curve is generated from the standard absorbance of the known concentrations using a 4-Parameter fit. Unknown samples are quantified according to the 4-Parameter regression.

To provide a semi-quantitative determination of AAV purity, the samples will then be normalized for genome titer and $5 \times 10^9$ GC separated on an SDS-polyacrylamide (SDS-PAGE) gel under reducing conditions. The gel is then stained with SYPRO Ruby dye. Any impurity bands are quantified by densitometry by comparison to co-electrophoresed BSA standards of 25, 50, and 100 ng of protein per lane. These quantities represent 1%, 2% and 4% of the total AAV protein sample. Stained bands that appear in addition to the three AAV specific proteins VP1, VP2 and VP3 are considered protein impurities. All impurity bands are compared to the reference proteins and the impurity mass percent as well as approximate molecular weight are reported. The SDS-PAGE gels will also be used to quantify the VP1, VP2 and VP3 proteins and determine their ratio.

Example 10: Biodistribution and Brain Enzyme

Adult cynomolgus macaques are injected suboccipitally with $1\times10^{12}$ GC/kg AAV9.CMV.hIDUA. 636 days later, tissues are harvested and immediately frozen down to $-80°$ C. Total cellular DNA is extracted from tissue using a QIAamp DNA Mini Kit (Qiagen, Valencia, Calif., USA). Detection and quantification of vector genomes in extracted DNA are performed by real-time PCR (TaqMan Universal Master Mix, Applied Biosystems, Foster City, Calif., USA) using primer and probe sets targeted to sequences within the SV40 polyA. The PCR conditions are set at 100 ng total cellular DNA as template, 300 nM primers, and 200 nM probes each. Cycles were for 10 min at 95.8° C., 40 cycles of 15 s at 95.8° C., and 1 min at 60.8° C.

Adult MPS I knockout mice are injected with $3\times10^8$, $3\times10^9$, or $3\times10^{10}$ GC/mouse AAV9.CB7.hIDUA into the right lateral ventricle. 21 days later whole brains are harvested and immediately frozen down to $-80°$ C. Tissue samples homogenized in lysis buffer (0.2% Triton-X100, 0.9% NaCl, pH 4.0), and briefly sonicated. Samples are then freeze-thawed and clarified by centrifugation. Protein concentrations are determined by BCA assay. IDUA activity is measured by incubating sample diluted in 0.1 ml water with 0.1 ml of 100 mmol/l 4 MU-iduronide (Toronto Research Chemicals, Toronto, Canada; Glycosynth, Warrington, England) in IDUA buffer (0.15 mol/l NaCl, 0.05% Triton-X100, 0.1 mol/l sodium acetate, pH 3.58) at 37° C. for 1-3 hours. The reaction is stopped by addition of 2 ml 290 mmol/l glycine, 180 mmol/l sodium citrate, pH 10.9. The liberated 4 MU is quantified by comparing fluorescence to standard dilutions of 4 MU. Units are given as nmol 4 MU liberated per hour per mg of protein.

Example 11: MPSI Biomarker

In the present study, metabolite profiling of CSF samples from MPS I dogs was performed, which revealed substantial disease related alterations in the CSF metabolome. The most striking difference was an over 30-fold elevation in spermine levels compared to normal controls. This finding was confirmed in MPS I patient samples, as well as in a feline model of MPS I. Spermine binds to HS, and cellular uptake of spermine is dependent on this interaction [M. Belting, S. Persson, L.-Å. Fransson, Proteoglycan involvement in polyamine uptake. Biochemical Journal 338, 317-323 (1999); J. E. Welch, P. Bengtson, K. Svensson, A. Wittrup, G. J. Jenniskens, G. B. Ten Dam, T. H. Van Kuppevelt, M. Belting, Single chain fragment anti-heparan sulfate antibody targets the polyamine transport system and attenuates polyamine-dependent cell proliferation. International journal of oncology 32, 749-756 (2008); published online Epub April]. Cell surface proteoglycans such as glypican-1 can bind spermine through their HS moieties, and after endocytosis of the glypican protein, intracellular cleavage of the HS chain releases bound spermine into the cell (K. Ding, S et al, The Journal of biological chemistry 276, 46779-46791 (2001); published online Epub December 14. Thus, intact HS recycling is essential for spermine uptake. In MPS I, extracellular spermine accumulation could occur through inhibition of this uptake mechanism due to inefficient HS recycling, or through simple binding of spermine to the extracellular GAGS that accumulate in MPS, shifting the spermine binding equilibrium to favor extracellular distribution. Future studies should address the relative contribution of these mechanisms to spermine accumulation in MPS I CSF.

We found that inhibitors of spermine synthesis blocked excess neurite growth in MPS neurons, and that neurite growth could be induced in WT neurons by spermine concentrations similar to those found in patient CSF. Gene therapy in the dog model of MPS I reversed spermine accumulation and normalized expression of GAP43, suggesting that the same pathway was impacted in vivo. We could not directly evaluate the impact of spermine synthesis inhibition in vivo, as available inhibitors do not cross the blood-brain barrier, and chronic direct CNS administration from birth is not feasible in our animal models. While our in vitro findings support a role for spermine in aberrant neurite growth in MPS I, it is important to note that inhibiting spermine synthesis did not completely reverse the phenotype, and spermine addition to normal neurons did not increase neurite growth to the level of MPS I neurons. The effects of spermine modulation may have been limited by the relatively short period of treatment. It is also possible that spermine accumulation is not the sole mediator contributing to neurite outgrowth in MPS I. Notably many neurotrophic factors bind through HS modified receptors, and interactions with HS in extracellular matrix can influence neurite growth [D. Van Vactor, et al, Heparan sulfate proteoglycans and the emergence of neuronal connectivity. Current opinion in neurobiology 16, 40-51 (2006); published online Epub February (10.1016/j.conb.2006.01.011)]. Spermine accumulation may therefore be one of several factors promoting abnormal neurite growth in MPS I.

Of the 15 MPS I dog CSF samples screened, only one fell within the normal range of spermine concentration. At 28 days of age, this was the youngest animal included in the study. This finding indicates that spermine accumulation may be age dependent. Future studies should evaluate CSF spermine levels longitudinally in MPS patients. If spermine increases with age in MPS patients, this could explain the kinetics of cognitive decline, as most patients experience 1-2 years of normal development before the onset of developmental delays.

The potential for impaired HS metabolism to trigger accumulation of a metabolite that alters neuron growth could point to a novel connection between enzyme deficiencies and the abnormal neurite growth phenotype in MPSI, which may explain the cognitive dysfunction associated with these disorders. These findings also indicate that CSF spermine may be useful as a noninvasive biomarker for assessing pharmacodynamics of novel CNS-directed therapies for MPSI.

Materials and Methods:

Experimental design: This study was initially designed to detect metabolites that were present at significantly different levels in MPS I patient CSF samples compared to samples from healthy controls. Due to the limited availability of CSF samples from children with MPS IH and healthy controls, the initial screen was performed using CSF samples from MPS I dogs, for which greater numbers were available, with the intention of subsequently evaluating candidate biomarkers in human samples. A total of 15 CSF samples from individual untreated MPS I dogs were available for analysis, and an additional 15 samples were obtained from healthy controls. Following identification of elevated spermine in MPS I dog CSF in the prospective metabolite screen, spermine was retrospectively measured in CSF samples from previous studies of MPS I dogs and cats treated with gene therapy, as well as patient samples. The number of subjects included in each group for these analyses was limited by sample availability and was not based on statistical considerations; therefore in some cases numbers are insufficient for statistical comparisons. For studies of in vitro neurite growth, the number of cells quantified for each condition was based on pilot experiments which indicated that >30 cells per condition was required to detect a 20% difference in arbor length, neurite number or neurite branches per cell. After cells were plated and treated with the designated drug, the wells were coded and the acquisition of cell images and the manual quantification of neurite length and branching were performed by a blinded reviewer. The comparison of wildtype and MPS mouse neurons was repeated using a different substrate [poly-L-lysine (Sigma) coated tissue culture plates rather than chamber slides (Sigma S6815)] with similar results. The comparison of wildtype neurons with and without spermine addition was performed four times using both substrates with similar results. CSF metabolite profiling: CSF metabolite profiling was performed by Metabolon.

Samples were stored at −80° C. until processing. Samples were prepared using the MicroLab STAR® system (Hamilton Company). A recovery standard was added prior to the first step in the extraction process for QC purposes. Proteins were precipitated with methanol under vigorous shaking for 2 min followed by centrifugation. The resulting extract was divided into five fractions: one for analysis by reverse phase (RP)UPLC-MS/MS with positive ion mode electrospray ionization, one for analysis by RP/UPLC-MS/MS with negative ion mode electrospray ionization, one for analysis by hydrophilic interaction chromatography (HILIC)/UPLC-MS/MS with negative ion mode electrospray ionization, one for analysis by GC-MS, and one sample was reserved for backup. Samples were placed briefly on a TurboVap® (Zymark) to remove the organic solvent. For LC, the samples were stored overnight under nitrogen before preparation for analysis. For GC, each sample was dried under vacuum overnight before preparation for analysis.

The LC/MS portion of the platform was based on a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. The sample extract was dried then reconstituted in solvents compatible to each of the LC/MS methods. Each reconstitution solvent contained a series of standards at fixed concentrations to ensure injection and chromatographic consistency. For RP chromatography, one aliquot was analyzed using acidic positive ion optimized conditions and the other using basic negative ion optimized conditions Each method utilized separate dedicated columns (Waters UPLC BEH C18-2.1× 100 mm, 1.7 μm). The extracts reconstituted in acidic conditions were gradient eluted using water and methanol containing 0.1% formic acid. The basic extracts were similarly eluted using methanol and water, however with 6.5 mM ammonium bicarbonate. The third aliquot was analyzed via negative ionization following elution from a HILIC column (Waters UPLC BEH Amide 2.1×150 mm, 1.7 μm) using a gradient consisting of water and acetonitrile with 10 mM ammonium formate. The MS analysis alternated between MS and data-dependent MSn scans using dynamic exclusion. The scan range varied slightly between methods but covered 80-1000 m/z.

The samples destined for analysis by GC-MS were dried under vacuum for a minimum of 18 h prior to being derivatized under dried nitrogen using bistrimethyl-silyltrifluoroacetamide. Derivatized samples were separated on a 5% diphenyl/95% dimethyl polysiloxane fused silica column (20 m×0.18 mm ID; 0.18 um film thickness) with helium as carrier gas and a temperature ramp from 60° to 340° C. in a 17.5 min period. Samples were analyzed on a Thermo-Finnigan Trace DSQ fast-scanning single-quadrupole mass spectrometer using electron impact ionization (EI) and operated at unit mass resolving power. The scan range was from 50-750 m/z.

Several types of controls were analyzed in concert with the experimental samples: a pooled matrix sample generated by taking a small volume of each experimental sample served as a technical replicate throughout the data set; extracted water samples served as process blanks; and a cocktail of QC standards that were carefully chosen not to interfere with the measurement of endogenous compounds were spiked into every analyzed sample, allowed instrument performance monitoring and aided chromatographic alignment. Instrument variability was determined by calculating the median relative standard deviation (RSD) for the standards that were added to each sample prior to injection into the mass spectrometers. Overall process variability was determined by calculating the median RSD for all endogenous metabolites (i.e., non-instrument standards) present in 100% of the pooled matrix samples. Experimental samples were randomized across the platform run with QC samples spaced evenly among the injections.

Metabolites were identified by automated comparison of the ion features in the experimental samples to a reference library of chemical standard entries that included retention time, molecular weight (m/z), preferred adducts, and in-source fragments as well as associated MS spectra and curated by visual inspection for quality control using software developed at Metabolon. Identification of known chemical entities was based on comparison to metabolomics library entries of purified standards. Peaks were quantified using area-under-the-curve measurements. Raw area counts for each metabolite in each sample were normalized to correct for variation resulting from instrument inter-day tuning differences by the median value for each run-day, therefore, setting the medians to 1.0 for each run. This preserved variation between samples but allowed metabolites of widely different raw peak areas to be compared on a similar graphical scale. Missing values were imputed with the observed minimum after normalization.

Quantitative MS assay: CSF samples (50 μL) were mixed with a spermine-d8 internal standard (IsoSciences). Samples were deproteinized by mixing with a 4-fold excess of methanol and centrifuging at 12,000×g at 4° C. The supernatant was dried under a stream of nitrogen, and then resuspended in 50 μL of water. An aliquot of 5 μL was subjected to LC-MS analysis. The LC separations were carried out using a Waters ACQUITY UPLC system (Waters Corp., Milford, Mass., USA) equipped with an Xbridge® C18 column (3.5 μm, 150×2.1 mm). The flow-rate was 0.15 mL/min, solvent A was 0.1% formic acid and solvent B was 98/2 acetonitrile/H2O (v/v) with 0.1% formic acid. The elution conditions were as follows: 2% B at 0 min, 2% B at 2 min, 60% B at 5 min, 80% B at 10 min, 98% B at 11 min, 98% B at 16 min, 2% B at 17 min, 2% B at 22 min, with the column temperature being 35° C. A Finnigan TSQ Quantum Ultra spectrometer (Thermo Fisher, San Jose, Calif.) was used to conduct MS/MS analysis in positive ion mode with the following parameters: spray voltage at 4000 V, capillary temperature at 270° C., sheath gas pressure at 35 arbitrary units, ion sweep gas pressure at 2 arbitrary units, auxiliary gas pressure at 10 arbitrary units, vaporizer temperature at 200° C., tube lens offset at 50, capillary offset at 35 and skimmer offset at 0. The following transitions were monitored: 203.1/112.1 (spermine); 211.1/120.1 (spermine-d8) with scan width of 0.002 m/z, and scan time being 0.15 s.

Animal procedures: All animal protocols were approved by the Institutional Animal Care and Use Committee of the University of Pennsylvania. For CSF metabolite screening, samples were collected by suboccipital puncture in normal dogs at 3-26 months of age, and in MPS I dogs at 1-18 months of age. Gene transfer studies in MPS I dogs and cats were performed as previously described (20, 22). CSF samples were collected 6-8 months after vector administration. For mouse cortical neuron experiments, primary cortical neuron cultures were prepared from E18 IDUA−/− or IDUA+/+ embryos.

Patient samples: CSF metabolite profiling: Metabolite profiling was performed as described (metabolon ref) Informed consent was obtained from each subject's parent or legal guardian. The protocol was approved by the Institutional Review Board of the University of Minnesota. CSF was collected by lumbar puncture. All MPS I patients had a diagnosis of Hurler syndrome and had not received enzyme replacement therapy or hematopoietic stem cell transplantation prior to sample collection. MPS I patients were 6-26 months of age. The healthy controls were 36 and 48 months of age.

Statistical analysis: The random forest analysis and heat map generation were performed using MetaboAnalyst 3.0 [R. G. Kalb, Development 120, 3063-3071 (1994); J. Zhong, et al, Journal of neurochemistry 64, 531-539 (1995) D. Van Vactor, D. P. W et al, Current opinion in neurobiology 16, 40-51 (2006); published online Epub February (10.1016/j.conb.2006.01.011). Raw peak data were log transformed and normalized to the mean of normal sample values. All other statistical analyses were performed with GraphPad Prism 6. Cultured neuron arbor length, neurite number, and branching were compared by ANOVA followed by Dunnett's test. CSF spermine and cortical GAP43 were compared by Kruskal-Wallis test followed by Dunn's test.

GAP43 western: Samples of frontal cortex were homogenized in 0.2% triton X-100 using a Qiagen Tissuelyser at 30 Hz for 5 min. Samples were clarified by centrifugation at 4° C. Protein concentration was determined in supernatants by BCA assay. Samples were incubated in NuPAGE LDS buffer with DTT (Thermo Fisher Scientific) at 70° C. for 1 hr and separated on a Bis-Tris 4-12% polyacrylamide gel in MOPS buffer. Protein was transferred to a PVDF membrane, and blocked for 1 hr in 5% nonfat dry milk. The membrane was probed with rabbit polyclonal anti-GAP43 antibody (Abcam) diluted to 1 mg/mL in 5% nonfat dry milk followed by an HRP conjugated polyclonal anti-rabbit antibody (Thermo Fisher Scientific) diluted 1:10,000 in 5% nonfat dry milk. Bands were detected using SuperSignal West Pico substrate (Thermo Fisher Scientific). Densitometry was performed using Image Lab 5.1 (Bio-Rad).

Neurite growth assay: Day 18 embryonic cortical neurons were harvested as described above, and plated at a concentration of 100,000 cells/mL on chamber slides (Sigma S6815) or poly-L-lysine (Sigma) coated tissue culture plates in serum-free Neurobasal medium (Gibco) supplemented by B27 (Gibco). Treatments were applied to duplicate wells 24 hours after plating (day 1). Phase-contrast images for quantification were taken on a Nikon Eclipse Ti at 20× using a 600 ms manual exposure and 1.70× gain on high contrast. An individual blind to treatment conditions captured 10-20 images per well and coded them. Images were converted to 8-bit format in ImageJ (NIH) and traced in NeuronJ by a blinded reviewer. Soma diameter, neurite number, branch points, and arbor length were traced manually. Images traced in NeuronJ were converted to micrometers using a conversion factor based on image size; 2560×1920 pixel images were converted to micrometers using a conversion factor of 0.17 micrometers/pixel.

Histology: Brain tissue processing and LIMP2 immunofluorescence were performed as previously described [C. Hinderer, et al, Molecular therapy: the journal of the American Society of Gene Therapy 22, 2018-2027 (2014); published online Epub December (10.1038/mt.2014.135)].

RT-PCR: Samples of frontal cortex from 3 normal dogs and 5 MPS dogs were immediately frozen on dry ice at necropsy. RNA was extracted with TRIzol reagent (Thermo Fisher Scientific), treated with DNAse I (Roche) for 20 min at room temperature, and purified using an RNeasy kit (Qiagen) according to the manufacturer's instructions. Purified RNA (500 ng) was reverse transcribed using the High Capacity cDNA Synthesis Kit (Applied Biosystems) with random hexamer primers. Transcripts for arginase, ornithine decarboxylase, spermine synthase, spermidine synthase, spermine-spermidine acetyltransferase and glyceraldehyde phosphate dehydrogenase were quantified by Sybr green PCR using an Applied Biosystems 7500.

Real-Time PCR System. A standard curve was generated for each target gene using four-fold dilutions of a pooled standard comprised of all individual samples. The highest standard was assigned an arbitrary transcript number, and Ct values for individual samples were converted to transcript numbers based on the standard curve. Values are expressed relative to the GAPDH control.

Statistical analysis: Random forest analysis and heat map generation were performed using MetaboAnalyst 3.0 [J. Xia, et al, MetaboAnalyst 2.0—a comprehensive server for metabolomic data analysis. Nucleic Acids Research, (2012); published online Epub May 2, 2012 (10.1093/nar/gks374); J. Xia, et al., MetaboAnalyst: a web server for metabolomic data analysis and interpretation. Nucleic Acids Research 37, W652-W660 (2009); published online Epub Jul. 1, 2009 (10.1093/nar/gkp356). J. Xia, et al, MetaboAnalyst 3.0—making metabolomics more meaningful. Nucleic Acids Research, (2015); published online Epub Apr. 20, 2015 (10.1093/nar/gkv380)]. Undetectable values in the metabolite screen were imputed with the minimum values observed in the data set. Raw peak data were normalized to the mean of normal sample values and log transformed. All other statistical analyses were performed with GraphPad Prism 6. Cultured neuron arbor length, neurite number, and branching were compared by ANOVA followed by Dunnett's test. CSF spermine and cortical GAP43 were compared by Kruskal-Wallis test followed by Dunn's test.

Results

1. Identification of Elevated CSF Spermine Through Metabolite Profiling

An initial screen of CSF metabolites was carried out using a canine model of MPS I. These animals carry a splice site mutation in the IDUA gene, resulting in complete loss of enzyme expression and development of clinical and histological features analogous to those of MPS I patients (K. P. Menon, et al, Genomics 14, 763-768 (1992); R. Shull, et al., The American journal of pathology 114, 487 (1984). CSF samples were collected from 15 normal dogs and 15 MPS I dogs. CSF samples were evaluated for relative quantities of metabolites by LC and GC-MS. A total of 281 metabolites could be positively identified in CSF samples by mass spectrometry. Of these, 47 (17%) were significantly elevated in MPS I dogs relative to controls, and 88 (31%) were decreased relative to controls. A heat map of the 50 metabolites most different between groups is shown in FIG. 17A. Metabolite profiling identified marked differences in polyamine, sphingolipid, acetylated amino acid, and nucleotide metabolism between MPS I and normal dogs. Random forest clustering analysis identified the polyamine spermine as the largest contributor to the metabolite differences between MPS I and normal dogs (FIG. 21). On average spermine was more than 30-fold elevated in MPS I dogs, with the exception of one MPS I dog that was under 1 month of age at the time of sample collection. A stable isotope dilution (SID)-LC-MS/MS assay was developed to quantitatively measure spermine in CSF. Samples were screened from 6 children with Hurler syndrome (ages 6-26 months), as well as 2 healthy controls (ages 36 and 48 months). Both healthy controls had CSF spermine levels below the limit of quantification (1 ng/mL) of the assay, whereas CSF samples from MPS I patients were on average 10-fold above the limit of quantification (FIG. 17B). Spermine elevation in MPS IH patients appeared consistent with the known role of HS in spermine binding and uptake (M. Belting, et al, Journal of Biological Chemistry 278, 47181-47189 (2003); M. Belting, et al, Proteoglycan involvement in polyamine uptake. Biochemical Journal 338, 317-323 (1999); J. E. Welch, et al, International journal of oncology 32, 749-756 (2008))]. Increased synthesis appeared unlikely as a cause of elevated CSF spermine, as normal and MPS I dog brain samples had similar mRNA expression levels for transcriptionally regulated enzymes in the polyamine synthetic pathway.

2. Role of Spermine in Abnormal Neurite Growth Associated with MPS

Following axon injury neurons upregulate polyamine synthesis, which promotes neurite outgrowth (D. Cai, et al, Neuron 35, 711-719 (2002); published online Epub August 15; K. Deng, et al, The Journal of neuroscience: the official journal of the Society for Neuroscience 29, 9545-9552 (2009); published online Epub July 29; Y. Gao, et al, Neuron 44, 609-621 (2004); published online Epub November 18; R. C. Schreiber, et al., Neuroscience 128, 741-749 (2004)). We therefore evaluated the role of spermine in the abnormal neurite overgrowth phenotype that has been described in MPS neurons (Hocquemiller, S., et al, Journal of neuroscience research 88, 202-213 (2010)). Cultures of E18 cortical neurons from MPS I mice exhibited greater neurite number, branching, and total arbor length after 4 days in culture than neurons derived from wild type mice from the colony (FIGS. 19A-F. Treatment of MPS neurons with APCHA, an inhibitor of spermine synthesis, significantly reduced neurite growth and branching. The effect was reversible by replacing spermine (FIGS. 18A-F). The same APCHA concentration did not affect the growth of normal neurons. Addition of spermine to wild type neuron cultures at concentrations similar to those identified in vivo resulted in significant increases in neurite growth and branching (FIGS. 18A-18F).

3. Impact of Gene Therapy on CSF Spermine and GAP43 Expression

In order to evaluate the effect of IDUA deficiency on GAP43 expression and spermine accumulation in vivo, we measured CSF spermine and brain GAP43 levels in untreated MPS I dogs as well as those treated with CNS directed gene therapy. We previously described five MPS I dogs that were treated with an intrathecal injection of an adeno-associated virus serotype 9 vector carrying the canine IDUA transgene (C. Hinderer, et al, Molecular therapy: the journal of the American Society of Gene Therapy 23, 1298-1307 (2015); published online Epub August). MPS I dogs can develop antibodies to the normal IDUA enzyme, so two of the dogs were pre-treated as newborns with hepatic IDUA gene transfer to induce immunological tolerance to the protein. Both tolerized dogs exhibited brain IDUA activity well above normal following AAV9 treatment. The three non-tolerized dogs exhibited varying levels of expression, with one animal reaching levels greater than normal and the other two exhibiting expression near normal (FIGS. 19A-D). CSF spermine reduction was inversely proportional to brain IDUA activity, with a 3-fold reduction relative to untreated animals in the two dogs with the lowest IDUA expression, and more than 20-fold reduction in the animal with the highest expression (FIGS. 19A-19D).GAP43 was upregulated in frontal cortex of MPS I dogs, and expression was normalized in all vector treated animals (FIGS. 19A-19D).

We further evaluated the relationship between CSF spermine levels and IDUA reconstitution in MPS I dogs treated with a range of vector doses. MPS I dogs previously tolerized to human IDUA by neonatal hepatic gene transfer were treated with intrathecal injection of an AAV9 vector expressing human IDUA at one of 3 doses (1010, 1011, 1012 GC/kg, n=2 per dose) (C. Hinderer, et al, Neonatal tolerance induction enables accurate evaluation of gene therapy for MPS I in a canine model. Molecular Genetics and Metabolism, dx.doi.org/10.1016/j.ymgme.2016.06.006)). CSF spermine was evaluated 6 months after injection (FIG. 20A-20B). Reduction of CSF spermine was dose dependent, with animals at the mid and high vector doses reaching the normal range, whereas CSF spermine was only partially reduced in the low dose animals. For independent verification of the connection between IDUA deficiency and CSF spermine accumulation, we evaluated CSF spermine levels in a feline model of MPS I. Using CSF samples from our previously reported gene therapy studies, we found that untreated MPS I cats exhibited elevated CSF spermine (FIG. 20A-20B) (C. Hinderer, et al, Molecular therapy: the journal of the American Society of Gene Therapy 22, 2018-2027 (2014); published online Epub December (10.1038/mt.2014.135)). Intrathecal administration of a high dose of an AAV9 vector expressing feline IDUA normalized CSF spermine levels (FIG. 20A).

C. Discussion

In the present study we performed metabolite profiling of CSF samples from MPS I dogs, which revealed substantial disease related alterations in the CSF metabolome. The most striking difference was an over 30-fold elevation in spermine levels compared to normal controls. This finding was confirmed in MPS I patient samples, as well as in a feline model of MPS I. Spermine binds directly to HS with high affinity, and cellular uptake of spermine is dependent on this interaction (M. Belting, S. PERSSON, L.-A. Fransson, Proteoglycan involvement in polyamine uptake. Biochemical Journal 338, 317-323 (1999); J. E. Welch, et al, International journal of oncology 32, 749-756 (2008)). Cell surface proteoglycans such as glypican-1 can bind spermine through their HS moieties, and after endocytosis of the glypican protein, intracellular cleavage of the HS chain releases bound spermine into the cell (Belting et al, cited above; K. Ding, et al, The Journal of biological chemistry 276, 46779-46791 (2001); published online Epub December 14). Thus, intact HS recycling is essential for spermine uptake. Inefficient HS recycling due to IDUA deficiency could inhibit this spermine uptake mechanism, leading to extracellular spermine accumulation. Alternatively, extracellular GAGS may sequester spermine, shifting the equilibrium to favor extracellular distribution. The methanol deproteinization step employed for LC-MS sample preparation in this study also precipitates soluble HS, suggesting that the spermine detected in CSF is unbound, and therefore that uptake inhibition rather than GAG binding is responsible for extracellular spermine accumulation (N. Volpi, Journal of chromatography. B, Biomedical applications 685, 27-34 (1996); published online Epub October 11). Formation and maintenance of functional neural networks requires precise control of neurite growth and synapse formation. During development, the CNS environment becomes increasingly inhibitory to neurite formation, with myelin associated proteins largely blocking neurite growth in the adult brain. This developmental shift toward decreased neurite growth is paralleled by a decrease in GAP43 expression (S. M. De la Monte, et al, Developmental Brain Research 46, 161-168 (1989); published online Epub4/1/). The persistent GAP43 expression and exaggerated neurite outgrowth exhibited by MPS neurons may interfere with this normal balance of inhibitory and growth promoting signals, resulting in abnormal connectivity and impaired cognition (Hocquemiller et al, cited above). How HS storage leads to this increase in neurite growth has not been established. A number of studies have implicated polyamines in neurite outgrowth; following axon injury, the rate-limiting enzymes for the synthesis of spermine and its precursors putrescine and spermidine are elevated, allowing for enhanced neurite outgrowth even in the presence of inhibitory signals from myelin (Cia (2002), Deng (2009), Gao (2004), all cited above-). Further, treatment of neurons with putrescine induces neurite growth when injected directly into CSF, an effect that is blocked by inhibitors of spermine synthesis (Deng (2009) cited above). The mechanism by which polyamines exert their effect on neurite growth is not known. One potential target is the NMDA receptor, activation of which is potentiated by spermine binding (J. Lerma, Neuron 8, 343-352 (1992); published online Epub2//(dx.doi.org/10.1016/0896-6273 (92)90300-3)). NMDA signaling induces neurite outgrowth, and the spermine sensitive subunit of the receptor is highly expressed during development (D. Georgiev, et al, Experimental cell research 314, 2603-2617 (2008); published online Epub August 15 (10.1016/j.yexcr.2008.06.009); R. G. Kalb, Regulation of motor neuron dendrite growth by NMDA receptor activation. Development 120, 3063-3071 (1994); J. Zhong, et al, Journal of neurochemistry 64, 531-539 (1995). Notably many neurotrophic factors bind through HS modified receptors, and interactions with HS in extracellular matrix can influence neurite growth (D. Van Vactor, et al, Current opinion in neurobiology 16, 40-51 (2006); published online Epub February (10.1016/j.conb.2006.01.011)). Spermine accumulation may therefore be one of several factors promoting abnormal neurite growth in MPS I. Of the 15 MPS I dog CSF samples screened, only one fell within the normal range of spermine concentration. At 28 days of age, this was the youngest animal included in the study. This finding indicates that spermine accumulation may be age dependent, although this study demonstrates that it is already elevated by 6 months of age in infants with Hurler syndrome. Future studies should evaluate CSF spermine levels longitudinally in MPS patients. If spermine increases with age in MPS patients, this could explain the kinetics of cognitive decline, as most patients experience 1-2 years of normal development before the onset of developmental delays. The potential for impaired HS metabolism to trigger accumulation of a metabolite that alters neuron growth could point to a novel connection between enzyme deficiencies and the abnormal neurite growth phenotype in MPS, which may explain the cognitive dysfunction associated with these disorders. Future studies should confirm spermine elevation in other MPSs. These findings also indicate that CSF spermine may be useful as a noninvasive biomarker for assessing pharmacodynamics of novel CNS-directed therapies for MPS. Future trials for CNS directed therapies should evaluate the correlation between cognitive endpoints and changes in CSF spermine.

Example 12: CT Guided ICV Delivery Device

A. Pre-Procedural Screening Assessments

1. Protocol Visit 1: Screening

The principal investigator will describe the screening process that leads up to the intracisternal (IC) procedure, the administration procedure itself, and all potential safety risks in order for the subject (or designated caregiver) to be fully informed upon signing the informed consent.

The following will be performed and provided to the neuroradiologist/neurosurgeon/anesthesiologist in their screening assessment of subject eligibility for the IC procedure: Medical history; concomitant medications; physical exam; vital signs; electrocardiogram (ECG); and laboratory testing results.

2. Interval: Screening to Study Visit 2

In order to allow adequate time to review eligibility, the following procedures should be performed at any time between the first screening visit and up to one week prior to study Visit 2 (Day 0):

Head/Neck Magnetic Resonance Imaging (MRI) with and without gadolinium [note: Subject must be suitable candidate to receive gadolinium (i.e., eGFR>30 mL/min/1.73 m$^2$)]

In addition to the Head/Neck MRI, the investigator will determine the need for any further evaluation of the neck via flexion/extension studies MRI protocol will include T1, T2, DTI, FLAIR, and CINE protocol images Head/Neck MRA/MRV as per institutional protocol (note: Subjects with a history of intra/transdural operations may be excluded or may need further testing (e.g., radionucleotide cisternography) that allows for adequate evaluation of CSF flow and identification of possible blockage or lack of communication between CSF spaces.

Neuroradiologist/neurosurgeon subject procedural evaluation meeting: The representatives from the 3 sites will have a conference call (or web-meeting) to discuss the eligibility of each subject for the IC procedures based on all available information (scans, medical history, physical exam, labs, etc.). All attempts should be made to achieve consensus on proceeding forward with the IC procedure or screen failing the subject (i.e., each member should be prepared to accept the decision made).

Anesthesia pre-op evaluation Day −28 to Day 1, with detailed assessment of airway, neck (shortened/thickened) and head range-of-motion (degree of neck flexion), keeping in mind the special physiologic needs of the MPS subject.

3. Day 1: Computerized Tomography Suite & Vector Preparation for Administration.

Prior to the IC procedure, the CT Suite will confirm the following equipment and medications are present:

Adult lumbar puncture (LP) kit (supplied per institution)

BD (Becton Dickinson) 22 or 25 gauge×3-7" spinal needle (Quincke bevel)

Coaxial introducer needle (e.g., 18 G×3.5"), used at the discretion of the interventionalist (for introduction of spinal needle)

4 way small bore stopcock with swivel (Spin) male luer lock

T-connector extension set (tubing) with female luer lock adapter, approximate length 6.7"

Omnipaque 180 (iohexol), for intrathecal administration

Iodinated contrast for intravenous (IV) administration

1% lidocaine solution for injection (if not supplied in adult LP kit)

Prefilled 10 cc normal saline (sterile) flush syringe

Radiopaque marker(s)

Surgical prep equipment/shaving razor

Pillows/supports to allow proper positioning of intubated subject

Endotracheal intubation equipment, general anesthesia machine and mechanical ventilator Intraoperative neurophysiological monitoring (IONM) equipment (and required personnel)

10 cc syringe containing AAV9.hIDUA vector; prepared and transported to CT/Operating Room (OR) suite in accordance with separate Pharmacy Manual 4. Day 1: Subject Preparation & Dosing Informed Consent for the study and procedure will be confirmed and documented within the medical record and/or study file. Separate consent for the procedure from radiology and anesthesiology staff will be obtained as per institutional requirements.

Study subject will have intravenous access placed within the appropriate hospital care unit according to institutional guidelines (e.g., two IV access sites). Intravenous fluids will be administered at the discretion of the anesthesiologist.

At the discretion of the anesthesiologist and per institutional guidelines, study subject will be induced and undergo endotracheal intubation with administration of general anesthesia in an appropriate patient care unit, holding area or the surgical/CT procedure suite.

A lumbar puncture will be performed, first to remove 5 cc of cerebrospinal fluid (CSF) and subsequently to inject contrast (Omnipaque 180) intrathecally to aid visualization of the cisterna magna. Appropriate subject positioning maneuvers will be performed to facilitate diffusion of contrast into the cisterna magna.

If not already done so, intraoperative neurophysiological monitoring (IONM) equipment will be attached to subject.

Subject will be placed onto the CT scanner table in the prone or lateral decubitus position.

If deemed appropriate, subject will be positioned in a manner that provides neck flexion to the degree determined to be safe during pre-operative evaluation and with normal neurophysiologic monitor signals documented after positioning.

The following study staff and investigator(s) will be confirmed to be present and identified on-site:
  Interventionalist/neurosurgeon performing the procedure
  Anesthesiologist and respiratory technician(s)
  Nurses and physician assistants
  CT (or OR) technicians
  Neurophysiology technician
  Site Research Coordinator The subject's skin under the skull base will be shaved as appropriate.

CT scout images will be performed, followed by a pre-procedure planning CT with IV contrast, if deemed necessary by the interventionalist to localize the target location and to image vasculature.

Once the target site (cisterna magna) is identified and needle trajectory planned, the skin will be prepped and draped using sterile technique as per institutional guidelines.

A radiopaque marker will be placed on the target skin location as indicated by the interventionalist.

The skin under the marker will be anesthetized via infiltration with 1% lidocaine.

A 22 G or 25 G spinal needle will be advanced towards the cisterna magna, with the option to use a coaxial introducer needle.

After needle advancement, CT images will be obtained using the thinnest CT slice thickness feasible using institutional equipment (ideally ≤2.5 mm). Serial CT images should use the lowest radiation dose possible that allows for adequate visualization of the needle and relevant soft tissues (e.g., paraspinal muscles, bone, brainstem, and spinal cord).

Correct needle placement will be confirmed by observation of CSF in the needle hub and visualization of needle tip within the cisterna magna.

The interventionalist will confirm the syringe containing vector is positioned close to, but outside of the sterile field. Prior to handling or administering vector, site will confirm gloves, mask, and eye protection are donned by staff assisting the procedure within the sterile field (other staff outside of sterile field do not need to take these procedures).

The short (~6") extension tubing will be attached to the inserted spinal needle, which will then be attached to the 4-way stop cock. Once this apparatus is "self-primed" with the subject's CSF, the 10 cc prefilled normal saline flush syringe will be attached to the 4-way stop cock.

The syringe containing vector will be handed to the interventionalist and attached to a port on the 4-way stop cock.

Once the stop cock port to the syringe containing vector is opened, the syringe contents are to be injected slowly (over approximately 1-2 minutes), with care taken not to apply excessive force onto the plunger during the injection.

Once the contents of the syringe containing AAV9.hIDUA test vector injected, the stop cock will be turned so that the stopcock and needle assembly can be flushed with 1-2 cc of normal saline using the attached prefilled syringe.

When ready, the interventionist will alert staff that he/she will remove the apparatus from the subject.

In a single motion, the needle, extension tubing, stopcock, and syringes will be slowly removed from the subject and placed onto a surgical tray for discarding into a biohazard waste receptacle or hard container (for the needle).

The needle insertion site will be examined for signs of bleeding or CSF leakage and treated as indicated by the investigator. Site will be dressed using gauze, surgical tape and/or Tegaderm dressing, as indicated.

Subject will be removed from the CT scanner and placed supine onto a stretcher.

Anesthesia will be discontinued and subject cared for following institutional guidelines for post-anesthesia care. Neurophysiologic monitors can be removed from study subject.

The head of the stretcher on which the subject lies should be slightly raised (~30 degrees) during recovery.

Subject will be transported to a suitable post-anesthesia care unit as per institutional guidelines.

After subject has adequately recovered consciousness and is in stable condition, he/she will be admitted to the appropriate floor/unit for protocol mandated assessments. Neurological assessments will be followed as per the protocol and the Primary Investigator will oversee subject care in collaboration with hospital and research staff.

Example 13: Evaluation of Intrathecal Routes of Administration in Large Animals

The purpose of this study was to evaluate more routine methods of administration into the CSF, including intraventricular (ICV) injection, and injection through a lumbar puncture. In brief, in this study ICV and IC AAV administration were compared in dogs. Vector administration was evaluated via lumbar puncture in nonhuman primates with some animals placed in Trendelenburg position after injection, a maneuver which has been suggested to improve cranial distribution of vector. In the dog study, ICV and IC vector administration resulted in similarly efficient transduction throughout brain and spinal cord. However, animals in the ICV cohort developed encephalitis, apparently due to a severe T cell response to the transgene product. The occurrence of this transgene-specific immune response only in the ICV cohort is suspected to be related to the presence of localized inflammation from the injection procedure at the site of transgene expression. In the NHP study, transduction efficiency following vector administration into the lumbar cistern was improved compared to our previous studies by using an extremely large injection volume (approximately 40% of total CSF volume). However, this approach was still less efficient than IC administration. Positioning animals in Trendelenburg after injection provided no additional benefit. However, it was found that large injection volumes could improve cranial distribution of the vector.

To maximize the effectiveness of intrathecal AAV delivery, it will be critical to determine the optimal route of vector administration into the CSF. We previously reported that vector injection into the cisterna magna (cerebellomedullary cistern) by suboccipital puncture achieved effective vector distribution in nonhuman primates, whereas injection via lumbar puncture resulted in substantially lower transduction of the spinal cord and virtually no distribution to the brain, underscoring the importance of the route of administration [Hinderer, Molecular Therapy Methods & Clinical Development. 12/10/online 2014; 1]. Others have suggested that vector delivery into the lateral ventricles, a common clinical procedure, results in effective vector distribution [Haurigot et al, J Clin Invest., August 2013; 123(8): 3254-3271]. It has also been reported that delivery via lumbar puncture can be improved by placing animals in the Trendelenburg position after injection to promote cranial vector distribution [Meyer et al, Molecular therapy: the journal of the American Society of Gene Therapy. Oct. 31, 2014]. In this study we compared intraventricular and intracisternal administration of an AAV9 vector expressing a green fluorescent protein (GFP) reporter gene in dogs. We found that both routes achieve effective distribution throughout the CNS, though intraventricular delivery may carry additional risks of a transgene-specific immune response. We also evaluated vector delivery by lumbar puncture in NHPs, and the impact of placing animals in the Trendelenburg position after injection. There was no clear effect of post-injection positioning, although we did find that large injection volumes could improve cranial distribution of the vector.

A. Materials and Methods:

1. Vector production: The GFP vector consisted of an AAV serotype 9 capsid carrying an expression cassette comprising a chicken beta actin promoter with cytomegalovirus immediate early enhancer, an artificial intron, the enhanced green fluorescent protein cDNA, a woodchuck hepatitis virus posttranscriptional regulatory element, and a rabbit beta globin polyadenylation sequence. The GUSB vector consisted of an AAV serotype 9 capsid carrying an expression cassette comprising a chicken beta actin promoter with cytomegalovirus immediate early enhancer, an artificial intron, the canine GUSB cDNA, and a rabbit beta globin polyadenylation sequence. The vectors were produced by triple transfection of HEK 293 cells and purified on an iodixanol gradient as previously described [Lock et al, Human gene therapy. October 2010; 21(10):1259-1271].

2. Animal experiments: All dogs were raised in the National Referral Center for Animal Models of Human Genetic Disease of the School of Veterinary Medicine of the University of Pennsylvania OD P40-010939) under National Institutes of Health and USDA guidelines for the care and use of animals in research.

3. NHP study: This study included 6 cynomolgus monkeys between 9 and 12 years of age. Animals were between 4 and 8 kg at the time of injection. The vector ($2\times10^{13}$ GC) was diluted in 5 mL of Omnipaque (Iohexol) 180 contrast material prior to injection. Injection of the vector via lumbar puncture was performed as previously described [Hinderer, Molecular Therapy—Methods & Clinical Development. 12/10/online 2014; 1]. Correct injection into the intrathecal space was verified by fluoroscopy. For animals in the Trendelenburg group, the head of the bed was lowered 30 degrees for 10 minutes immediately following injection. Euthanasia and tissue collection were performed as previously described [Hinderer, Molecular Therapy—Methods & Clinical Development. 12/10/online 2014; 1].

4. Dog study: This study included 6 one-year-old MPS I dogs. Baseline MRIs were performed on all ICV treated dogs to plan the injection coordinates. Intracisternal injection was performed as previously described [Hinderer et al, Molecular therapy: the journal of the American Society of Gene Therapy. August 2015; 23(8):1298-1307]. For ICV injection, dogs were anesthetized with intravenous propofol, endotracheally intubated, maintained under anesthesia with isoflurane and placed in a stereotaxic frame. The skin was sterilely prepped, and an incision was made over the injection site. A single burr hole was drilled at the injection site, through which a 26-gauge needle was advanced to the predetermined depth. Placement was confirmed by CSF return. The vector ($1.8\times10^{13}$ GC in 1 mL) was slowly infused over one to two minutes. Euthanasia and tissue collection were performed as previously described [Hinderer et al, Molecular therapy: the journal of the American Society of Gene Therapy. August 2015; 23(8):1298-1307].

5. Histology: Brains were processed as described for evaluation of GFP expression [Hinderer, Molecular Therapy—Methods & Clinical Development. 12/10/online 2014; 1]. GUSB enzyme stains and GM3 stains were performed as previously described [Gurda et al, Molecular therapy: the journal of the American Society of Gene Therapy. Oct. 8 2015.]

6. ELISPOT: At the time of necropsy blood was collected from vector treated dogs in heparinized tubes. Peripheral blood mononuclear cells were isolated by Ficoll gradient centrifugation. T cell responses to AAV9 capsid peptides and GFP peptides were evaluated by interferon gamma ELISPOT. AAV9 and GFP peptide libraries were synthesized as 15-mers with 10 amino acid overlap (Mimotopes). The AAV9 peptide library was grouped in 3 pools: Pool A from peptide 1 to 50, Pool B from peptide 51 to 100 and Pool C from peptide 101 to 146. The GFP peptide library was also grouped in 3 pools. Phorbol 12-myristate 13-acetate plus Ionomycin salt (PMA+ION) were used as positive control. DMSO was used as negative control. Cells were stimulated with peptide and interferon gamma secretion was detected as described. A response was considered positive if it was both greater than 55 Spots Forming Units (SFU) per million lymphocytes and at least 3 times the DMSO negative control value.

7. Biodistribution: At the time of necropsy tissues for biodistribution were immediately frozen on dry ice. DNA isolation and quantification of vector genomes by TaqMan PCR was performed as described [Wang et al, Human gene therapy. November 2011; 22(11):1389-1401].

8. GUSB enzyme assay: GUSB activity was measured in CSF as described [Gurda et al, Molecular therapy: the journal of the American Society of Gene Therapy. Oct. 8, 2015].

B. Results

1. Comparison of Intraventricular and Intracisternal Vector Delivery in Dogs

Our previous studies using a canine model of the lysosomal storage disease mucopolysaccharidosis type I (MPS I) demonstrated that AAV9 injection into the cisterna magna could effectively target the entire brain and spinal cord [Hinderer et al, Molecular therapy: the journal of the American Society of Gene Therapy. August 2015; 23(8):1298-1307]. In this study, we compared distribution of an AAV9 vector expressing a GFP reporter gene administered into the cisterna magna or lateral ventricle of adult MPS I dogs. Three dogs were treated with a single 1 mL injection of the vector ($1.8 \times 10^{13}$ genome copies) into the cisterna magna. Three additional dogs received a single vector injection of the same vector into the lateral ventricle. For dogs treated by ICV injection, a baseline MRI was performed to select the larger lateral ventricle for injection and to define the target coordinates. Injection was performed using a stereotaxic frame to accurately target the designated ventricle.

The three dogs treated with IC vector injection appeared healthy throughout the study. They were euthanized two weeks after vector injection for evaluation of vector biodistribution and transgene expression. No gross or microscopic brain lesions were observed in any IC treated dogs (FIG. 14). Measurement of vector genomes by quantitative PCR revealed vector deposition throughout all sampled regions of the brain and spinal cord (FIG. 15). Consistent with the distribution of vector genomes, robust transgene expression was detectable in most regions of cerebral cortex, as well as throughout the spinal cord. Spinal cord histology was notable for strong transduction of alpha motor neurons, with a gradient of transduction favoring thoracic and lumbar segments.

The three dogs treated with vector injected ICV initially appeared healthy following the procedure. However, one animal (I-567) was found dead 12 days after injection. The other two animals survived to the designated 14 day necropsy time point, although one animal (I-565) became stuporous prior to euthanasia, and the other (1-568) began to exhibit weakness of facial muscles. These clinical findings correlated with significant gross brain lesions. Brains from all three animals exhibited discoloration surrounding the needle track, with associated hemorrhage in the animal that was found dead. Histological evaluation revealed severe lymphocytic inflammation in the region surrounding the injection site. Perivascular lymphocytic infiltration was also observed throughout the brain of each animal. Given this evidence for immunological toxicity, T cell responses to both the AAV9 capsid protein and the GFP transgene were evaluated in peripheral blood samples collected from one of the ICV-treated dogs (I-565) at the time of necropsy. An interferon gamma ELISPOT showed a strong T cell response directed against GFP, with no evidence of a response to capsid peptides. This suggests that the encephalitis observed was caused by a cell-mediated immune response against the transgene product.

Vector distribution in the ICV treated animals was similar to that observed in the IC treated group, although spinal cord transduction was somewhat greater in the IC cohort (FIG. 15). GFP expression was observed throughout the CNS regions examined in the ICV treated animals.

The toxicity associated with ICV administration of an AAV9 vector expressing GFP was consistent with an immune response against the transgene product. Such an immune response might be particularly severe because the GFP transgene is entirely foreign; animals may be more immunologically tolerant to a transgene that is similar to an endogenous protein.

2. Impact of the Trendelenburg Position on CNS Transduction after AAV9 Administration by Lumbar Puncture in NHP We previously compared AAV9 injection into the cisterna magna or lumbar cistern of NHPs and found that the lumbar route was 10-fold less efficient for targeting the spinal cord and 100-fold less efficient for targeting the brain [C. Hinderer, et al, Molecular Therapy—Methods & Clinical Development. 12/10/online 2014; 1]. Other investigators have since demonstrated better transduction using AAV9 administration by lumbar puncture, with improvements in cranial distribution of the vector achieved by placing animals in the Trendelenburg position after injection [Myer et al, Molecular therapy: the journal of the American Society of Gene Therapy. Oct. 31, 2014]. In this approach the vector is diluted into an excess volume of contrast material to increase the density of the solution and promote gravity driven distribution while in Trendelenburg. Six adult cynomolgus monkeys were treated with a single injection of AAV9 expressing GFP ($2 \times 10^{13}$ genome copies) in the L3-4 interspace. The vector was diluted to a final volume of 5 mL in Iohexol 180 contrast material. Four of the animals were positioned with the head of the procedure table at a −30° angle for 10 minutes immediately after injection. After 10 minutes fluoroscopic images were captured to verify contrast distribution in the CSF. Notably with this large injection volume (approximately 40% of the total CSF volume of the animal) [Reiselbach et al, New England Journal of Medicine. 1962; 267(25):1273-1278] contrast material was rapidly distributed along the entire spinal subarachnoid space and into the basal cisterns even in animals that were not placed in Trendelenburg position (FIG. 18). Analysis of vector genome distribution by PCR (FIG. 19) and GFP expression (FIG. 20) demonstrated transduction throughout the brain and spinal cord. There was no apparent impact of post-injection positioning on the number or distribution of transduced cells. As previously reported, there was vector escape to the periphery and hepatic transduction after intrathecal AAV administration [Hinderer et al, Molecular Therapy—Methods & Clinical Development. 12/10/online 2014; 1; Haurigot et al, Journal of Clinical Investigation. August 2013; 123(8): 3254-3271]. The extent of liver transduction was dependent on the presence of pre-existing neutralizing antibodies (NAb) against AAV9. Four out of six animals had no detectable baseline AAV9 NAbs (titer <1:5) and two animals (4051 and 07-11) had detectable pre-existing antibodies to AAV9 with a titer of 1:40. Consistent with previous results, pre-existing antibodies blocked liver transduction, and resulted in increased vector distribution to the spleen [Wang et al, Human gene therapy. November 2011; 22(11):1389-1401, but had no impact on CNS transduction; Haurigot et al, Journal of Clinical Investigation. August 2013; 123(8):3254-3271].

C. Discussion

Because suboccipital puncture is not a common procedure in clinical practice, we evaluated more routine sites of CSF access, including the lateral ventricle and the lumbar cistern. Here we evaluated a method employing vector solutions with higher density and post-injection Trendelenburg positioning to improve vector distribution cranially from the lumbar region.

In the dog study, both IC and ICV vector injection yielded similarly effective vector distribution, but encephalitis occurred only in the ICV group. A T cell response against the GFP transgene was detectable in one of the ICV treated dogs, suggesting that the lymphocytic encephalitis observed in these animals was due to a transgene-specific immune response. Induction of a T cell response to a new antigen requires two elements—recognition of an epitope from the protein by a naïve T cell, and an inflammatory "danger signal" that promotes activation of the T cell. AAV is believed to be capable of expressing foreign transgenes without eliciting immunity against the transgene product because it does not activate the innate immune system, thereby avoiding inflammatory signals and promoting tolerance rather than immunity when naïve lymphocytes encounter the newly expressed antigen. Local inflammation caused by the trauma of penetrating the brain parenchyma, occurring at the same location that the foreign transgene product is expressed, may provide the danger signal needed to induce an immune response to the transgene product. This is supported by previous studies in MPS I dogs, which develop cell-mediated immune responses to an enzyme expressed from an AAV vector delivered by direct brain injection but not by IC injection [Ciron et al, Annals of Neurology. August 2006; 60(2):204-213; Hinderer, et al, Molecular therapy: the journal of the American Society of Gene Therapy. August 2015; 23(8):1298-1307]. The potential for such an immune response will depend on whether the transgene product is recognized as foreign—for delivery of vectors expressing a protein that is also produced endogenously, even an inflammatory response caused by injection may not break tolerance to the self protein. The same may be true for patients with recessive diseases who carry missense mutations that allow for production of a protein similar to the transgene product. Risk of immunity could, therefore, vary depending on patient population and transgene product, and in some cases immunosuppression may be necessary to prevent destructive T cell responses to a transgene. The present findings suggest that the risk of deleterious immune responses can likely be mitigated by using an IC rather than ICV route of administration.

The study of AAV9 administration via lumbar puncture in NHPs showed greater transduction throughout the CNS than we have previously observed with this route of administration. This difference appears to be due to the large injection volume in the present study, which was necessary in order to dilute the vector into an excess volume of contrast material. Previous studies have shown that such large volume injections (approximately 40% of CSF volume) can drive injected material directly into the basal cisterns and even the ventricular CSF of macaques [Reiselbach, cited above]. The potential to translate this approach to humans is unclear, given that replicating this approach would require extremely large injection volumes (>60 mL) that are not routinely administered to patients. Moreover, even with this high volume approach, injection via lumbar puncture was less efficient than previous results with IC delivery. In this previous study, animals were dosed by weight, so only one animal received an IC vector dose equivalent to that used here [Hinderer, et al, Molecular Therapy—Methods & Clinical Development. 12/10/online 2014; 1]. That animal had on average 3-fold higher vector distribution in the brain and spinal cord, indicating that even very large volume vector delivery to the lumbar cistern is less efficient than IC delivery. In contrast to reports in the literature, we found no additional benefit to placing animals in the Trendelenburg position after lumbar vector injection [Meyer et al, Molecular therapy: the journal of the American Society of Gene Therapy. Oct. 31, 2014].

Together these findings support vector administration at the level of the cisterna magna, as this approach achieves more efficient vector distribution than administration via lumbar puncture, and appears to carry less risk of immunity to the transgene product than ICV administration. Vector delivery to the cisterna magna could be carried out clinically using the suboccipital puncture approach that was used in preclinical studies. Additionally, injection into the subarachnoid space between the first and second cervical vertebra using a lateral approach (C1-2 puncture) is likely to produce similar vector distribution given the proximity of the injection site to the cisterna magna. The C1-2 approach has the additional advantage that, unlike suboccipital puncture, it is widely used clinically for CSF access, particularly for intrathecal contrast administration.

This application contains a sequence listing, which is hereby incorporated by reference, as are U.S. Patent Application No. 62/616,106, filed Jan. 11, 2018, U.S. Patent Application No. 62/530,614, filed Jul. 10, 2017, U.S. 62/529,385, filed Jul. 6, 2017. All publications, patents, and patent applications cited in this application are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

TABLE (Sequence Listing Free Text)
The following information is provided for sequences containing free text under numeric identifier <223>.

| SEQ ID NO | Free Text under <223> |
|---|---|
| 3 | <223> CB7.CI.hIDUAco.RBG |
|  | <220> |
|  | <221> misc_feature |
|  | <222> (1) ... (130) |
|  | <223> 5"ITR |
|  | <220> |
|  | <221> promoter |
|  | <222> (198) ... (579) |
|  | <223> CMV IE promoter |
|  | <220> |
|  | <221> promoter |
|  | <222> (582) ... (863) |
|  | <223> CB promoter |
|  | <220> |
|  | <221> TATA_signal |
|  | <222> (836) ... (839) |
|  | <220> |
|  | <221> Intron |
|  | <222> (956) ... (1928) |
|  | <223> chicken beta-actin intron |
|  | <220> |
|  | <221> CDS |
|  | <222> (1990) ... (3948) |
|  | <223> human IDUA co |
|  | <220> |
|  | <221> polyA_signal |
|  | <222> (4000) ... (4126) |
|  | <223> rabbit globin polyA |
| 5 | <223> Vector genome - TBG.PI.hIDUAco.RBG |
|  | <220> |
|  | <221> repeat_region |
|  | <222> (1) ... (130) |
|  | <223> 5' ITR |
|  | <220> |
|  | <221> enhancer |
|  | <222> (221) ... (320) |
|  | <223> Alpha mic/Bik |
|  | <220> |
|  | <221> enhancer |
|  | <222> (327) ... (426) |
|  | <223> Alpha mic/Bik |
|  | <220> |
|  | <221> promoter |
|  | <222> (442) ... (901) |
|  | <223> TBG |
|  | <220> |

TABLE-continued (Sequence Listing Free Text)
The following information is provided for sequences containing free text under numeric identifier <223>.

| SEQ ID NO | Free Text under <223> |
|---|---|
|  | <221> TATA_signal |
|  | <222> (885) ... (888) |
|  | <220> |
|  | <221> Intron |
|  | <222> (1027) ... (1157) |
|  | <220> |
|  | <221> misc_feature |
|  | <222> (1251) ... (3212) |
|  | <223> Human alpha-L-IDUA coding sequence |
|  | <220> |
|  | <221> polyA_signal |
|  | <222> (3261) ... (3387) |
|  | <223> rabbit globin poly A |
|  | <220> |
|  | <221> repeat_region |
|  | <222> (3476) ... (3605) |
| 6 | <223> Vector genome: CMV.PI.hIDUAco.SV40 |
|  | <220> |
|  | <221> repeat_region |
|  | <222> (1) ... (130) |
|  | <223> 5' ITR |
|  | <220> |
|  | <221> misc_feature |
|  | <222> (143) ... (181) |
|  | <223> CMV enhancer and promoter |
|  | <220> |
|  | <221> TATA_signal |
|  | <222> (910) ... (916) |
|  | <220> |
|  | <221> Intron |
|  | <222> (1024) ... (1221) |
|  | <223> chimeric intron |
|  | <220> |
|  | <221> misc_feature |
|  | <222> (1284) ... (3246) |
|  | <223> human IDUA coding sequence |
|  | <220> |
|  | <221> polyA_signal |
|  | <222> (3258) ... (3496) |
|  | <220> |
|  | <221> repeat_region |
|  | <222> (3562) ... (3691) |
| 7 | <220> |
|  | <223> hu14/Adeno-associated virus 9 |

The invention claimed is:

1. A therapeutic regimen useful for treatment of an alpha-L-iduronidase deficiency in a human patient, wherein the regimen comprises administering to a patient:
  (a) a recombinant adeno-associated virus (rAAV) having an AAV9 capsid and a nucleic acid comprising a sequence encoding human α-L-iduronidase (hIDUA) under control of regulatory sequences which direct expression thereof in the patient, wherein the hIDUA coding sequence has the nucleotide sequence of nucleotides 1 to 1962 of SEQ ID NO: 1 or a sequence at least 80% identical to nucleotides 1 to 1962 of SEQ ID NO:

1 which encodes a functional hIDUA, wherein the regulatory sequences comprise a cytomegalovirus immediate early (CMV IE) enhancer, a chicken beta-actin promoter, a chicken beta actin intron, and a rabbit beta globin polyadenylation (poly A) signal sequence, (b) at least a first immunosuppressive agent which is an intravenous corticosteroid; and (c) at least a second immunosuppressive agent which is an oral corticosteroid, wherein administration of at least one immunosuppressive agent begins prior to or on the same day as delivery of the rAAV; and wherein administration of at least one of the immunosuppressive agents continues for at least 8 weeks post-rAAV administration.

2. The therapeutic regimen according to claim 1, wherein the therapeutic regimen comprises further administering to a patient one or more immunosuppressive agents comprising one or more macrolides.

3. The therapeutic regimen according to claim 2, wherein the one or more macrolides comprises tacrolimus, sirolimus, or combination of tacrolimus and sirolimus.

4. The therapeutic regimen according to claim 1, wherein corticosteroids administration is discontinued 12-weeks post rAAV administration.

5. The therapeutic regimen according to claim 2, wherein the immunosuppressive agent which is tacrolimus is administered on day 2 post-rAAV administration.

6. The therapeutic regimen according to claim 2, wherein the immunosuppressive agent which is sirolimus is administered on day −2 prior to rAAV administration.

7. The therapeutic regimen according to claim 2, wherein when the immunosuppressive agents comprise both tacrolimus and sirolimus, a low dose of each is used to maintain a blood trough level of (i) 2 ng/ml to 4 ng/ml, or about 4 ng/ml to about 8 ng/ml, or a total of about 8 ng/ml to about 16 ng/ml of tacrolimus, and (ii) 1 ng/ml to 3 ng/ml of sirolimus.

8. The therapeutic regimen according to claim 2, wherein when the immunosuppressive agents comprise only one of tacrolimus or sirolimus, the total dose is in the range of about 16 ng/ml to about 24 ng/ml.

9. The therapeutic regimen according to claim 2, wherein when the immunosuppressive agents comprise both tacrolimus and sirolimus, the initial loading dose of sirolimus is about 1 mg/m$^2$.

10. The therapeutic regimen according to claim 1, wherein the immunosuppressive therapy is started at about day −14 to day −1 prior to rAAV administration.

11. The therapeutic regimen according to claim 1, wherein the encoded hIDUA has the sequence of:

(a) amino acids 1 to 653 of SEQ ID NO: 2 (Genbank NP_000193); or (b) a synthetic human enzyme comprising a heterologous leader sequence fused to amino acids 27 to 653 of SEQ ID NO: 2.

12. The therapeutic regimen according to claim 1, wherein the rAAV is in a suspension having a pH of 6 to 9.

13. The therapeutic regimen according to claim 12, wherein the rAAV is delivered via intrathecal injection.

14. The therapeutic regimen according to claim 13, further Comprising co-administering an rAAV comprising the hIDUA gene intravenously.

15. The therapeutic regimen according to claim 1, wherein the efficacy of therapy is assessed by measuring auditory capacity changes, optionally by auditory brainstem testing.

16. The therapeutic regimen according to claim 1, wherein the rAAV is formulated for intrathecal injection to a human subject, to administer a total flat dose of:

(i) about $1.2 \times 10^{12}$ to about $6.0 \times 10^{12}$ GC or about $6.0 \times 10^{12}$ to about $3.0 \times 10^{13}$ GC to a human subject ≥4 months to <9 months of age;

(ii) about $2 \times 10^{12}$ to about $6.0 \times 10^{13}$ or about $1.0 \times 10^{13}$ to about $5.0 \times 10^{13}$ GC to a human subject ≥9 months to <18 months of age; or (iii) about $2.2 \times 10^{12}$ to about $1.1 \times 10^{13}$ GC or about $1.1 \times 10^{13}$ to about $5.5 \times 10^{13}$ GC to a human subject ≥9 months to <18 months of age.

17. The therapeutic regimen according to claim 1, wherein the patient is pre-dosed initially with the intravenous immunosuppressive agent which is a corticosteroid prior to rAAV administration.

18. The therapeutic regimen according to claim 1, wherein the patient is dosed with the oral immunosuppressive agent which is a corticosteroid following rAAV administration.

19. The therapeutic regimen according to claim 1, wherein the rAAV comprises a vector genome comprising a nucleic acid sequence having the sequence of nucleotides 1 to 4344 of SEQ ID NO: 3.

20. The therapeutic regimen according to claim 5, wherein administering the patient with tacrolimus is discontinued 32-weeks post rAAV administration.

21. The therapeutic regimen according to claim 6, wherein administering the patient with sirolimus is discontinued 48-weeks post rAAV administration.

22. The therapeutic regimen according to claim 2, wherein when the immunosuppressive agents comprise both tacrolimus and sirolimus, the initial dose of tacrolimus is 0.05 mg/kg twice daily.

23. The therapeutic regimen according to claim 1, wherein the hIDUA coding sequence comprises a nucleic acid sequence having the sequence of nucleotides 1 to 1962 of SEQ ID NO: 1.

24. The therapeutic regimen according to claim 23, wherein the regimen comprises dosing the patient with tacrolimus to a blood trough level of about 4 ng/mL to about 8 ng/ml.

25. The therapeutic regimen according to claim 23, wherein the regimen comprises dosing the patient with sirolimus to a blood trough level of about 1 ng/mL to about 3 ng/ml.

26. The therapeutic regimen according to claim 1, wherein the rAAV is administrable by intracerebroventricular or intracisternal delivery.

27. The therapeutic regimen according to claim 1, wherein the rAAV is administrable by intrathecal injection at a dose of about $10^9$ to $10^{11}$ GC/g brain mass.

28. The therapeutic regimen according to claim 1, wherein the rAAV comprises an expression cassette comprising a nucleic acid sequence having the sequence of nucleotides 198 to 4126 of SEQ ID NO: 3.

29. The therapeutic regimen according to claim 28, wherein the rAAV is administrable by intracerebroventricular or intracisternal delivery.

30. The therapeutic regimen according to claim 29, wherein the regimen comprises dosing a patient with tacrolimus to a blood trough level of about 4 ng/mL to about 8 ng/ml.

31. The therapeutic regimen according to claim 29, wherein the regimen comprises dosing the patient with sirolimus to a blood trough level of about 1 ng/mL to about 3 ng/ml.

32. The therapeutic regimen according to claim 29, wherein the patient is predosed initially with the intravenous corticosteroid prior to rAAV delivery.

33. The therapeutic regimen according to claim 29, wherein the intravenous corticosteroid is methylprednisolone given at 10 mg/kg on Day 1 prior to rAAV delivery.

34. The therapeutic regimen according to claim 33, wherein the patient is dosed with the oral corticosteroid following rAAV delivery.

35. The therapeutic regimen according to claim 34, wherein the oral corticosteroid is prednisone given starting at 0.5 mg/kg/day on Day 2 after rAAV delivery.

36. The therapeutic regimen according to claim 1, wherein the intravenous corticosteroid is methylprednisolone given at 10 mg/kg once on Day 1 prior to rAAV delivery.

37. The therapeutic regimen according to claim 1, wherein the oral corticosteroid is prednisone given starting at 0.5 mg/kg/day on Day 2 after rAAV delivery.

* * * * *

SEQUENCE LISTING

<160> NUMBER OF SEQ ID NOS: 7

<210> SEQ ID NO 1
<211> LENGTH: 1971
<212> TYPE: DNA
<213> ORGANISM: Homo sapiens
<220> FEATURE:
<221> NAME/KEY: CDS
<222> LOCATION: (1)..(1971)

<400> SEQUENCE: 1

```
atg cgg ccc ctg agg cct aga gct gct ctg ctg gca ctg ctg gcc agt      48
Met Arg Pro Leu Arg Pro Arg Ala Ala Leu Leu Ala Leu Leu Ala Ser
 1               5                  10                  15 ctg ctg gct gcc cct cct gtg gcc cct gcc gaa gcc cct cac ctg gtg      96
Leu Leu Ala Ala Pro Pro Val Ala Pro Ala Glu Ala Pro His Leu Val
             20                  25                  30 cat gtg gat gcc gcc aga gcc ctg tgg cct ctg cgg aga ttc tgg cgg     144
```

```
His Val Asp Ala Ala Arg Ala Leu Trp Pro Leu Arg Arg Phe Trp Arg
        35                  40                  45 agc acc ggc ttt tgc ccc cca ctg cct cac agc cag gcc gac cag tac      192
Ser Thr Gly Phe Cys Pro Pro Leu Pro His Ser Gln Ala Asp Gln Tyr
 50                  55                  60 gtg ctg agc tgg gac cag cag ctg aac ctg gcc tac gtg ggc gcc gtg      240
Val Leu Ser Trp Asp Gln Gln Leu Asn Leu Ala Tyr Val Gly Ala Val
 65                  70                  75                  80 ccc cac aga ggc atc aaa cag gtg aga acc cac tgg ctg ctg gaa ctg      288
Pro His Arg Gly Ile Lys Gln Val Arg Thr His Trp Leu Leu Glu Leu
                 85                  90                  95 gtg aca acc cgg ggc tcc acc ggc aga ggc ctg agc tac aac ttc acc      336
Val Thr Thr Arg Gly Ser Thr Gly Arg Gly Leu Ser Tyr Asn Phe Thr
                100                 105                 110 cac ctg gac ggc tac ctg gac ctg ctg aga gag aac cag ctg ctg ccc      384
His Leu Asp Gly Tyr Leu Asp Leu Leu Arg Glu Asn Gln Leu Leu Pro
                115                 120                 125 ggc ttc gag ctg atg ggc agc gcc agc ggc cac ttc acc gac ttc gag      432
Gly Phe Glu Leu Met Gly Ser Ala Ser Gly His Phe Thr Asp Phe Glu
130                 135                 140 gac aag cag caa gtc ttt gag tgg aag gac ctg gtg tcc agc ctg gcc      480
Asp Lys Gln Gln Val Phe Glu Trp Lys Asp Leu Val Ser Ser Leu Ala
145                 150                 155                 160 aga cgg tac atc ggc aga tac gga ctg gcc cac gtg tcc aag tgg aac      528
Arg Arg Tyr Ile Gly Arg Tyr Gly Leu Ala His Val Ser Lys Trp Asn
                165                 170                 175 ttc gag aca tgg aac gag ccc gac cac cac gac ttc gac aac gtg tca      576
Phe Glu Thr Trp Asn Glu Pro Asp His His Asp Phe Asp Asn Val Ser
                180                 185                 190 atg acc atg cag ggc ttt ctg aac tac tac gac gcc tgc tcc gag ggc      624
Met Thr Met Gln Gly Phe Leu Asn Tyr Tyr Asp Ala Cys Ser Glu Gly
                195                 200                 205 ctg aga gcc gcc agt cct gcc ctg aga ctg ggc gga ccc ggc gat agc      672
Leu Arg Ala Ala Ser Pro Ala Leu Arg Leu Gly Gly Pro Gly Asp Ser
210                 215                 220 ttc cac acc ccc cca aga agc ccc ctg agc tgg ggc ctg ctg aga cac      720
Phe His Thr Pro Pro Arg Ser Pro Leu Ser Trp Gly Leu Leu Arg His
225                 230                 235                 240 tgc cac gac ggc acc aat ttc ttc acc ggc gag gcc ggc gtg cgg ctg      768
Cys His Asp Gly Thr Asn Phe Phe Thr Gly Glu Ala Gly Val Arg Leu
                245                 250                 255 gac tac atc agc ctg cac cgg aag ggc gcc aga agc agc atc agc atc      816
Asp Tyr Ile Ser Leu His Arg Lys Gly Ala Arg Ser Ser Ile Ser Ile
                260                 265                 270 ctg gaa cag gaa aag gtc gtc gcc cag cag atc cgg cag ctg ttc ccc      864
Leu Glu Gln Glu Lys Val Val Ala Gln Gln Ile Arg Gln Leu Phe Pro
                275                 280                 285 aag ttc gcc gac acc ccc atc tac aac gac gag gcc gac ccc ctg gtg      912
Lys Phe Ala Asp Thr Pro Ile Tyr Asn Asp Glu Ala Asp Pro Leu Val
290                 295                 300 gga tgg tca ctg cct cag cct tgg aga gcc gac gtg acc tac gcc gct      960
Gly Trp Ser Leu Pro Gln Pro Trp Arg Ala Asp Val Thr Tyr Ala Ala
305                 310                 315                 320 atg gtg gtg aaa gtg atc gcc cag cat cag aac ctg ctg ctg gcc aac     1008
Met Val Val Lys Val Ile Ala Gln His Gln Asn Leu Leu Leu Ala Asn
                325                 330                 335 acc acc agc gcc ttc cct tac gcc ctg ctg agc aac gac aac gcc ttc     1056
Thr Thr Ser Ala Phe Pro Tyr Ala Leu Leu Ser Asn Asp Asn Ala Phe
                340                 345                 350
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | agc | tac | cac | ccc | cac | ccc | ttc | gcc | cag | aga | acc | ctg | acc | gcc | cgg | 1104 |
| Leu | Ser | Tyr | His | Pro | His | Pro | Phe | Ala | Gln | Arg | Thr | Leu | Thr | Ala | Arg |      |
|     | 355 |     |     |     | 360 |     |     |     |     | 365 |     |     |     |     |     |      |

| | | | | | | | | | | | | | | | | |
|---|---|---|---|---|---|---|---|---|---|---|---|---|---|---|---|---|
| ttc | cag | gtg | aac | aac | acc | aga | ccc | ccc | cac | gtg | cag | ctg | ctg | aga | aag | 1152 |
| Phe | Gln | Val | Asn | Asn | Thr | Arg | Pro | Pro | His | Val | Gln | Leu | Leu | Arg | Lys | |
| | 370 | | | | | 375 | | | | | 380 | | | | | |

| | | | | | | | | | | | | | | | | |
|---|---|---|---|---|---|---|---|---|---|---|---|---|---|---|---|---|
| ccc | gtg | ctg | acc | gct | atg | gga | ctg | ctg | gct | ctg | ctg | gac | gag | gaa | cag | 1200 |
| Pro | Val | Leu | Thr | Ala | Met | Gly | Leu | Leu | Ala | Leu | Leu | Asp | Glu | Glu | Gln | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| ctg | tgg | gcc | gaa | gtg | tcc | cag | gcc | ggc | acc | gtg | ctg | gac | agc | aat | cat | 1248 |
| Leu | Trp | Ala | Glu | Val | Ser | Gln | Ala | Gly | Thr | Val | Leu | Asp | Ser | Asn | His | |
| | | | | 405 | | | | | 410 | | | | | 415 | | |

| | | | | | | | | | | | | | | | | |
|---|---|---|---|---|---|---|---|---|---|---|---|---|---|---|---|---|
| aca | gtg | ggc | gtg | ctg | gcc | tcc | gcc | cac | aga | cct | cag | gga | ccc | gcc | gat | 1296 |
| Thr | Val | Gly | Val | Leu | Ala | Ser | Ala | His | Arg | Pro | Gln | Gly | Pro | Ala | Asp | |
| | | 420 | | | | | 425 | | | | | 430 | | | | |

| | | | | | | | | | | | | | | | | |
|---|---|---|---|---|---|---|---|---|---|---|---|---|---|---|---|---|
| gct | tgg | cgg | gct | gcc | gtg | ctg | atc | tac | gcc | agc | gac | gat | acc | aga | gcc | 1344 |
| Ala | Trp | Arg | Ala | Ala | Val | Leu | Ile | Tyr | Ala | Ser | Asp | Asp | Thr | Arg | Ala | |
| | | 435 | | | | | 440 | | | | | 445 | | | | |

| | | | | | | | | | | | | | | | | |
|---|---|---|---|---|---|---|---|---|---|---|---|---|---|---|---|---|
| cac | ccc | aac | aga | tcc | gtg | gcc | gtg | acc | ctg | cgg | ctg | aga | ggc | gtg | cca | 1392 |
| His | Pro | Asn | Arg | Ser | Val | Ala | Val | Thr | Leu | Arg | Leu | Arg | Gly | Val | Pro | |
| 450 | | | | | 455 | | | | | 460 | | | | | | |

| | | | | | | | | | | | | | | | | |
|---|---|---|---|---|---|---|---|---|---|---|---|---|---|---|---|---|
| cca | ggc | cct | gga | ctg | gtg | tac | gtg | acc | aga | tac | ctg | gac | aac | ggc | ctg | 1440 |
| Pro | Gly | Pro | Gly | Leu | Val | Tyr | Val | Thr | Arg | Tyr | Leu | Asp | Asn | Gly | Leu | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| tgc | agc | ccc | gac | ggc | gaa | tgg | cgc | aga | ctg | ggc | aga | cct | gtg | ttc | ccc | 1488 |
| Cys | Ser | Pro | Asp | Gly | Glu | Trp | Arg | Arg | Leu | Gly | Arg | Pro | Val | Phe | Pro | |
| | | | | 485 | | | | | 490 | | | | | 495 | | |

| | | | | | | | | | | | | | | | | |
|---|---|---|---|---|---|---|---|---|---|---|---|---|---|---|---|---|
| acc | gcc | gag | cag | ttc | cgg | cgg | atg | aga | gcc | gct | gag | gat | cct | gtg | gct | 1536 |
| Thr | Ala | Glu | Gln | Phe | Arg | Arg | Met | Arg | Ala | Ala | Glu | Asp | Pro | Val | Ala | |
| | | | 500 | | | | | 505 | | | | | 510 | | | |

| | | | | | | | | | | | | | | | | |
|---|---|---|---|---|---|---|---|---|---|---|---|---|---|---|---|---|
| gct | gcc | cct | aga | cct | ctg | cct | gct | ggc | ggc | aga | ctg | acc | ctg | agg | ccc | 1584 |
| Ala | Ala | Pro | Arg | Pro | Leu | Pro | Ala | Gly | Gly | Arg | Leu | Thr | Leu | Arg | Pro | |
| | | | 515 | | | | | 520 | | | | | 525 | | | |

| | | | | | | | | | | | | | | | | |
|---|---|---|---|---|---|---|---|---|---|---|---|---|---|---|---|---|
| gct | ctg | aga | ctg | cct | agt | ctg | ctg | ctg | gtg | cac | gtg | tgc | gcc | agg | ccc | 1632 |
| Ala | Leu | Arg | Leu | Pro | Ser | Leu | Leu | Leu | Val | His | Val | Cys | Ala | Arg | Pro | |
| | 530 | | | | | 535 | | | | | 540 | | | | | |

| | | | | | | | | | | | | | | | | |
|---|---|---|---|---|---|---|---|---|---|---|---|---|---|---|---|---|
| gag | aag | cct | ccc | ggc | cag | gtg | aca | aga | ctg | aga | gcc | ctg | ccc | ctg | acc | 1680 |
| Glu | Lys | Pro | Pro | Gly | Gln | Val | Thr | Arg | Leu | Arg | Ala | Leu | Pro | Leu | Thr | |
| 545 | | | | | 550 | | | | | 555 | | | | | 560 | |

| | | | | | | | | | | | | | | | | |
|---|---|---|---|---|---|---|---|---|---|---|---|---|---|---|---|---|
| cag | ggc | cag | ctg | gtg | ctg | gtg | tgg | tcc | gat | gag | cac | gtg | ggc | agc | aag | 1728 |
| Gln | Gly | Gln | Leu | Val | Leu | Val | Trp | Ser | Asp | Glu | His | Val | Gly | Ser | Lys | |
| | | | | 565 | | | | | 570 | | | | | 575 | | |

| | | | | | | | | | | | | | | | | |
|---|---|---|---|---|---|---|---|---|---|---|---|---|---|---|---|---|
| tgc | ctg | tgg | acc | tac | gag | atc | cag | ttc | agc | cag | gac | ggc | aag | gcc | tac | 1776 |
| Cys | Leu | Trp | Thr | Tyr | Glu | Ile | Gln | Phe | Ser | Gln | Asp | Gly | Lys | Ala | Tyr | |
| | | | 580 | | | | | 585 | | | | | 590 | | | |

| | | | | | | | | | | | | | | | | |
|---|---|---|---|---|---|---|---|---|---|---|---|---|---|---|---|---|
| acc | ccc | gtg | tcc | cgg | aag | ccc | agc | acc | ttc | aac | ctg | ttc | gtg | ttc | agc | 1824 |
| Thr | Pro | Val | Ser | Arg | Lys | Pro | Ser | Thr | Phe | Asn | Leu | Phe | Val | Phe | Ser | |
| | | 595 | | | | | 600 | | | | | 605 | | | | |

| | | | | | | | | | | | | | | | | |
|---|---|---|---|---|---|---|---|---|---|---|---|---|---|---|---|---|
| ccc | gat | aca | ggc | gcc | gtg | tcc | ggc | tct | tat | aga | gtg | cgg | gcc | ctg | gac | 1872 |
| Pro | Asp | Thr | Gly | Ala | Val | Ser | Gly | Ser | Tyr | Arg | Val | Arg | Ala | Leu | Asp | |
| | | 610 | | | | | 615 | | | | | 620 | | | | |

| | | | | | | | | | | | | | | | | |
|---|---|---|---|---|---|---|---|---|---|---|---|---|---|---|---|---|
| tac | tgg | gcc | aga | ccc | ggc | cct | ttc | agc | gac | ccc | gtg | ccc | tac | ctg | gaa | 1920 |
| Tyr | Trp | Ala | Arg | Pro | Gly | Pro | Phe | Ser | Asp | Pro | Val | Pro | Tyr | Leu | Glu | |
| 625 | | | | | 630 | | | | | 635 | | | | | 640 | |

| | | | | | | | | | | | | | | | | |
|---|---|---|---|---|---|---|---|---|---|---|---|---|---|---|---|---|
| gtg | ccc | gtg | cct | aga | ggc | ccc | tct | agc | ccc | ggc | aac | cct | tga | gtc | gac | 1968 |
| Val | Pro | Val | Pro | Arg | Gly | Pro | Ser | Ser | Pro | Gly | Asn | Pro |  | Val | Asp | |
| | | | 645 | | | | | 650 | | | | | | 655 | | |

| | | |
|---|---|---|
| ccg | | 1971 |
| Pro | | |

<210> SEQ ID NO 2
<211> LENGTH: 653
<212> TYPE: PRT
<213> ORGANISM: Homo sapiens

<400> SEQUENCE: 2

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380
```

```
Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
            405                 410                 415

Thr Val Gly Val Leu Ala Ser Ala His Arg Pro Gln Gly Pro Ala Asp
        420                 425                 430

Ala Trp Arg Ala Ala Val Leu Ile Tyr Ala Ser Asp Asp Thr Arg Ala
    435                 440                 445

His Pro Asn Arg Ser Val Ala Val Thr Leu Arg Leu Arg Gly Val Pro
450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
            485                 490                 495

Thr Ala Glu Gln Phe Arg Arg Met Arg Ala Ala Glu Asp Pro Val Ala
        500                 505                 510

Ala Ala Pro Arg Pro Leu Pro Ala Gly Gly Arg Leu Thr Leu Arg Pro
    515                 520                 525

Ala Leu Arg Leu Pro Ser Leu Leu Leu Val His Val Cys Ala Arg Pro
530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
            565                 570                 575

Cys Leu Trp Thr Tyr Glu Ile Gln Phe Ser Gln Asp Gly Lys Ala Tyr
        580                 585                 590

Thr Pro Val Ser Arg Lys Pro Ser Thr Phe Asn Leu Phe Val Phe Ser
    595                 600                 605

Pro Asp Thr Gly Ala Val Ser Gly Ser Tyr Arg Val Arg Ala Leu Asp
610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
            645                 650

<210> SEQ ID NO 3
<211> LENGTH: 4344
<212> TYPE: DNA
<213> ORGANISM: Artificial sequence
<220> FEATURE:
<223> OTHER INFORMATION: CB7.CI.hIDUAco.RBG
<220> FEATURE:
<221> NAME/KEY: misc_feature
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: chicken beta-actin intron
<220> FEATURE:
```

```
<221> NAME/KEY: CDS
<222> LOCATION: (1990)..(3948)
<223> OTHER INFORMATION: human IDUA co
<220> FEATURE:
<221> NAME/KEY: polyA_signal
<222> LOCATION: (4000)..(4126)
<223> OTHER INFORMATION: rabbit globin polyA
<220> FEATURE:
<221> NAME/KEY: misc_feature
<222> LOCATION: (4215)..(4344)

<400> SEQUENCE: 3
```

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctaccag | ggtaatgggg | 180 |
| atcctctaga | actatagcta | gtcgacattg | attattgact | agttattaat | agtaatcaat | 240 |
| tacgggtca | ttagttcata | gcccatatat | ggagttccgc | gttacataac | ttacggtaaa | 300 |
| tggcccgcct | ggctgaccgc | ccaacgaccc | ccgcccattg | acgtcaataa | tgacgtatgt | 360 |
| tcccatagta | acgccaatag | ggactttcca | ttgacgtcaa | tgggtggagt | atttacggta | 420 |
| aactgcccac | ttggcagtac | atcaagtgta | tcatatgcca | agtacgcccc | ctattgacgt | 480 |
| caatgacggt | aaatggcccg | cctggcatta | tgcccagtac | atgaccttat | gggactttcc | 540 |
| tacttggcag | tacatctacg | tattagtcat | cgctattacc | atggtcgagg | tgagccccac | 600 |
| gttctgcttc | actctcccca | tctcccccc | ctccccaccc | ccaattttgt | atttatttat | 660 |
| tttttaatta | ttttgtgcag | cgatggggc | ggggggggg | gggggcgcg | cgccaggcgg | 720 |
| ggcggggcgg | ggcgaggggc | ggggcgggc | gaggcggaga | ggtgcggcgg | cagccaatca | 780 |
| gagcggcgcg | ctccgaaagt | ttccttttat | ggcgaggcgg | cggcggcggc | ggccctataa | 840 |
| aaagcgaagc | gcgcggcggg | cgggagtcgc | tgcgcgctgc | cttcgccccg | tgccccgctc | 900 |
| cgccgccgcc | tcgcgccgcc | cgccccggct | ctgactgacc | gcgttactcc | cacaggtgag | 960 |
| cgggcgggac | ggcccttctc | ctccgggctg | taattagcgc | ttggtttaat | gacggcttgt | 1020 |
| ttcttttctg | tggctgcgtg | aaagccttga | ggggctccgg | gagggccctt | tgtgcggggg | 1080 |
| gagcggctcg | gggggtgcgt | gcgtgtgtgt | gtgcgtgggg | agcgccgcgt | gcggctccgc | 1140 |
| gctgcccggc | ggctgtgagc | gctgcgggcg | cggcgcgggg | ctttgtgcgc | tccgcagtgt | 1200 |
| gcgcgagggg | agcgcggccg | ggggcggtgc | cccgcggtgc | ggggggggct | gcgaggggaa | 1260 |
| caaaggctgc | gtgcggggtg | tgtgcgtggg | ggggtgagca | gggggtgtgg | gcgcgtcggt | 1320 |
| cgggctgcaa | ccccccctgc | accccctcc | ccgagttgct | gagcacgcc | cggcttcggg | 1380 |
| tgcggggctc | cgtacggggc | gtggcgcggg | gctcgccgtg | ccgggcgggg | ggtggcggca | 1440 |
| ggtggggtg | ccgggcgggg | cggggccgcc | tcggccgggg | gagggctcgg | gggaggggcg | 1500 |
| cggcggcccc | cggagcgccg | gcggctgtcg | aggcgcggcg | agccgcagcc | attgcctttt | 1560 |
| atggtaatcg | tgcgagaggg | cgcagggact | tcctttgtcc | caaatctgtg | cggagccgaa | 1620 |
| atctgggagg | cgccgccgca | ccccctctag | cgggcgcggg | gcgaagcggt | gcggcgccgg | 1680 |
| caggaaggaa | atgggcgggg | agggccttcg | tgcgtcgccg | cgccgccgtc | ccttctcccc | 1740 |
| tctccagcct | cggggctgtc | cgcggggga | cggctgcctt | cggggggac | ggggcagggc | 1800 |
| ggggttcggc | ttctggcgtg | tgaccggcgg | ctctagagcc | tctgctaacc | atgttcatgc | 1860 |
| cttcttcttt | ttcctacagc | tcctgggcaa | cgtgctggtt | attgtgctgt | ctcatcattt | 1920 |
| tggcaaagaa | ttcacgcgtg | gtacctctag | agtcgacccg | gcggcctcg | agaattcacg | 1980 |

```
cgtgccacc atg cgg ccc ctg agg cct aga gct gct ctg ctg gca ctg ctg         2031
          Met Arg Pro Leu Arg Pro Arg Ala Ala Leu Leu Ala Leu Leu
          1               5                   10 gcc agt ctg ctg gct gcc cct cct gtg gcc cct gcc gaa gcc cct cac           2079
Ala Ser Leu Leu Ala Ala Pro Pro Val Ala Pro Ala Glu Ala Pro His
15                  20                  25                  30 ctg gtg cat gtg gat gcc gcc aga gcc ctg tgg cct ctg cgg aga ttc           2127
Leu Val His Val Asp Ala Ala Arg Ala Leu Trp Pro Leu Arg Arg Phe
                35                  40                  45 tgg cgg agc acc ggc ttt tgc ccc cca ctg cct cac agc cag gcc gac           2175
Trp Arg Ser Thr Gly Phe Cys Pro Pro Leu Pro His Ser Gln Ala Asp
50                  55                  60 cag tac gtg ctg agc tgg gac cag cag ctg aac ctg gcc tac gtg ggc           2223
Gln Tyr Val Leu Ser Trp Asp Gln Gln Leu Asn Leu Ala Tyr Val Gly
            65                  70                  75 gcc gtg ccc cac aga ggc atc aaa cag gtg aga acc cac tgg ctg ctg           2271
Ala Val Pro His Arg Gly Ile Lys Gln Val Arg Thr His Trp Leu Leu
80                  85                  90 gaa ctg gtg aca acc cgg ggc tcc acc ggc aga ggc ctg agc tac aac           2319
Glu Leu Val Thr Thr Arg Gly Ser Thr Gly Arg Gly Leu Ser Tyr Asn
95                  100                 105                 110 ttc acc cac ctg gac ggc tac ctg gac ctg ctg aga gag aac cag ctg           2367
Phe Thr His Leu Asp Gly Tyr Leu Asp Leu Leu Arg Glu Asn Gln Leu
            115                 120                 125 ctg ccc ggc ttc gag ctg atg ggc agc gcc agc ggc cac ttc acc gac           2415
Leu Pro Gly Phe Glu Leu Met Gly Ser Ala Ser Gly His Phe Thr Asp
            130                 135                 140 ttc gag gac aag cag caa gtc ttt gag tgg aag gac ctg gtg tcc agc           2463
Phe Glu Asp Lys Gln Gln Val Phe Glu Trp Lys Asp Leu Val Ser Ser
145                 150                 155 ctg gcc aga cgg tac atc ggc aga tac gga ctg gcc cac gtg tcc aag           2511
Leu Ala Arg Arg Tyr Ile Gly Arg Tyr Gly Leu Ala His Val Ser Lys
160                 165                 170 tgg aac ttc gag aca tgg aac gag ccc gac cac cac gac ttc gac aac           2559
Trp Asn Phe Glu Thr Trp Asn Glu Pro Asp His His Asp Phe Asp Asn
175                 180                 185                 190 gtg tca atg acc atg cag ggc ttt ctg aac tac tac gac gcc tgc tcc           2607
Val Ser Met Thr Met Gln Gly Phe Leu Asn Tyr Tyr Asp Ala Cys Ser
                195                 200                 205 gag ggc ctg aga gcc gcc agt cct gcc ctg aga ctg ggc gga ccc ggc           2655
Glu Gly Leu Arg Ala Ala Ser Pro Ala Leu Arg Leu Gly Gly Pro Gly
            210                 215                 220 gat agc ttc cac acc ccc ccc aga agc ccc ctg agc tgg ggc ctg ctg           2703
Asp Ser Phe His Thr Pro Pro Arg Ser Pro Leu Ser Trp Gly Leu Leu
            225                 230                 235 aga cac tgc cac gac ggc acc aat ttc ttc acc ggc gag gcc ggc gtg           2751
Arg His Cys His Asp Gly Thr Asn Phe Phe Thr Gly Glu Ala Gly Val
240                 245                 250 cgg ctg gac tac atc agc ctg cac cgg aag ggc gcc aga agc agc atc           2799
Arg Leu Asp Tyr Ile Ser Leu His Arg Lys Gly Ala Arg Ser Ser Ile
255                 260                 265                 270 agc atc ctg gaa cag gaa aag gtc gtc gcc cag cag atc cgg cag ctg           2847
Ser Ile Leu Glu Gln Glu Lys Val Val Ala Gln Gln Ile Arg Gln Leu
                275                 280                 285 ttc ccc aag ttc gcc gac acc ccc atc tac aac gac gag gcc gac ccc           2895
Phe Pro Lys Phe Ala Asp Thr Pro Ile Tyr Asn Asp Glu Ala Asp Pro
            290                 295                 300 ctg gtg gga tgg tca ctg cct cag cct tgg aga gcc gac gtg acc tac           2943
Leu Val Gly Trp Ser Leu Pro Gln Pro Trp Arg Ala Asp Val Thr Tyr
            305                 310                 315
```

| | | |
|---|---|---|
| gcc gct atg gtg gtg aaa gtg atc gcc cag cat cag aac ctg ctg ctg<br>Ala Ala Met Val Val Lys Val Ile Ala Gln His Gln Asn Leu Leu Leu<br>320                          325                         330 | 2991 | |
| gcc aac acc acc agc gcc ttc cct tac gcc ctg ctg agc aac gac aac<br>Ala Asn Thr Thr Ser Ala Phe Pro Tyr Ala Leu Leu Ser Asn Asp Asn<br>335                          340                         345                  350 | 3039 | |
| gcc ttc ctg agc tac cac ccc cac ccc ttc gcc cag aga acc ctg acc<br>Ala Phe Leu Ser Tyr His Pro His Pro Phe Ala Gln Arg Thr Leu Thr<br>                      355                         360                       365 | 3087 | |
| gcc cgg ttc cag gtg aac aac acc aga ccc ccc cac gtg cag ctg ctg<br>Ala Arg Phe Gln Val Asn Asn Thr Arg Pro Pro His Val Gln Leu Leu<br>                370                         375                       380 | 3135 | |
| aga aag ccc gtg ctg acc gct atg gga ctg ctg gct ctg ctg gac gag<br>Arg Lys Pro Val Leu Thr Ala Met Gly Leu Leu Ala Leu Leu Asp Glu<br>385                          390                         395 | 3183 | |
| gaa cag ctg tgg gcc gaa gtg tcc cag gcc ggc acc gtg ctg gac agc<br>Glu Gln Leu Trp Ala Glu Val Ser Gln Ala Gly Thr Val Leu Asp Ser<br>            400                       405                       410 | 3231 | |
| aat cat aca gtg ggc gtg ctg gcc tcc gcc cac aga cct cag gga ccc<br>Asn His Thr Val Gly Val Leu Ala Ser Ala His Arg Pro Gln Gly Pro<br>415                          420                       425                  430 | 3279 | |
| gcc gat gct tgg cgg gct gcc gtg ctg atc tac gcc agc gac gat acc<br>Ala Asp Ala Trp Arg Ala Ala Val Leu Ile Tyr Ala Ser Asp Asp Thr<br>                         435                       440                       445 | 3327 | |
| aga gcc cac ccc aac aga tcc gtg gcc gtg acc ctg cgg ctg aga ggc<br>Arg Ala His Pro Asn Arg Ser Val Ala Val Thr Leu Arg Leu Arg Gly<br>                      450                         455                       460 | 3375 | |
| gtg cca cca ggc cct gga ctg gtg tac gtg acc aga tac ctg gac aac<br>Val Pro Pro Gly Pro Gly Leu Val Tyr Val Thr Arg Tyr Leu Asp Asn<br>            465                       470                       475 | 3423 | |
| ggc ctg tgc agc ccc gac ggc gaa tgg cgc aga ctg ggc aga cct gtg<br>Gly Leu Cys Ser Pro Asp Gly Glu Trp Arg Arg Leu Gly Arg Pro Val<br>480                          485                         490 | 3471 | |
| ttc ccc acc gcc gag cag ttc cgg cgg atg aga gcc gct gag gat cct<br>Phe Pro Thr Ala Glu Gln Phe Arg Arg Met Arg Ala Ala Glu Asp Pro<br>495                          500                       505                  510 | 3519 | |
| gtg gct gct gcc cct aga cct ctg cct gct ggc ggc aga ctg acc ctg<br>Val Ala Ala Ala Pro Arg Pro Leu Pro Ala Gly Gly Arg Leu Thr Leu<br>                        515                       520                       525 | 3567 | |
| agg ccc gct ctg aga ctg cct agt ctg ctg ctg gtg cac gtg tgc gcc<br>Arg Pro Ala Leu Arg Leu Pro Ser Leu Leu Leu Val His Val Cys Ala<br>                    530                       535                     540 | 3615 | |
| agg ccc gag aag cct ccc ggc cag gtg aca aga ctg aga gcc ctg ccc<br>Arg Pro Glu Lys Pro Pro Gly Gln Val Thr Arg Leu Arg Ala Leu Pro<br>545                          550                       555 | 3663 | |
| ctg acc cag ggc cag ctg gtg ctg gtg tgg tcc gat gag cac gtg ggc<br>Leu Thr Gln Gly Gln Leu Val Leu Val Trp Ser Asp Glu His Val Gly<br>560                          565                       570 | 3711 | |
| agc aag tgc ctg tgg acc tac gag atc cag ttc agc cag gac ggc aag<br>Ser Lys Cys Leu Trp Thr Tyr Glu Ile Gln Phe Ser Gln Asp Gly Lys<br>575                          580                       585                  590 | 3759 | |
| gcc tac acc ccc gtg tcc cgg aag ccc agc acc ttc aac ctg ttc gtg<br>Ala Tyr Thr Pro Val Ser Arg Lys Pro Ser Thr Phe Asn Leu Phe Val<br>                        595                       600                     605 | 3807 | |
| ttc agc ccc gat aca ggc gcc gtg tcc ggc tct tat aga gtg cgg gcc<br>Phe Ser Pro Asp Thr Gly Ala Val Ser Gly Ser Tyr Arg Val Arg Ala<br>                    610                       615                     620 | 3855 | |
| ctg gac tac tgg gcc aga ccc ggc cct ttc agc gac ccc gtg ccc tac<br>Leu Asp Tyr Trp Ala Arg Pro Gly Pro Phe Ser Asp Pro Val Pro Tyr | 3903 | |

```
                  625                 630                 635
ctg gaa gtg ccc gtg cct aga ggc ccc cct agc ccc ggc aac cct        3948
Leu Glu Val Pro Val Pro Arg Gly Pro Pro Ser Pro Gly Asn Pro
        640                 645                 650 tgagtcgacc cgggcggcct cgaggacggg gtgaactacg cctgaggatc cgatcttttt   4008
ccctctgcca aaaattatgg ggacatcatg aagcccttg agcatctgac ttctggctaa    4068
taaaggaaat ttattttcat tgcaatagtg tgttggaatt ttttgtgtct ctcactcgga   4128
agcaattcgt tgatctgaat ttcgaccacc cataataccc attaccctgg tagataagta   4188
gcatggcggg ttaatcatta actacaagga acccctagtg atggagttgg ccactccctc   4248
tctgcgcgct cgctcgctca ctgaggccgg gcgaccaaag gtcgcccgac gcccgggctt   4308
tgcccgggcg gcctcagtga gcgagcgagc gcgcag                              4344
```

<210> SEQ ID NO 4
<211> LENGTH: 653
<212> TYPE: PRT
<213> ORGANISM: Artificial sequence
<220> FEATURE:
<223> OTHER INFORMATION: Synthetic Construct

<400> SEQUENCE: 4

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
```

```
                260                 265                 270
Leu Glu Gln Glu Lys Val Ala Gln Gln Ile Arg Gln Leu Phe Pro
                275                 280                 285

Lys Phe Ala Asp Thr Pro Ile Tyr Asn Asp Glu Ala Asp Pro Leu Val
            290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
        370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
        450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Val His Val Cys Ala Arg Pro
        530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
        610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```

<210> SEQ ID NO 5
<211> LENGTH: 3605
<212> TYPE: DNA
<213> ORGANISM: Artificial sequence

```
<220> FEATURE:
<223> OTHER INFORMATION: Vector genome - TBG.PI.hIDUAco.RBG
<220> FEATURE:
<221> NAME/KEY: repeat_region
<222> LOCATION: (1)..(130)
<223> OTHER INFORMATION: 5' ITR
<220> FEATURE:
<221> NAME/KEY: enhancer
<222> LOCATION: (221)..(320)
<223> OTHER INFORMATION: Alpha mic/Bik
<220> FEATURE:
<221> NAME/KEY: enhancer
<222> LOCATION: (327)..(426)
<223> OTHER INFORMATION: Alpha mic/Bik
<220> FEATURE:
<221> NAME/KEY: promoter
<222> LOCATION: (442)..(901)
<223> OTHER INFORMATION: TBG
<220> FEATURE:
<221> NAME/KEY: TATA_signal
<222> LOCATION: (885)..(888)
<220> FEATURE:
<221> NAME/KEY: Intron
<222> LOCATION: (1027)..(1157)
<220> FEATURE:
<221> NAME/KEY: misc_feature
<222> LOCATION: (1251)..(3212)
<223> OTHER INFORMATION: Human alpha-L-IDUA coding sequence
<220> FEATURE:
<221> NAME/KEY: polyA_signal
<222> LOCATION: (3261)..(3387)
<223> OTHER INFORMATION: rabbit globin poly A
<220> FEATURE:
<221> NAME/KEY: repeat_region
<222> LOCATION: (3476)..(3605)

<400> SEQUENCE: 5
ctgcgcgctc gctcgctcac tgaggccgcc cgggcaaagc ccgggcgtcg ggcgaccttt      60
ggtcgcccgg cctcagtgag cgagcgagcg cgcagagagg gagtgggcaa ctccatcact     120
aggggttcct tgtagttaat gattaacccg ccatgctact tatctaccag ggtaatgggg     180
atcctctaga actatagcta gaattcgccc ttaagctagc aggttaattt ttaaaaagca     240
gtcaaaagtc caagtggccc ttggcagcat ttactctctc tgtttgctct ggttaataat     300
ctcaggagca caaacattcc agatccaggt taatttttaa aaagcagtca aaagtccaag     360
tggcccttgg cagcatttac tctctctgtt tgctctggtt aataatctca ggagcacaaa     420
cattccagat ccgcgcgcc agggctggaa gctacctttg acatcatttc ctctgcgaat      480
gcatgtataa tttctacaga acctattaga aaggatcacc cagcctctgc ttttgtacaa     540
ctttccctta aaaactgcc aattccactg ctgtttggcc caatagtgag aactttttcc      600
tgctgcctct tggtgctttt gcctatggcc cctattctgc ctgctgaaga cactcttgcc     660
agcatggact taaaccccte cagctctgac aatcctcttt ctcttttgtt ttacatgaag     720
ggtctggcag ccaaagcaat cactcaaagt tcaaaccta tcattttttg ctttgttcct     780
cttggccttg gttttgtaca tcagctttga aaataccatc ccagggttaa tgctggggtt     840
aatttataac taagagtgct ctagttttgc aatacaggac atgctataaa aatgaaagga     900
tgttgctttc tgagagacag ctttattgcg gtagtttatc acagttaaat tgctaacgca     960
gtcagtgctt ctgacacaac agtctcgaac ttaagctgca gaagttggtc gtgaggcact    1020
gggcaggtaa gtatcaaggt tacaagacag gtttaaggag accaatagaa actgggcttg    1080
tcgagacaga aagactctt gcgtttctga taggcaccta ttggtcttac tgacatccac     1140
tttgcctttc tctccacagg tgtccactcc cagttcaatt acagctctta aggctagagt    1200
acttaatacg actcactata ggctagcctc gagaattcac gcgtgccacc atgcggcccc    1260
```

```
tgaggcctag agctgctctg ctggcactgc tggccagtct gctggctgcc cctcctgtgg    1320
cccctgccga agcccctcac ctggtgcatg tggatgccgc cagagccctg tggcctctgc    1380
ggagattctg gcggagcacc ggcttttgcc ccccactgcc tcacagccag gccgaccagt    1440
acgtgctgag ctgggaccag cagctgaacc tggcctacgt gggcgccgtg ccccacagag    1500
gcatcaaaca ggtgagaacc cactggctgc tggaactggt gacaacccgg ggctccaccg    1560
gcagaggcct gagctacaac ttcacccacc tggacggcta cctggacctg ctgagagaga    1620
accagctgct gcccggcttc gagctgatgg gcagcgccag cggccacttc accgacttcg    1680
aggacaagca gcaagtcttt gagtggaagg acctggtgtc cagcctggcc agacggtaca    1740
tcggcagata cggactggcc cacgtgtcca gtggaacttt cgagacatgg aacgagcccg    1800
accaccacga cttcgacaac gtgtcaatga ccatgcaggg cttctgaac tactacgacg    1860 cctgctccga gggcctgaga ccgccagtc ctgccctgag actgggcgga cccggcgata    1920
gcttccacac ccccccagag agcccctga gctgggcct gctgagacac tgccacgacg    1980
gcaccaattt cttcaccggc gaggccggcg tgcggctgga ctacatcagc ctgcaccgga    2040
agggcgccag aagcagcatc agcatcctgg aacaggaaaa ggtcgtcgcc cagcagatcc    2100
ggcagctgtt ccccaagttc gccgacaccc ccatctacaa cgacgaggcc gacccctgg    2160 tgggatggtc actgcctcag ccttggagag ccgacgtgac ctacgccgct atggtggtga    2220
aagtgatcgc ccagcatcag aacctgctgc tggccaacac caccagcgcc ttcccttacg    2280
ccctgctgag caacgacaac gccttcctga gctaccaccc ccaccccttc gcccagagaa    2340
ccctgaccgc ccggttccag gtgaacaaca ccagacccccc cacgtgcag ctgctgagaa    2400 agcccgtgct gaccgctatg ggactgctgg ctctgctgga cgaggaacag ctgtgggccg    2460
aagtgtccca ggccggcacc gtgctggaca gcaatcatac agtgggcgtg ctggcctccg    2520
cccacagacc tcagggaccc gccgatgctt ggcgggctgc cgtgctgatc tacgccagcg    2580
acgataccag agcccacccc aacagatccg tggccgtgac cctgcggctg agaggcgtgc    2640
caccaggccc tggactggtg tacgtgacca gataccctgga caacggcctg tgcagccccg    2700
acggcgaatg gcgcagactg ggcagacctg tgttccccac cgccgagcag ttccggcgga    2760
tgagagccgc tgaggatcct gtggctgctg cccctagacc tctgcctgct ggcggcagac    2820
tgaccctgag gcccgctctg agactgccta gtctgctgct ggtgcacgtg tgcgccaggc    2880
ccgagaagcc tcccggccag gtgacaagac tgagagccct gccctgacc cagggccagc    2940 tggtgctggt gtggtccgat gagcacgtgg gcagcaagtg cctgtggacc tacgagatcc    3000
agttcagcca ggacggcaag gcctacaccc ccgtgtcccg gaagcccagc accttcaacc    3060
tgttcgtgtt cagcccccgat acaggcgccg tgtccggctc ttatagagtg cgggccctgg    3120
actactgggc cagacccggc cctttcagcg acccccgtgcc ctacctggaa gtgcccgtgc    3180
ctagaggccc ccctagcccc ggcaacccctt gagtcgaccc gggcggcctc gaggacgggg    3240
tgaactacgc ctgaggatcc gatcttttc cctctgccaa aaattatggg gacatcatga    3300
agccccttga gcatctgact tctggctaat aaaggaaatt tattttcatt gcaatagtgt    3360
gttggaattt tttgtgtctc tcactcggaa gcaattcgtt gatctgaatt cgaccaccc    3420 ataatacca ttacctggt agataagtag catggcgggt taatcattaa ctacaaggaa    3480
cccctagtga tggagttggc cactccctct ctgcgcgctc gctcgctcac tgaggccggg    3540
cgaccaaagg tcgcccgacg cccgggcttt gcccgggcgg cctcagtgag cgagcgagcg    3600
``` cgcag 3605

<210> SEQ ID NO 6
<211> LENGTH: 3691
<212> TYPE: DNA
<213> ORGANISM: Artificial sequence
<220> FEATURE:
<223> OTHER INFORMATION: Vector genome: CMV.PI.hIDUAco.SV40
<220> FEATURE:
<221> NAME/KEY: repeat_region
<222> LOCATION: (1)..(130)
<223> OTHER INFORMATION: 5' ITR
<220> FEATURE:
<221> NAME/KEY: misc_feature
<222> LOCATION: (143)..(181)
<223> OTHER INFORMATION: CMV enhancer and promoter
<220> FEATURE:
<221> NAME/KEY: TATA_signal
<222> LOCATION: (910)..(916)
<220> FEATURE:
<221> NAME/KEY: Intron
<222> LOCATION: (1024)..(1221)
<223> OTHER INFORMATION: chimeric intron
<220> FEATURE:
<221> NAME/KEY: misc_feature
<222> LOCATION: (1284)..(3246)
<223> OTHER INFORMATION: human IDUA coding sequence
<220> FEATURE:
<221> NAME/KEY: polyA_signal
<222> LOCATION: (3258)..(3496)
<220> FEATURE:
<221> NAME/KEY: repeat_region
<222> LOCATION: (3562)..(3691)

<400> SEQUENCE: 6

| | | | | | |
|---|---|---|---|---|---|
| ggccttaatt | aggctgcgcg | ctcgctcgct | cactgaggcc | gcccgggcaa | agcccgggcg | 60 |
| tcgggcgacc | tttggtcgcc | cggcctcagt | gagcgagcga | gcgcgcagag | agggagtggc | 120 |
| caactccatc | actaggggtt | ccttgtagtt | aatgattaac | ccgccatgct | acttatctac | 180 |
| gtagccatgc | tctaggaaga | tcttcaatat | tggccattag | ccatattatt | cattggttat | 240 |
| atagcataaa | tcaatattgg | ctattggcca | ttgcatacgt | tgtatctata | tcataatatg | 300 |
| tacatttata | ttggctcatg | tccaatatga | ccgccatgtt | ggcattgatt | attgactagt | 360 |
| tattaatagt | aatcaattac | ggggtcatta | gttcatagcc | catatatgga | gttccgcgtt | 420 |
| acataactta | cggtaaatgg | cccgcctggc | tgaccgccca | acgacccccg | cccattgacg | 480 |
| tcaataatga | cgtatgttcc | catagtaacg | ccaataggga | ctttccattg | acgtcaatgg | 540 |
| gtggagtatt | tacggtaaac | tgcccacttg | gcagtacatc | aagtgtatca | tatgccaagt | 600 |
| ccgcccccta | ttgacgtcaa | tgacggtaaa | tggcccgcct | ggcattatgc | ccagtacatg | 660 |
| accttacggg | actttcctac | ttggcagtac | atctacgtat | tagtcatcgc | tattaccatg | 720 |
| gtgatgcggt | tttggcagta | caccaatggg | cgtggatagc | ggtttgactc | acggggattt | 780 |
| ccaagtctcc | accccattga | cgtcaatggg | agtttgtttt | ggcaccaaaa | tcaacgggac | 840 |
| tttccaaaat | gtcgtaataa | ccccgccccg | ttgacgcaaa | tgggcggtag | gcgtgtacgg | 900 |
| tgggaggtct | atataagcag | agctcgttta | gtgaaccgtc | agatcactag | aagctttatt | 960 |
| gcggtagttt | atcacagtta | aattgctaac | gcagtcagtg | cttctgacac | aacagtctcg | 1020 |
| aacttaagct | gcagaagttg | gtcgtgaggc | actgggcagg | taagtatcaa | ggttacaaga | 1080 |
| caggtttaag | gagaccaata | gaaactgggc | ttgtcgagac | agagaagact | cttgcgtttc | 1140 |
| tgataggcac | ctattggtct | tactgacatc | cactttgcct | ttctctccac | aggtgtccac | 1200 |
| tcccagttca | attacagctc | ttaaggctag | agtacttaat | acgactcact | ataggctagc | 1260 |

```
ctcgagaatt cacgcgtgcc accatgcggc ccctgaggcc tagagctgct ctgctggcac    1320
tgctggccag tctgctggct gcccctcctg tggcccctgc cgaagcccct cacctggtgc    1380
atgtggatgc cgccagagcc ctgtggcctc tgcggagatt ctggcggagc accggctttt    1440
gccccccact gcctcacagc caggccgacc agtacgtgct gagctgggac cagcagctga    1500
acctggccta cgtgggcgcc gtgccccaca gaggcatcaa acaggtgaga acccactggc    1560
tgctggaact ggtgacaacc cggggctcca ccggcagagg cctgagctac aacttcaccc    1620
acctggacgg ctacctggac ctgctgagag agaaccagct gctgcccggc ttcgagctga    1680
tgggcagcgc cagcggccac ttcaccgact cgaggacaa gcagcaagtc tttgagtgga    1740
aggacctggt gtccagcctg ccagacggt acatcggcag atacggactg gcccacgtgt    1800
ccaagtggaa cttcgagaca tggaacgagc ccgaccacca cgacttcgac aacgtgtcaa    1860
tgaccatgca gggcttttctg aactactacg acgcctgctc cgagggcctg agagccgcca    1920
gtcctgccct gagactgggc ggacccggcg atagcttcca cacccccccc agaagccccc    1980
tgagctgggg cctgctgaga cactgccacg acggcaccaa tttcttcacc ggcgaggccg    2040
gcgtgcggct ggactacatc agcctgcacc ggaagggcgc cagaagcagc atcagcatcc    2100
tggaacagga aaaggtcgtc gcccagcaga tccggcagct gttccccaag ttcgccgaca    2160
cccccatcta caacgacgag gccgaccccc tggtgggatg gtcactgcct cagccttgga    2220
gagccgacgt gacctacgcc gctatggtgg tgaaagtgat cgcccagcat cagaacctgc    2280
tgctggccaa caccaccagc gccttcccctt acgccctgct gagcaacgac aacgccttcc    2340
tgagctacca ccccccacccc ttcgcccaga gaacccctgac cgcccggttc caggtgaaca    2400
acaccagacc ccccccacgtg cagctgctga aaagcccgt gctgaccgct atgggactgc    2460
tggctctgct ggacgaggaa cagctgtggg ccgaagtgtc ccaggccggc accgtgctgg    2520
acagcaatca tacagtgggc gtgctggcct ccgcccacag acctcaggga cccgccgatg    2580
cttggcgggc tgccgtgctg atctacgcca gcgacgatac cagagcccac cccaacagat    2640
ccgtggccgt gaccctgcgg ctgagaggcg tgccaccagg ccctggactg gtgtacgtga    2700
ccagataccct ggacaacggc ctgtgcagcc ccgacgcga atggcgcaga ctgggcagac    2760
ctgtgttccc caccgccgag cagttccggc ggatgagagc cgctgaggat cctgtggctg    2820
ctgcccctag acctctgcct gctggcggca gactgaccct gaggcccgct ctgagactgc    2880
ctagtctgct gctggtgcac gtgtgcgcca ggcccgagaa gcctcccggc caggtgacaa    2940
gactgagagc cctgccccctg acccaggggc agctggtgct ggtgtggtcc gatgagcacg    3000
tgggcagcaa gtgcctgtgg acctacgaga tccagttcag ccaggacggc aaggcctaca    3060
cccccgtgtc ccggaagccc agcaccttca acctgttcgt gttcagcccc gatacaggcg    3120
ccgtgtccgg ctcttataga gtgcgggccc tggactactg ggccagaccc ggcccttttca    3180
gcgacccgt gccctacctg gaagtgcccg tgcctagagg ccccctagc ccggcaacc    3240
cttgagtcga cccgggcggc cgcttcgagc agacatgata agatacattg atgagtttgg    3300
acaaaccaca actagaatgc agtgaaaaaa atgctttatt tgtgaaattt gtgatgctat    3360
tgctttattt gtaaccatta taagctgcaa taaacaagtt aacaacaaca attgcattca    3420
ttttatgttt caggttcagg gggagatgtg ggaggttttt taaagcaagt aaaacctcta    3480
caaatgtggt aaaatcgata aggatcttcc tagagcatgg ctacgtagat aagtagcatg    3540
gcgggttaat cattaactac aaggaacccc tagtgatgga gttggccact ccctctctgc    3600
gcgctcgctc gctcactgag gccgggcgac caaaggtcgc ccgacgcccg gctttgccc    3660
```

-continued

```
gggcggcctc agtgagcgag cgagcgcgca g                                    3691
```

<210> SEQ ID NO 7
<211> LENGTH: 736
<212> TYPE: PRT
<213> ORGANISM: Artificial sequence
<220> FEATURE:
<223> OTHER INFORMATION: hu14/Adeno-associated virus 9

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350
```

Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735